(12) United States Patent
Shelton, IV et al.

(10) Patent No.: US 11,389,192 B2
(45) Date of Patent: Jul. 19, 2022

(54) METHOD OF SUTURING A TROCAR PATH INCISION

(71) Applicant: ETHICON LLC, Guaynabo, PR (US)

(72) Inventors: Frederick E. Shelton, IV, Hillsboro, OH (US); Gregory J. Bakos, Mason, OH (US); Layne D. Christopher, Cincinnati, OH (US); Rebecca J. Gettinger, Loveland, OH (US); Jason L. Harris, Lebanon, OH (US); Christopher J. Hess, Blue Ash, OH (US); Zhifan F. Huang, Mason, OH (US); John V. Hunt, Cincinnati, OH (US); Michael Jacobs, Villa Hills, KY (US); Anil R. Jadhav, Pune (IN); John A. Jast, Morrow, OH (US); Nichole Y. Kwee, Cincinnati, OH (US); Kevin A. Larson, South Lebanon, OH (US); James G. Lee, Cincinnati, OH (US); David T. Martin, Milford, OH (US); Jerome R. Morgan, Cincinnati, OH (US); Michael A. Murray, Bellevue, KY (US); Shailendra K. Parihar, Mason, OH (US); Sol Posada, Cincinnati, OH (US); Devanathan Raghavan, Mason, OH (US); Brian D. Schings, Cincinnati, OH (US); Patrick M. Schleitweiler, West Chester, OH (US); Nicholas Seipelt, Milford, OH (US); Melinda Tellmann, Franklin, OH (US); Tamara S. Vetro Widenhouse, Clarksville, OH (US)

(73) Assignee: Cilag GmbH International, Zug (CH)

( * ) Notice: Subject to any disclaimer, the term of this patent is extended or adjusted under 35 U.S.C. 154(b) by 697 days.

(21) Appl. No.: 15/637,778

(22) Filed: Jun. 29, 2017

(65) Prior Publication Data

US 2019/0000496 A1   Jan. 3, 2019

(51) Int. Cl.
    *A61B 17/04* (2006.01)
    *A61B 17/34* (2006.01)
    (Continued)

(52) U.S. Cl.
    CPC ...... *A61B 17/3211* (2013.01); *A61B 17/0057* (2013.01); *A61B 17/3417* (2013.01);
    (Continued)

(58) Field of Classification Search
    CPC ............ A61B 17/0057; A61B 17/3421; A61B 17/3423; A61B 17/0482; A61B 17/0469;
    (Continued)

(56) References Cited

U.S. PATENT DOCUMENTS 5,281,237 A * 1/1994 Gimpelson ........ A61B 17/0469
                                                 606/139
5,507,755 A * 4/1996 Gresl ................. A61B 17/0469
                                                 606/139
(Continued)

OTHER PUBLICATIONS

U.S. Appl. No. 15/637,683, filed Jun. 29, 2017.
(Continued)

*Primary Examiner* — Katherine M Rodjom
(74) *Attorney, Agent, or Firm* — Frost Brown Todd LLC

(57) ABSTRACT

A method of suturing a trocar path incision in a tissue of a patient with an obturator includes inserting the obturator through the tissue such that a shaft of the obturator extends through a tissue opening about the trocar path incision and a distal tip of the obturator is positioned within a cavity of the patient. The method also includes directing the suture via a suturing feature with the obturator inserted through the tissue in order to direct the suture relative to the tissue. Furthermore, the method includes closing the tissue opening about the trocar path incision with the suture.

9 Claims, 103 Drawing Sheets

(51) Int. Cl.
  *A61B 17/3211*  (2006.01)
  *A61B 17/00*  (2006.01)
  *A61B 17/06*  (2006.01)

(52) U.S. Cl.
  CPC ...... *A61B 17/3421* (2013.01); *A61B 17/3423* (2013.01); *A61B 17/3494* (2013.01); *A61B 17/0469* (2013.01); *A61B 17/0482* (2013.01); *A61B 17/3462* (2013.01); *A61B 17/3474* (2013.01); *A61B 2017/00637* (2013.01); *A61B 2017/00663* (2013.01); *A61B 2017/06042* (2013.01); *A61B 2017/346* (2013.01); *A61B 2017/3445* (2013.01); *A61B 2017/3466* (2013.01)

(58) Field of Classification Search
  CPC .......... A61B 2017/00637; A61B 2017/00663; A61B 2017/346; A61B 17/3417
  See application file for complete search history.

(56) References Cited

U.S. PATENT DOCUMENTS

| | | | |
|---|---|---|---|
| 5,792,135 A | 8/1998 | Madhani et al. | |
| 5,817,084 A | 10/1998 | Jensen | |
| 5,878,193 A | 3/1999 | Wang et al. | |
| 6,231,565 B1 | 5/2001 | Tovey et al. | |
| 6,364,888 B1 | 4/2002 | Niemeyer et al. | |
| 6,783,524 B2 | 8/2004 | Anderson et al. | |
| 7,524,320 B2 | 4/2009 | Tierney | |
| 7,691,098 B2 | 4/2010 | Wallace et al. | |
| 7,806,891 B2 | 10/2010 | Nowlin et al. | |
| 7,981,092 B2 | 7/2011 | Duke | |
| 8,068,649 B2 | 11/2011 | Green | |
| 8,226,553 B2 | 7/2012 | Shelton, IV et al. | |
| 8,251,900 B2 | 8/2012 | Ortiz et al. | |
| 8,479,969 B2 | 7/2013 | Shelton, IV | |
| 8,517,933 B2 | 8/2013 | Mohr | |
| 8,545,515 B2 | 10/2013 | Prisco et al. | |
| 8,551,115 B2 | 10/2013 | Steger et al. | |
| 8,568,362 B2 | 10/2013 | Moreno et al. | |
| 8,573,461 B2 | 11/2013 | Shelton, IV et al. | |
| 8,573,465 B2 | 11/2013 | Shelton, IV | |
| 8,579,807 B2 | 11/2013 | Moreno et al. | |
| 8,602,288 B2 | 12/2013 | Shelton, IV et al. | |
| 8,616,431 B2 | 12/2013 | Timm et al. | |
| 8,623,028 B2 | 1/2014 | Rogers et al. | |
| 8,636,686 B2 | 1/2014 | Minnelli et al. | |
| 8,690,831 B2 | 4/2014 | Duke | |
| 8,771,180 B2 | 7/2014 | Mohr | |
| 8,783,541 B2 | 7/2014 | Shelton, IV et al. | |
| 8,800,838 B2 | 8/2014 | Shelton, IV | |
| 8,820,605 B2 | 9/2014 | Shelton, IV | |
| 8,844,789 B2 | 9/2014 | Shelton, IV et al. | |
| 8,888,789 B2 | 11/2014 | Prisco et al. | |
| 9,254,178 B2 | 2/2016 | Prisco et al. | |
| 9,283,050 B2 | 3/2016 | Prisco et al. | |
| 9,301,759 B2 | 4/2016 | Spivey et al. | |
| 9,320,416 B2 | 4/2016 | Cooper et al. | |
| 9,339,341 B2 | 5/2016 | Cooper | |
| 9,358,074 B2 | 6/2016 | Schena et al. | |
| 9,572,481 B2 | 2/2017 | Duindam et al. | |
| 9,636,186 B2 | 5/2017 | Kumar et al. | |
| 9,687,226 B2 | 6/2017 | Hodgkinson et al. | |
| 9,700,303 B2 | 7/2017 | Prior et al. | |
| 2006/0030868 A1* | 2/2006 | Bennett, III ........ | A61B 17/0057 606/148 |
| 2007/0208312 A1* | 9/2007 | Norton ............... | A61B 17/3421 604/284 |
| 2008/0200950 A1 | 8/2008 | Wohlert | |
| 2013/0310856 A1* | 11/2013 | Sherts ................. | A61B 50/30 606/148 |
| 2014/0066717 A1 | 3/2014 | Rogers et al. | |
| 2015/0038793 A1 | 2/2015 | Prior et al. | |
| 2017/0128041 A1 | 5/2017 | Hasser et al. | |
| 2017/0128144 A1 | 5/2017 | Hasser et al. | |
| 2017/0128145 A1 | 5/2017 | Hasser et al. | |
| 2017/0281154 A1 | 10/2017 | Hess et al. | |

OTHER PUBLICATIONS

U.S. Appl. No. 15/637,688, filed Jun. 29, 2017.
U.S. Appl. No. 15/637,690, filed Jun. 29, 2017.
U.S. Appl. No. 15/637,696, filed Jun. 29, 2017.
U.S. Appl. No. 15/637,702, filed Jun. 29, 2017.
U.S. Appl. No. 15/637,707, filed Jun. 29, 2017.
U.S. Appl. No. 15/637,712, filed Jun. 29, 2017.
U.S. Appl. No. 15/637,735, filed Jun. 29, 2017.

* cited by examiner

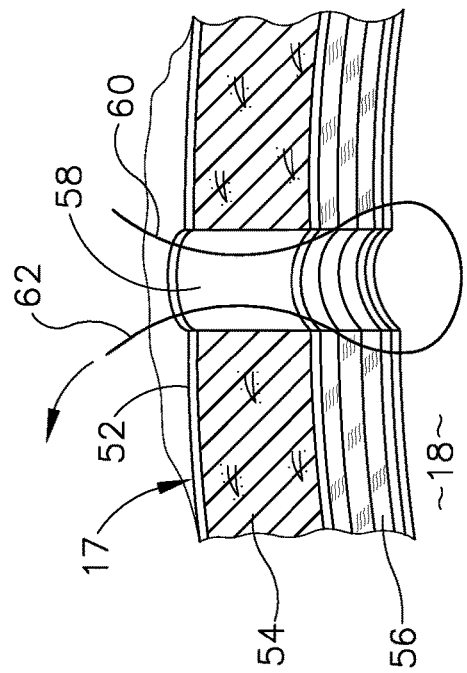
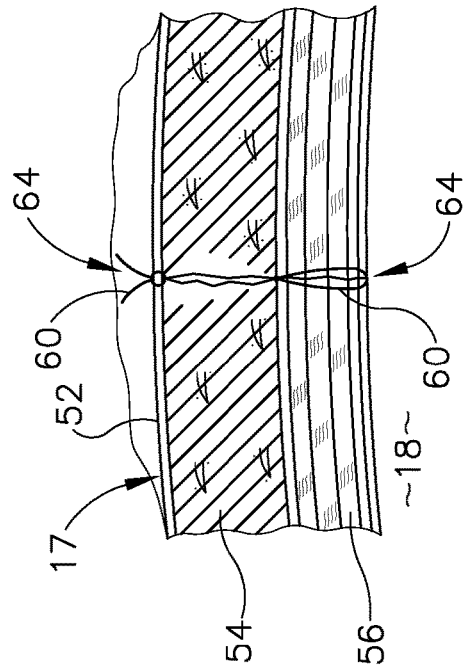
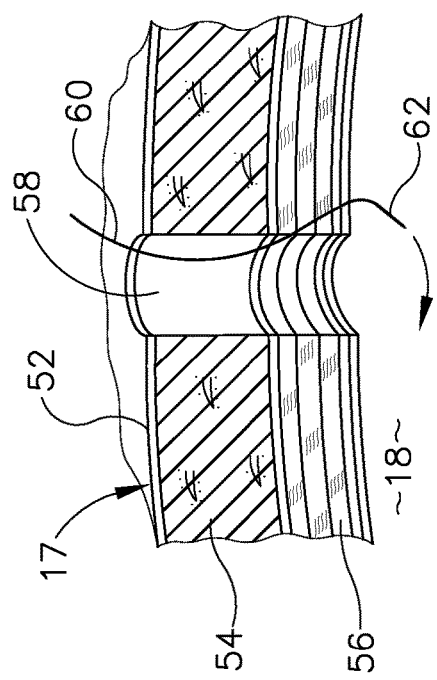
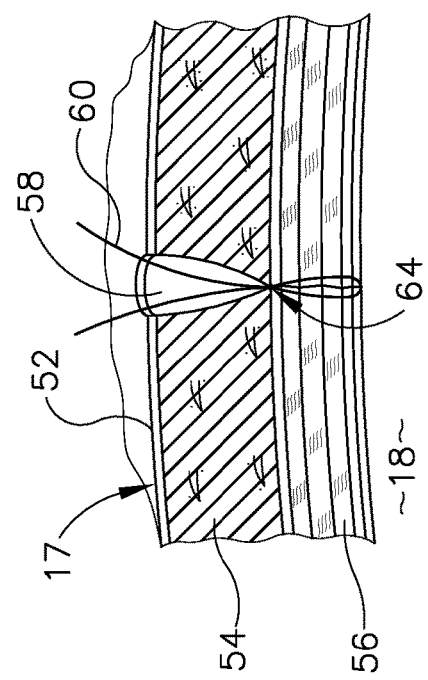

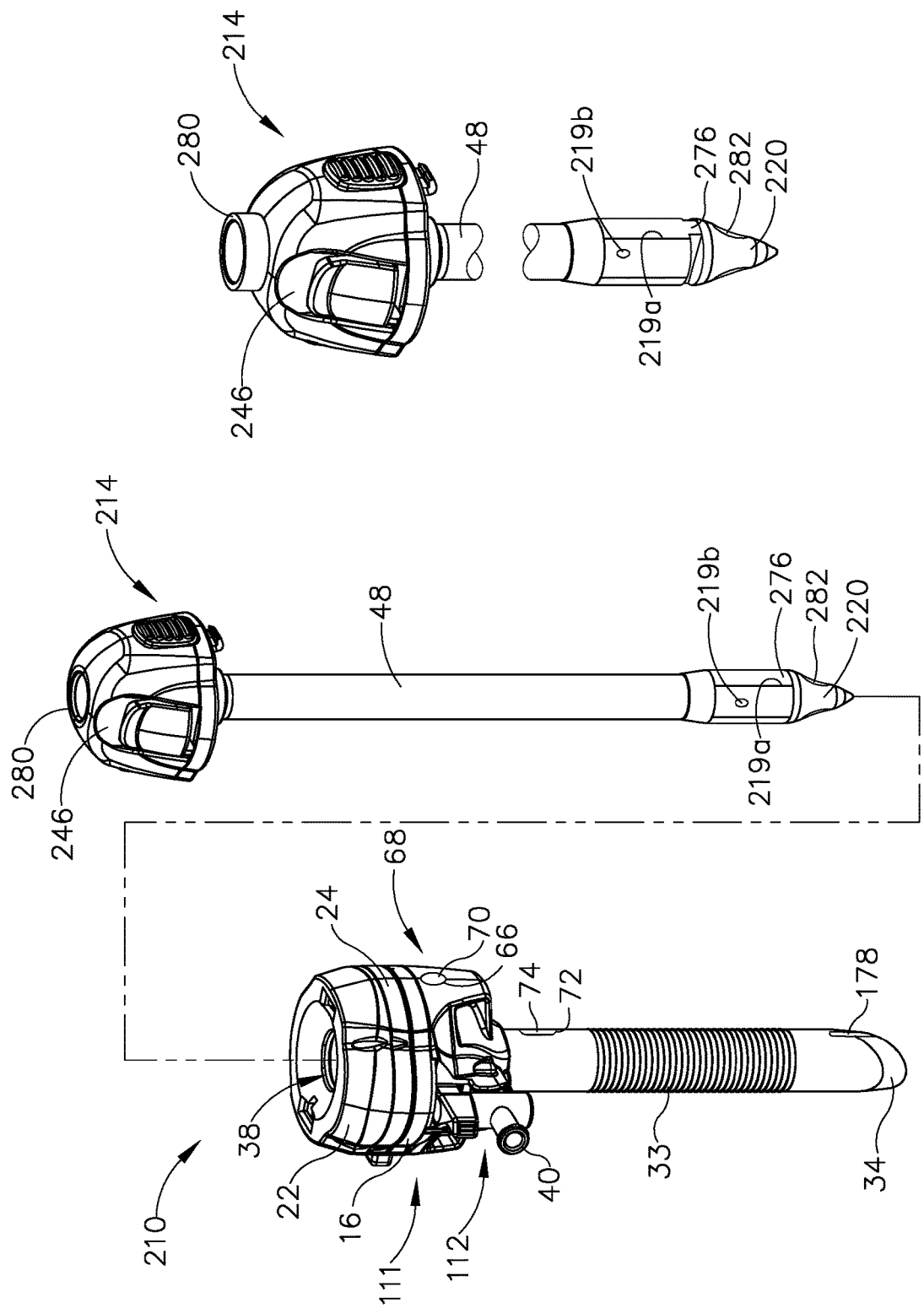

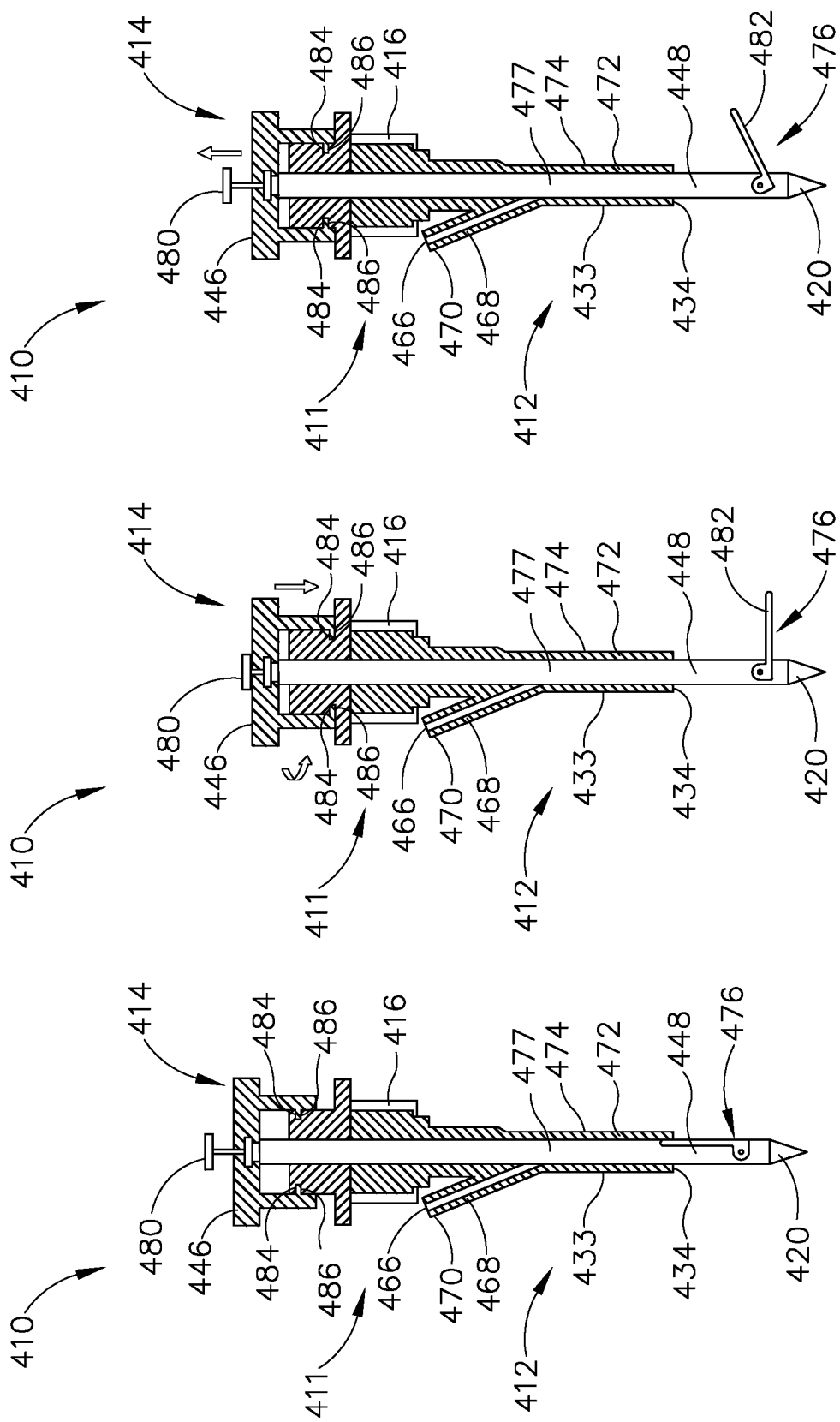

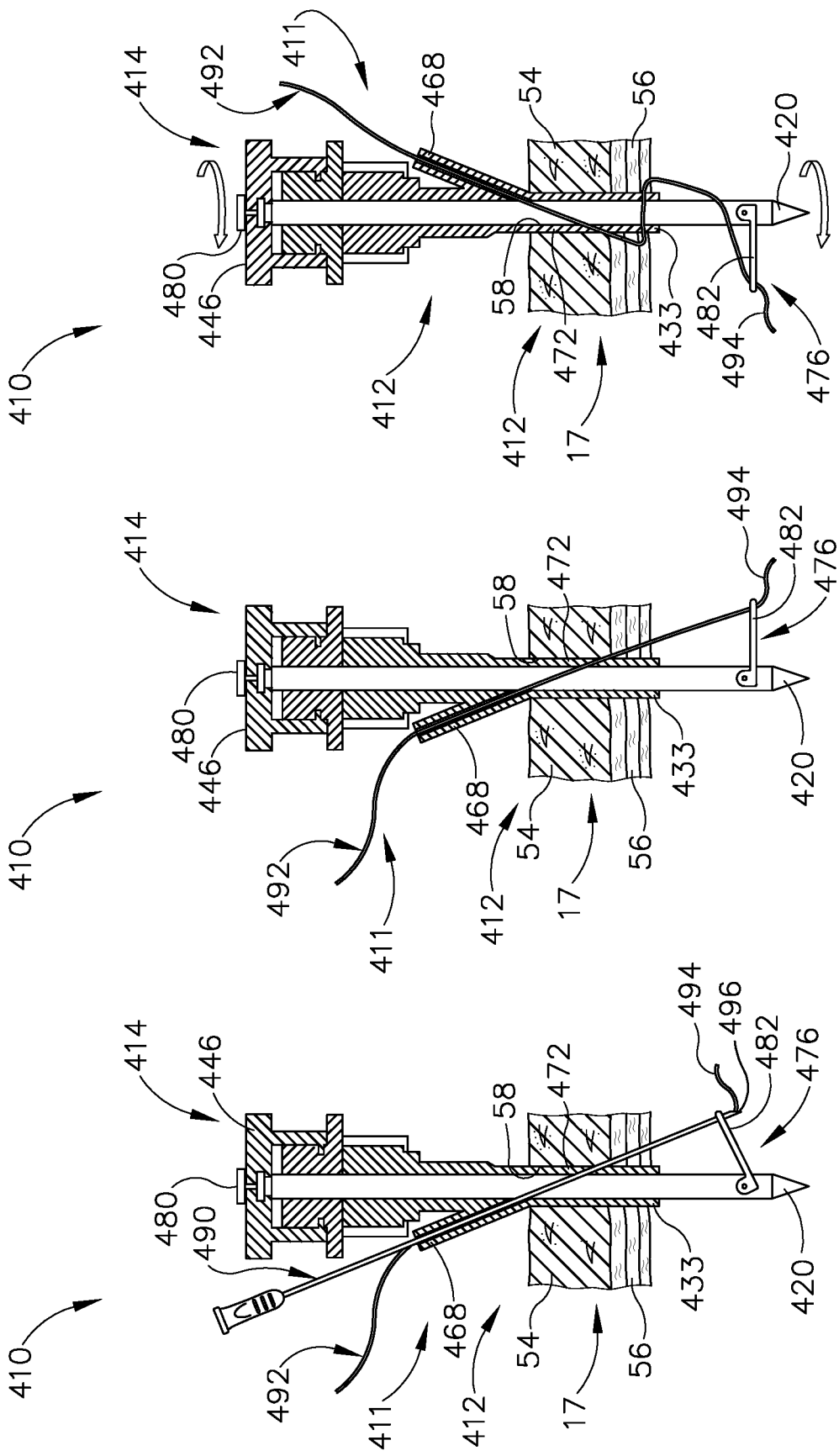

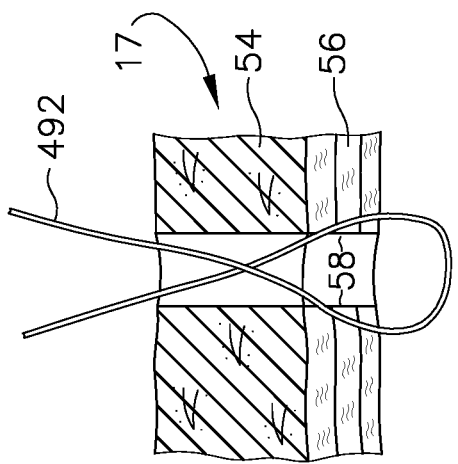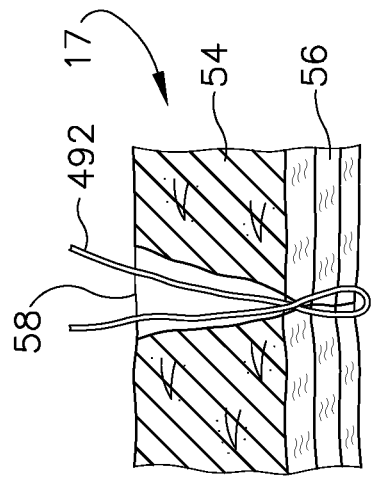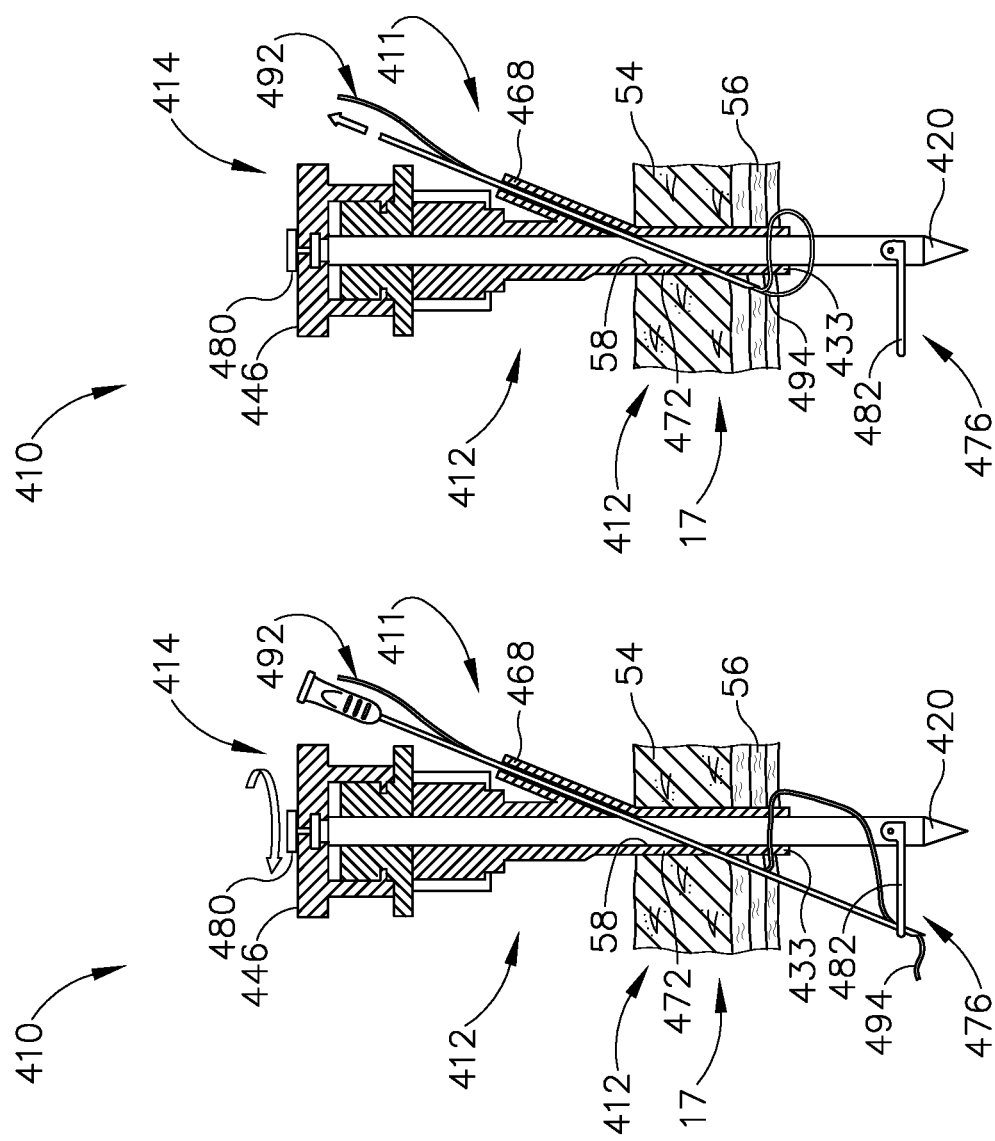

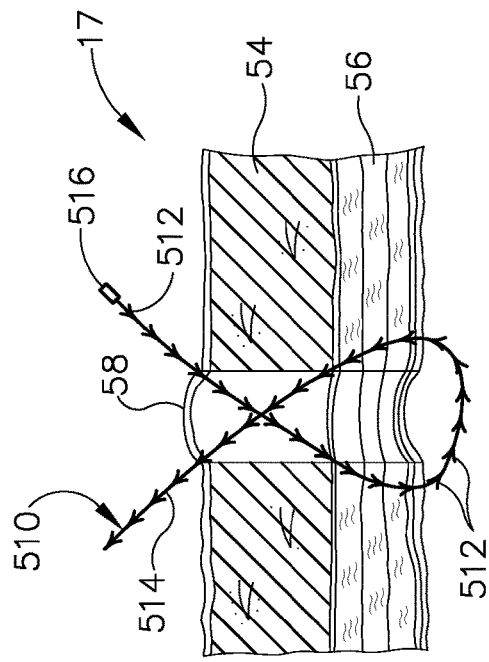
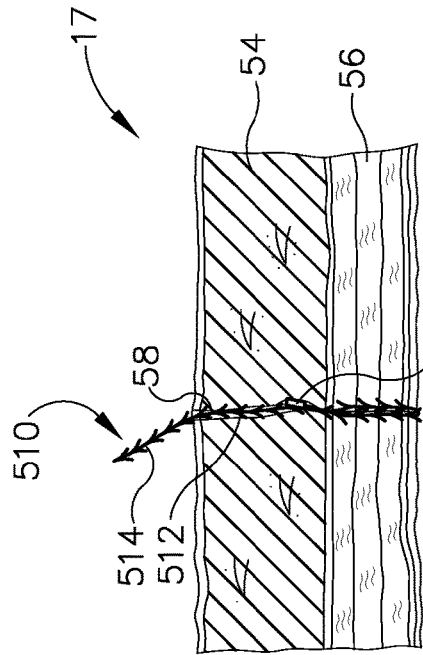
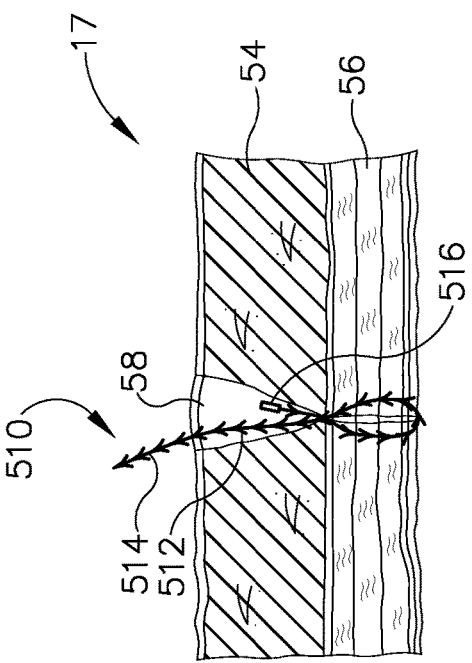
Fig.19A
Fig.19B
Fig.19C

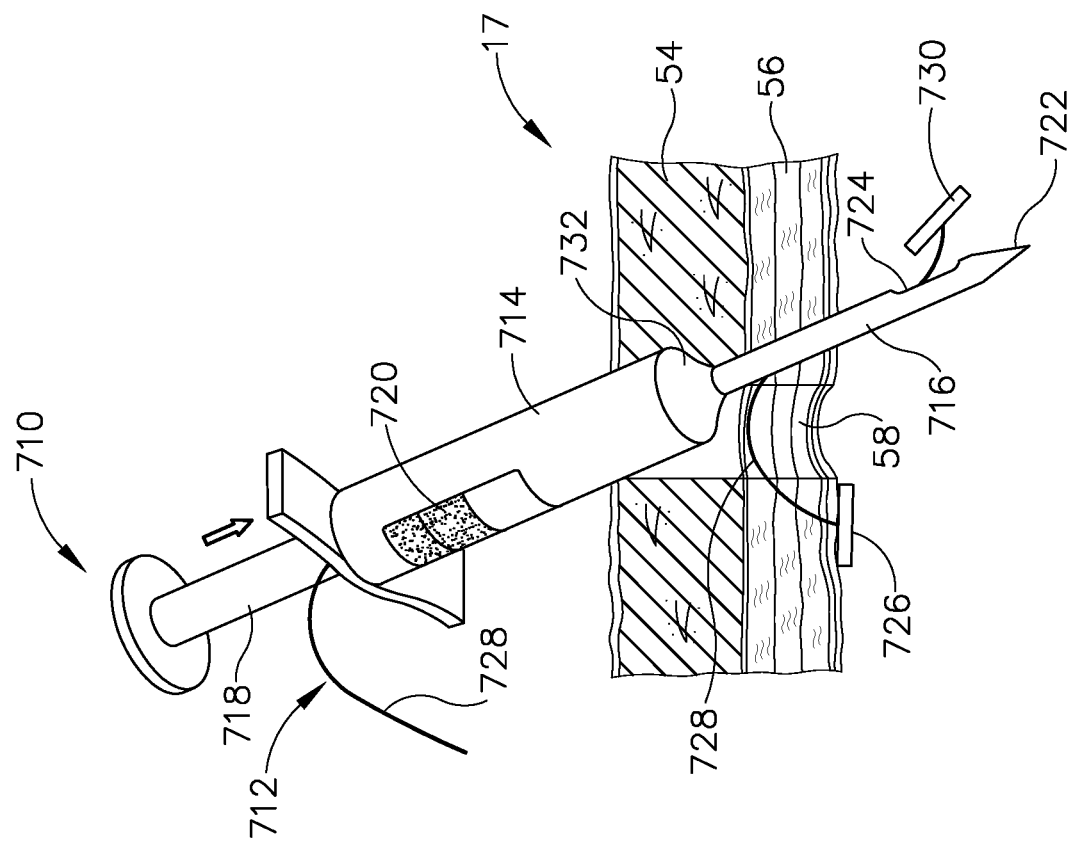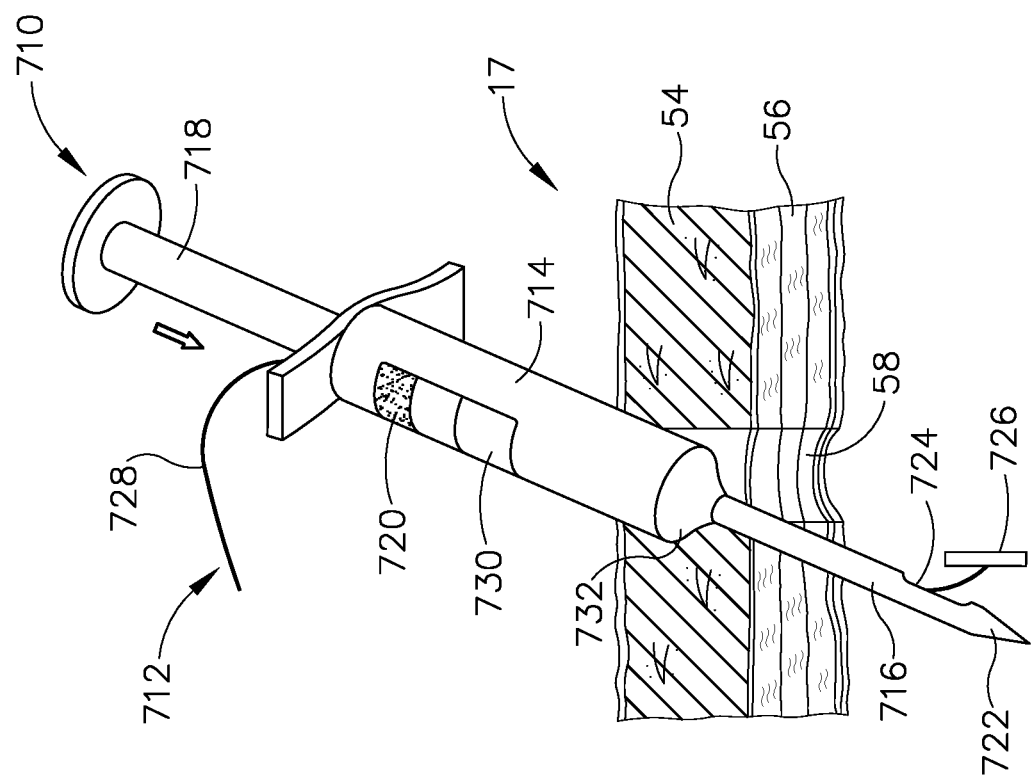
Fig.28A
Fig.28B

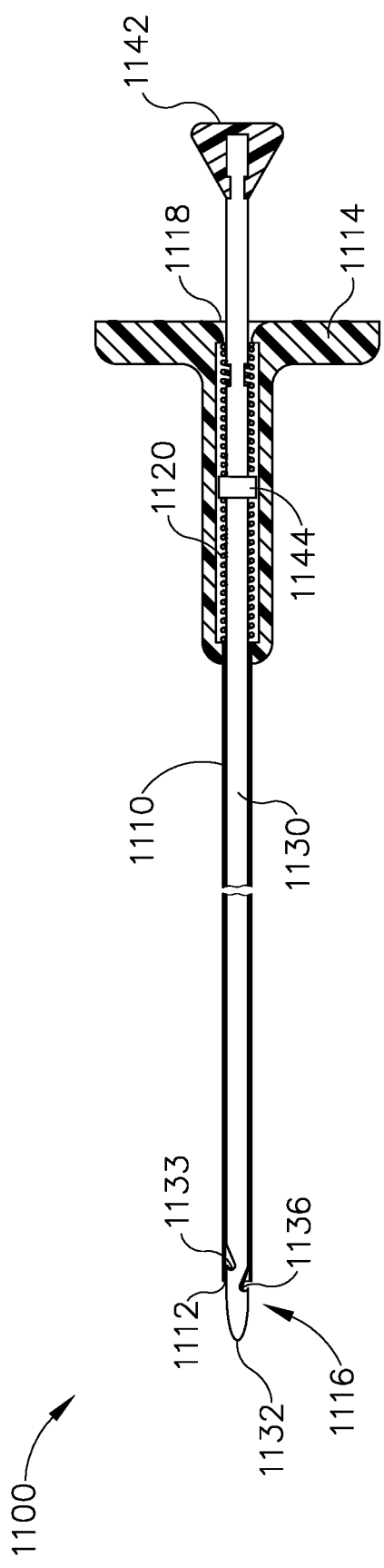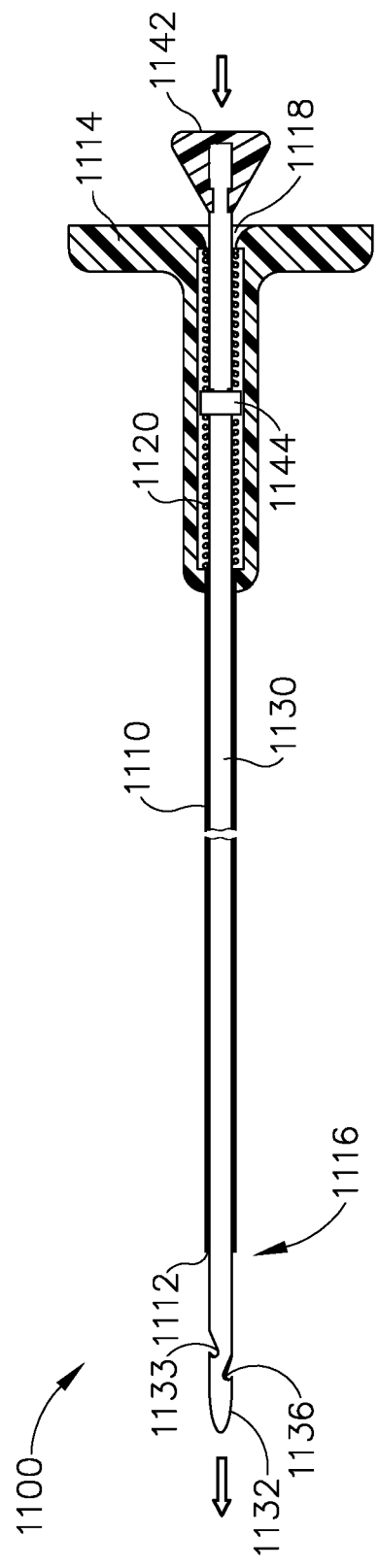

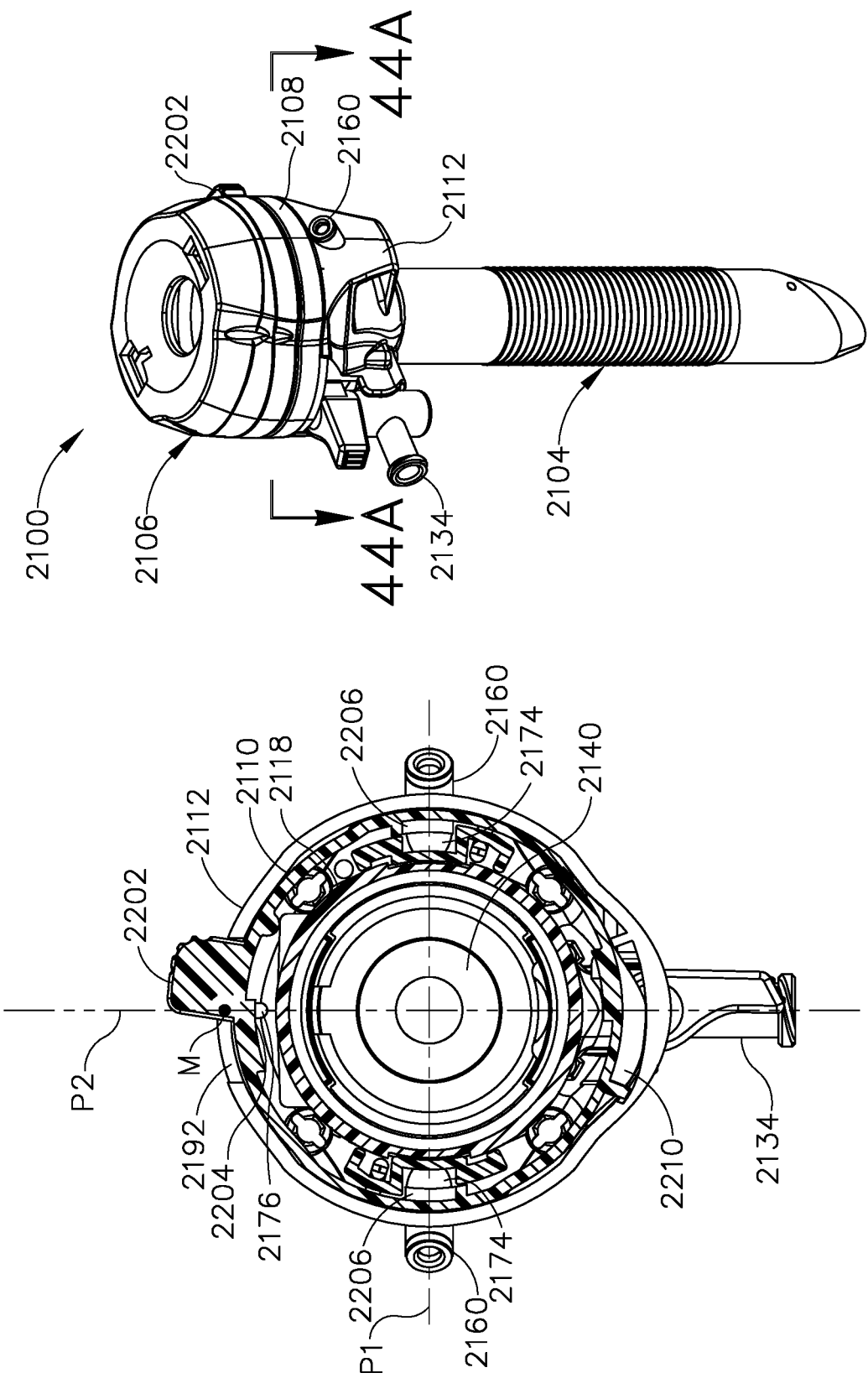

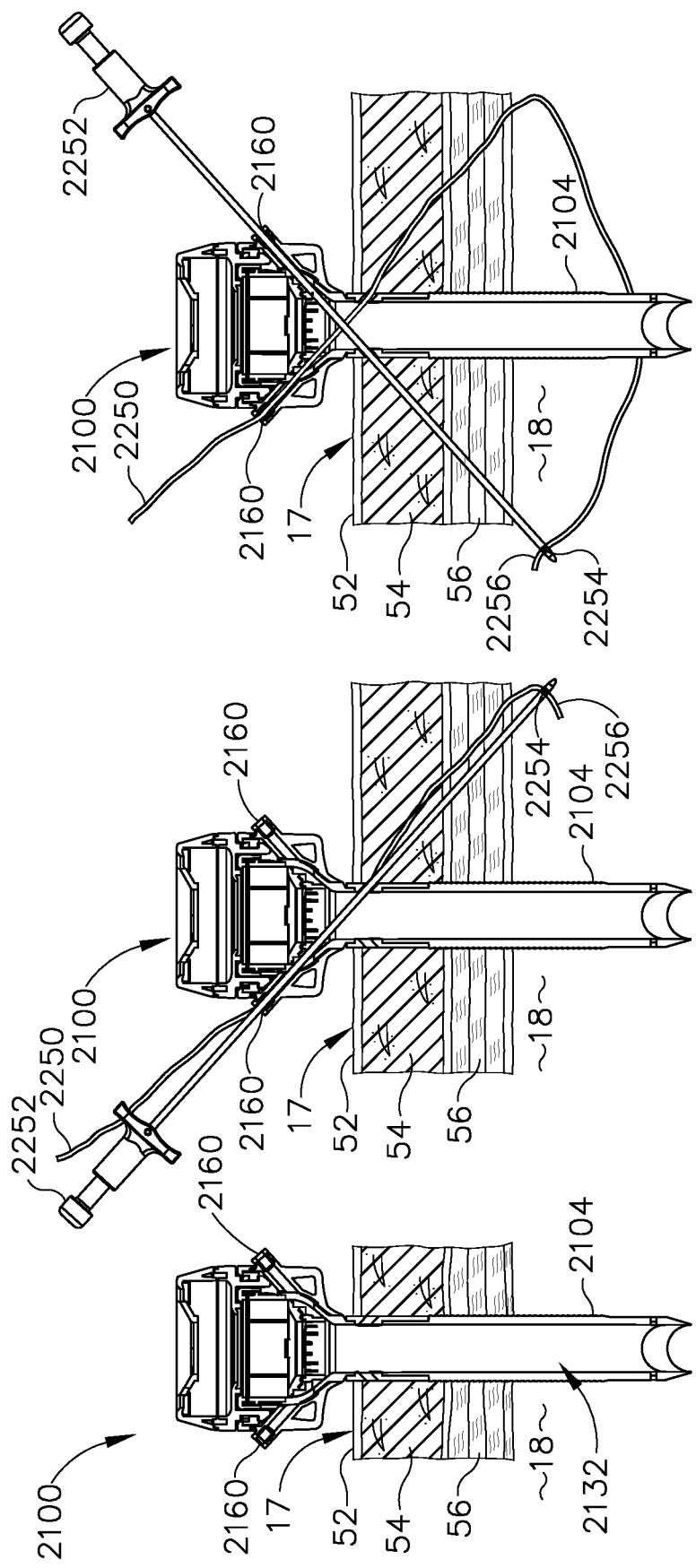

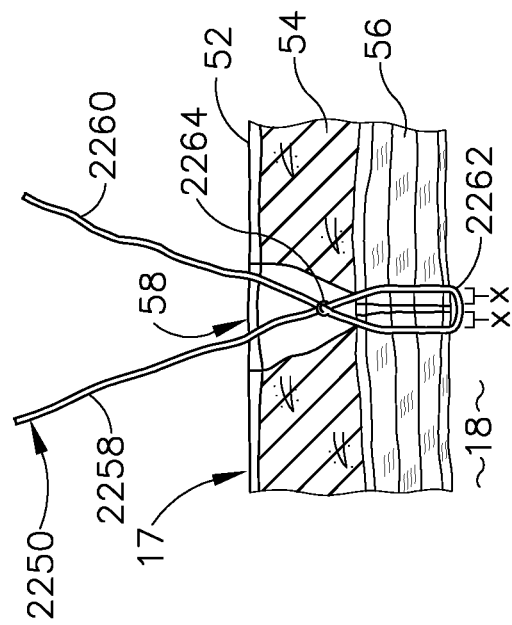
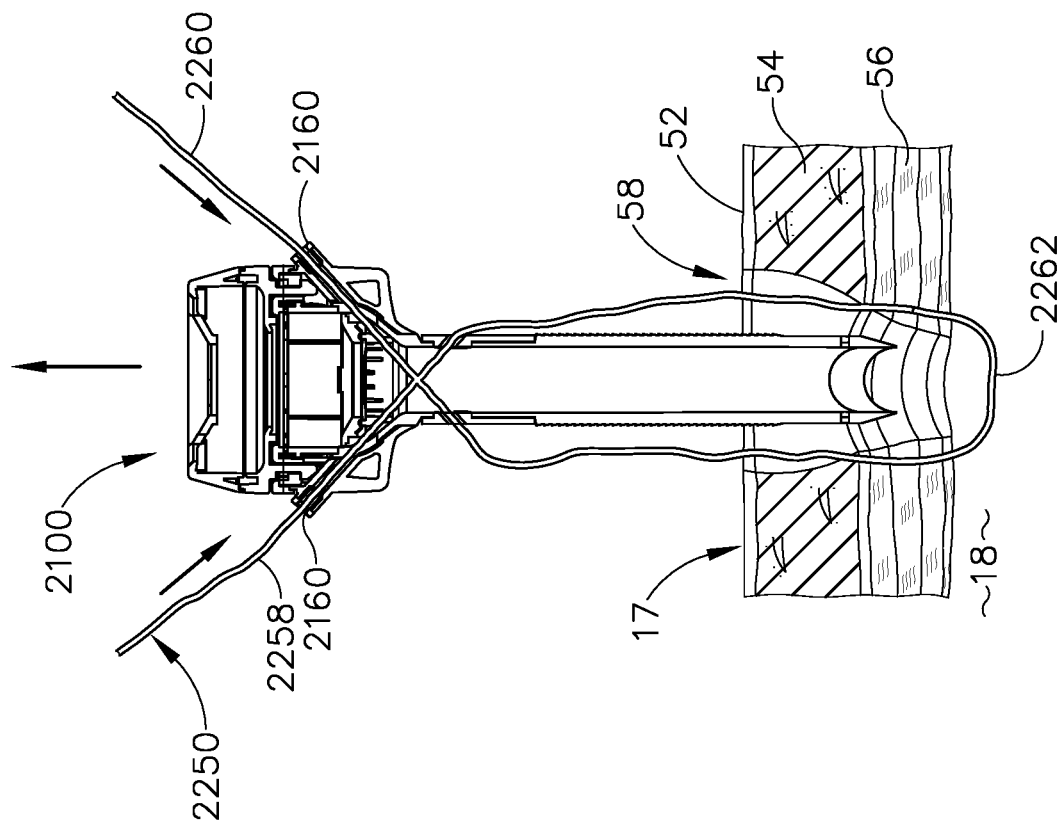
Fig.50E
Fig.50D

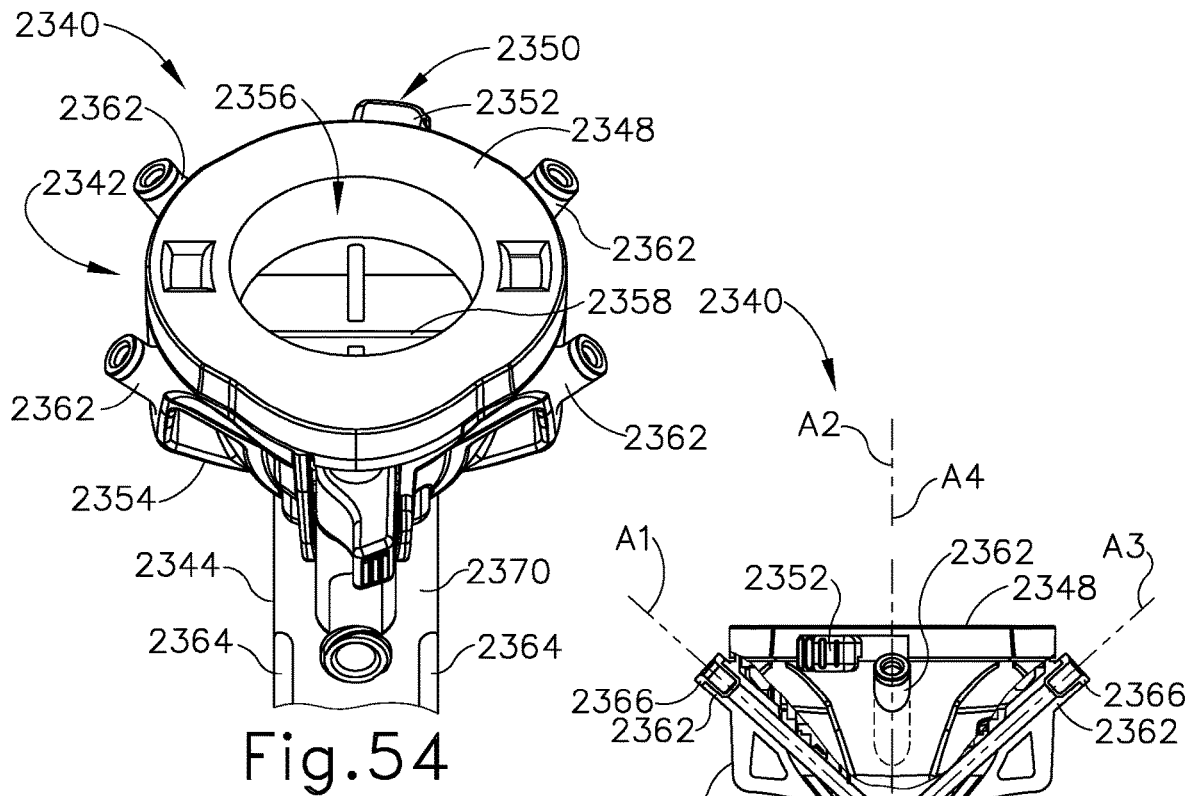
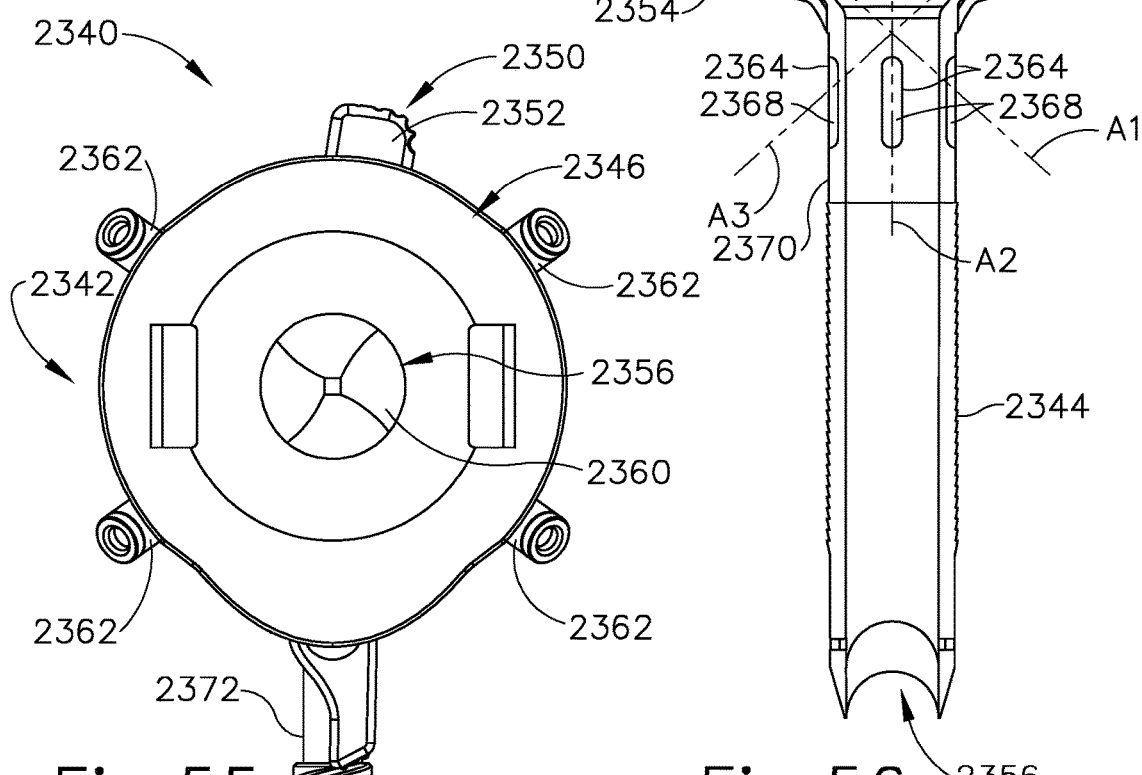

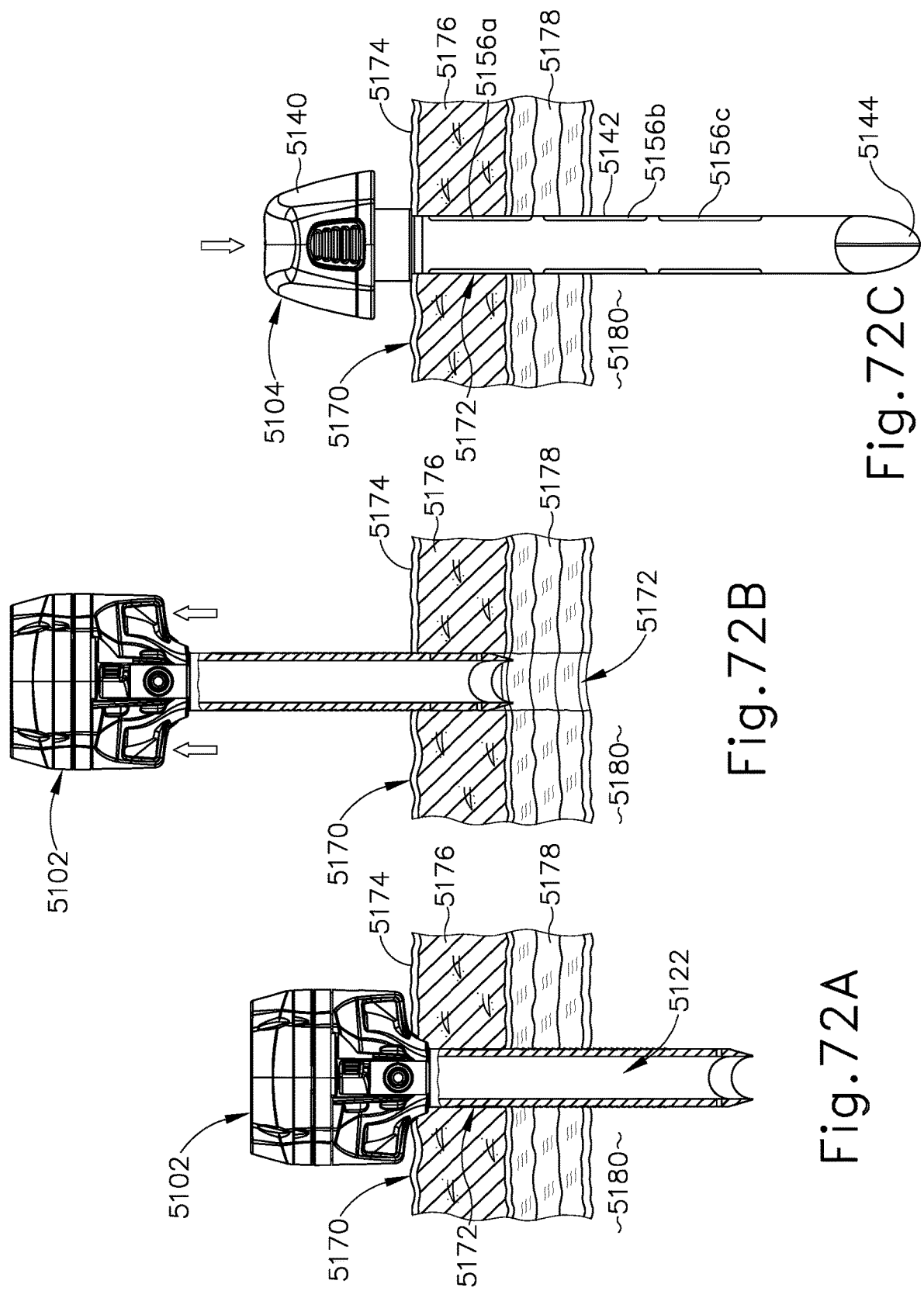

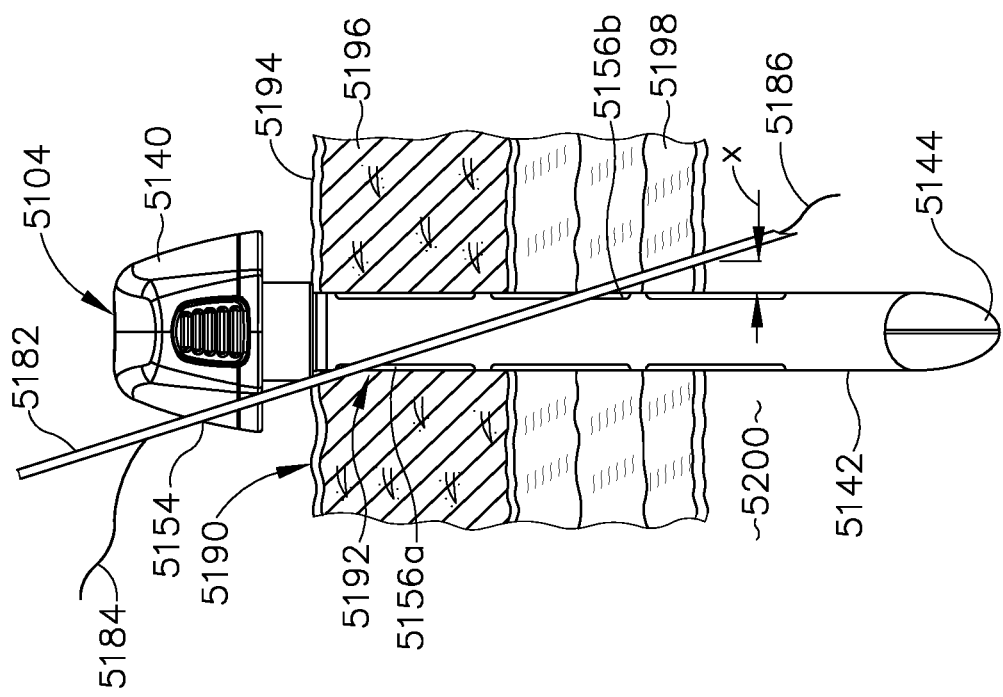
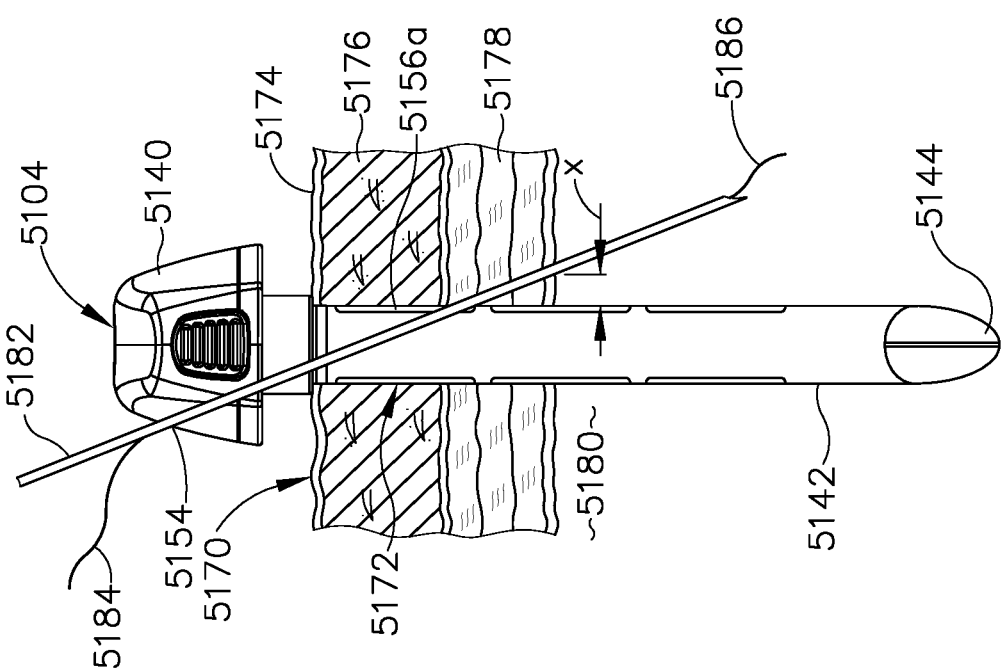

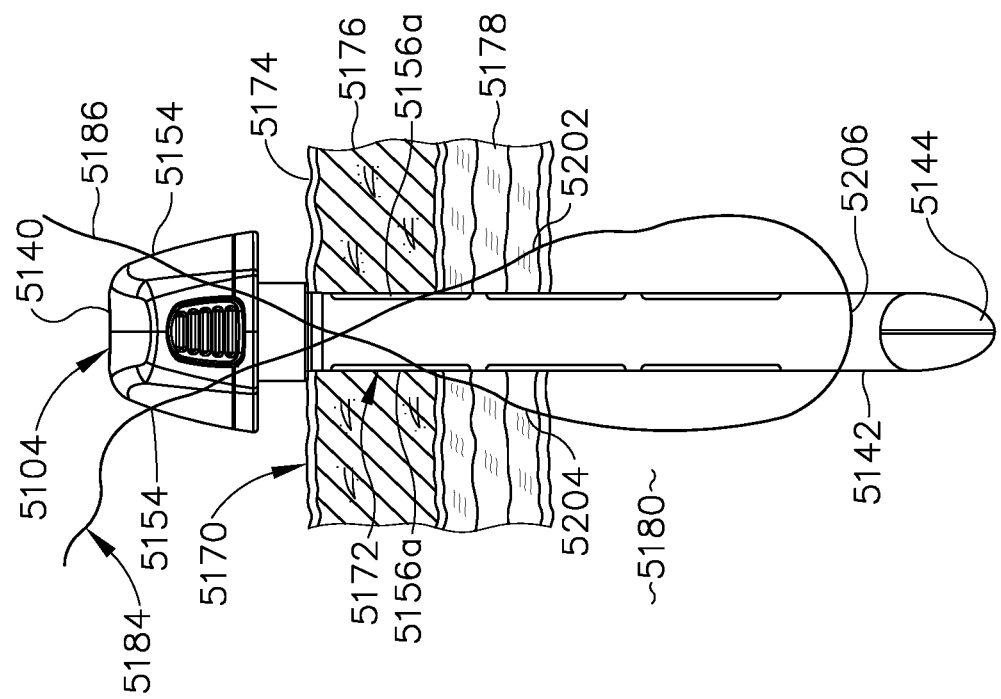
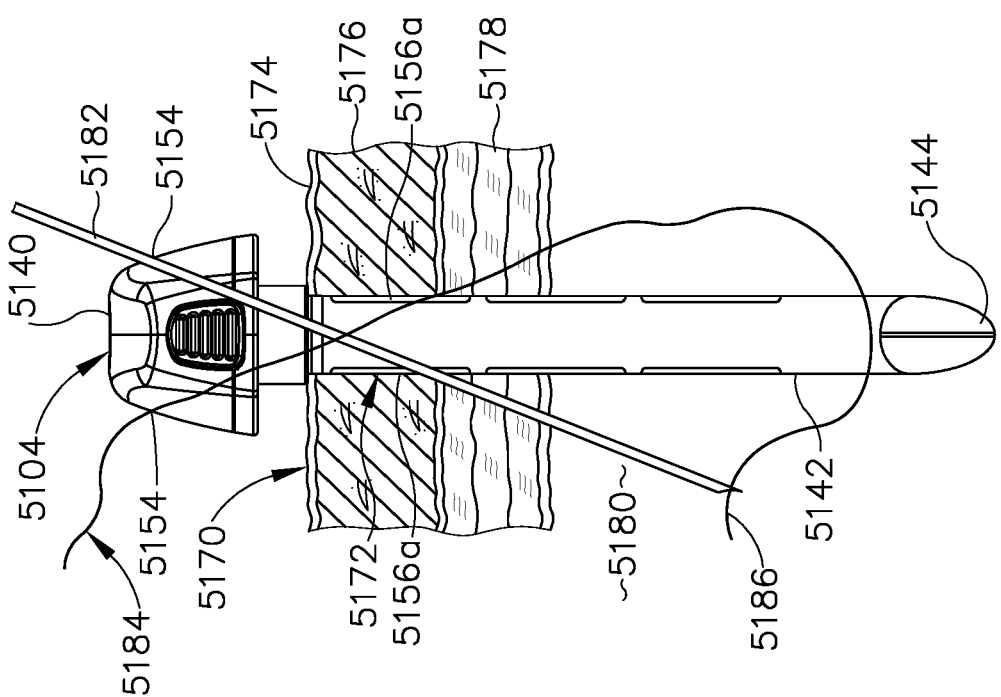

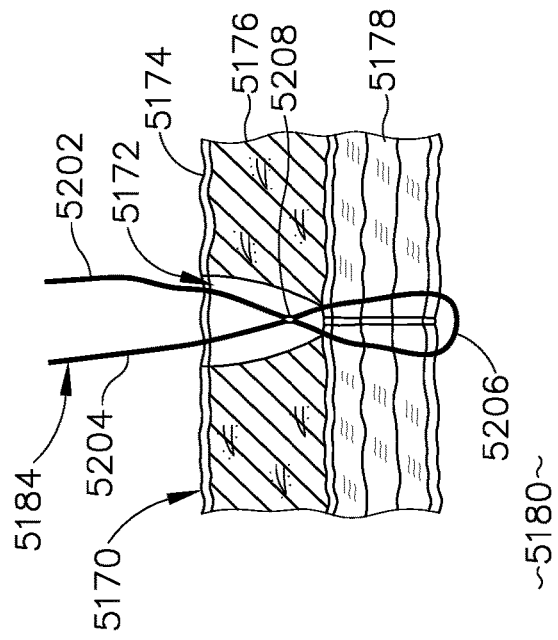
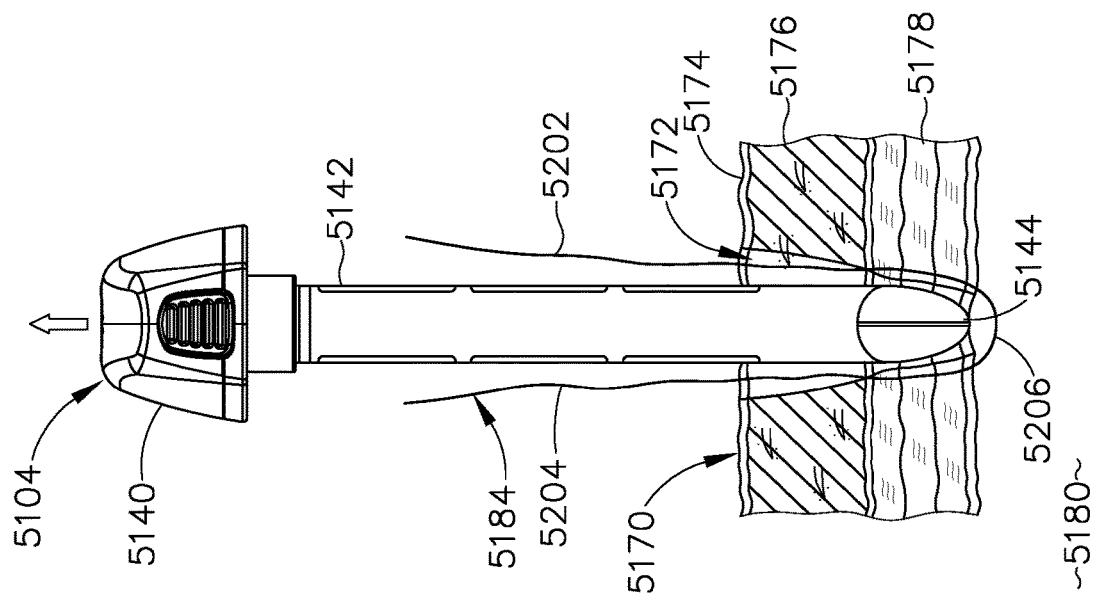

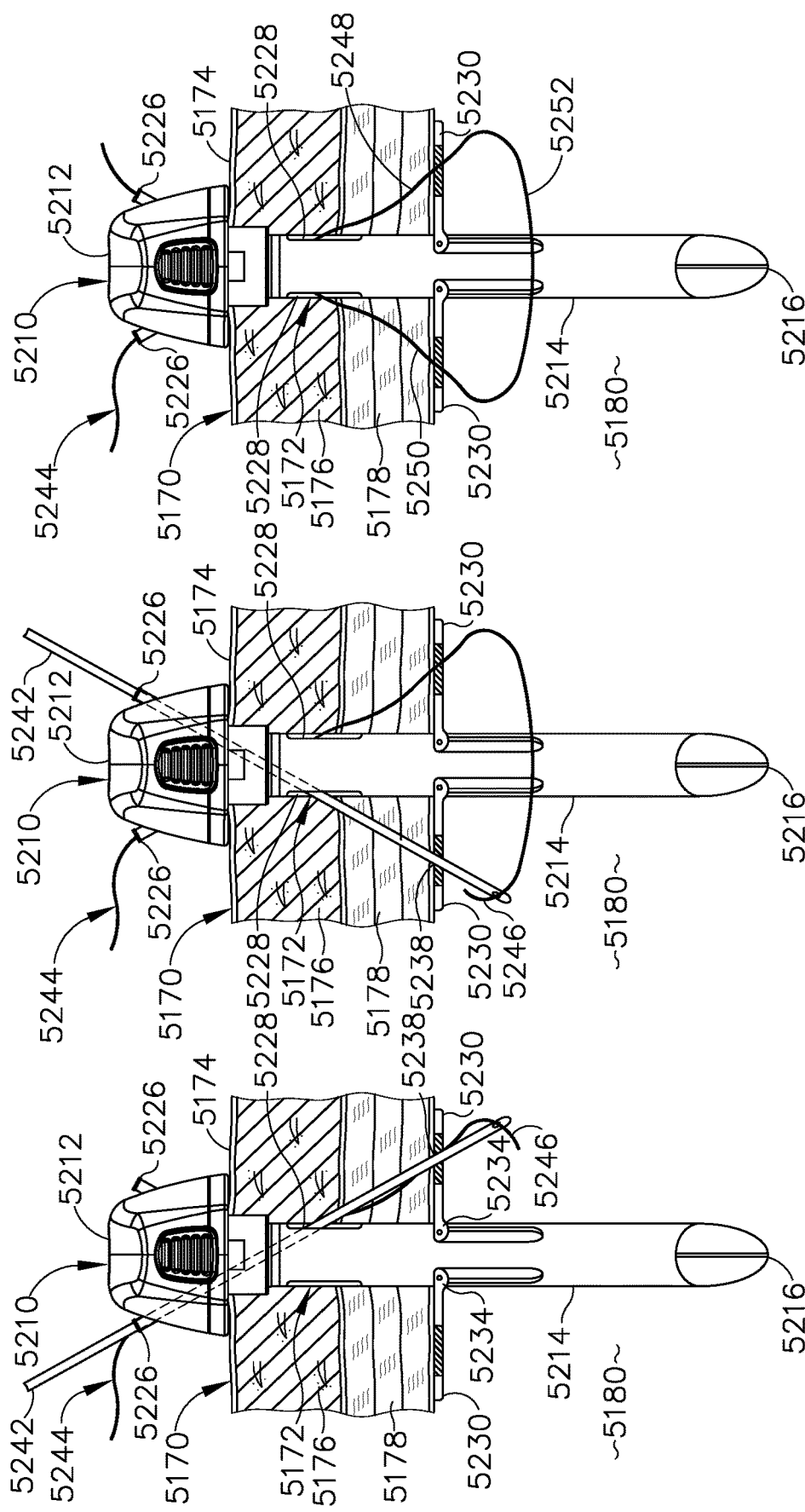

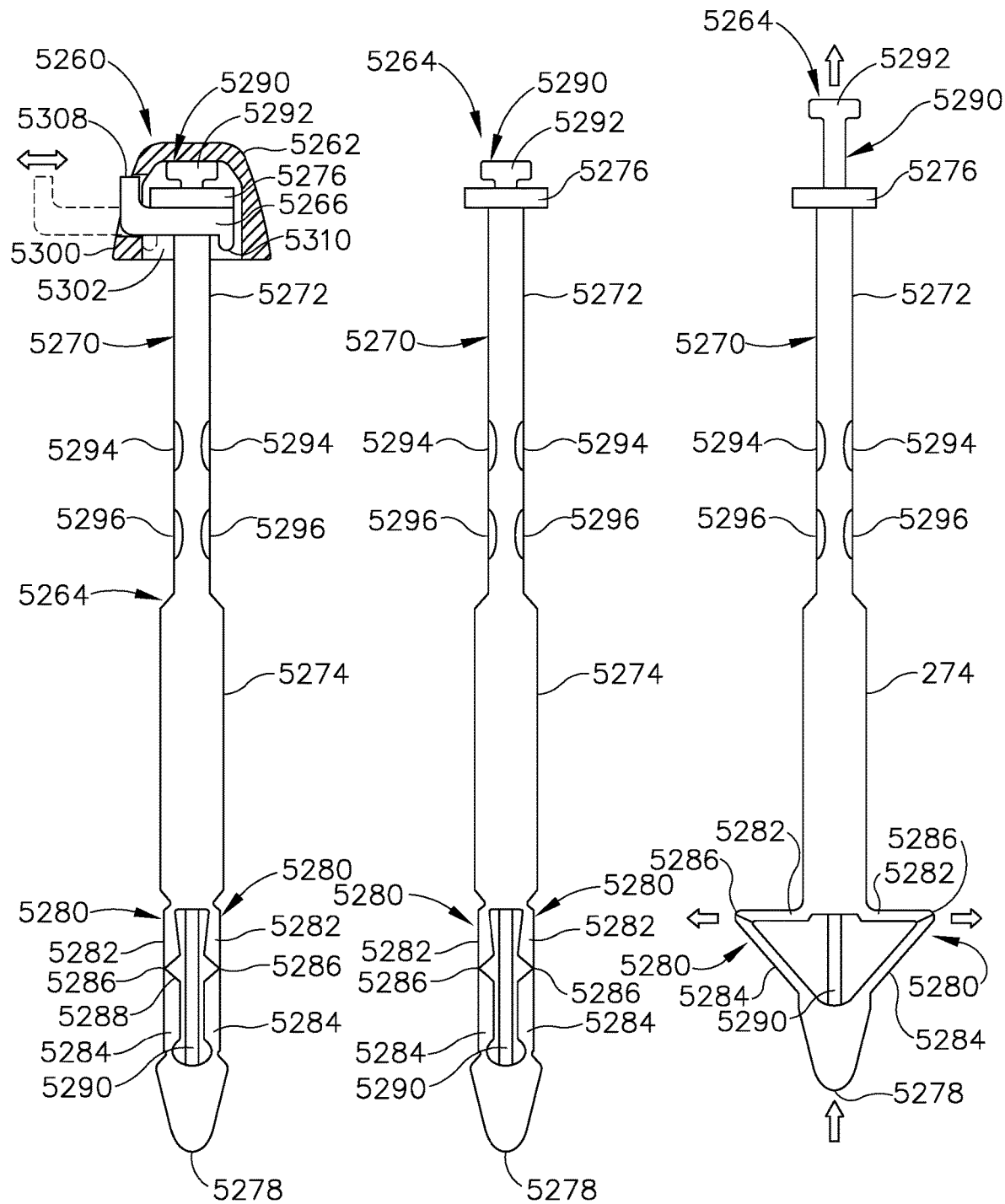

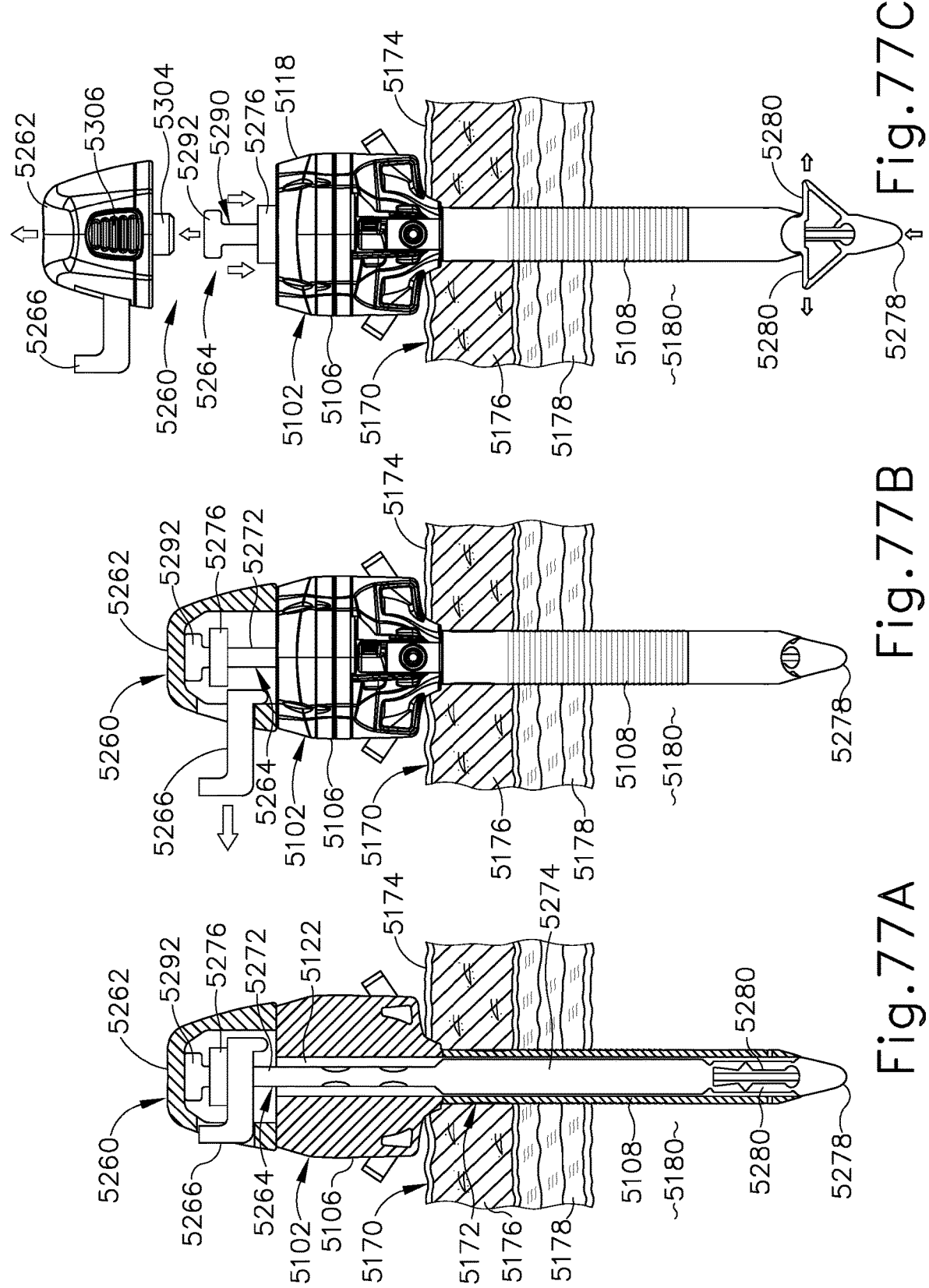

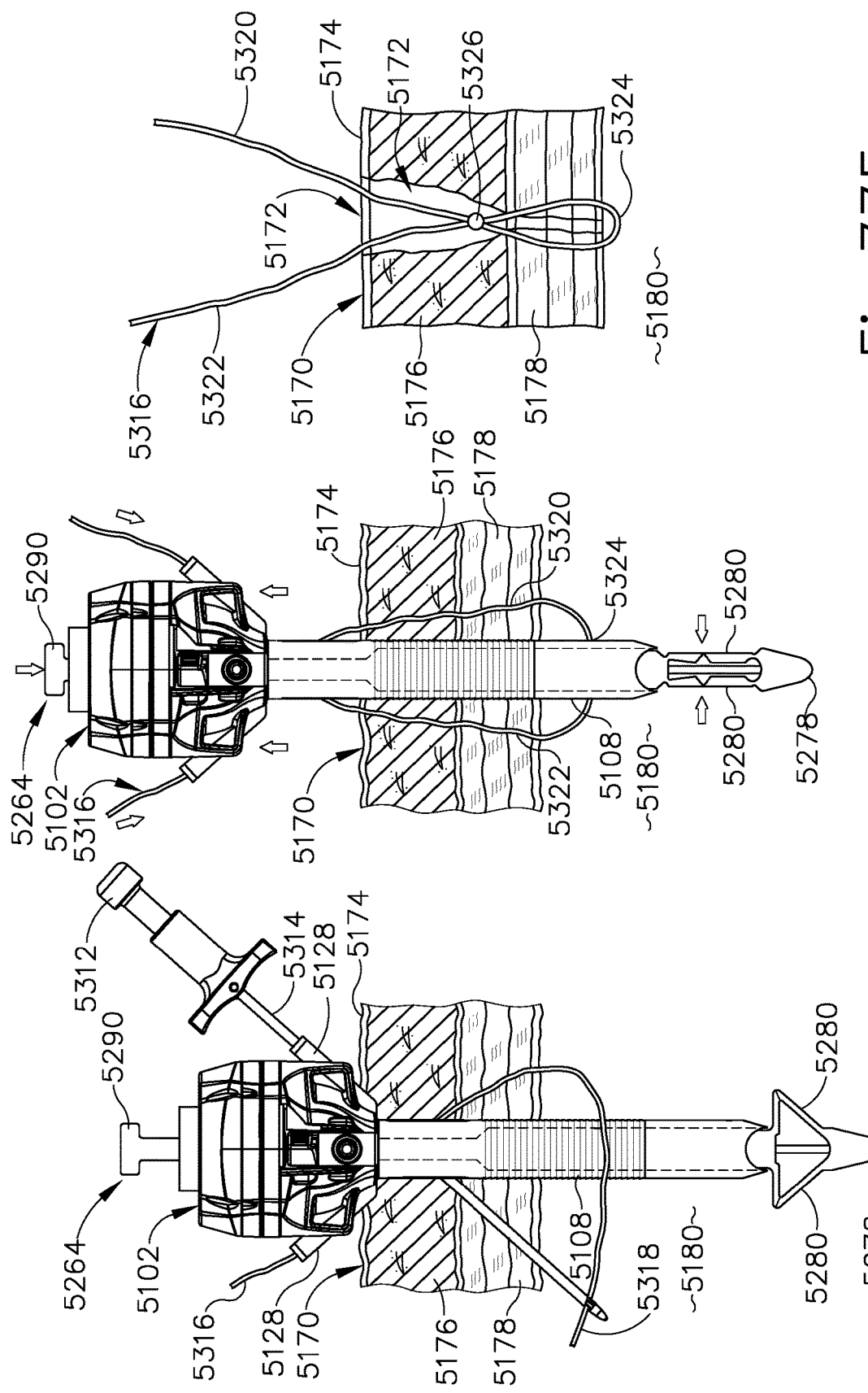

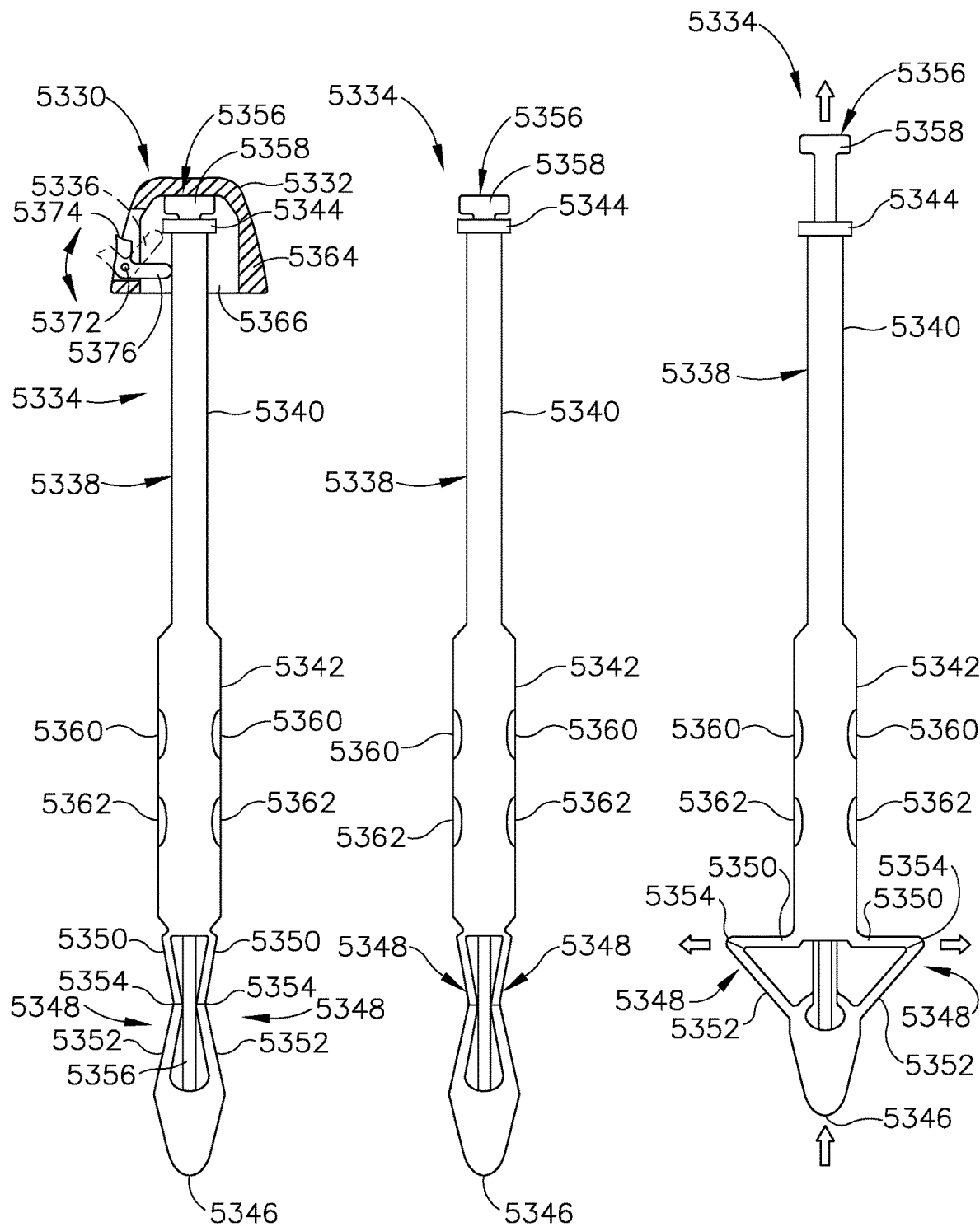

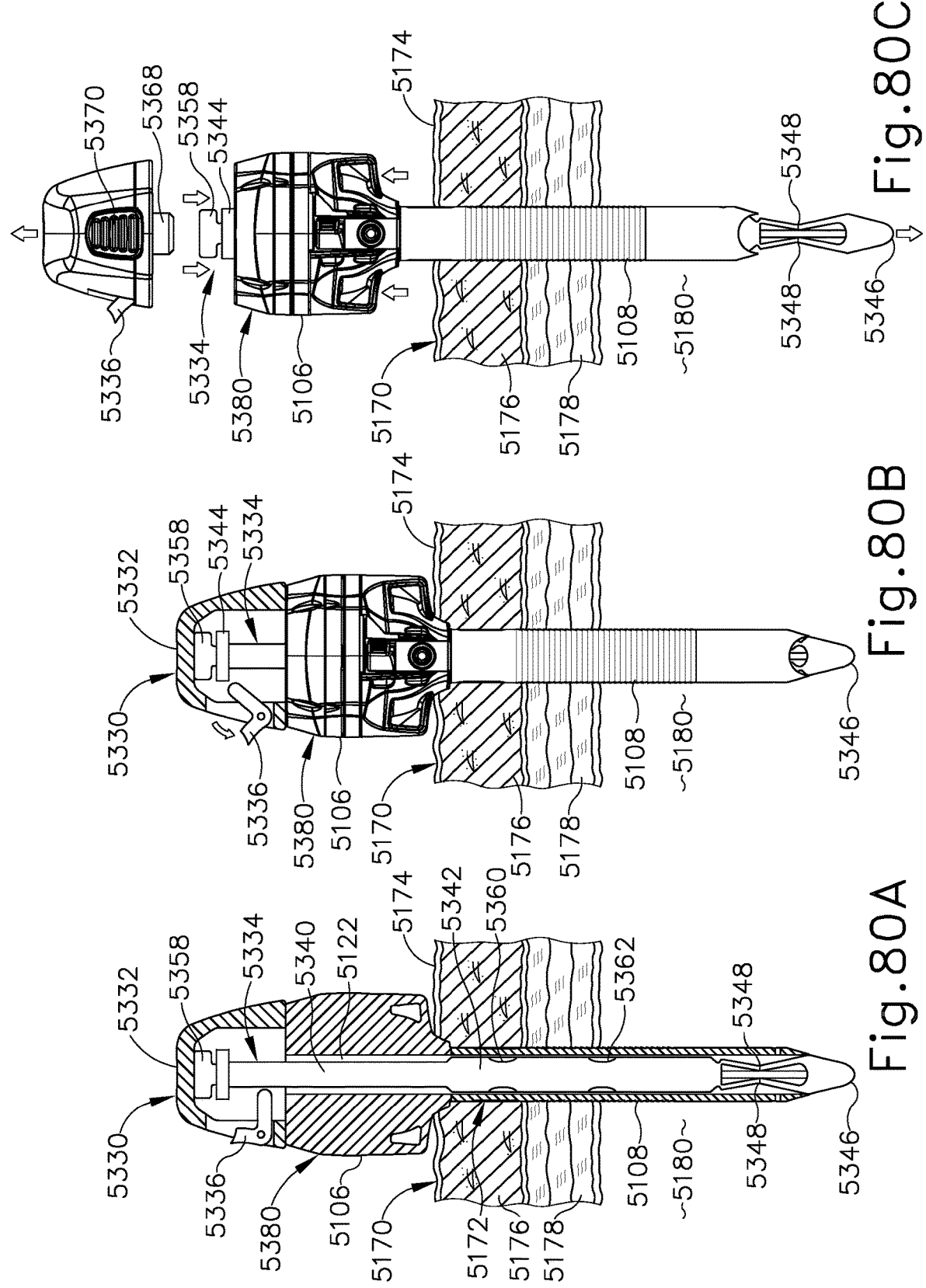

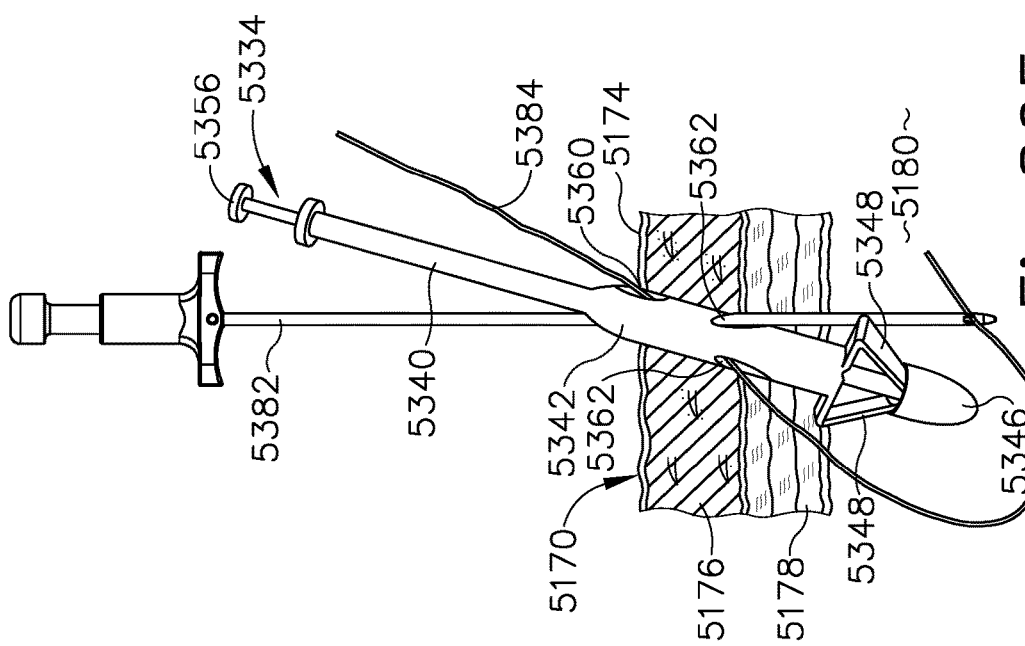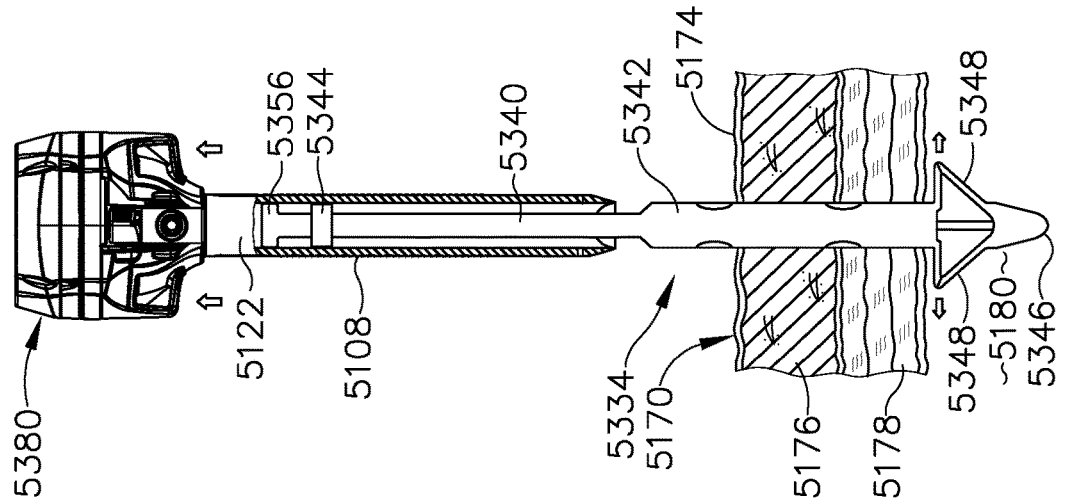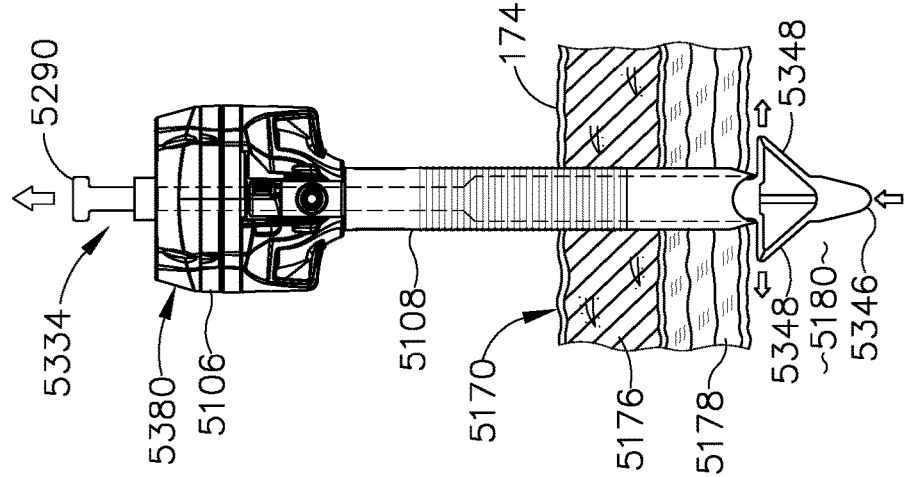

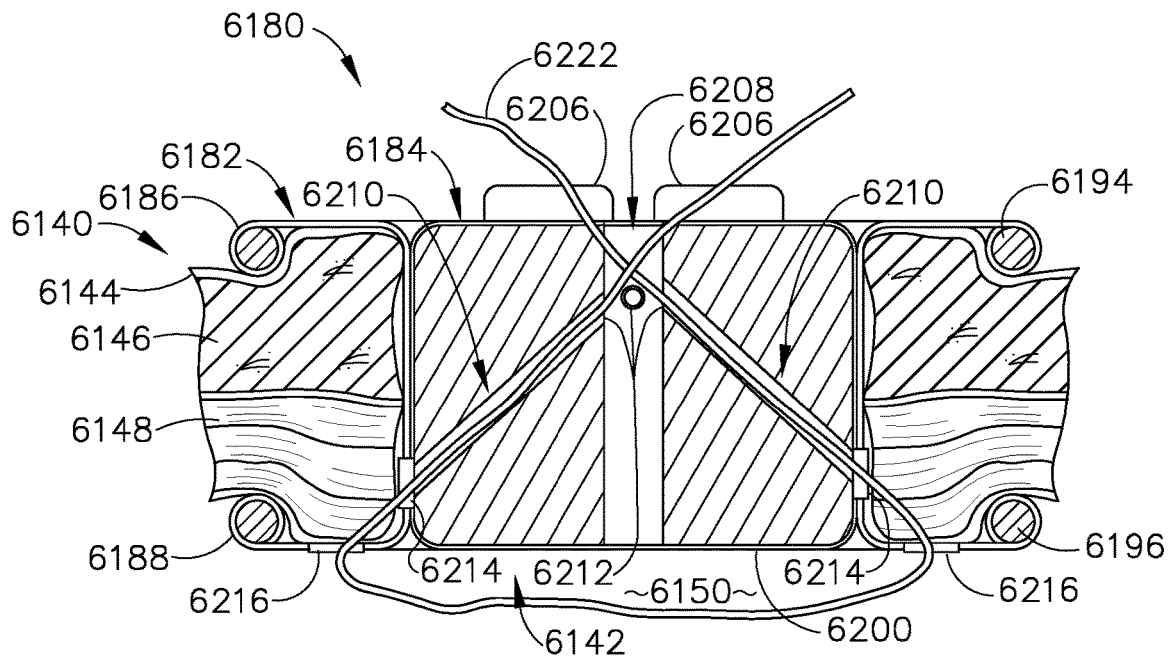
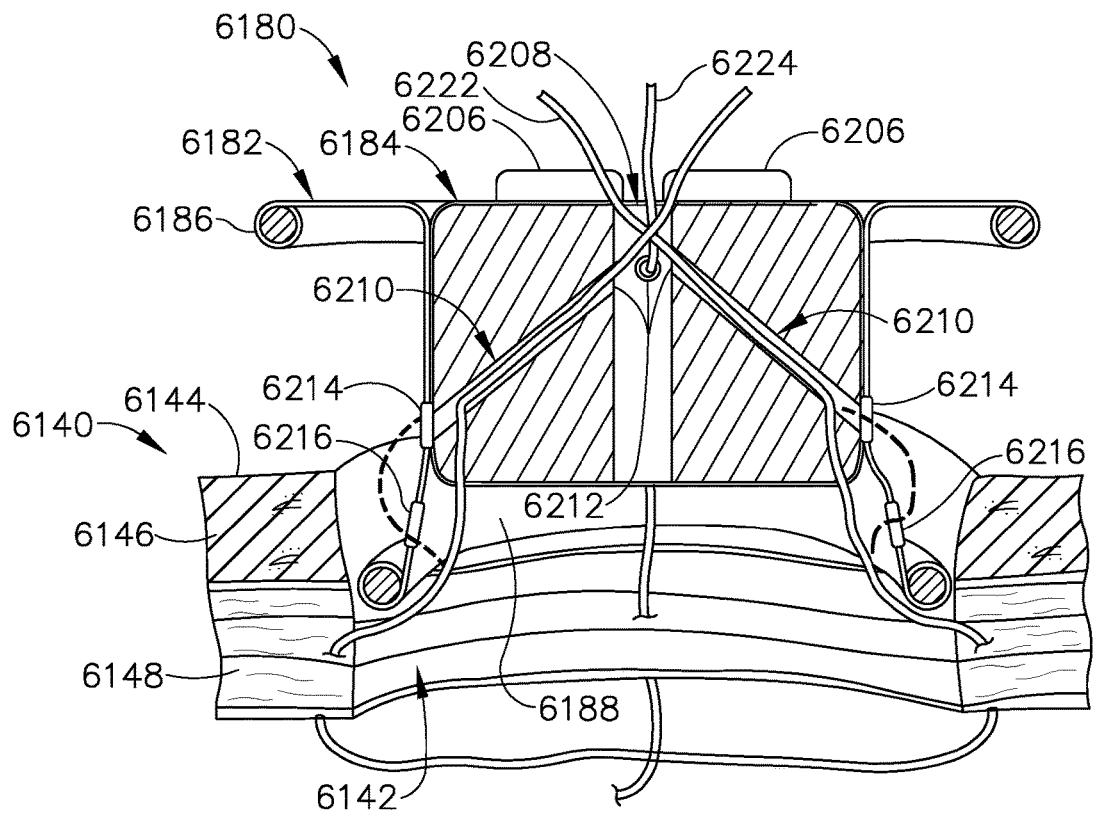

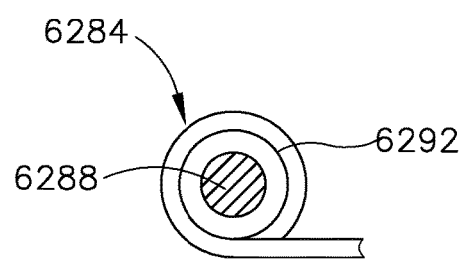
Fig.95
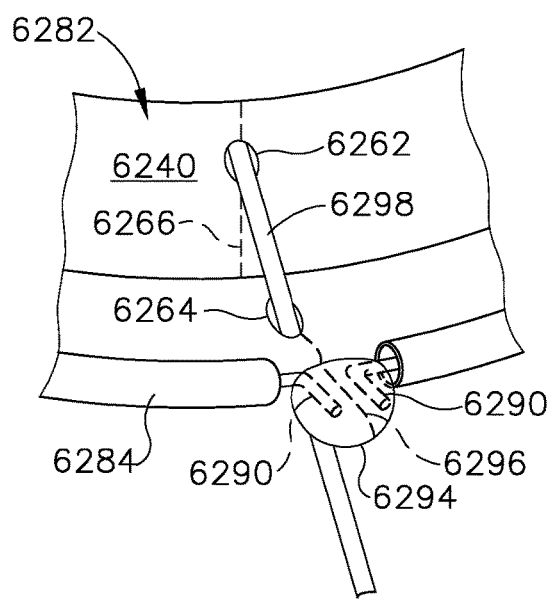 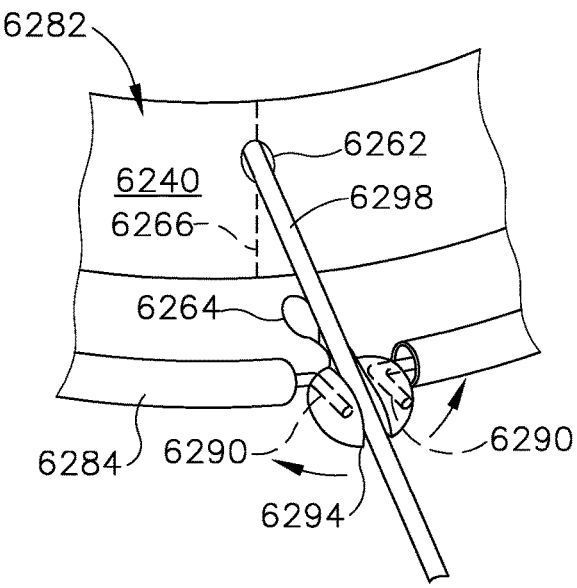
Fig.96A  Fig.96B

METHOD OF SUTURING A TROCAR PATH INCISION

BACKGROUND

Surgical procedures may require a clinician to gain access to a cavity or other desirable surgical site within a body of a patient. To perform such a surgical procedure, an incision may be made through a tissue of the patient into the cavity. Some conventional surgical procedures may apply a knife, such as a scalpel, to the tissue for the incision, while some less invasive surgical procedures, such as laparoscopic and endoscopic surgical procedures, may access the cavity through a trocar assembly. Trocar assemblies generally include a trocar obturator received within a trocar cannula. In use, the clinician directs the trocar obturator and the cannula through the tissue in order to access the cavity of the desirable surgical site. Once accessed, the clinician withdraws the trocar obturator from the trocar cannula so that the trocar cannula may be used to introduce surgical instruments into the cavity for treatment.

Merely exemplary trocar assemblies, components thereof, and other varieties of surgical access devices and wound closure devices are provided for in U.S. Pat. No. 7,981,092, entitled "Vibratory Trocar," issued Jul. 19, 2011; U.S. Pat. No. 8,226,553, entitled "Access Device with Insert," issued on Jul. 24, 2012; U.S. Pat. No. 8,251,900, entitled "Surgical Access Devices and Methods Providing Seal Movement in Predefined Paths," issued on Aug. 28, 2012; U.S. Pat. No. 8,579,807, entitled "Absorbing Fluids in a Surgical Access Device," issued on Nov. 12, 2013; U.S. Pat. No. 8,568,362, entitled "Surgical Access Device with Sorbents," issued on Oct. 29, 2013; U.S. Pat. No. 8,636,686, entitled "Surgical Access Device," issued on Jan. 28, 2014; U.S. Pat. No. 8,690,831, entitled "Gas Jet Fluid Removal in a Trocar," issued on Apr. 8, 2014; U.S. Pat. Pub. No. 2008/0200950, entitled "Surgical Hook," published on Aug. 21, 2008, now abandoned; U.S. Pat. Pub. No. 2015/0038793, entitled "Devices, Systems, and Methods for Providing Surgical Access and Facilitating Closure of Surgical Access Openings," published on Feb. 5, 2015; issued as U.S. Pat. No. 10,258,324 on Apr. 16, 2019; U.S. Pat Pub. No. 2015/0038994, entitled "Devices, Systems, and Methods for Providing Surgical Access and Facilitating Closure of Surgical Access Openings," published on Feb. 5, 2015, issued as U.S. Pat. No. 9,700,303 on Jul. 11, 2017; and U.S. Pat. Pub. No. 2015/0094741, entitled "Wound Closure Device including Mesh Barrier." Published on Apr. 2, 2015, issued as U.S. Pat. No. 9,687,226 on Jun. 27, 2017. The disclosure of each of the above-cited U.S. patents and Publications is incorporated by reference herein.

Surgical instruments for use with such surgical access devices may have a distal end effector for engaging tissue through the access device in a number of ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Laparoscopic and endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the cavity of the patient. Positioning of an end effector may be further facilitated through inclusion of one or more articulation joints or features, enabling the end effector to be selectively articulated or otherwise deflected relative to the longitudinal axis of the shaft.

While various kinds of surgical instruments, including trocar assemblies and end effectors or other surgical access devices, and other associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 4A depicts another sectional side view of the tissue shown in FIGS. 3A-3D following removal of the trocar assembly of FIG. 1, with an opening through the tissue and a suture thread being introduced into a portion of the tissue for suturing the opening closed;

FIG. 4B depicts a sectional side view of the tissue of FIG. 4A, with the suture thread being introduced though another portion of the tissue and pulled through the tissue;

FIG. 4C depicts a sectional side view of the tissue of FIG. 4A, with the suture thread tightened and knotted for at least partially closing the opening;

FIG. 4D depicts a sectional side view of the tissue of FIG. 4A, with additional suturing for further closing the opening;

FIG. 9 depicts a partially exploded perspective view of a second suturing trocar assembly having a cannula assembly and an obturator assembly with a second catch arm for releasably capturing a suture thread;

FIG. 10A depicts a perspective view of the suturing trocar assembly of FIG. 9 with the catch arm in a retracted position;

FIG. 14A depicts a cross-sectional view of the suturing trocar assembly of FIG. 13A taken along a longitudinal centerline thereof;

FIG. 14B depicts a cross-sectional view of the suturing trocar assembly of FIG. 13B taken along the longitudinal centerline thereof;

FIG. 14C depicts a cross-sectional view of the suturing trocar assembly of FIG. 13C taken along the longitudinal centerline thereof;

FIG. 15A depicts a cross-sectional view of the suturing trocar assembly of FIG. 13A taken along a longitudinal centerline thereof positioned within a tissue opening and receiving a needle with a suture thread;

FIG. 15B depicts the cross-sectional view of the suturing trocar assembly similar to FIG. 15A, but showing the needle removed therefrom and the suture thread releasably captured by the catch arm in a catch deployed position;

FIG. 15C depicts the cross-sectional view of the suturing trocar assembly similar to FIG. 15B, but with the catch arm and the suture thread rotated to a release deployed position;

FIG. 15D depicts the cross-sectional view of the suturing trocar assembly similar to FIG. 15C, but with the needle again received within the suturing trocar assembly and reattaching to the suture thread;

FIG. 15E depicts the cross-sectional view of the suturing trocar assembly similar to FIG. 15D, but with the needle and the suture thread being withdrawn from the suturing trocar assembly;

FIG. 15F depicts the cross-sectional view of the tissue having received the suture thread from the suturing trocar assembly of FIG. 15E, but with the suturing trocar assembly removed from the tissue opening such that the suture thread remains therein;

FIG. 15G depicts the cross-sectional view of the suture thread of FIG. 15F, but with the suture thread closing the tissue opening to form a suture;

FIG. 19A depicts a cross-sectional view of a tissue having received the unidirectional barbed suture of FIG. 16 within a tissue opening;

FIG. 19B depicts the cross-sectional view of the tissue and the unidirectional barbed suture similar to FIG. 19A, but showing the unidirectional barbed suture closing the tissue opening;

FIG. 19C depicts the cross-sectional view of the tissue and the unidirectional barbed suture similar to FIG. 19B, but showing the unidirectional barbed suture having closed the tissue opening;

FIG. 28A depicts a perspective sectional view of the suturing surgical instrument and the slip pledget suture thread of FIG. 23 inserted into a tissue opening of a tissue to position a pledget into a tissue portion about the tissue opening;

FIG. 28B depicts the perspective sectional view of the suturing surgical instrument and the slip pledget suture thread similar to FIG. 28A, but with another pledget inserted into another tissue portion about the tissue opening;

FIG. 31A depicts a cross-sectional side view of the suture passer of FIG. 29 taken along a centerline thereof with the needle in a retracted position and the biasing member in an expanded state;

FIG. 31B depicts the cross-sectional side view of the suture passer similar to FIG. 31A, but with the needle in an extended position and the biasing member in a compressed state;

FIG. 44A depicts a top sectional view of the trocar of FIG. 40A, taken along section line 44A-44A shown in FIG. 44B, showing a latch ring of the trocar housing in a first exemplary rotational position;

FIG. 44B depicts a front perspective view of the trocar of FIG. 40A, showing a proximal housing of the trocar housing in a coupled state corresponding to the latch ring rotational position of FIG. 44A;

FIG. 50A depicts a schematic side sectional view of tissue of a patient and the trocar of FIG. 40A positioned through an opening formed in the tissue such that the cannula extends distally into a cavity of the patient, according to a first step of an exemplary suturing procedure;

FIG. 50B depicts a schematic side sectional view of the tissue and trocar of FIG. 50A, showing completion of an exemplary second step of the suturing procedure in which a suture thread end is directed by a suture passer device distally through the trocar and fascia layers of the tissue into the cavity along a first oblique suture path;

FIG. 50C depicts a schematic side sectional view of the tissue and trocar of FIG. 50A, showing completion of an exemplary third step of the suturing procedure in which the suture passer device is re-inserted distally through the trocar and the tissue fascia layers along a second oblique suture path to capture the free suture thread end located within the cavity;

FIG. 50D depicts a schematic side sectional view of the tissue and trocar of FIG. 50A, showing completion of an exemplary fourth step of the suturing procedure in which the suture passer device and suture thread end are removed proximally such that the suture thread passes through two portions of the tissue fascia layers and proximally through the trocar, and the trocar is removed proximally from the tissue opening;

FIG. 50E depicts a schematic side sectional view of the tissue and trocar of FIG. 50A, showing completion of an exemplary fifth step of the suturing procedure in which the suture thread is pulled and knotted to draw together the tissue fascia layers;

FIG. 54 depicts a top perspective view of another exemplary trocar having four circumferentially spaced needle guide structures and corresponding needle ports;

FIG. 55 depicts a top elevational view of the trocar of FIG. 54;

FIG. 56 depicts a side elevational view of the trocar of FIG. 54, showing suture paths extending through the needle guide structures and the corresponding needle ports;

FIG. 65D depicts the partial sectional view of the suture passer similar to FIG. 65C, but with the needle head in an expanded state and the tissue tented outwards to thereby atraumatically indicate an anticipated puncture site;

FIG. 65E depicts the partial sectional view of the suture passer similar to FIG. 65D, but with the needle head and the inner needle respectively returned to the contracted state and the retracted position;

FIG. 65F depicts the partial sectional view of the suture passer similar to FIG. 65E, but with the outer needle puncturing through the tissue;

FIG. 65G depicts the partial cross-sectional view of the suture passer similar to FIG. 65F, but with the outer needle retracted from outer layer of skin thereby creating a tissue opening;

FIG. 66 depicts an enlarged perspective view of a second exemplary suture passer with an inner needle slidably received within an outer needle having a circular sharpened edge;

FIG. 67 depicts a partial cross-sectional view of the suture passer of FIG. 66, taken generally along a centerline thereof, with the suture passer driven into the outer layer of skin and the inner needle in a retracted position contained within the outer needle;

FIG. 68 depicts an enlarged perspective view of a third exemplary alternative suture passer with a pointed tip and a bulbous shape;

FIG. 69A depicts an enlarged top view of the suture passer of FIG. 68, with an inner needle in a retracted position contained within an outer needle and a head of the inner needle in a contracted state;

FIG. 69B depicts the enlarged top view of the suture passer similar to FIG. 69A, but with the inner needle in an extended position and the needle head in an expanded state;

FIG. 70 depicts a disassembled perspective view of an exemplary trocar assembly including a trocar and an obturator configured for use as a wound closure device;

FIG. 71 depicts a perspective view of the obturator of FIG. 70;

FIG. 72A depicts a schematic side sectional view showing the trocar of FIG. 70 inserted through an opening in tissue to access an internal body cavity of a patient;

Figure 71:
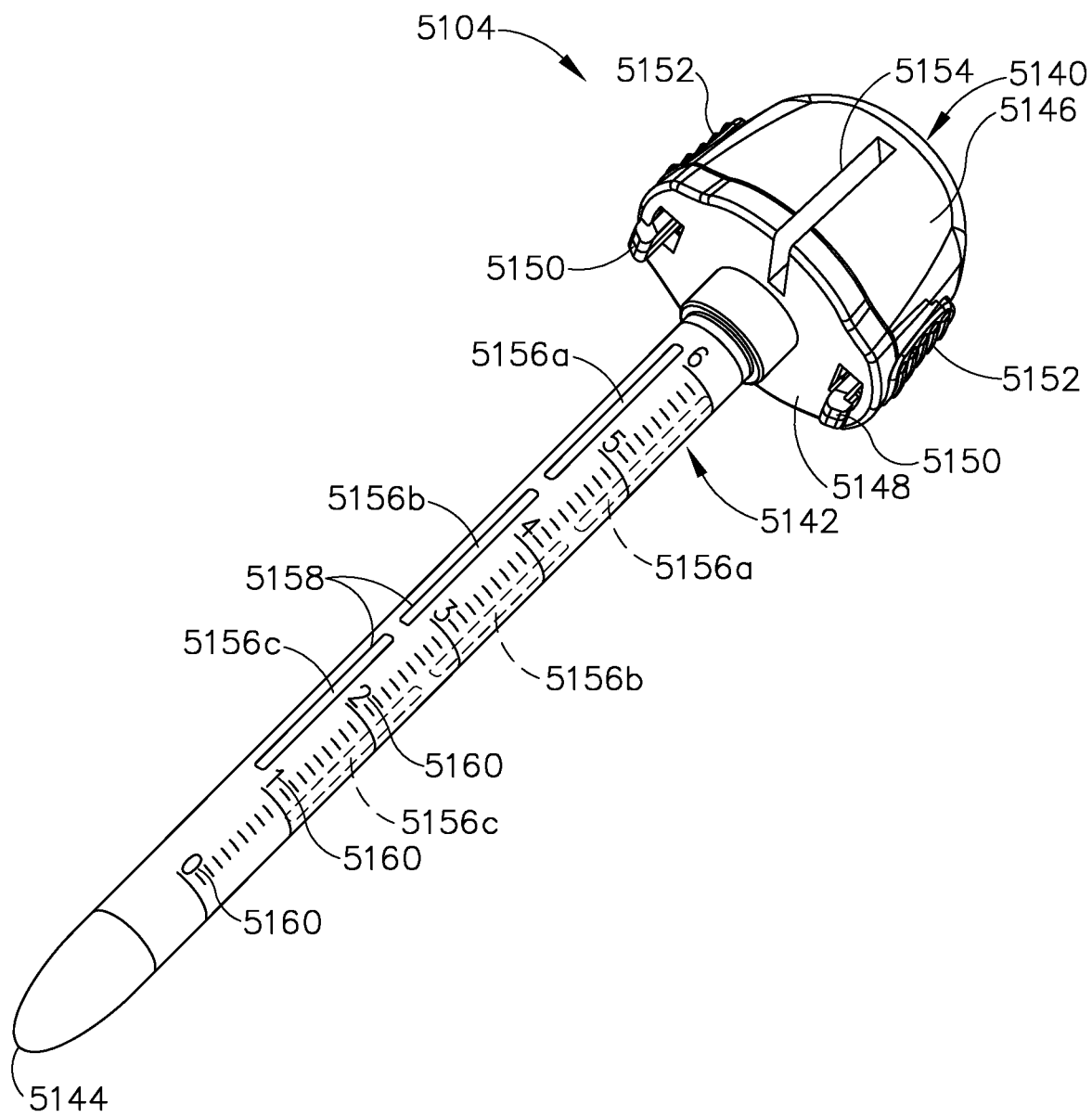
Figures 73A, 73B:
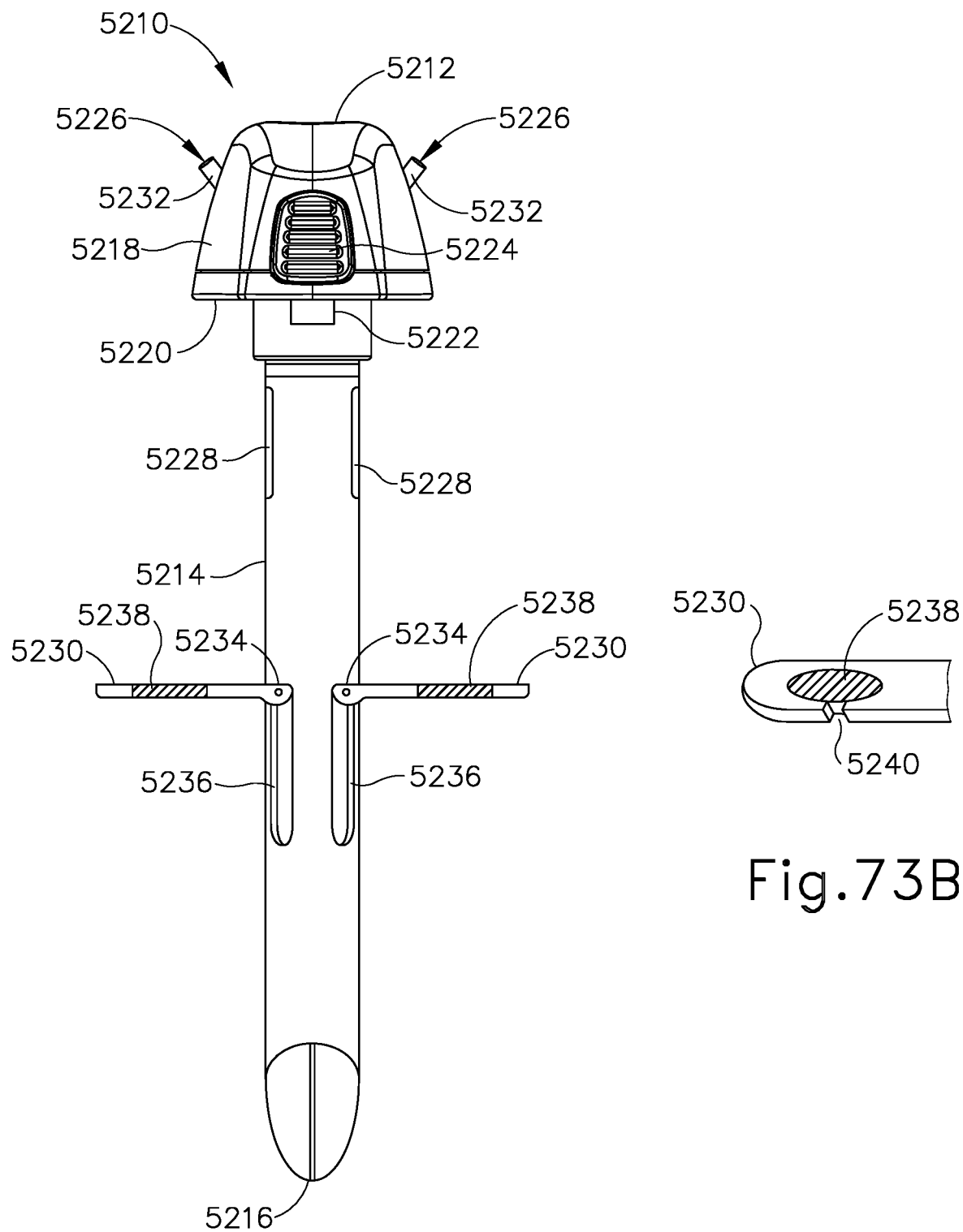
Figure 74E:
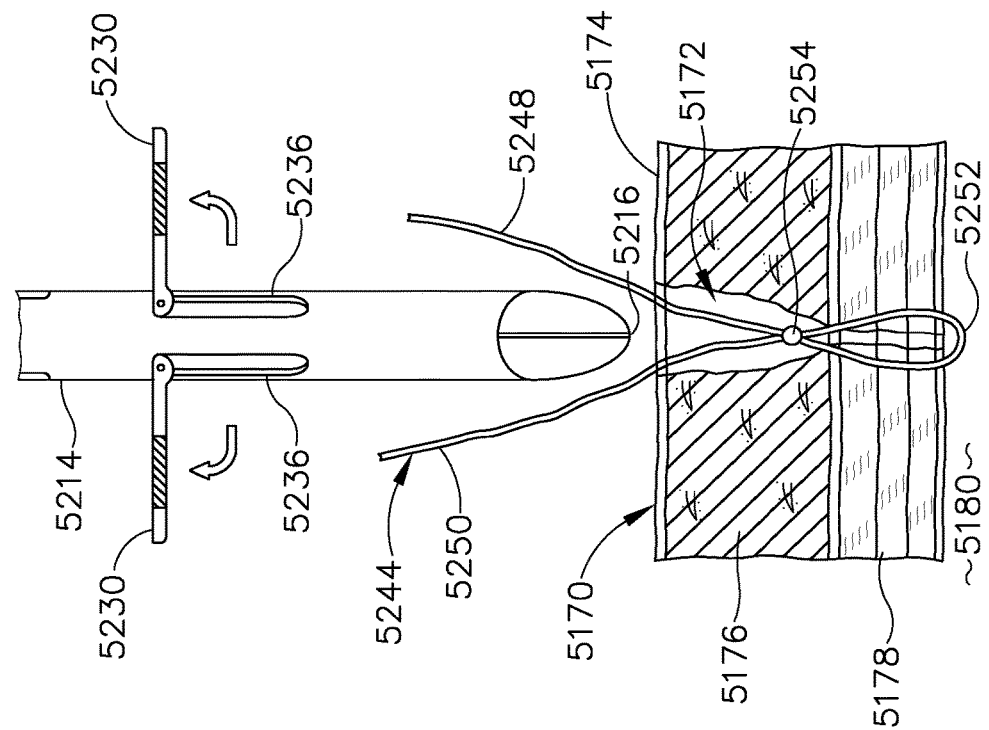
Figure 74D:
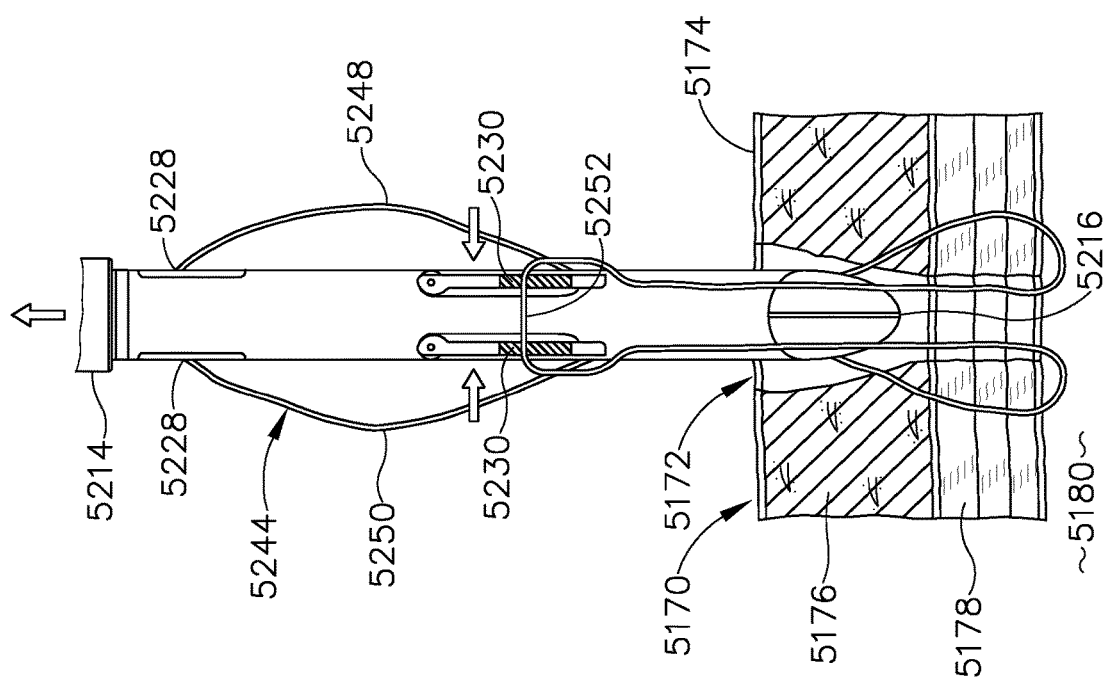
Figure 81:
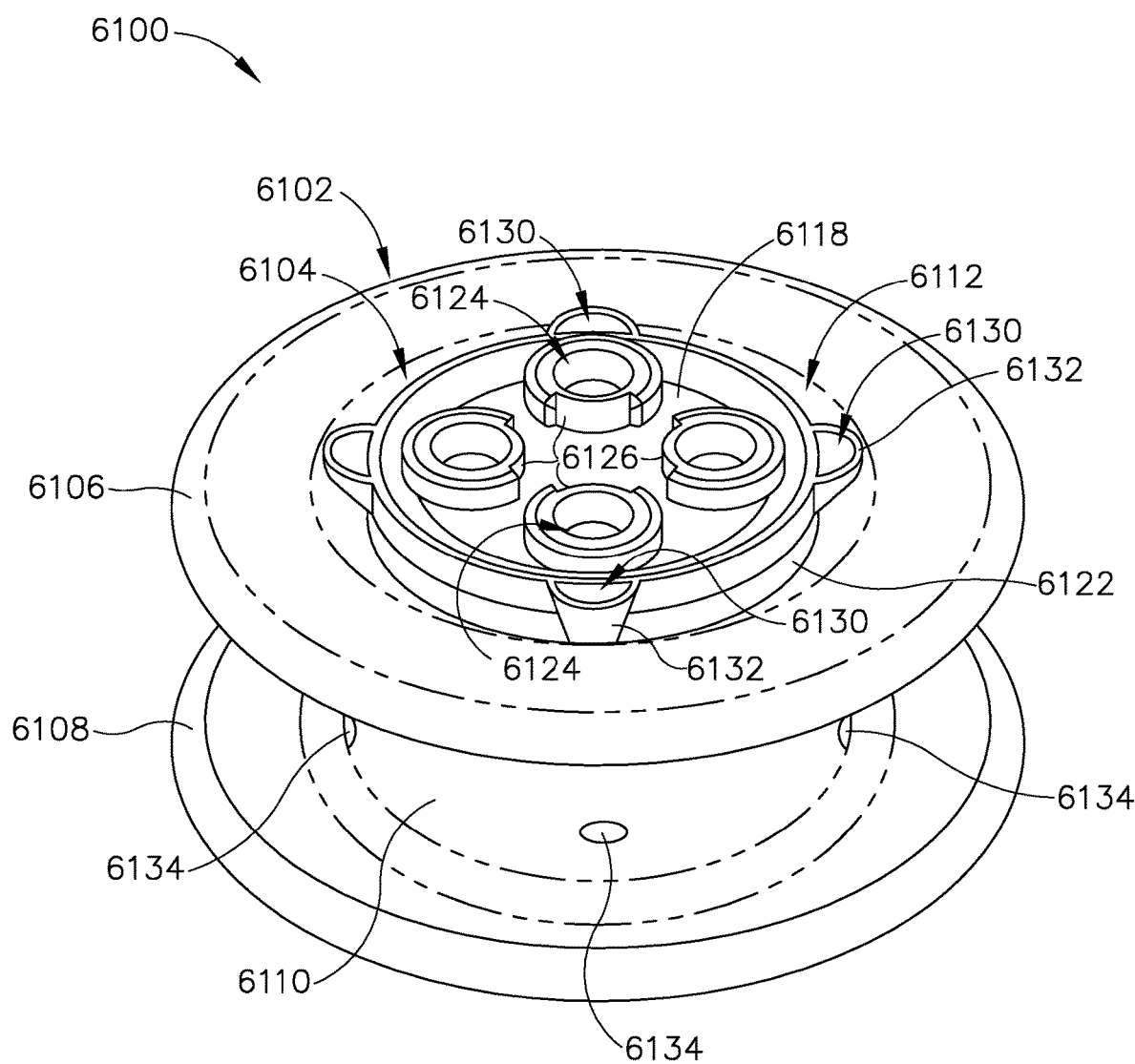
Figure 82:
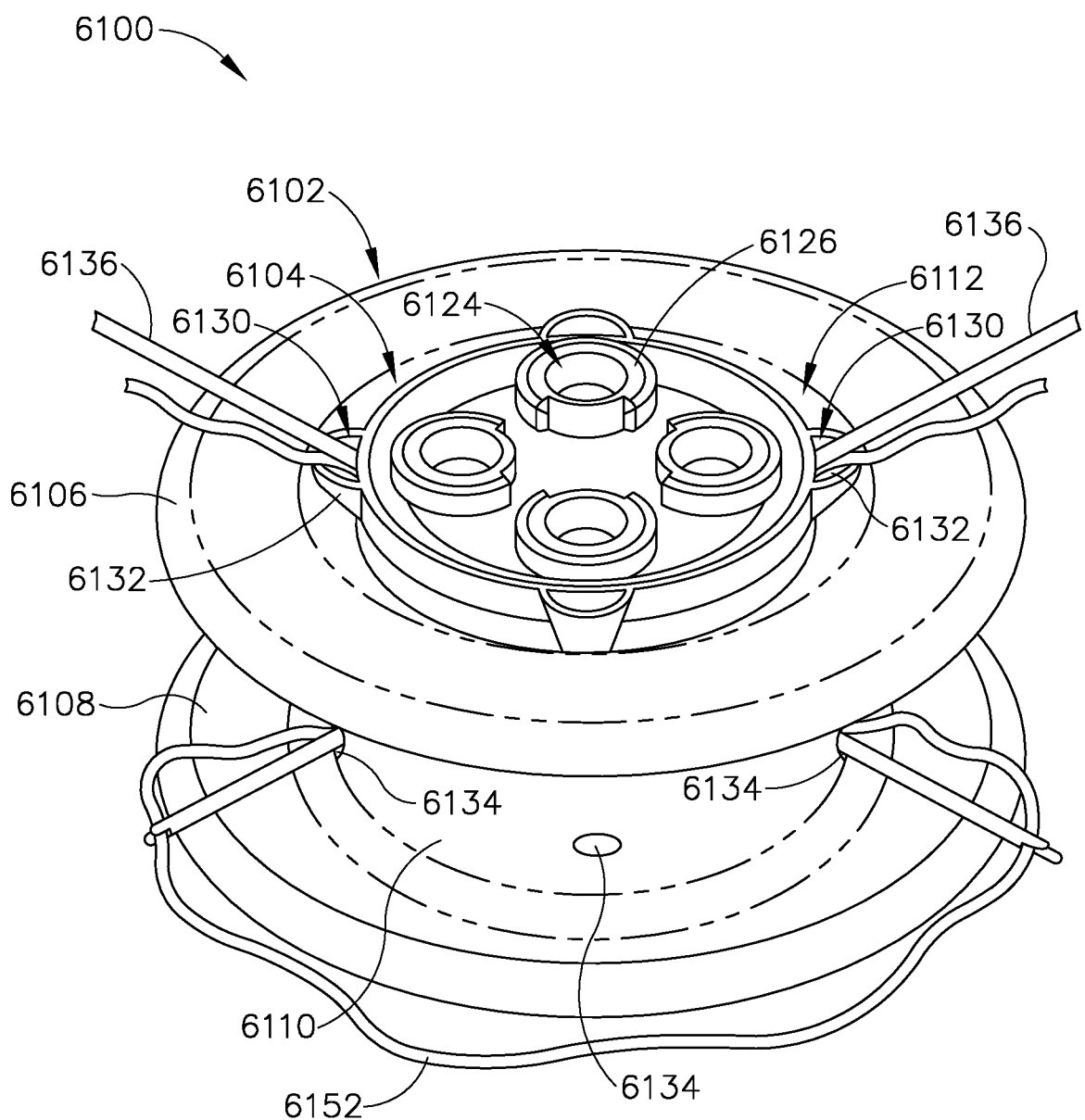
Figure 83:
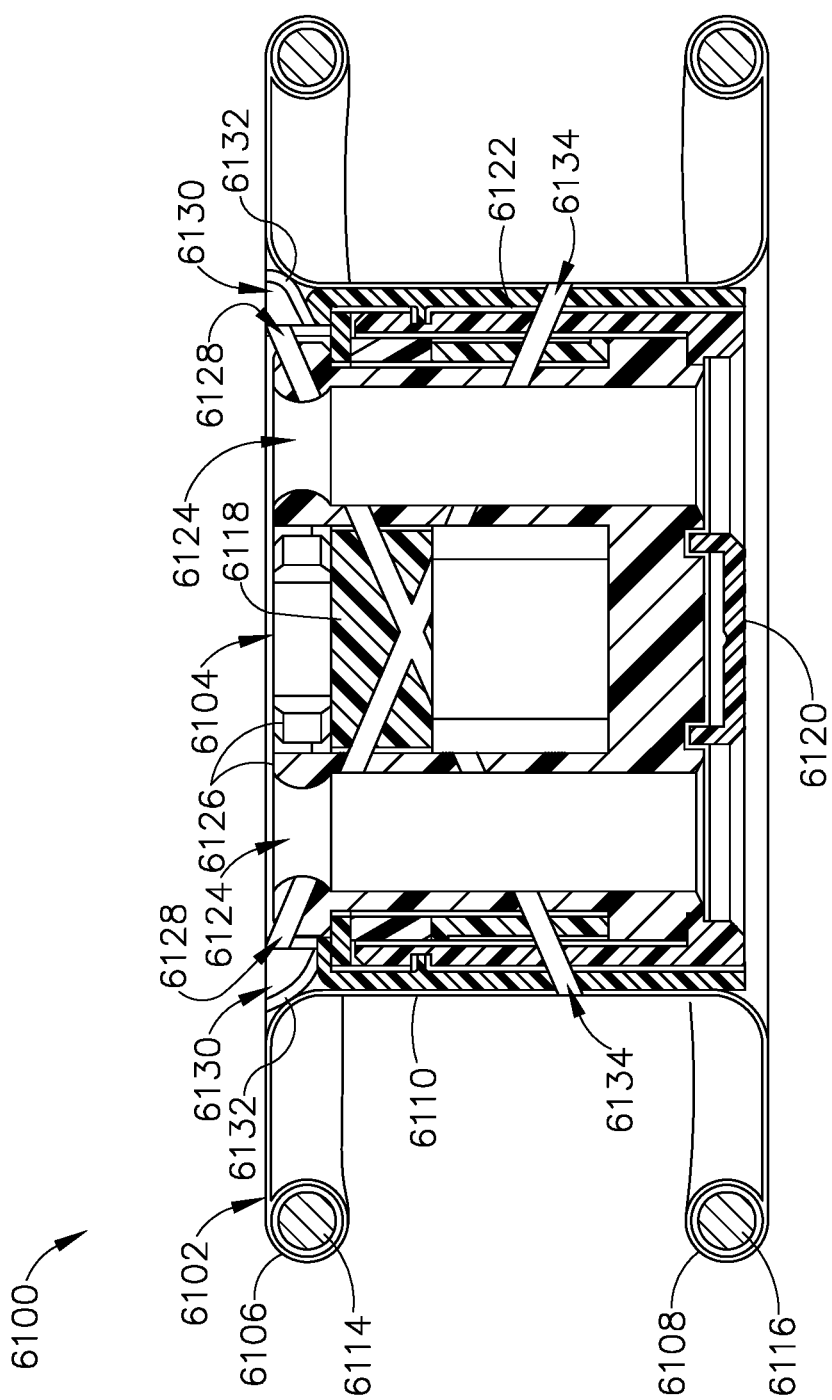
Figure 84A:
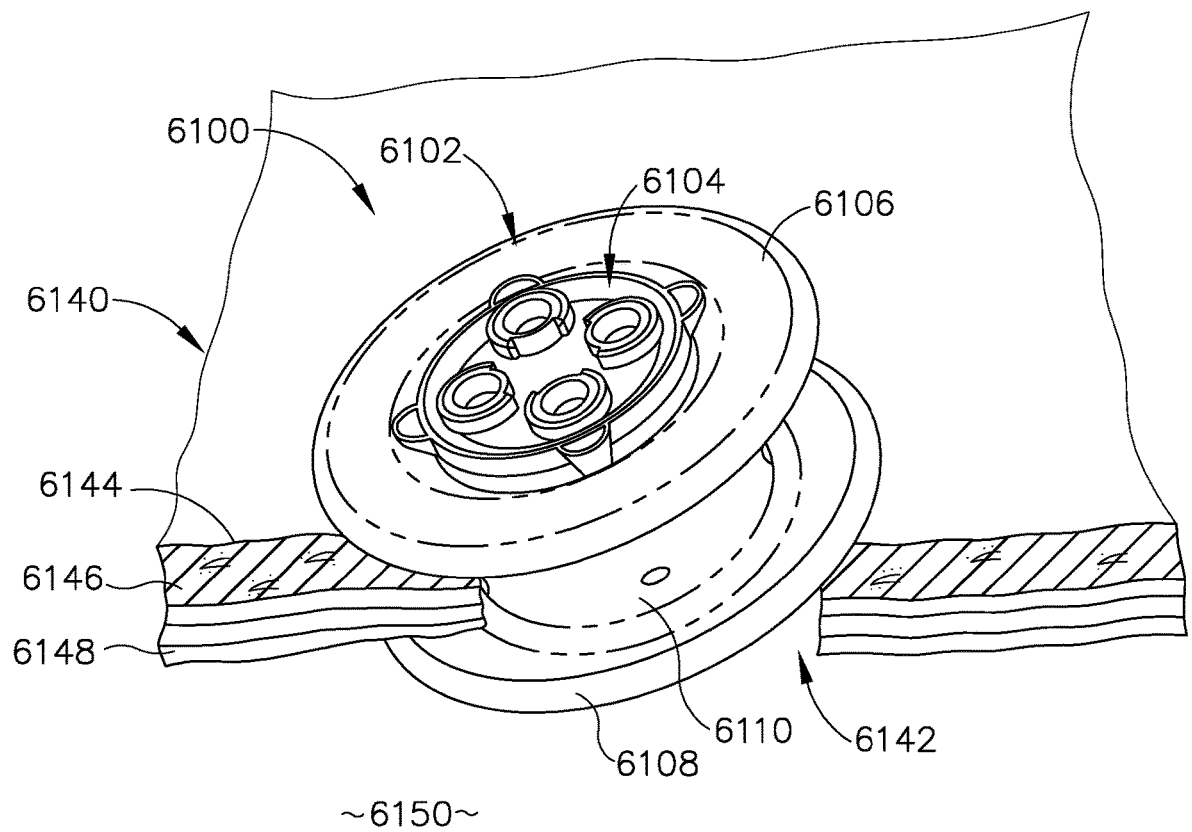
Figure 84B:
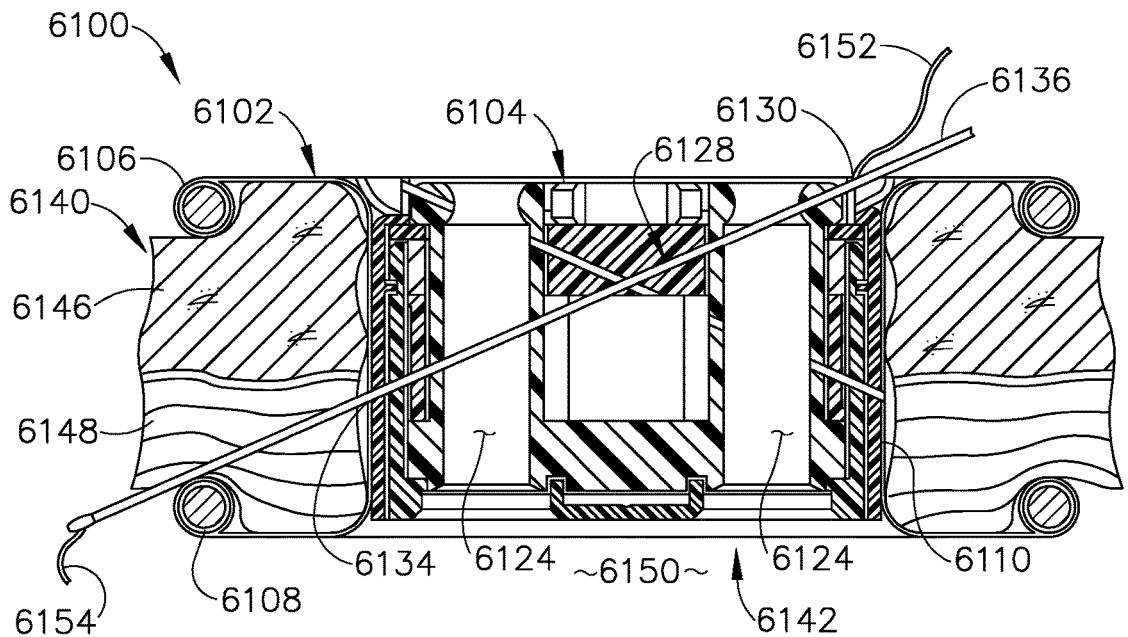
Figure 84C:
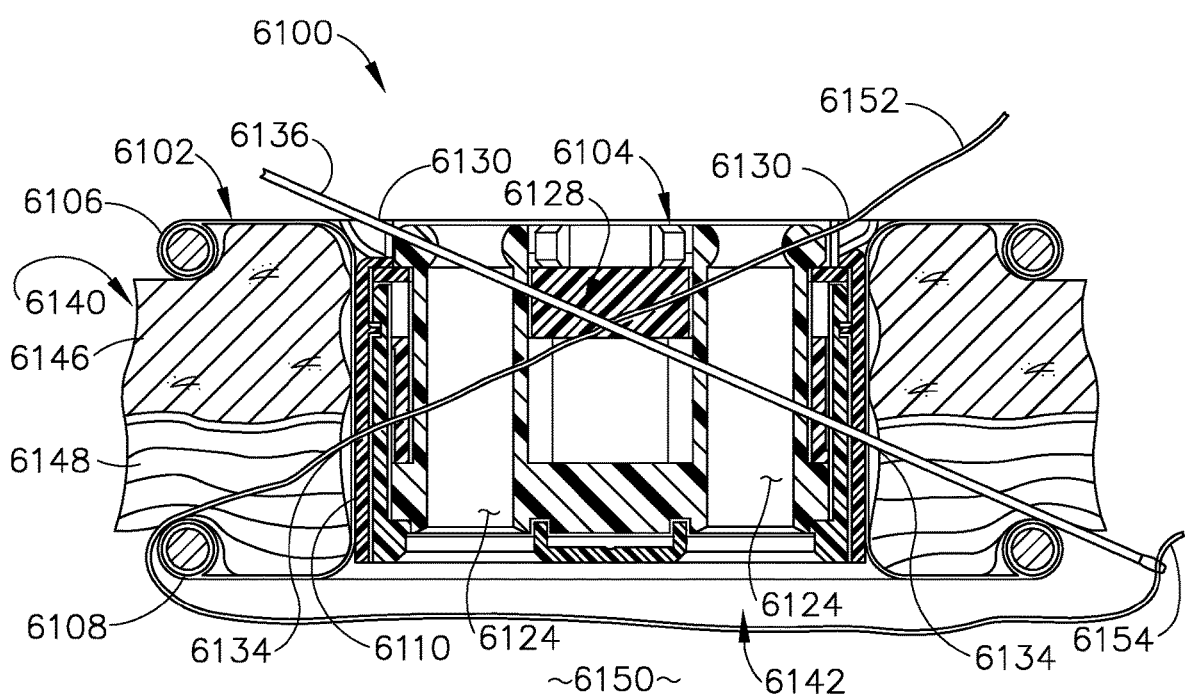
Figure 84D:
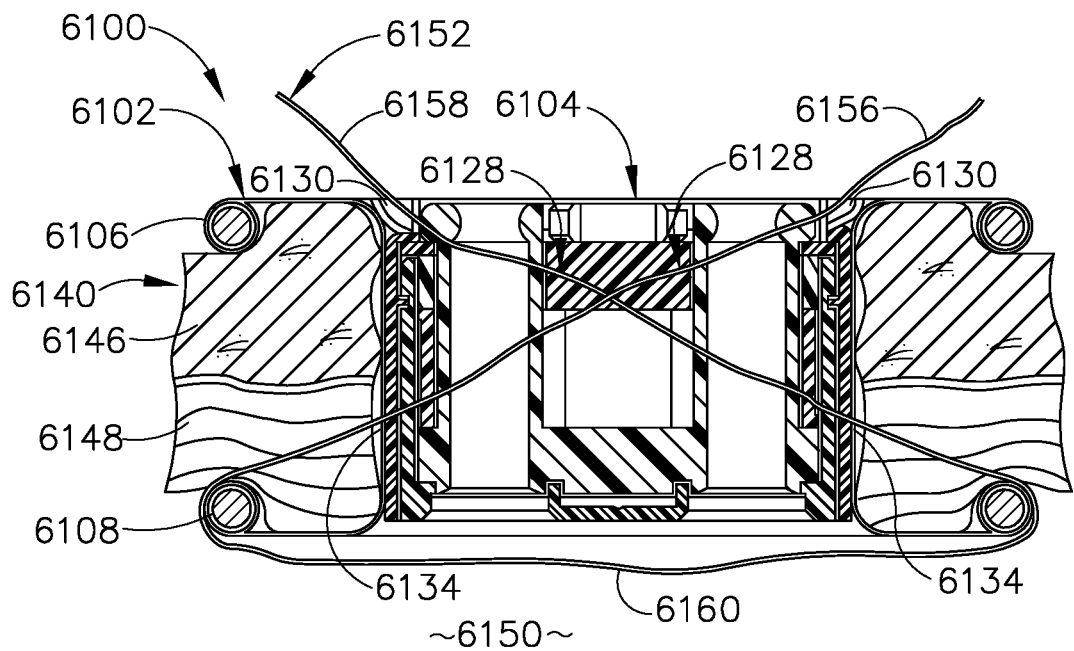
Figure 84E:
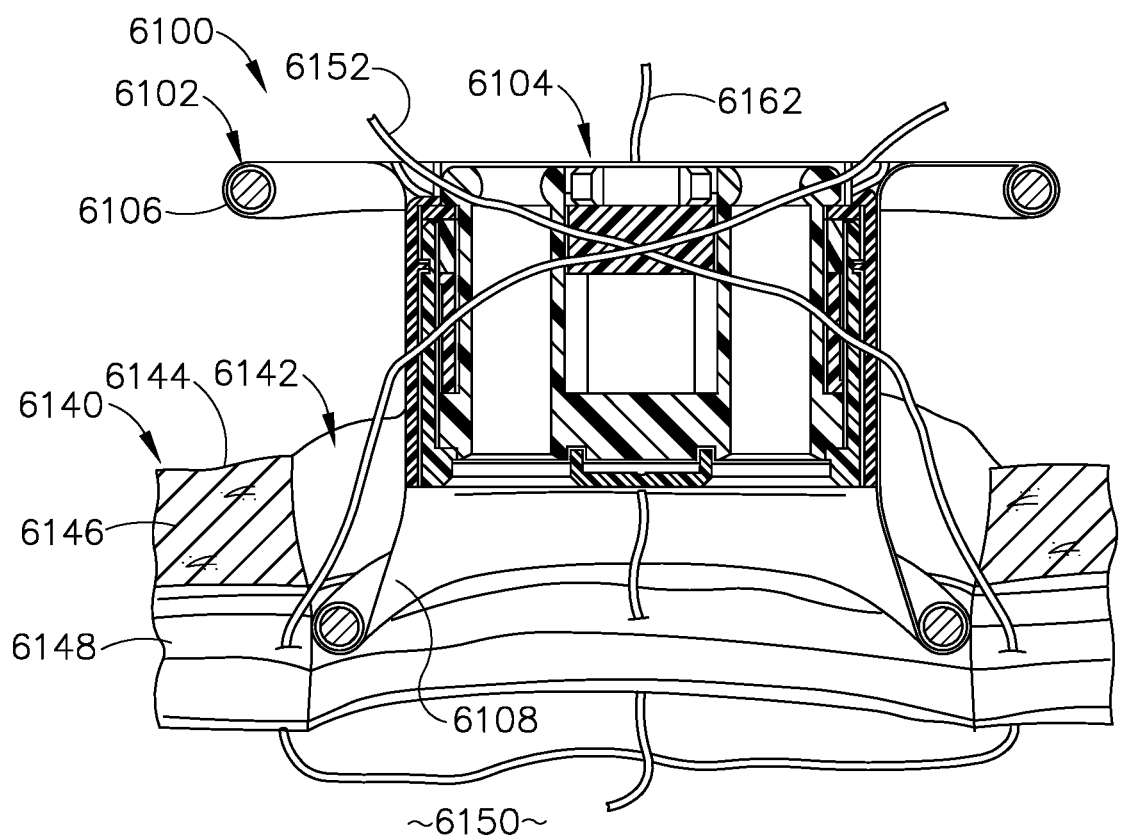
Figure 84F:
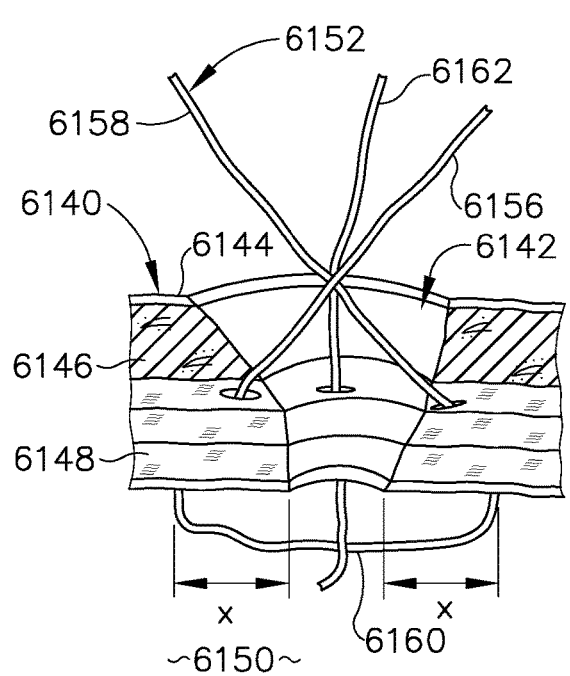
Figure 84G:
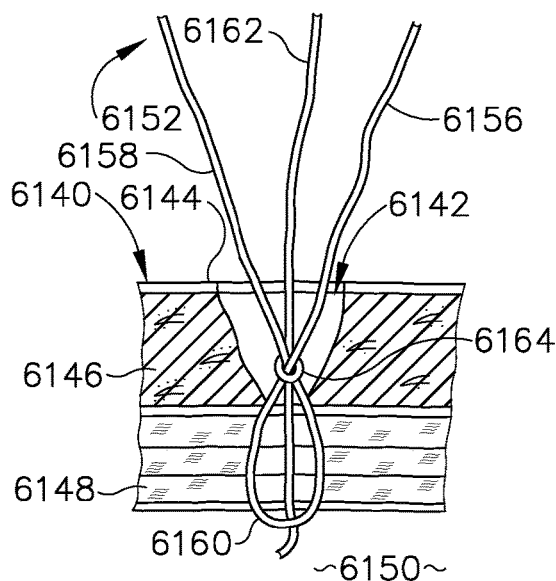
Figure 84H:
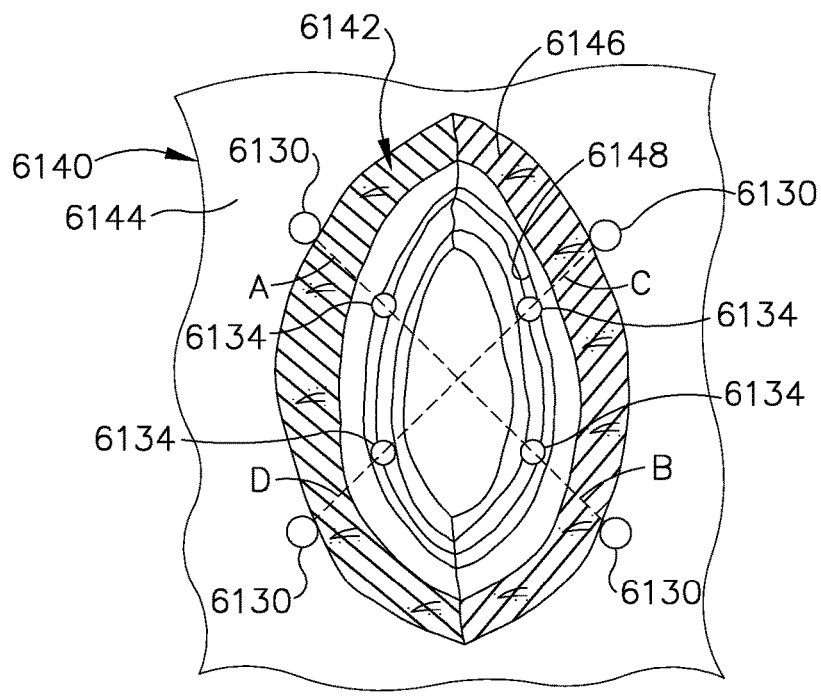
Figure 85A:
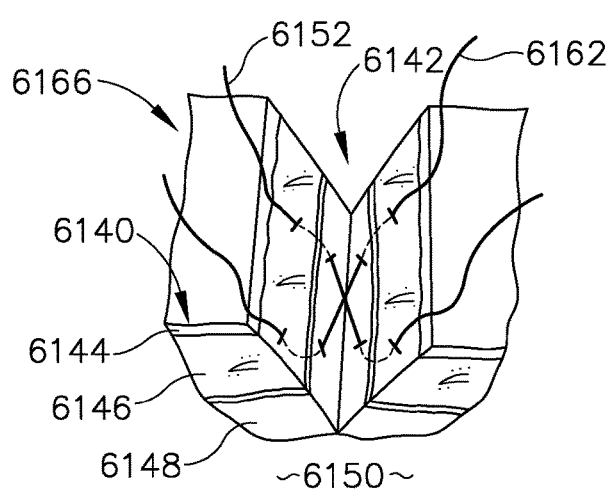
Figure 85B:
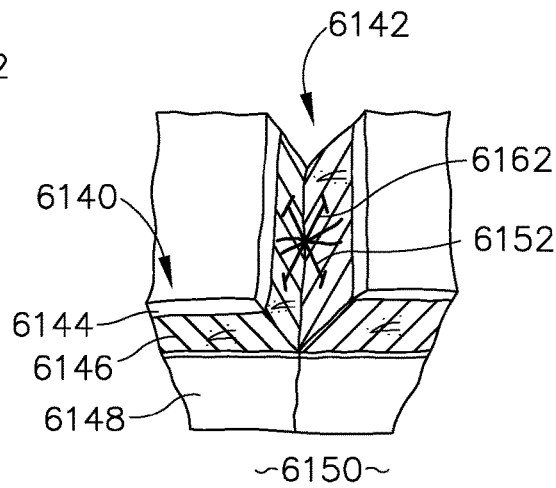
Figure 85C:
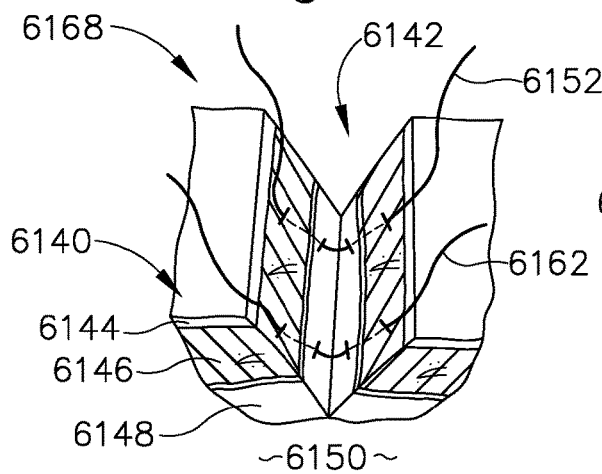
Figure 85D:
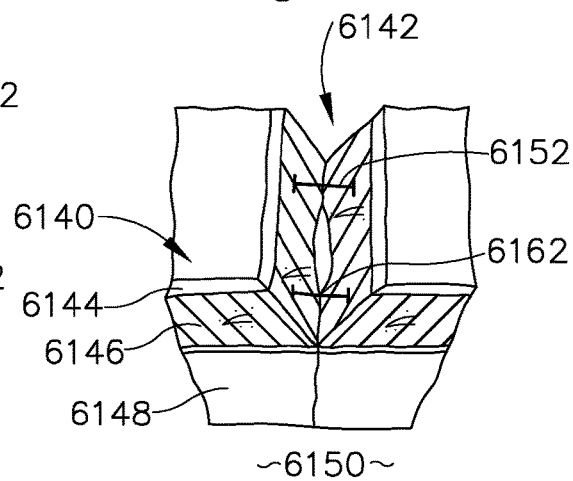
Figure 85E:
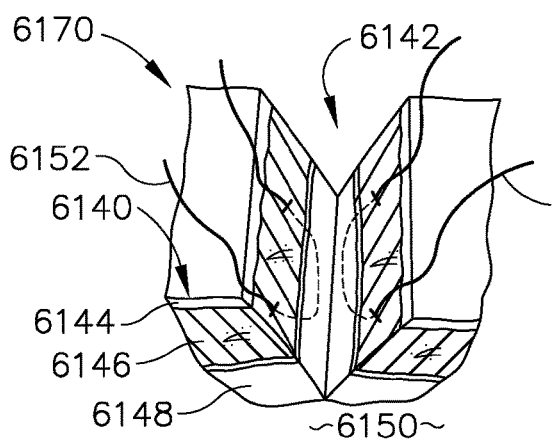
Figure 85F:
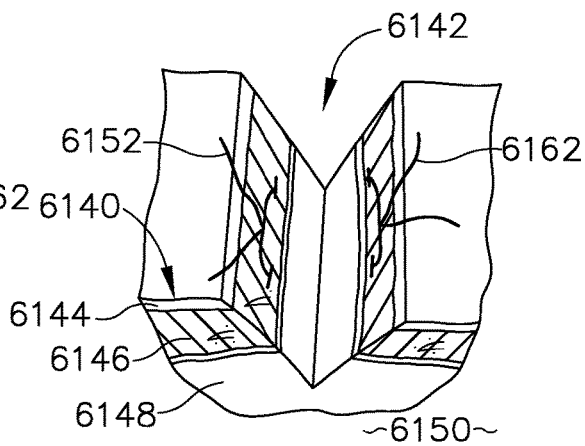
Figure 86:
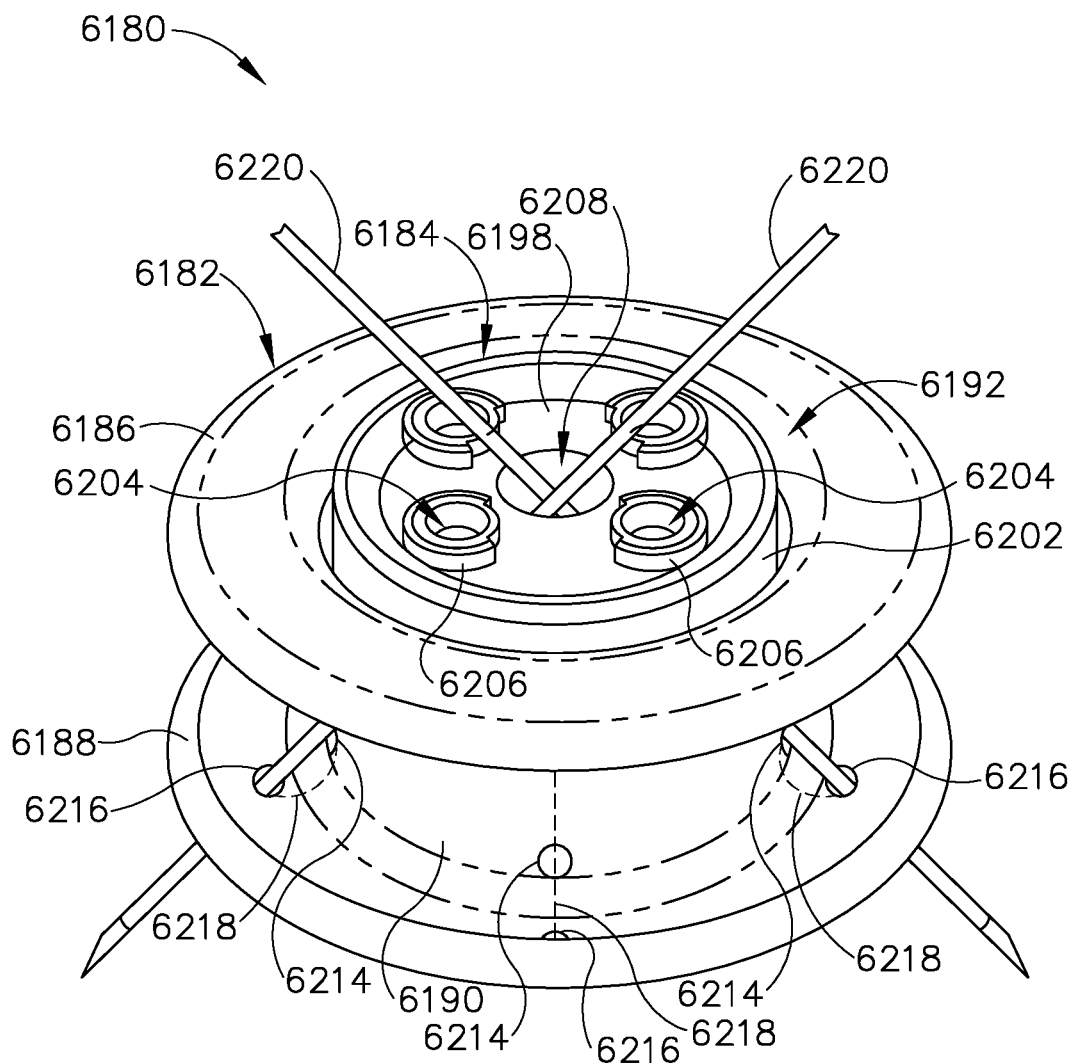
Figure 87:
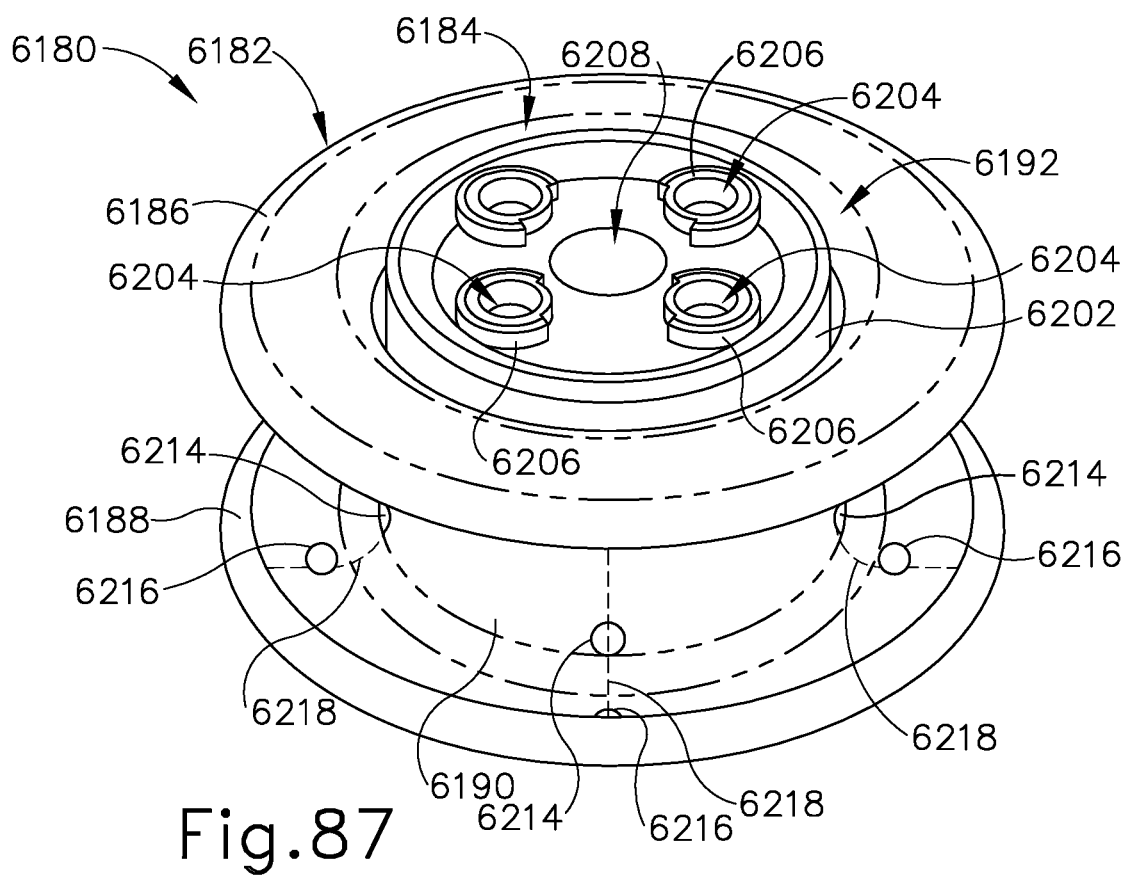
Figure 88:
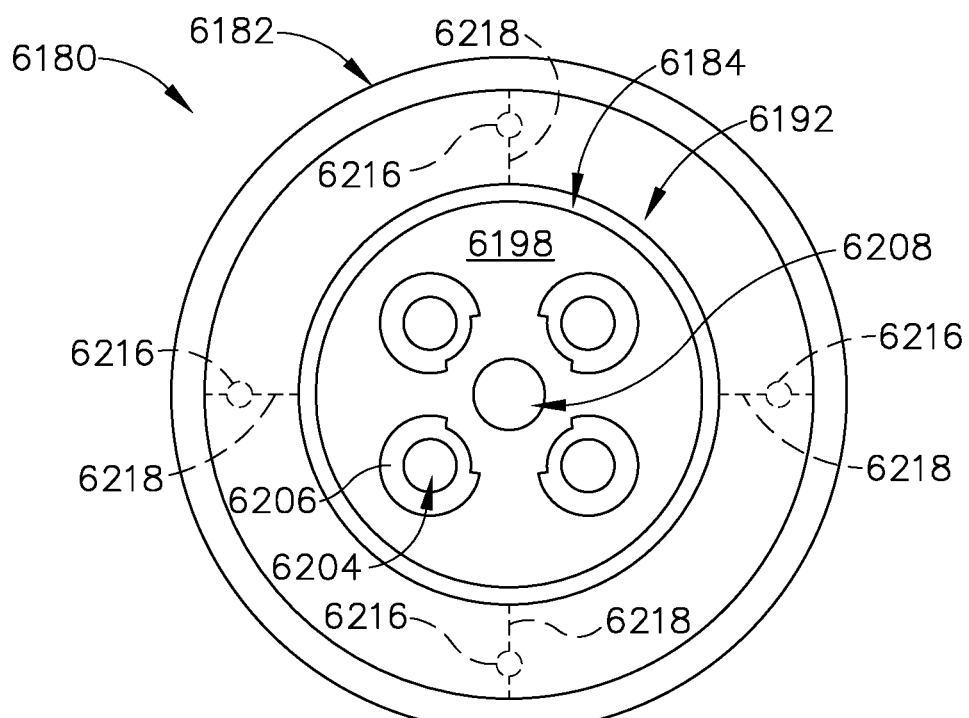
Figure 90:
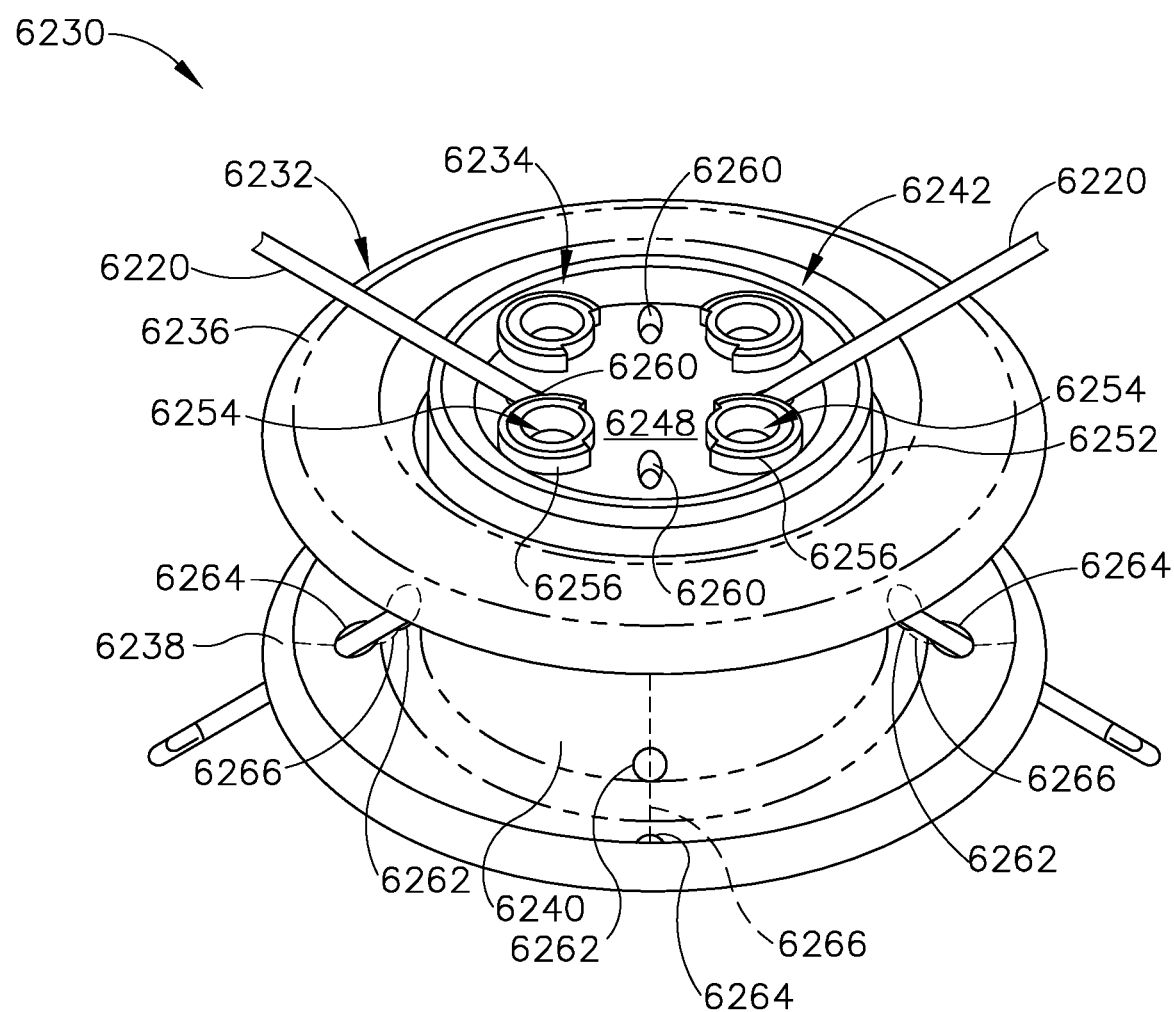
Figure 91:
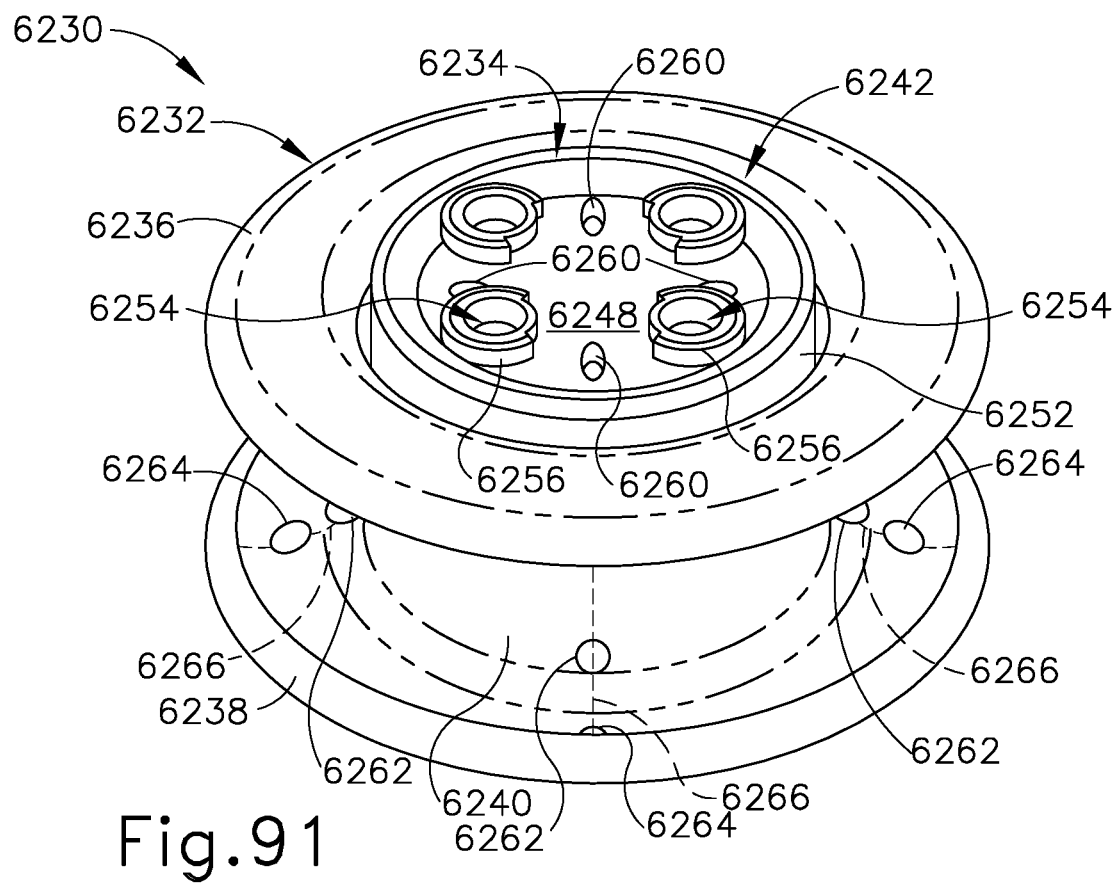
Figure 92:
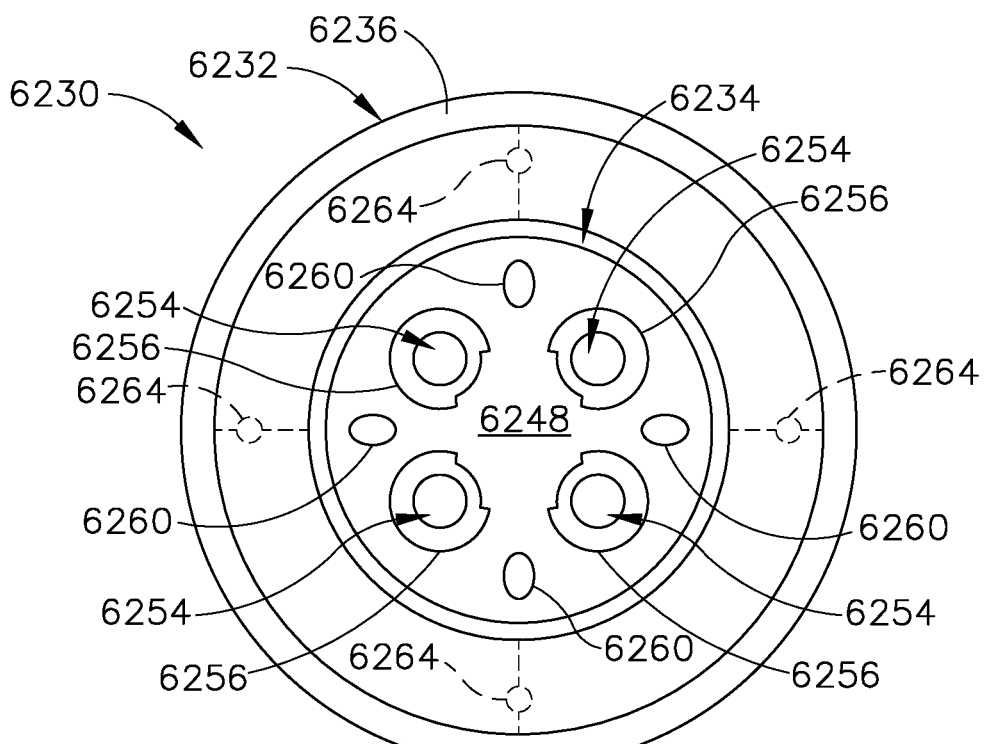
Figure 93A:
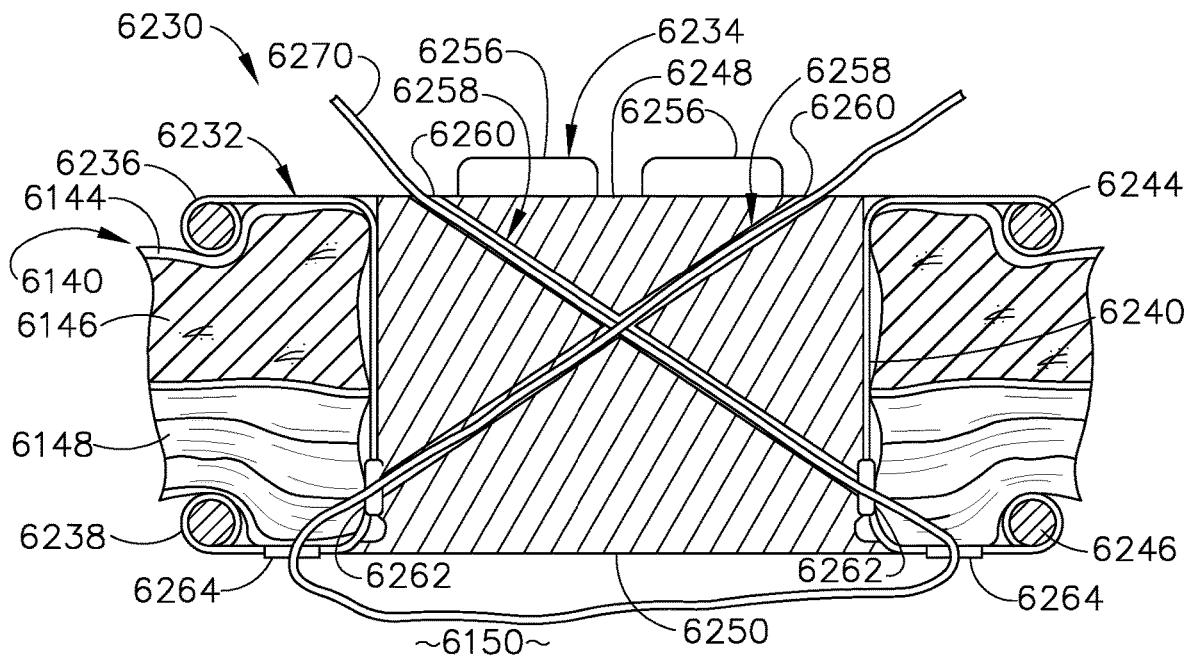
Figure 93B:
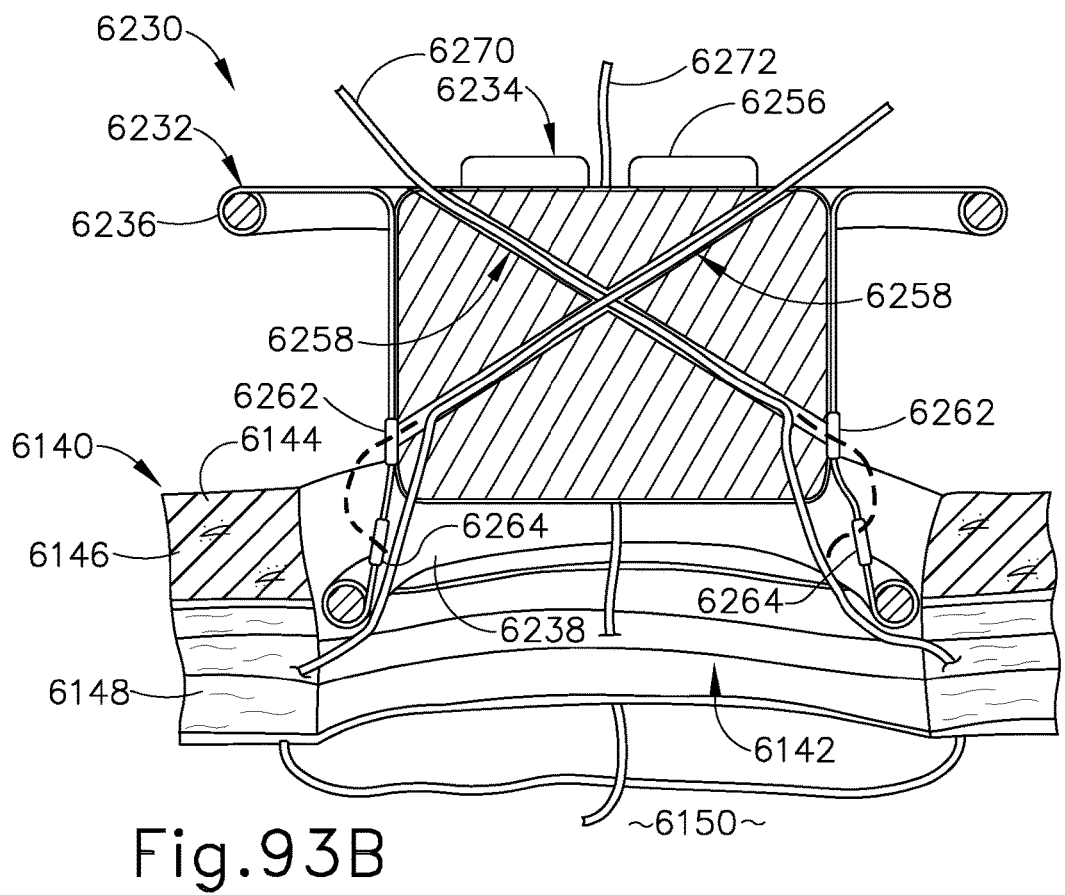
Figure 94:
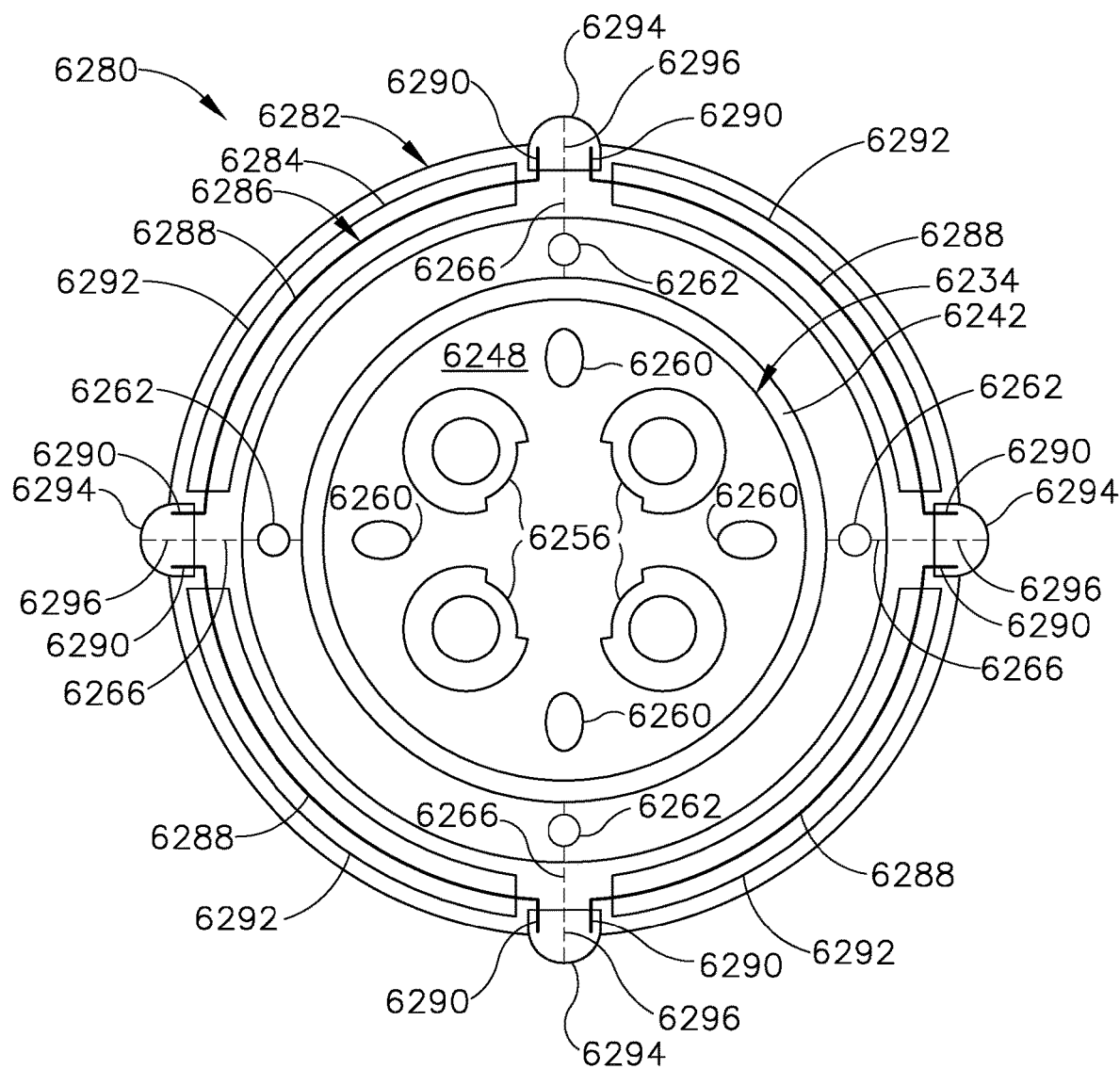
Figure 97A:
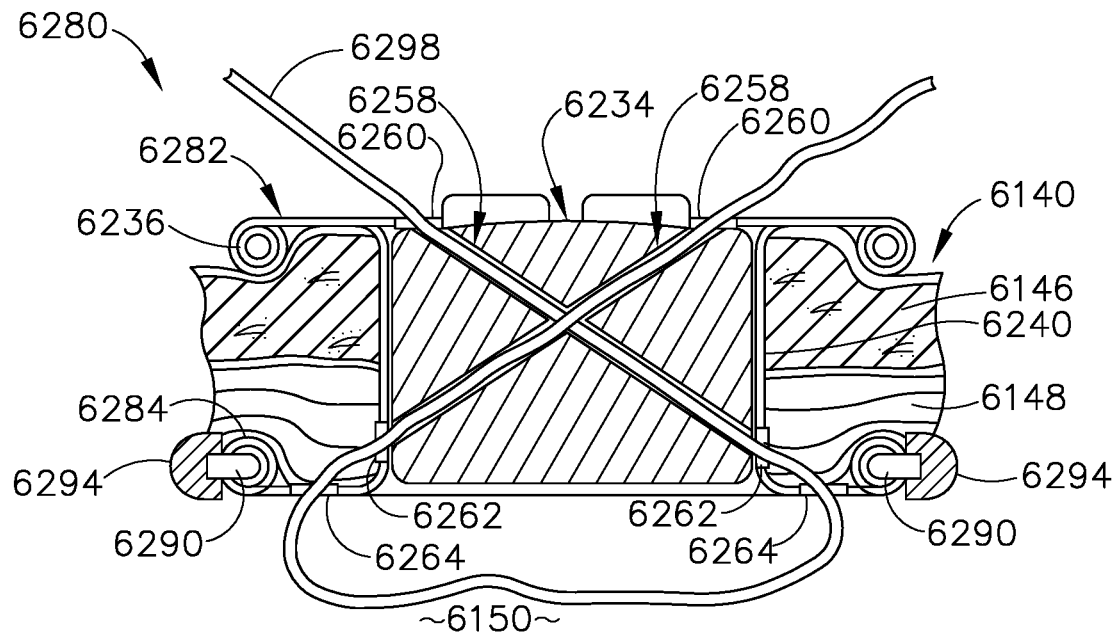
Figure 97B:
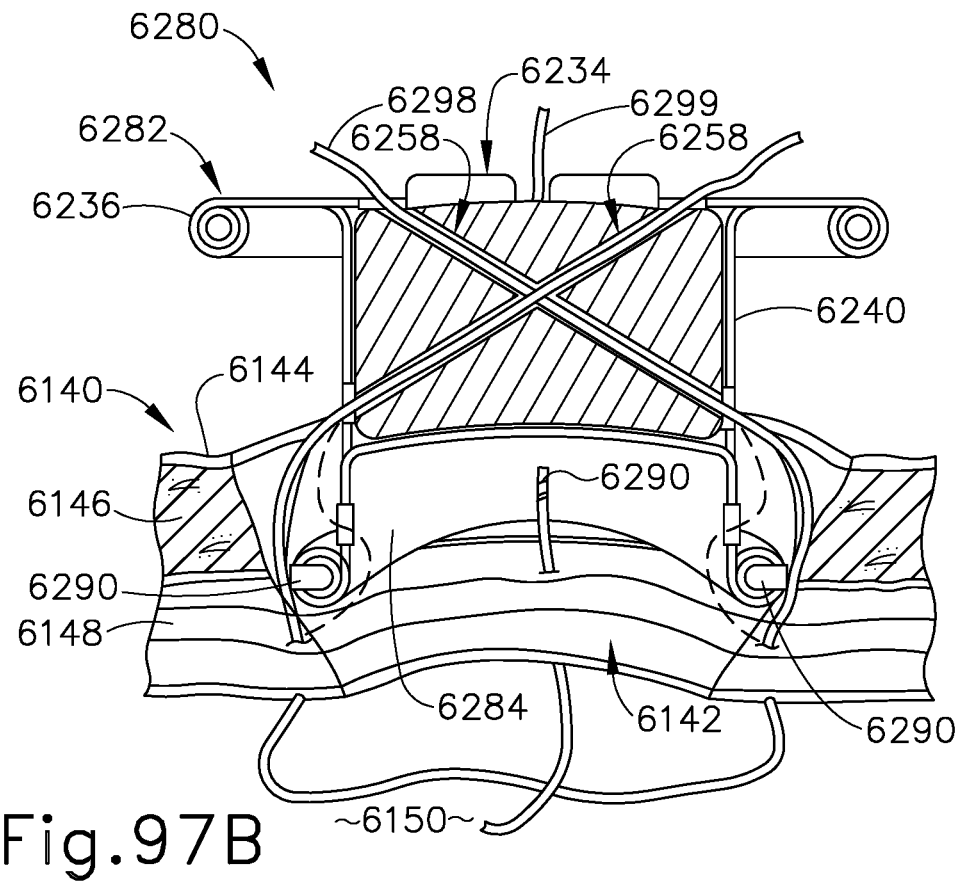
Figure 98:
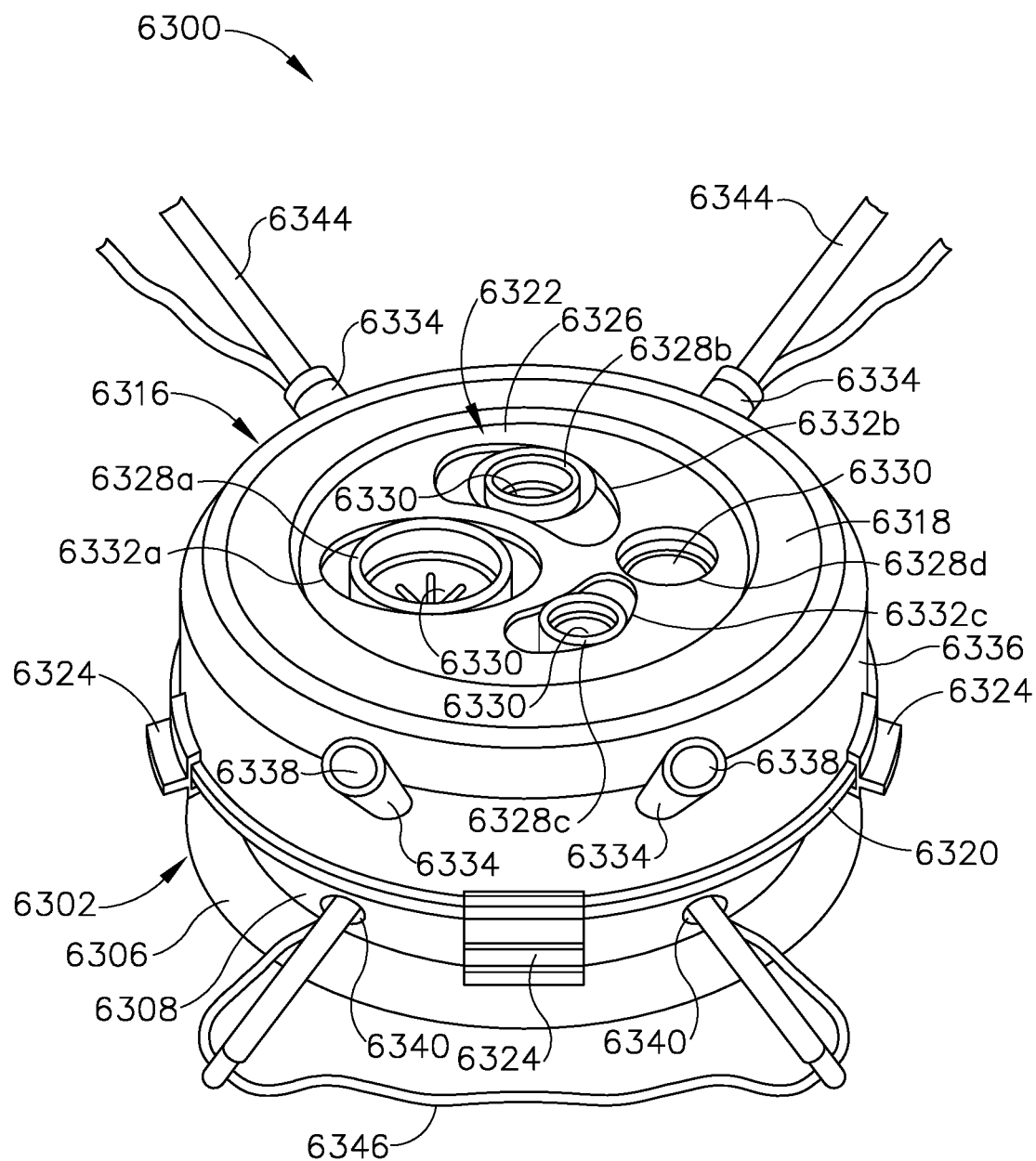
Figure 99:
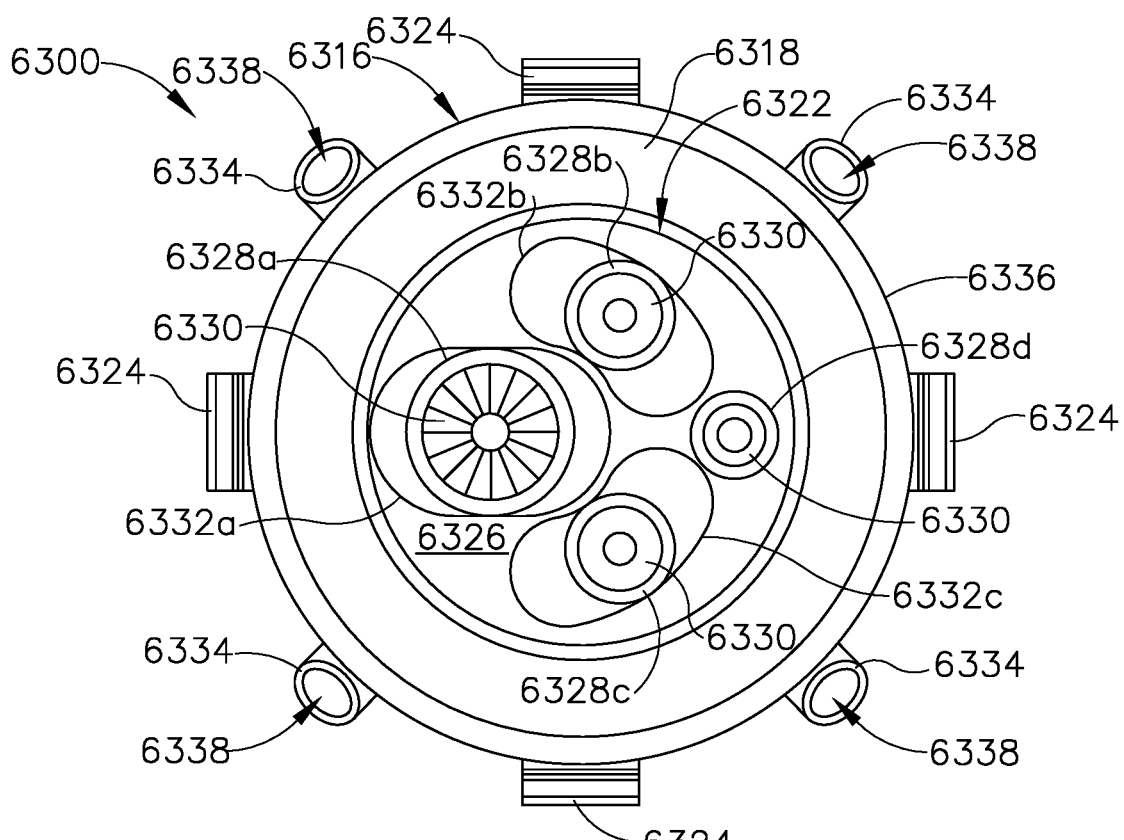
Figure 100:
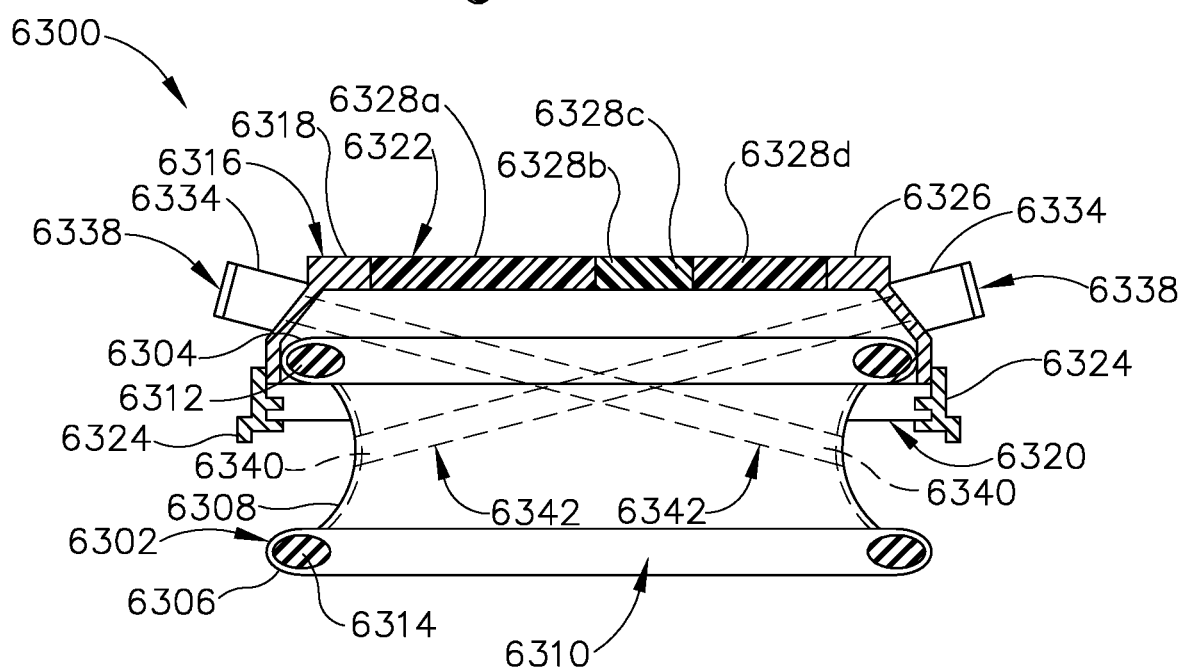
Figure 101:
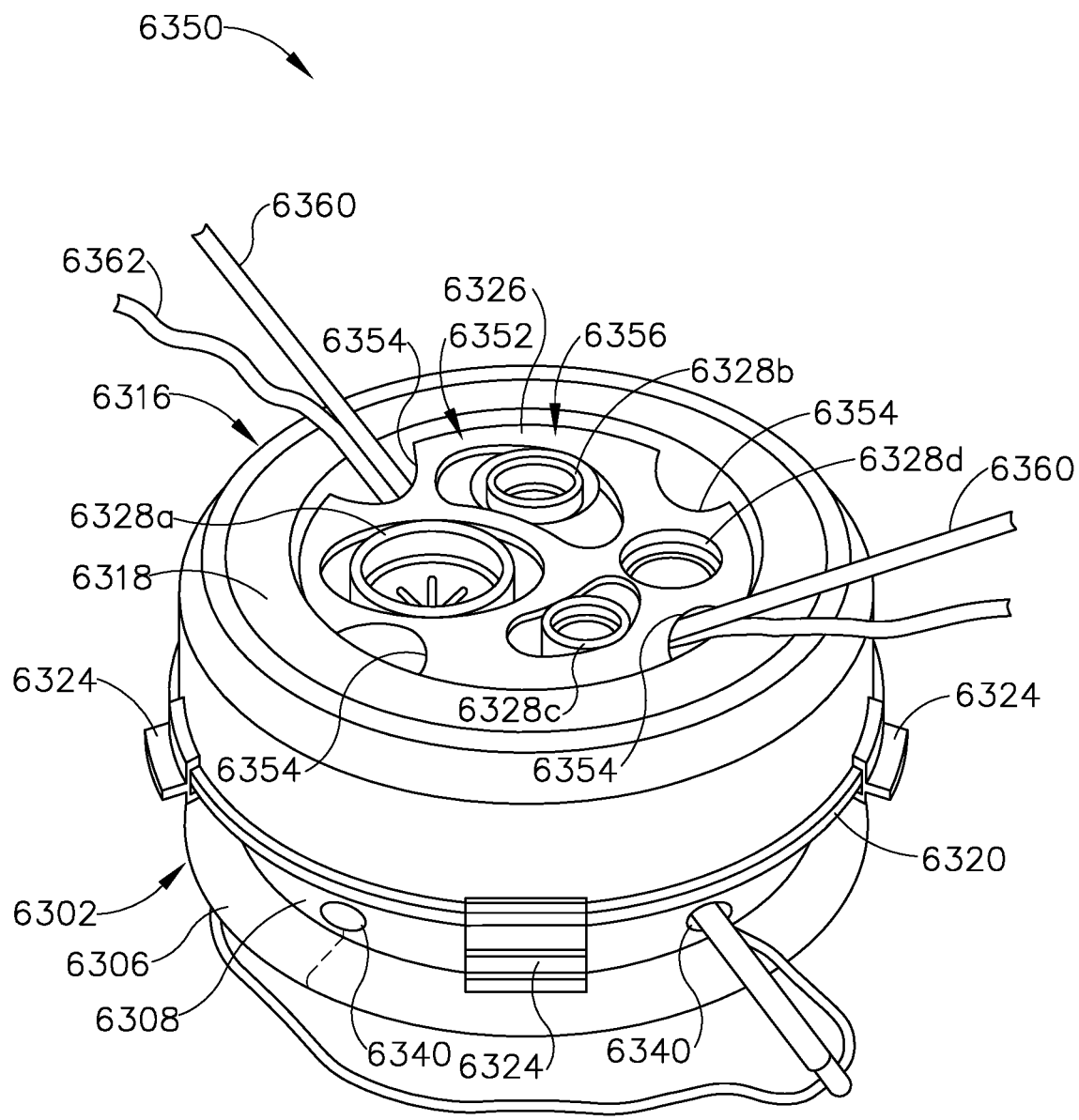
Figure 102:
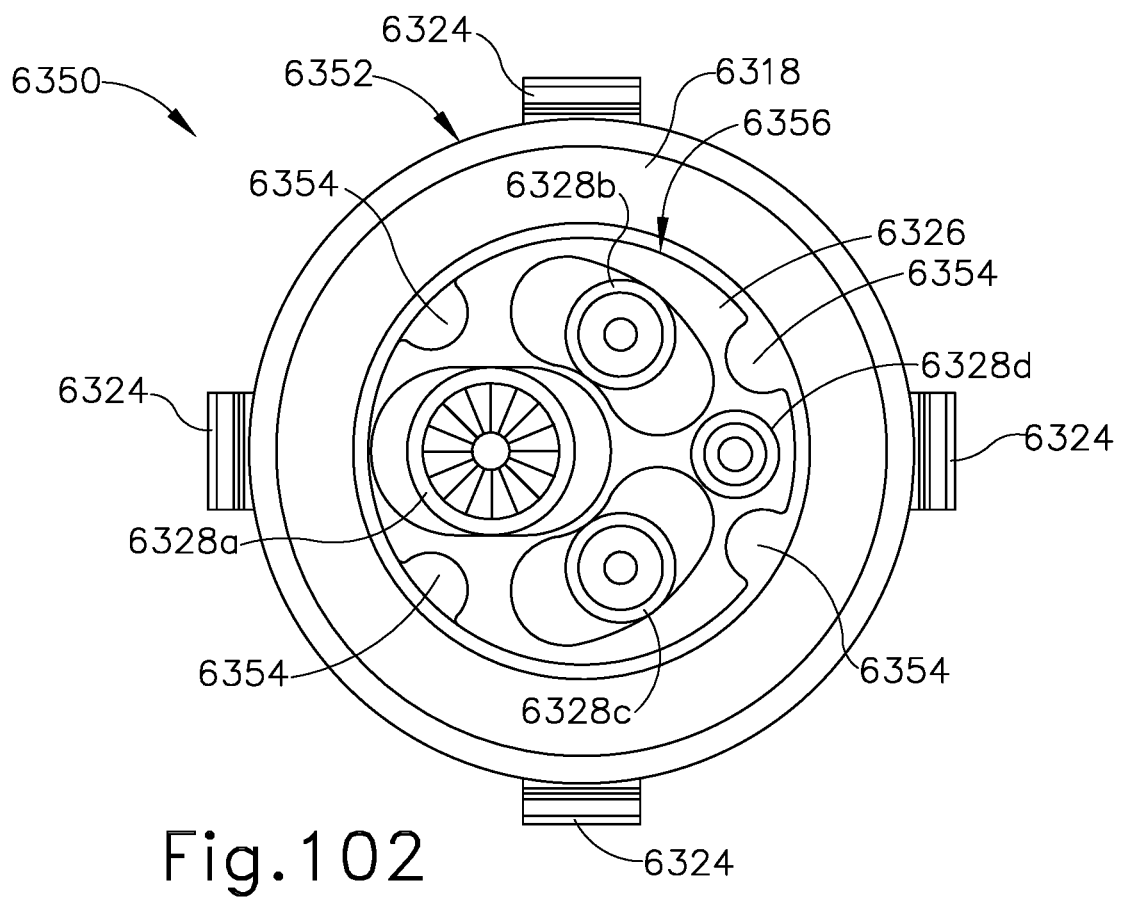
Figure 103:
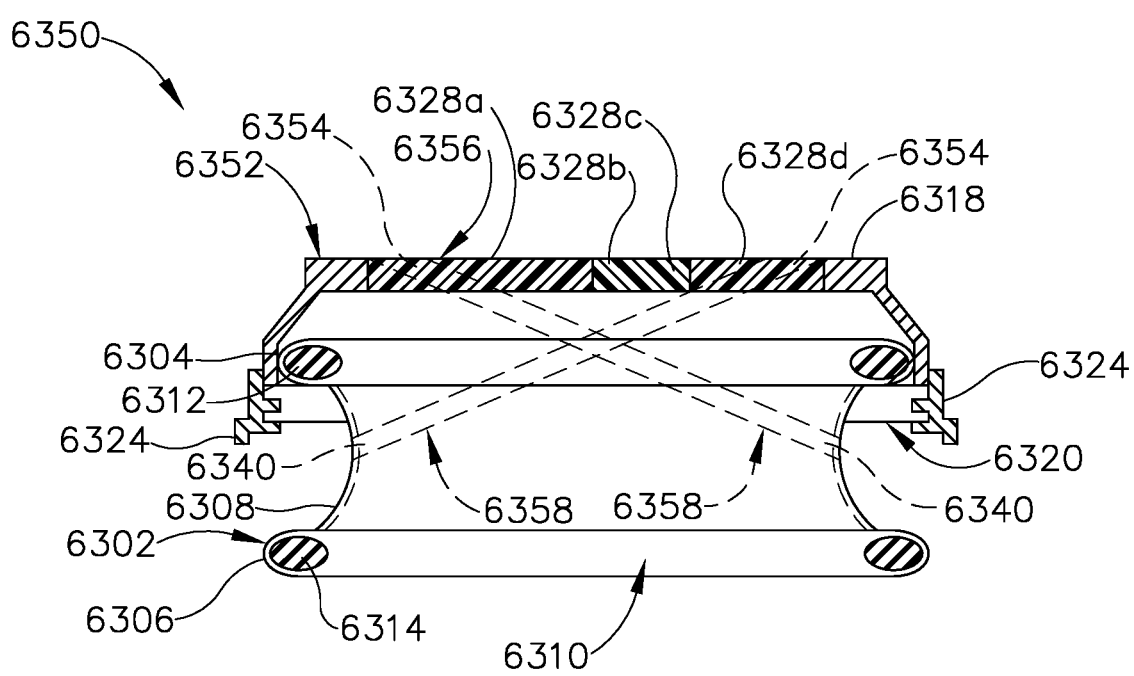
Figure 104A:
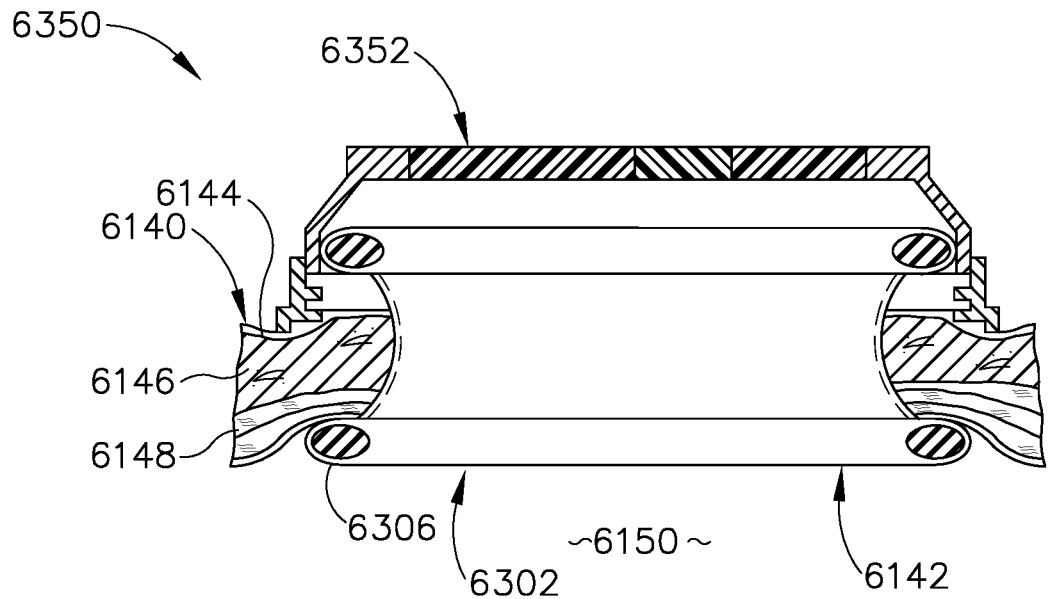
Figure 104B:
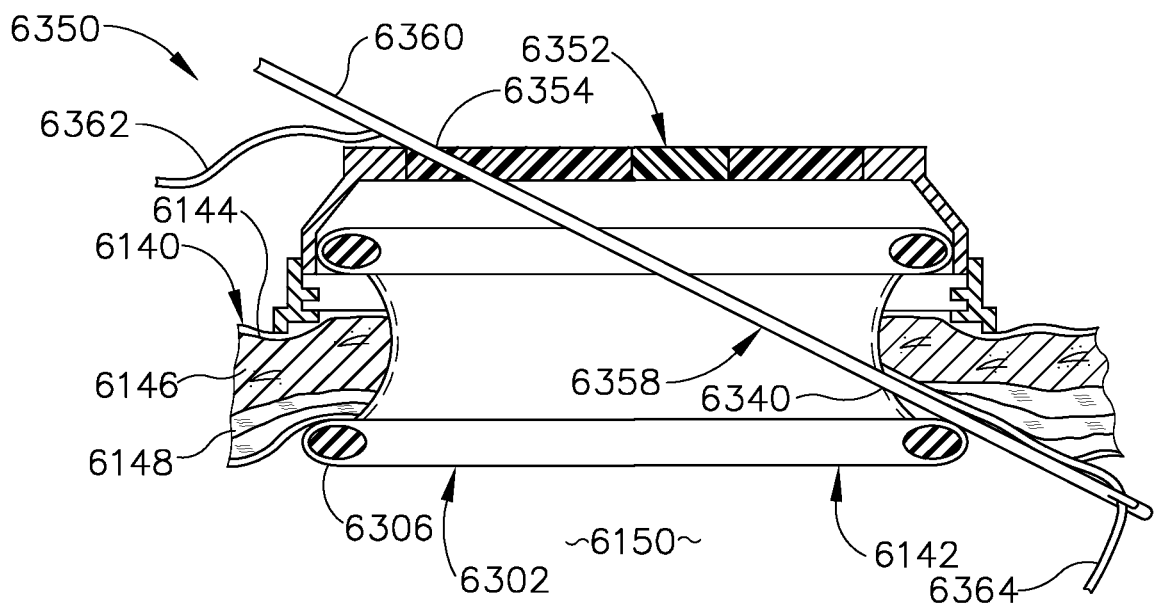
Figure 104C:
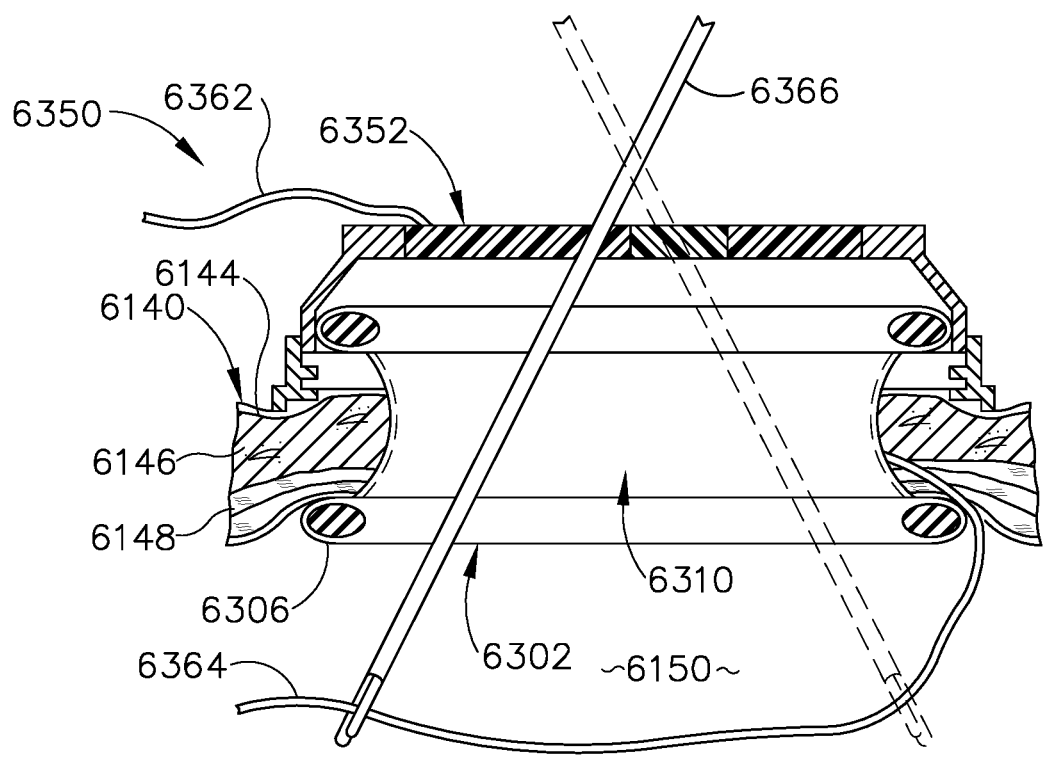
Figure 104D:
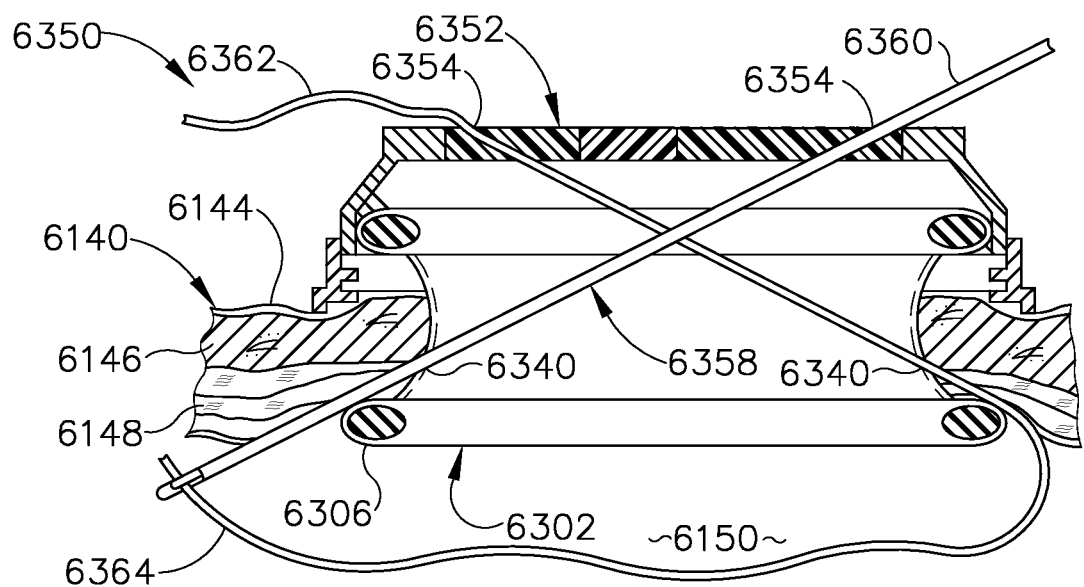
Figure 104E:
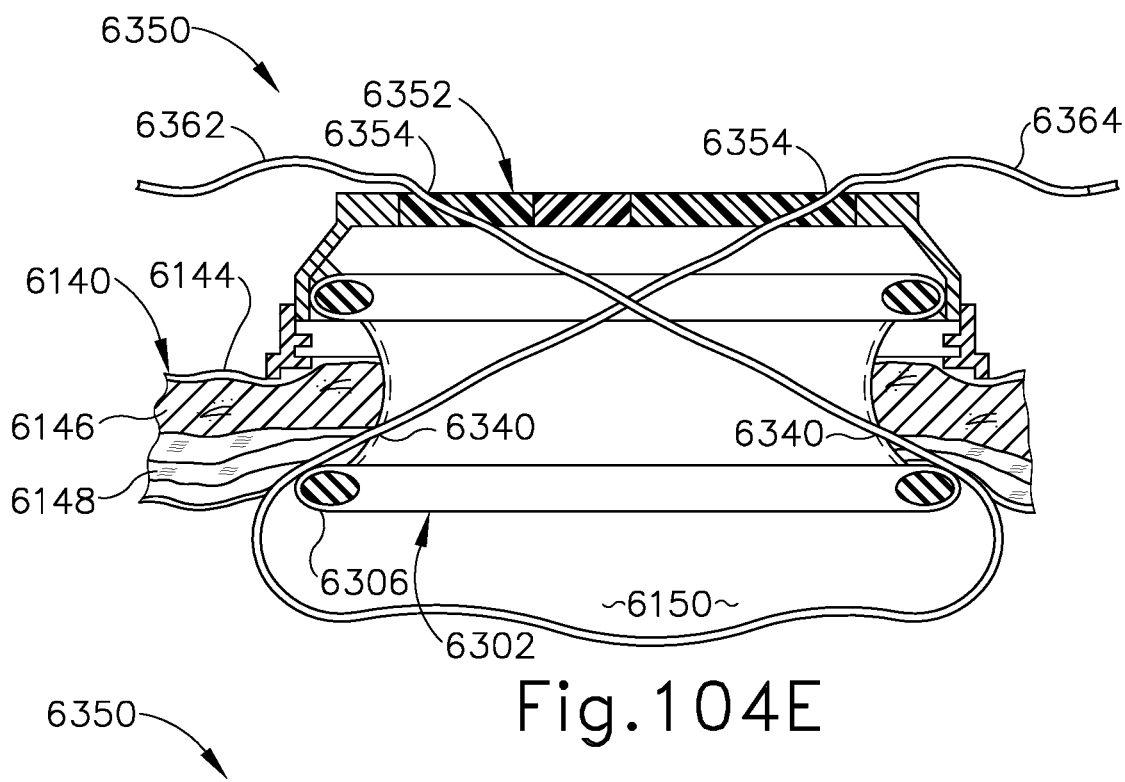
Figure 104F:
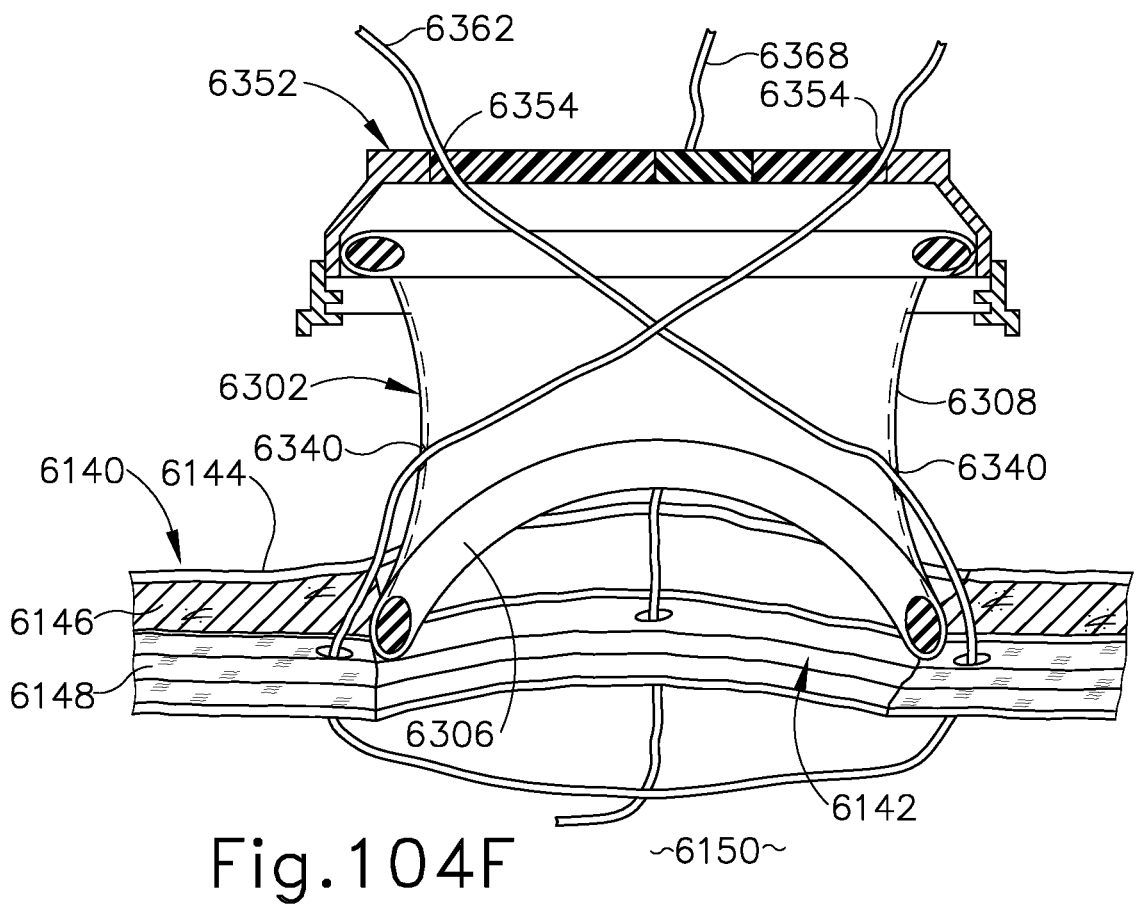
Figure 105:
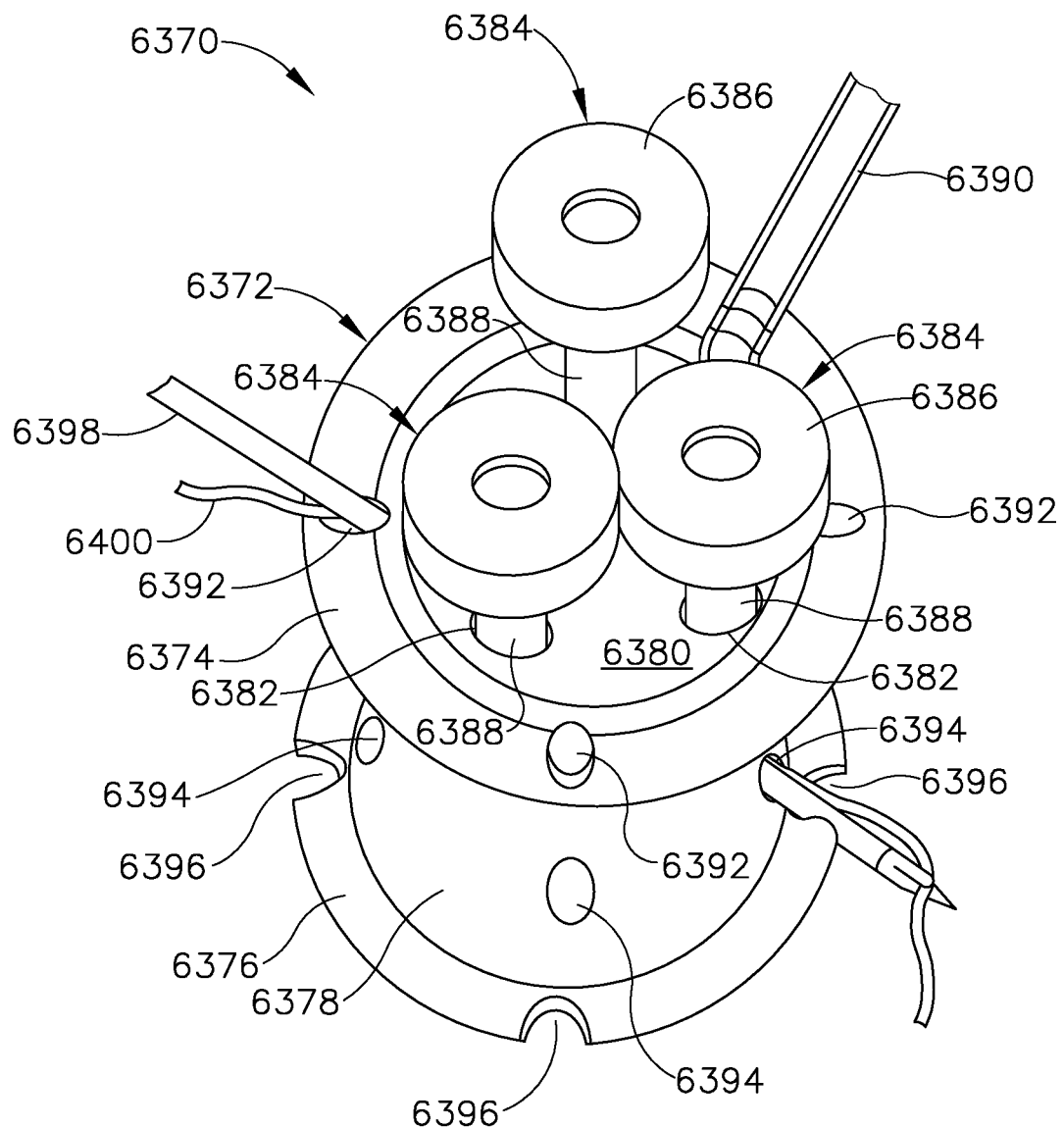
Figure 106:
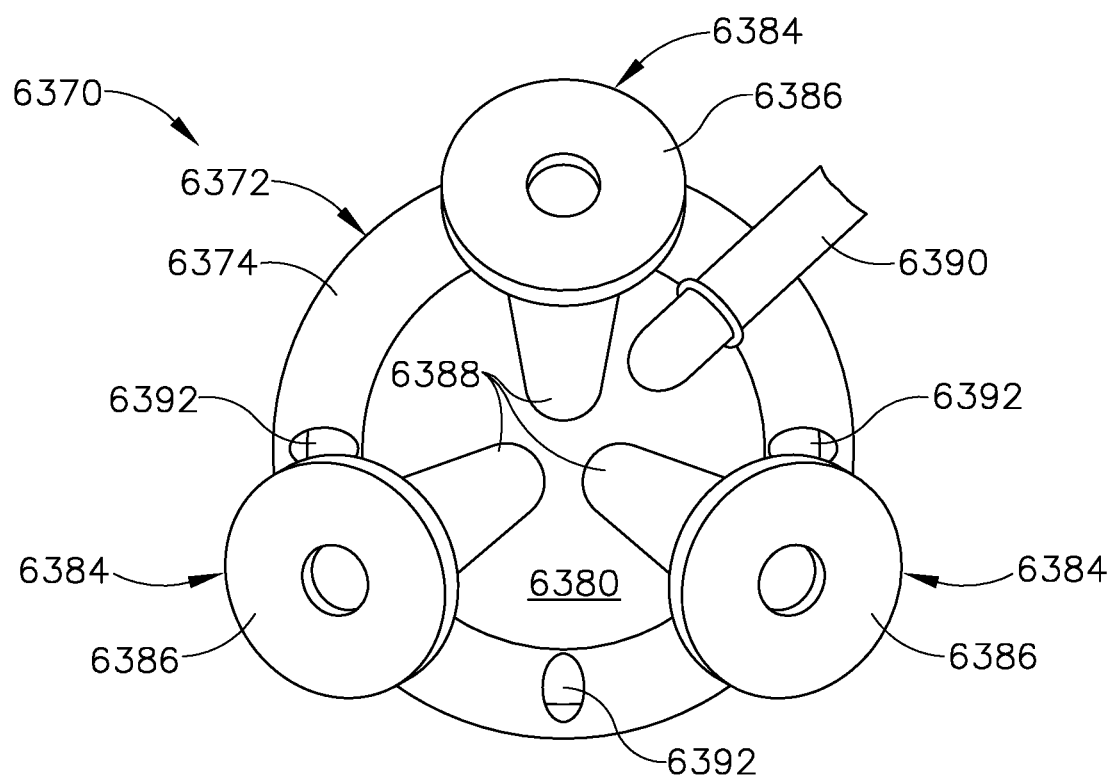
Figure 107:
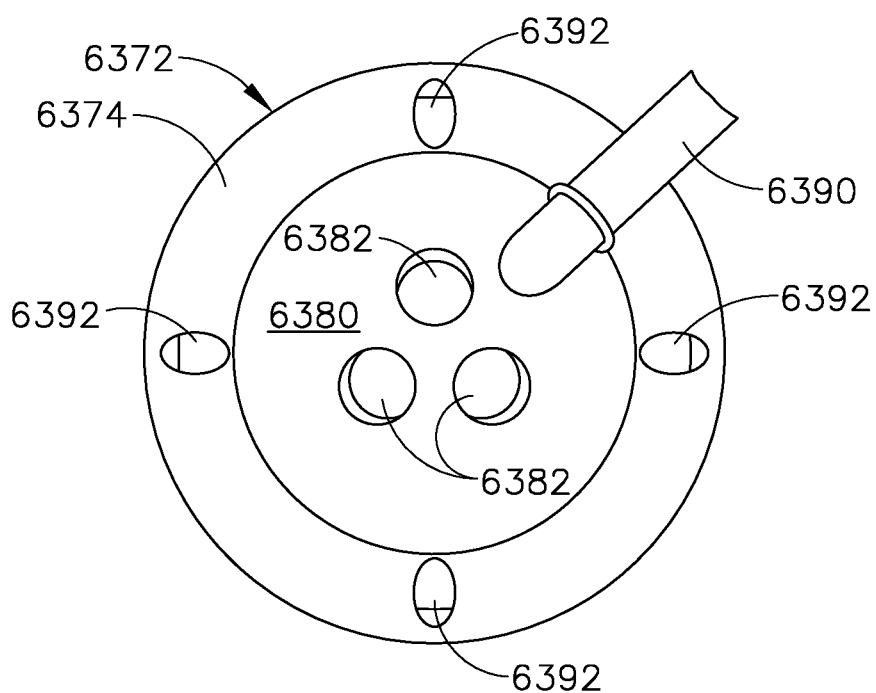
Figure 108:
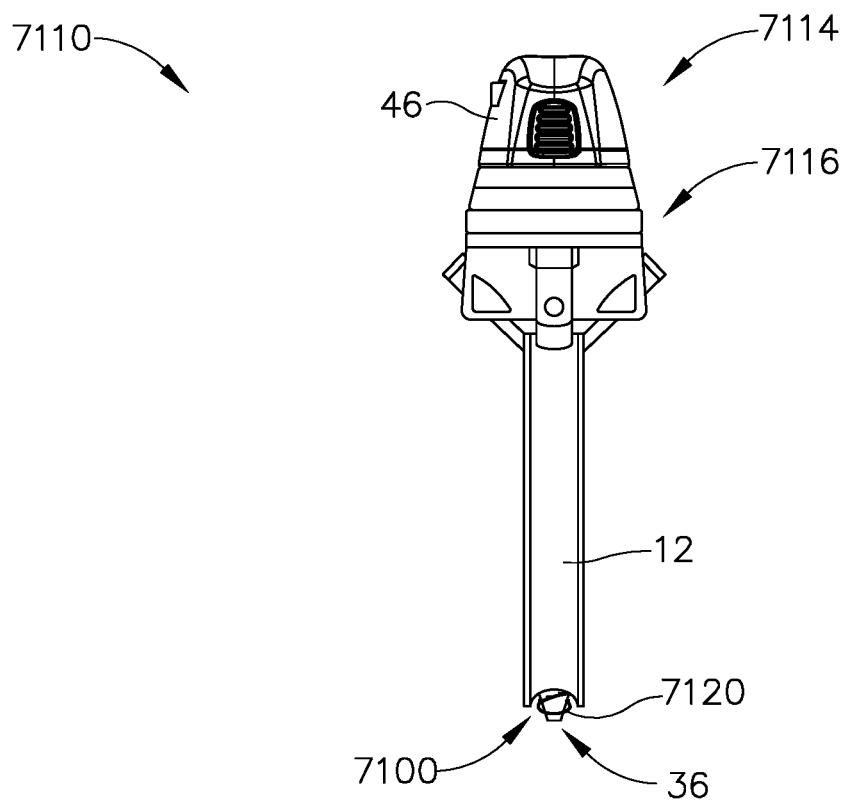
Figure 109:
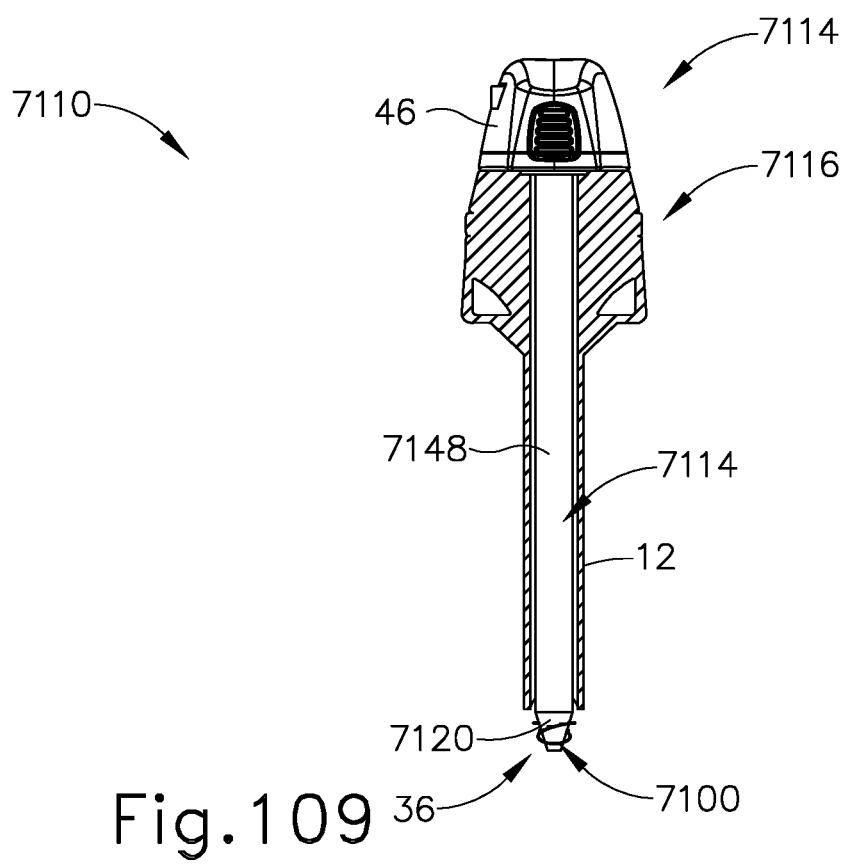
Figure 110:
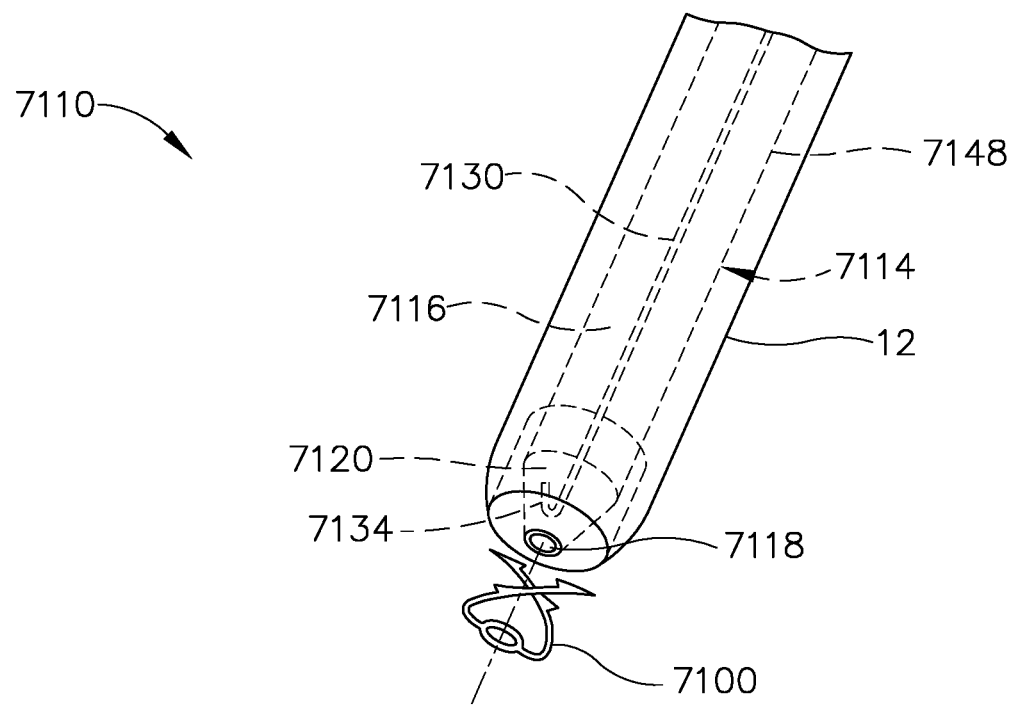
Figure 111:
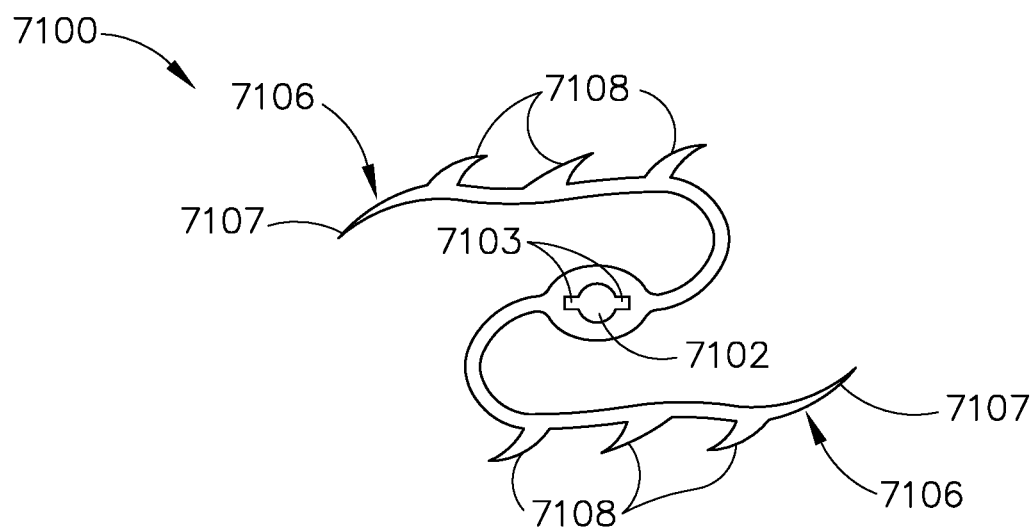
Figure 112:
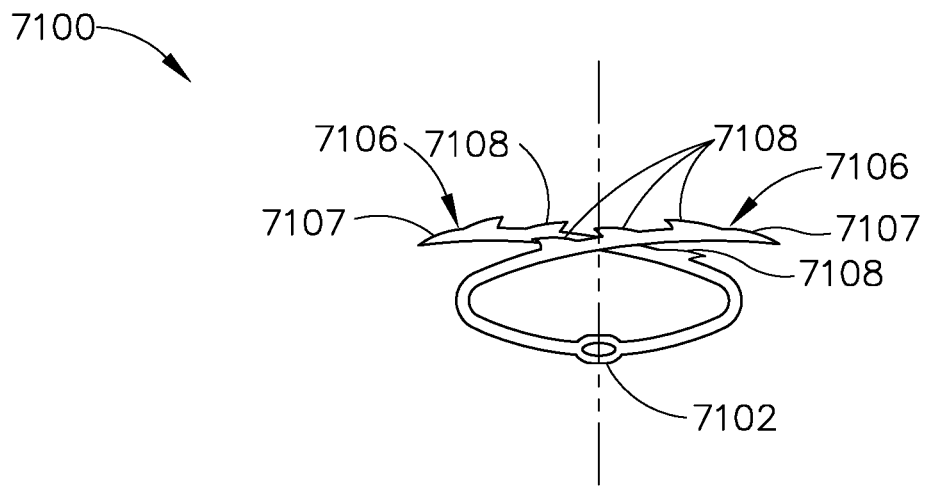
Figure 113A:
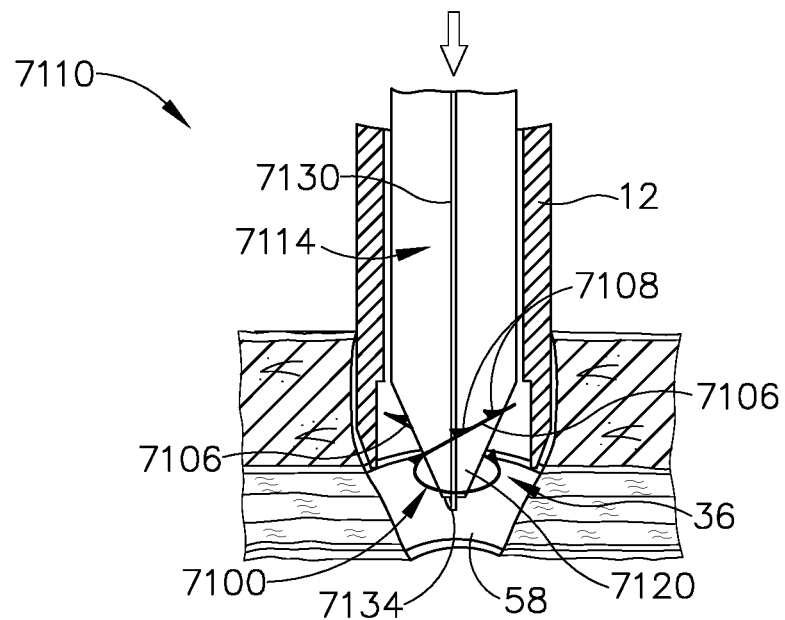
Figure 113B:
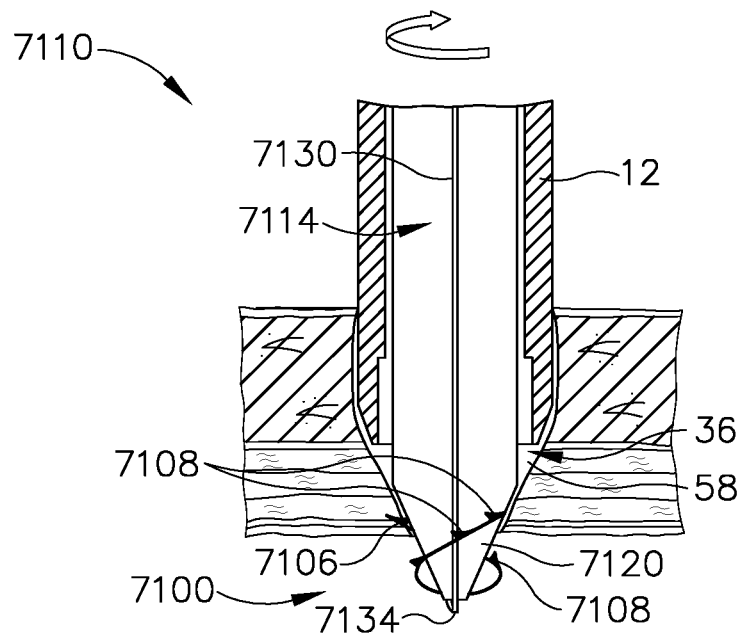
Figure 113C:
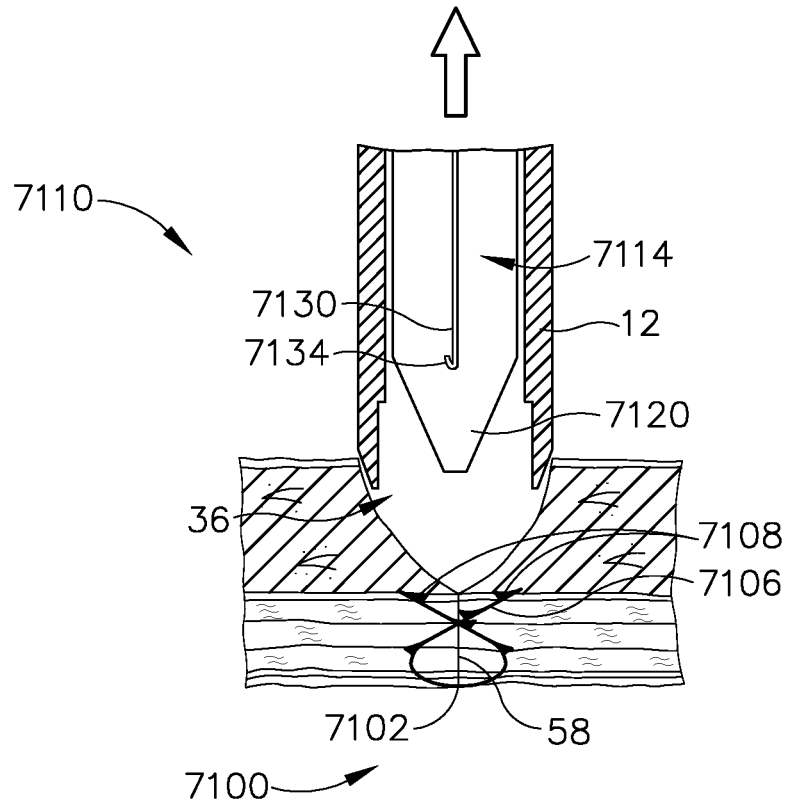
Figure 114A:
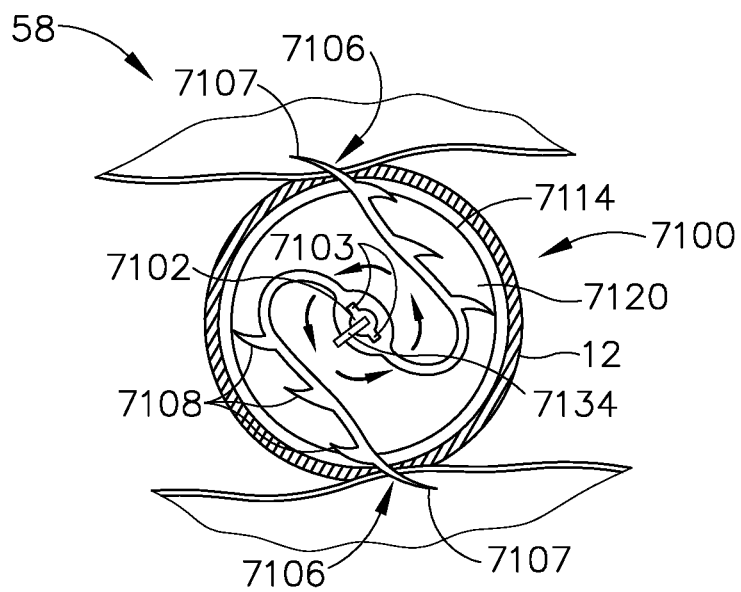
Figure 114B:
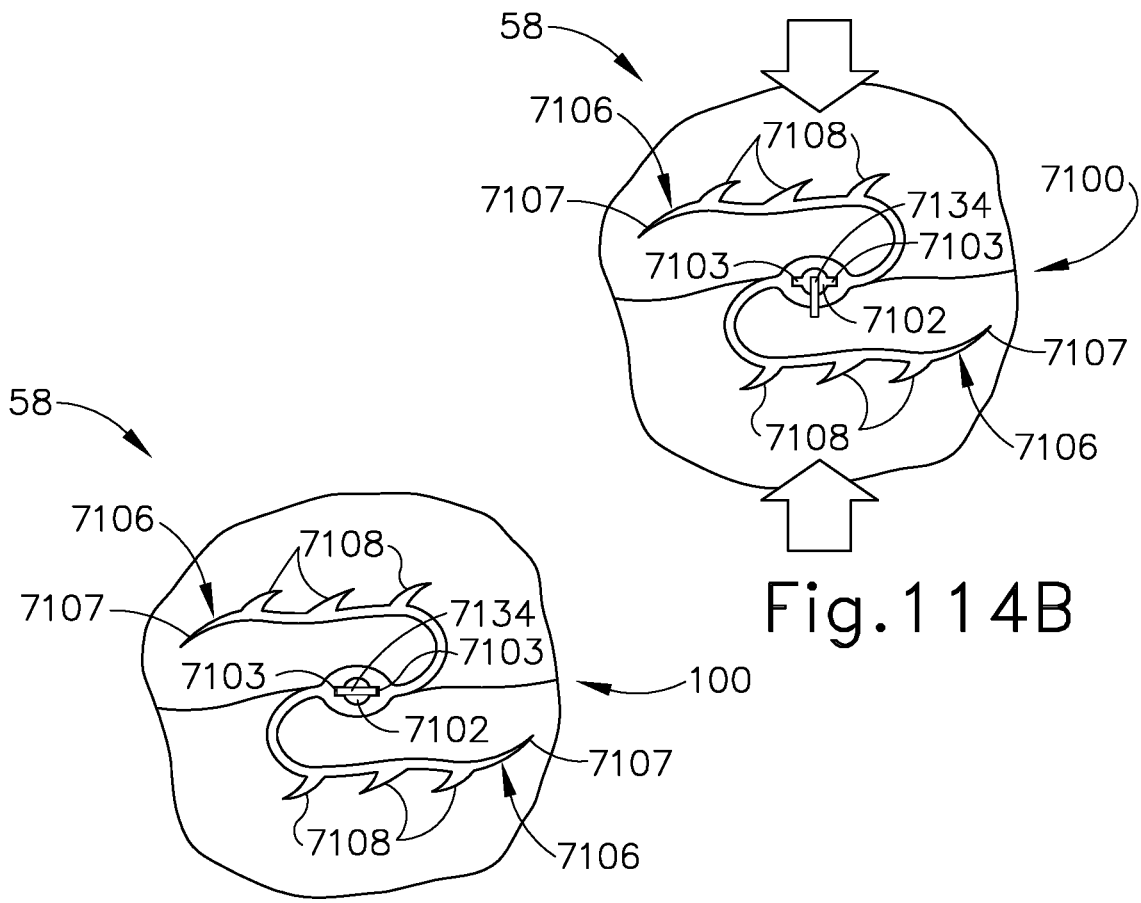
Figure 114C:
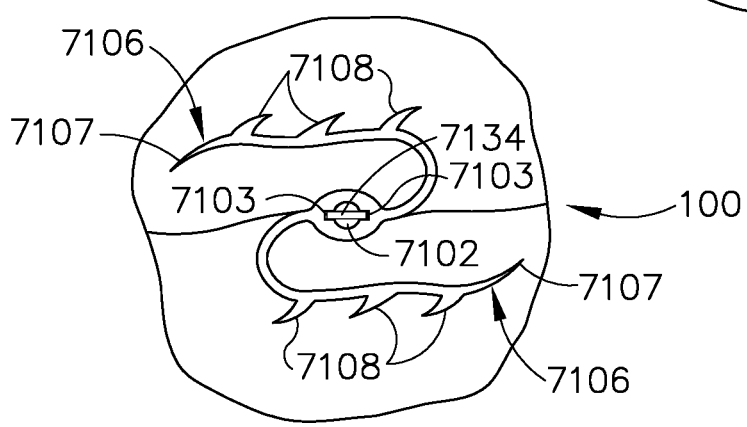
Figure 115A:
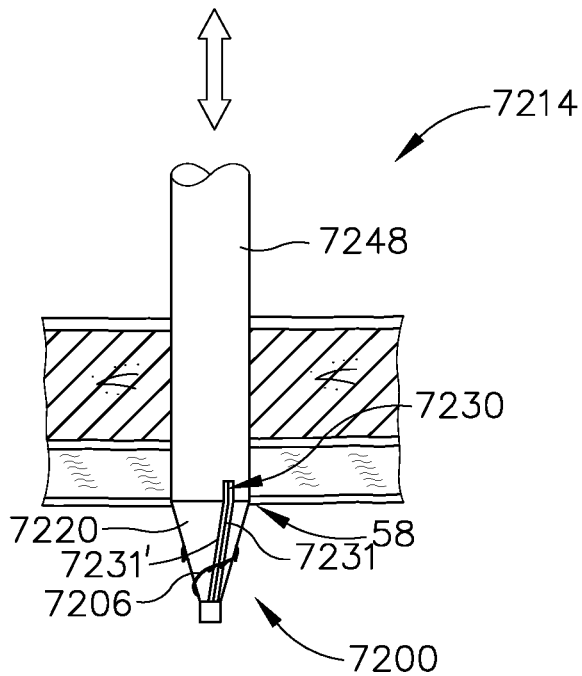
Figure 115B:
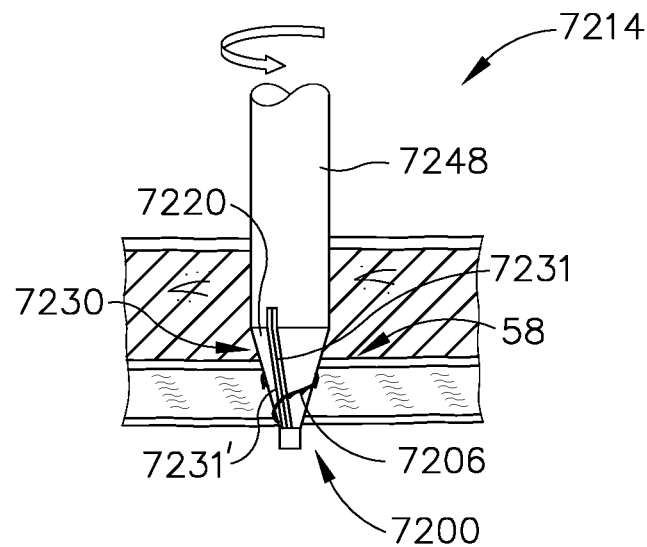
Figure 115C:
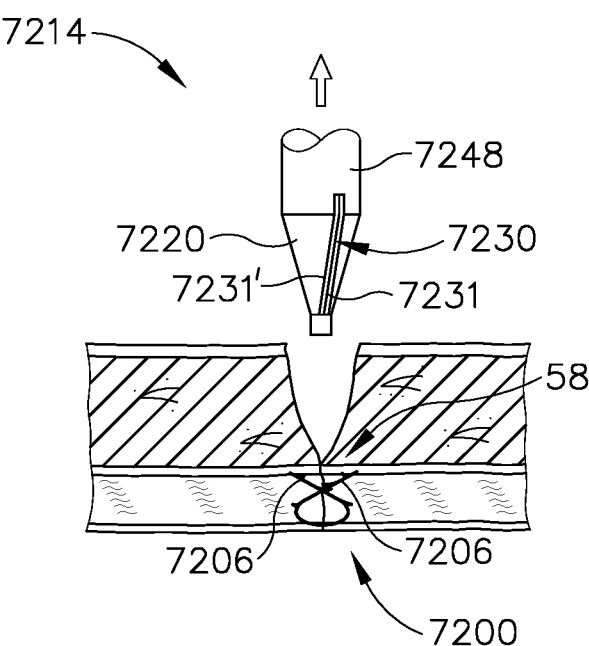

FIG. 72B depicts a schematic side sectional view showing proximal removal of the trocar of FIG. 72A from the tissue opening;

FIG. 72C depicts a schematic side sectional view showing insertion of the obturator of FIG. 71 distally through the tissue opening;

FIG. 72D depicts a schematic side sectional view of the obturator of FIG. 72C positioned within tissue of a first thickness, showing insertion of a suture passer needle and a suture thread end distally through the obturator and tissue fascia along a first suture path defining a first oblique angle relative to a central axis of the obturator;

FIG. 72E depicts a schematic side sectional view of the obturator of FIG. 72C positioned within tissue of a second thickness, showing insertion of a suture passer needle and a suture thread end distally through the obturator and tissue fascia along an alternative first suture path defining a second oblique angle relative to the central axis of the obturator;

FIG. 72F depicts a schematic side sectional view of the obturator and tissue of FIG. 72D, showing insertion of a suture passer needle distally through the obturator and tissue fascia along a second suture path defining an oblique angle relative to the central axis of the obturator, showing the suture thread end being captured by a distal end of the suture passer needle within the body cavity;

FIG. 72G depicts a schematic side sectional view of the obturator and tissue of FIG. 72F following proximal withdrawal of the suture passer needle along the second suture path, showing first and second portions of the suture thread extending through the obturator and tissue fascia along the respective first and second suture paths;

FIG. 72H depicts a schematic side sectional view of the obturator and tissue of FIG. 7G, showing proximal withdrawal of the obturator from the tissue opening and release of the suture thread from the obturator;

FIG. 72I depicts a schematic side sectional view of the tissue and suture thread of FIG. 72H, showing formation of a suture knot that closes a distal portion of the tissue opening;

FIG. 73A depicts a side elevational view of another exemplary trocar obturator configured for use as a wound closure device, showing needle guide arms of the obturator arranged in deployed positions;

FIG. 73B depicts an enlarged top perspective view of a needle guide arm of the obturator of FIG. 73A;

FIG. 74A depicts a schematic side sectional view of the obturator of FIG. 73A positioned within an opening in tissue to a patient body cavity, showing insertion of a suture passer needle and a suture thread end distally through the obturator, tissue fascia, and first needle guide arm along a first suture path defining a first oblique angle relative to a central axis of the obturator;

FIG. 74B depicts a schematic side sectional view of the obturator and tissue of FIG. 74A, showing insertion of a suture passer needle distally through the obturator, tissue fascia, and second needle guide arm along a second suture path defining a second oblique angle relative to a central axis of the obturator, showing the suture thread end being captured by a distal end of the suture passer needle within the body cavity;

FIG. 74C depicts a schematic side sectional view of the obturator and tissue of FIG. 74B, following proximal withdrawal of the suture passer needle along the second suture path, showing first and second portions of the suture thread extending through the obturator and tissue fascia along the respective first and second suture paths;

FIG. 74D depicts a schematic side sectional view of the obturator and tissue of FIG. 74C, showing proximal withdrawal of the obturator from the tissue opening with the needle guide arms in retracted positions;

FIG. 74E depicts a schematic side sectional view of the obturator and tissue of FIG. 74D, showing the needle guide arms in the deployed positions to release the suture thread, and subsequent formation of a suture knot that closes a distal portion of the tissue opening;

FIG. 75 depicts a side partial-sectional view of another exemplary trocar obturator configured for use as a wound closure device, having a shaft assembly and a head releasably coupled to the shaft assembly;

FIG. 76A depicts a side elevational view of the obturator shaft assembly of FIG. 75, showing a plunger in a distal position and anchor feet members in corresponding retracted positions;

FIG. 76B depicts a side elevational view of the obturator shaft assembly of FIG. 76A, showing the plunger in a proximal position and anchor feet members in corresponding deployed positions;

FIG. 77A depicts a schematic side sectional view of a trocar assembly including the obturator of FIG. 75 coupled with a trocar, showing the trocar assembly positioned within a tissue opening;

FIG. 77B depicts a schematic side sectional view of the trocar assembly and tissue of FIG. 77A, showing movement of a latch of the obturator head to an unlatched position;

FIG. 77C depicts a schematic side sectional view of the trocar assembly and tissue of FIG. 77B, showing removal of the obturator head from the obturator shaft assembly, and simultaneous distal movement of the shaft assembly within the trocar and proximal actuation of a plunger to deploy anchor feet members;

FIG. 77D depicts a schematic side sectional view the trocar assembly and tissue of FIG. 77C following insertion of a suture passer needle and suture thread end distally through the trocar assembly and tissue fascia along a first oblique suture path, showing insertion of the suture passer needle distally through the trocar assembly and tissue fascia along a second oblique suture path to capture the suture thread end;

FIG. 77E depicts a schematic side sectional view the trocar assembly and tissue of FIG. 77D, showing distal actuation of the plunger to retract the anchor feet members and proximal withdrawal of the trocar assembly from the tissue opening;

FIG. 77F depicts a schematic side sectional view of the suture thread and tissue of FIG. 77E, showing formation of a suture knot that closes a distal portion of the tissue opening;

FIG. 78 depicts a side partial-sectional view of another exemplary trocar obturator configured for use as a wound closure device, having a shaft assembly and a head releasably coupled to the shaft assembly;

FIG. 79A depicts a side elevational view of the obturator shaft assembly of FIG. 78, showing a plunger in a distal position and anchor feet members in corresponding retracted positions;

FIG. 79B depicts a side elevational view of the obturator shaft assembly of FIG. 79A, showing the plunger in a proximal position and anchor feet members in corresponding deployed positions;

FIG. 80A depicts a schematic side sectional view of a trocar assembly including the obturator of FIG. 78 coupled with a trocar, showing the trocar assembly positioned within a tissue opening;

FIG. 80B depicts a schematic side sectional view of the trocar assembly and tissue of FIG. 80A, showing movement of a latch of the obturator head to an unlatched position FIG. 80C depicts a schematic side sectional view of the trocar assembly and tissue of FIG. 80B, showing removal of the obturator head from the obturator shaft assembly, and simultaneous proximal movement of the trocar and distal movement of the shaft assembly within the trocar to expose the obturator anchor feet members;

FIG. 80D depicts a schematic side sectional view of the trocar assembly and tissue of FIG. 80C, showing proximal actuation of the obturator plunger to deploy the anchor feet within the patient body cavity;

FIG. 80E depicts a schematic side sectional view of the trocar assembly and tissue of FIG. 80D, showing proximal withdrawal of the trocar from the tissue opening while the obturator shaft assembly remains anchored within the tissue opening and passes through a working channel of the trocar;

FIG. 80F depicts a schematic side sectional view of the obturator shaft assembly and tissue of FIG. 80E, showing insertion of a suture passer needle distally through the shaft assembly and tissue fascia along a second oblique suture path to capture a distal thread end of suture thread extending through the shaft assembly and tissue fascia along a first oblique suture path;

FIG. 81 depicts a perspective view of an exemplary single-incision surgical access device FIG. 82 depicts a perspective view of the surgical access device of FIG. 81, showing a suture passer needle and a suture thread directed through first and second needle channels of the device;

FIG. 83 depicts a side sectional view of the surgical access device of FIG. 81, showing first and second needle channels of the device;

FIG. 84A depicts a perspective, partial side sectional view of the surgical access device of FIG. 81, showing the device being positioned within a tissue opening;

FIG. 84B depicts a schematic side sectional view of the surgical access device and tissue of FIG. 84A, showing a suture passer needle and a suture thread being directed along a first suture path extending through a first needle channel of the device and adjacent tissue;

FIG. 84C depicts a schematic side sectional view of the surgical access device and tissue of FIG. 84B, showing the suture passer needle being directed along a second suture path extending through a second needle channel of the device and adjacent tissue to recapture a deposited end of the suture thread;

FIG. 84D depicts a schematic side sectional view of the surgical access device and tissue of FIG. 84C, showing the suture thread extending through the device and tissue along the first and second suture paths;

FIG. 84E depicts a schematic side sectional view of the surgical access device and tissue of FIG. 84D, showing proximal removal of the device from the tissue opening following application of a second suture thread along third and fourth suture paths extending through third and fourth needle channels of the device;

FIG. 84F depicts a schematic side sectional view of the first and second suture threads and tissue of FIG. 84E, showing the tissue opening prior to closure;

FIG. 84G depicts a schematic side sectional view of the first and second suture threads and tissue of FIG. 84F, showing closure of the tissue opening via formation of an exemplary suture knot;

FIG. 84H depicts a schematic top elevational view of the tissue of FIG. 84F, showing an exemplary suture path pattern along which the first and second sutures are directed by the needle channels of the surgical access device of FIG. 82;

FIG. 85A depicts a schematic top perspective view showing first and second suture threads directed through tissue according to another exemplary suture path pattern for closing a tissue opening;

FIG. 85B depicts a schematic top perspective view showing the suture threads and tissue of FIG. 85A, showing closure of the tissue opening;

FIG. 85C depicts a schematic top perspective view showing first and second suture threads directed through tissue according to another exemplary suture path pattern for closing a tissue opening;

FIG. 85D depicts a schematic top perspective view showing the suture threads and tissue of FIG. 85C, showing closure of the tissue opening;

FIG. 85E depicts a schematic top perspective view showing first and second suture threads directed through tissue according to another exemplary suture path pattern for closing a tissue opening;

FIG. 85F depicts a schematic top perspective view showing the suture threads and tissue of FIG. 85E, showing partial closure of the tissue opening;

FIG. 86 depicts a perspective view of another exemplary single-incision surgical access device, showing a suture passer needle directed through first and second needle channels of the device;

FIG. 87 depicts another perspective view of the surgical access device of FIG. 86;

FIG. 88 depicts a top elevational view of the surgical access device of FIG. 86;

FIG. 89A depicts a schematic side sectional view of the surgical access device of FIG. 86, showing the device positioned within a tissue opening and a suture thread directed along first and second suture paths extending through first and second needle channels of the device and adjacent tissue;

FIG. 89B depicts a schematic side sectional view of the surgical access device and tissue of FIG. 89A, showing proximal removal of the device from the tissue opening following application of a second suture thread along third and fourth suture paths extending through third and fourth needle channels of the device and adjacent tissue;

FIG. 90 depicts a perspective view of another exemplary single-incision surgical access device, showing a suture passer needle directed through first and second needle channels of the device;

FIG. 91 depicts another perspective view of the surgical access device of FIG. 90;

FIG. 92 depicts a top elevational view of the surgical access device of FIG. 90;

FIG. 93A depicts a schematic side sectional view of the surgical access device of FIG. 90, showing the device positioned within a tissue opening and a suture thread directed along first and second suture paths extending through first and second needle channels of the device and adjacent tissue;

FIG. 93B depicts a schematic side sectional view of the surgical access device and tissue of FIG. 93A, showing proximal removal of the device from the tissue opening following application of a second suture thread along third and fourth suture paths extending through third and fourth needle channels of the device and adjacent tissue;

FIG. 94 depicts a schematic top elevational view of another exemplary single-incision surgical access device, wherein a proximal flange of a tissue retractor of the device is omitted to show details of a distal flange of the tissue retractor;

FIG. 95 depicts a side sectional view of the distal flange of the surgical access device of FIG. 94;

FIG. 96A depicts an enlarged perspective view of the distal flange and a medial body portion of the tissue retractor of FIG. 94, showing a suture thread exiting the medial body portion and extending through the distal flange at a location aligned with adjacent ends of ring segments of a resilient ring housed within the distal flange;

FIG. 96B depicts an enlarged perspective view of the distal flange and medial body portion of FIG. 96A, showing decoupling of the adjacent ends of the ring segments and separation of adjacent portions of the distal flange to thereby enable the suture thread to be freed from the distal flange;

FIG. 97A depicts a schematic side sectional view of the surgical access device of FIG. 94, showing the device positioned within a tissue opening and a suture thread directed along first and second suture paths extending through first and second needle channels of the device and adjacent tissue;

FIG. 97B depicts a schematic side sectional view of the surgical access device and tissue of FIG. 97A, showing proximal removal of the device from the tissue opening following application of a second suture thread along third and fourth suture paths extending through third and fourth needle channels of the device and adjacent tissue, and following decoupling of adjacent resilient ring segments and separation of adjacent distal flange portions as shown in FIG. 96B;

FIG. 98 depicts another exemplary single-incision surgical access device having a proximal housing, showing a suture passer needle and a suture thread directed through first and second needle channels of the device;

FIG. 99 depicts a top elevational view of the surgical access device of FIG. 98;

FIG. 100 depicts a schematic side sectional view of the surgical access device of FIG. 98;

FIG. 101 depicts a perspective view of another exemplary single-incision surgical access device having a proximal housing, showing a suture passer needle and a suture thread directed through first and second needle channels of the device;

FIG. 102 depicts a top elevational view of the surgical access device of FIG. 101;

FIG. 103 depicts a schematic side sectional view of the surgical access device of FIG. 101;

FIG. 104A depicts a schematic side sectional view of the surgical access device of FIG. 101, showing the device positioned within a tissue opening;

FIG. 104B depicts a schematic side sectional view of the surgical access device and tissue of FIG. 104A, showing a suture passer needle and a suture thread being directed along a first suture path extending through a first needle channel of the device and adjacent tissue;

FIG. 104C depicts a schematic side sectional view of the surgical access device and tissue of FIG. 104B, showing a surgical instrument directed distally through an instrument channel of the device to move a deposited end of the suture thread within a body cavity from a first side of the device toward a second side of the device;

FIG. 104D depicts a schematic side sectional view of the surgical access device and tissue of FIG. 104C, showing the suture passer needle being directed along a second suture path extending through a second needle channel of the device and adjacent tissue to recapture the deposited end of the suture thread;

FIG. 104E depicts a schematic side sectional view of the surgical access device and tissue of FIG. 104D, showing the suture thread extending through the device and tissue along the first and second suture paths;

FIG. 104F depicts a schematic side sectional view of the surgical access device and tissue of FIG. 104E, showing proximal removal of the device from the tissue opening following application of a second suture thread along third and fourth suture paths extending through third and fourth needle channels of the device and adjacent tissue;

FIG. 105 depicts a perspective view of another exemplary single-incision surgical access device, showing a suture passer needle and a suture thread directed through a first needle channel of the device;

FIG. 106 depicts a top perspective view of the surgical access device of FIG. 105, showing cannula devices positioned within instrument channels of the surgical access device;

FIG. 107 depicts a top perspective view of the surgical access device of FIG. 106, showing the surgical access device without the cannula devices of FIG. 106;

FIG. 108 depicts a side elevational view of an exemplary alternative trocar assembly with a tissue fastener attached to an obturator via a first securement mechanism;

FIG. 109 depicts a cross-sectional side view of the trocar assembly of FIG. 108, taken along a centerline thereof;

FIG. 110 depicts a partially exploded view of the trocar assembly of FIG. 108, with the tissue fastener detached from the obturator;

FIG. 111 depicts a distal end plan view of the tissue fastener of FIG. 108;

FIG. 112 depicts a side elevational view of the tissue fastener of FIG. 108;

FIG. 113A depicts a partial cross-sectional side view of the trocar assembly of FIG. 108, taken along a centerline thereof, with the obturator in a retracted position and adjacent to a tissue opening;

FIG. 113B depicts the partial cross-sectional side view of the trocar assembly similar to FIG. 113A, but with the obturator advanced into the tissue opening and the tissue fastener rotatably driven against the tissue to suture the opening closed;

FIG. 113C depicts the partial cross-sectional side view of the trocar assembly similar to FIG. 113B, but with the obturator retracted from the tissue opening and the tissue fastener detached from the obturator and securely fastened to the tissue;

FIG. 114A depicts a distal end plan view of the tissue fastener of FIG. 108, taken along a centerline thereof, with the tissue fastener inserted into the tissue opening for suturing the opening closed, and an internal hook in a locked position;

FIG. 114B depicts the distal end plan view of the tissue fastener similar to FIG. 114A, but with the tissue fastener rotatably driven against the tissue to fully close the opening;

FIG. 114C depicts the distal end plan view of the tissue fastener similar to FIG. 114B, but with the tissue fastener securely fastened to the tissue to close the opening and the internal hook in an unlocked position;

FIG. 115A depicts a partial side elevational view of another exemplary alternative trocar assembly with an obturator including a second securement mechanism, with a securement slot and the tissue fastener attached thereon;

FIG. 115B depicts the partial side elevational view of the trocar assembly similar to FIG. 115A, but with the obturator and the tissue fastener rotatably driven against tissue for suturing the opening closed; and FIG. 115C depicts the partial side elevational view of the trocar assembly similar to FIG. 115B, but with the obturator retracted from the tissue opening and the tissue fastener securely fastened to the tissue to close the opening.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Access Device

Figure 1:
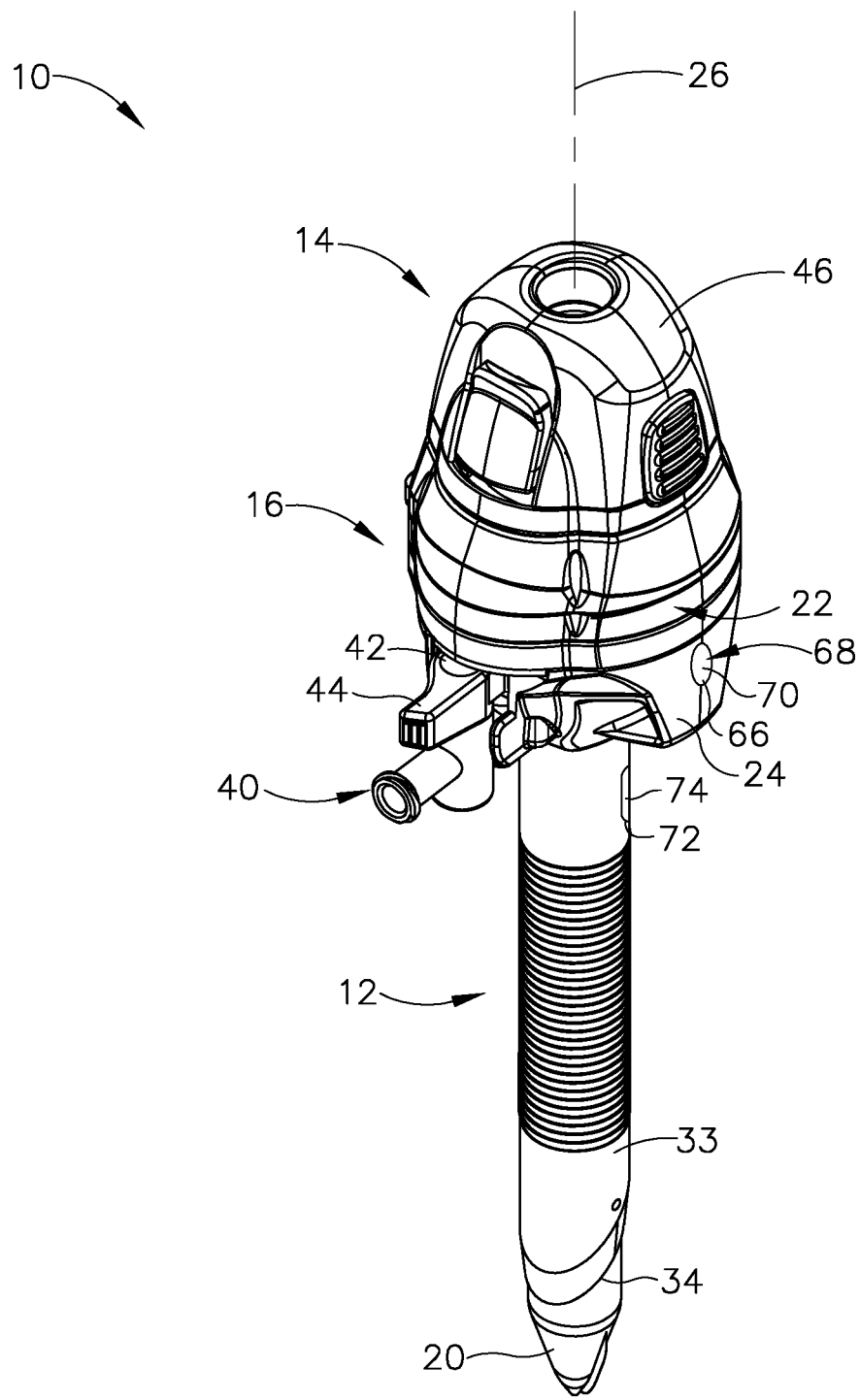
FIG. 1 depicts a perspective view of an exemplary trocar assembly.
Figure 2:
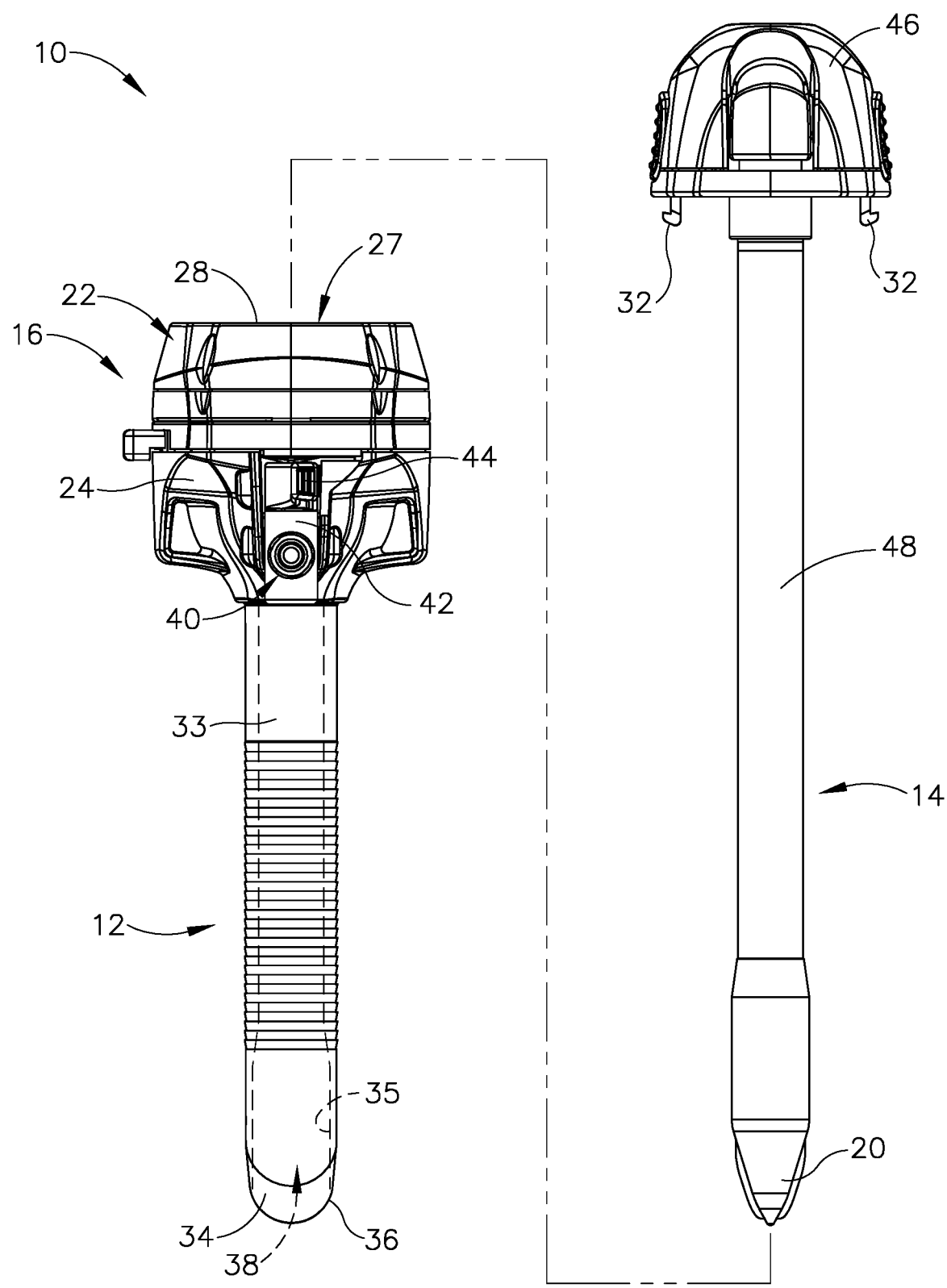
FIG. 2 depicts a partially exploded side elevational view of the trocar assembly of FIG. 1 having a trocar housing, a trocar cannula, and an obturator.

FIGS. 1-2 depict an exemplary surgical access device in the form of a first exemplary trocar assembly (10) that includes a cannula assembly (11) having a trocar cannula (12) and a trocar obturator assembly (14). Trocar obturator assembly (14) is removably received within trocar cannula (12) through a trocar housing (16) of cannula assembly (11). As shown in FIG. 1 with trocar obturator assembly (14) positioned within trocar cannula (12), a clinician inserts trocar assembly (10) through tissue (17) (see FIG. 3A) of a patient at a desirable surgical site for accessing a cavity (18) (see FIG. 3A) within the patient. By way of example only, trocar assembly (10) may be inserted in a patient's abdomen, between two of the patient's ribs, or elsewhere. A tip (20) of trocar obturator assembly (14) projects distally from trocar cannula (12) to penetrate tissue (17) (see FIG. 3A) for introducing a distal end portion of trocar cannula (12) into cavity (18) (see FIG. 3B). The clinician proximally withdraws trocar obturator assembly (14) from trocar cannula (12) such that cavity (18) (see FIG. 3C) within the patient is in communication with a surgical environment via trocar cannula (12). The clinician may then introduce a fluid, such as a gas, through trocar cannula (12) for inflating cavity (18) (see FIG. 3A) and/or an end effector of a surgical instrument through trocar cannula (12) for engaging tissue (17) to achieve a diagnostic or therapeutic effect.

It should be understood that terms such as "proximal" and "distal" are used herein with reference to the clinician gripping trocar housing (16). Thus, tip (20) is distal with respect to the more proximal trocar housing (16). It will be further appreciated that for convenience and clarity, spatial terms such as "vertical" and "horizontal" are used herein with respect to the drawings. However, surgical instruments are used in many orientations and positions, and these terms are not intended to be limiting and absolute. Further, in some instances, components are referred to interchangeably with and without the term "assembly," e.g., a trocar and a trocar assembly. There is no particular intention for the terms to refer to different components. Likewise, terms such as "instrument" and "device" may be used interchangeably.

A. Exemplary Trocar Assembly with Cannula and Obturator

Trocar assembly (10) of FIGS. 1-2 includes cannula (12) extending distally from trocar housing (16). In the present example, trocar housing (16) has a generally cylindrical shape with a proximal removable cap (22) atop a distal housing chamber (not shown). Cap (22) is selectively attachable and detachable from housing chamber (not shown). Trocar housing (16) includes a housing sidewall (24) that extends circumferentially around a central longitudinal axis (26) through trocar assembly (10), and thus along trocar cannula (12). Trocar housing (16) further includes a central lumen (27) extending from a proximal housing end opening (28) to a distal housing end opening (not shown). As shown, cap (22) selectively mates with housing sidewall (24) via distal mating members (not shown) and further includes proximal mating members, such as slots (not shown), configured to removably connect to a pair of tabs (32), respectively, that extend distally from a portion of obturator (14). However, it will be appreciated that alternative structures and devices may also be removably connected to cap (22) during use.

Cannula (12) extends distally from trocar housing (16), and is also generally defined by a cannula sidewall (33) extending circumferentially around central longitudinal axis (26). Cannula sidewall (33) extends distally to a beveled end (34) such that cannula sidewall (33) and beveled end (34) are configured to be inserted through tissue (17) (see FIG. 3A) as discussed below in greater detail for accessing cavity (18) (see FIG. 3A). To this end, cannula (12) generally has a smaller diameter than trocar housing (16), which is configured to remain exterior of tissue (17) (see FIG. 3C). In addition, cannula (12) defines an interior lumen (35) with a proximal cannula end opening (not shown) and a distal cannula end opening (36), which extends through beveled end (34). In the present example, distal housing end opening (not shown) of trocar housing (16) fluidly connects to proximal cannula end opening (not shown) such that central lumen (27) of trocar housing (16) and interior lumen (35) of cannula (12) define a working channel (38). Working channel (38) thus extends from proximal housing end opening (28) to distal cannula end opening (36) and is configured to receive one or more surgical instruments therethrough for accessing cavity (18).

Furthermore, an insufflation port (40) is operatively connected to trocar housing (16) to control the flow of an insufflation fluid, such as carbon dioxide, through a portion of cannula (12) and into cavity (18). More particularly, insufflation port (40) includes a stopcock valve (42) and a cock valve lever (44), which can work together to allow and/or prevent passage of the insufflation fluid into tubing (not shown), through trocar housing (16), and into trocar cannula (12). Trocar housing (16) and cannula (12) respectively have proximal and distal seal assemblies (not shown) positioned within central lumen (27) and interior lumen (35) of working channel (38). In the present example, the proximal seal assembly is an instrument seal (not shown), whereas the distal seal assembly (not shown) is a zero-closure seal, such as a duckbill seal (not shown). Instrument seal (not shown) is retained with cap (22) and configured to fluidly seal against a surgical instrument extending through working channel (38). In contrast, duckbill seal (not shown) is configured to form a seal in working channel (38) when no instrument is disposed therethrough to thereby inhibit the leakage of insufflation fluid during use. Of course, it will be appreciated that alternative seal assemblies may be positioned within working channel (38) for inhibiting such leakage of insufflation fluid.

Duckbill seal (not shown) is further configured to be manipulated to provide an opening to working channel (38) that is larger than a corresponding opening provided by instrument seal. This larger opening provided by duckbill seal (not shown) may facilitate extraction of bodily tissue through trocar housing (16) during a surgical procedure. In particular, cap (22) may be removed, and proximal instrument seal (not shown) along with it, to expose the duckbill seal (not shown) and thereby enable a surgeon to extract bodily tissue proximally through the duckbill seal opening (not shown) that would otherwise be too large to extract proximally through the instrument seal opening (not shown).

As discussed briefly above, obturator (14) is used in conjunction with cannula (12) for inserting trocar assembly (10) into the patient. Obturator (14) of the present example, includes a handle head (46) with a cylindrical shaft (48) extending distally therefrom to tip (20), which is generally configured to penetrate tissue (17) (see FIG. 3A) as described below in greater detail. Handle head (46) is configured to be gripped by the clinician during use and includes selectively movable tabs (32) extending distally to removably connect with trocar housing (16) for selective securement. Shaft (48) is received through working channel (38) such that tip (20) extends distally from beveled end (34). Of course, obturator (14) may be selectively removed from cannula (12) and trocar housing (16) to free working channel (38) for use. While the present example of trocar assembly (10) has obturator (14), it will be appreciated that cannula (12) may be inserted in some examples without obturator (14) or may be alternatively configured to aid insertion without using obturator (14).

B. Exemplary Method of Accessing a Cavity within a Patient

Figure 3A:
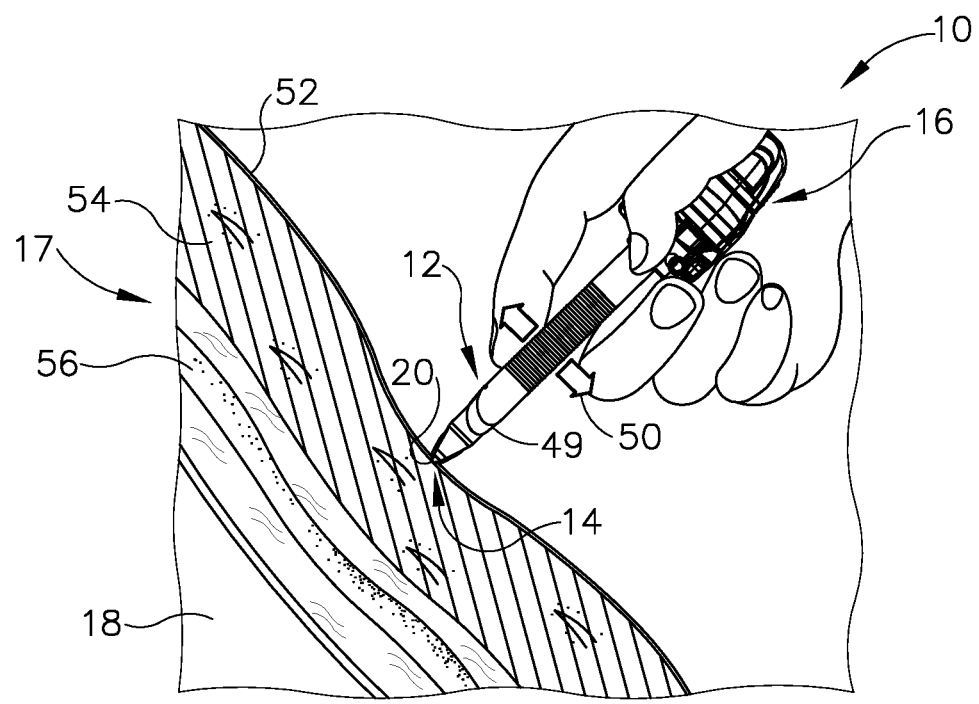
FIG. 3A depicts a sectional side view of tissue of a patient with the trocar assembly of FIG. 1 being manipulated by a clinician through the tissue.
Figure 3B:
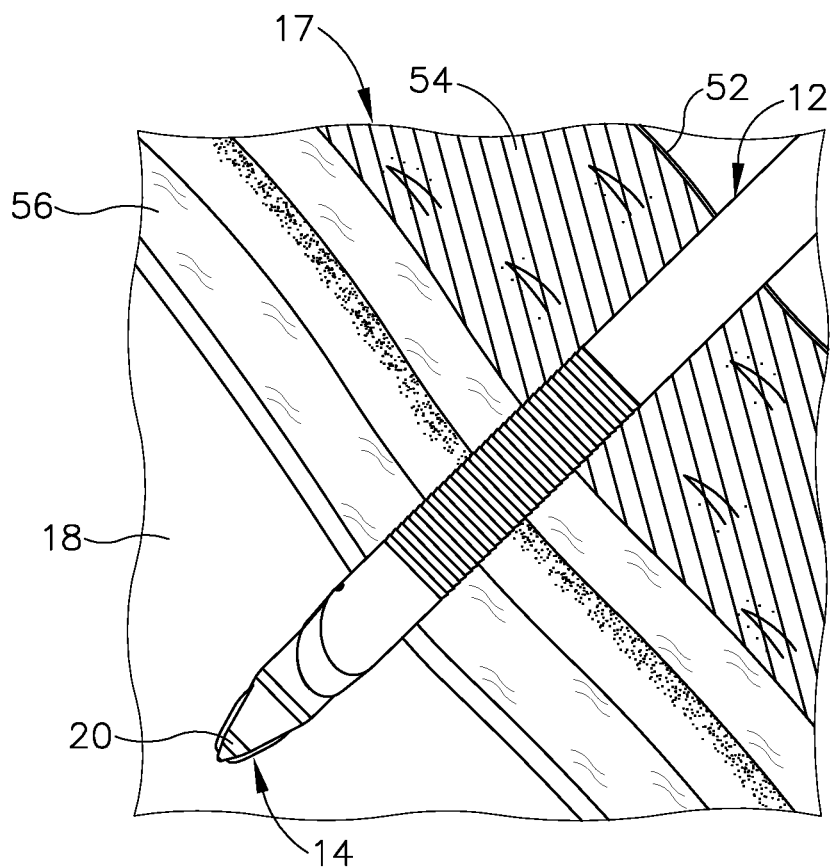
FIG. 3B depicts a sectional side view of the tissue and trocar assembly of FIG. 3A, with the trocar assembly of FIG. 1 inserted through the tissue and received within a cavity of the patient.
Figure 3C:
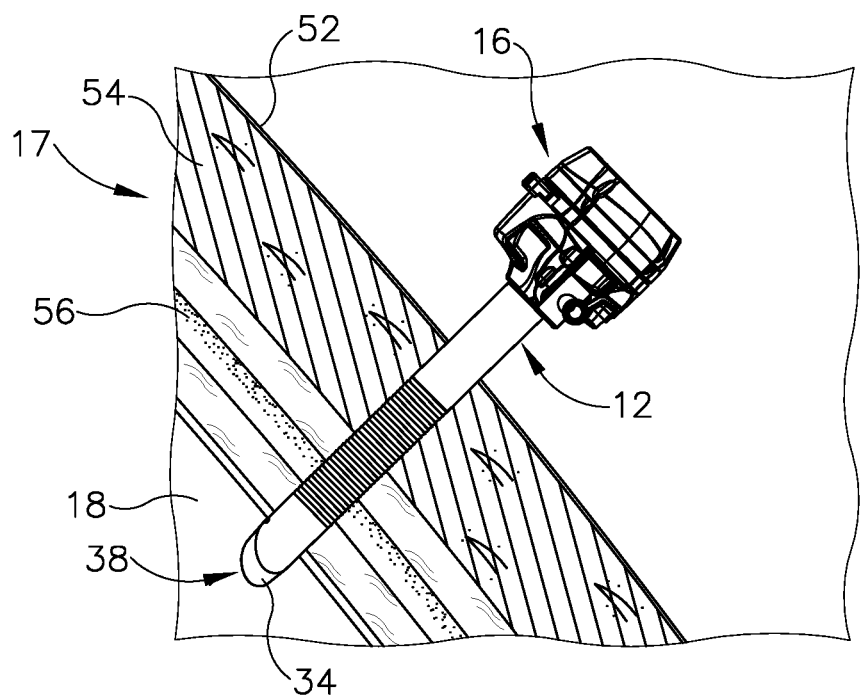
FIG. 3C depicts a sectional side view of the tissue and the trocar assembly of FIG. 3A, with the obturator withdrawn from the trocar cannula for accessing the cavity via a working channel through the trocar cannula and the trocar housing.
Figure 3D:
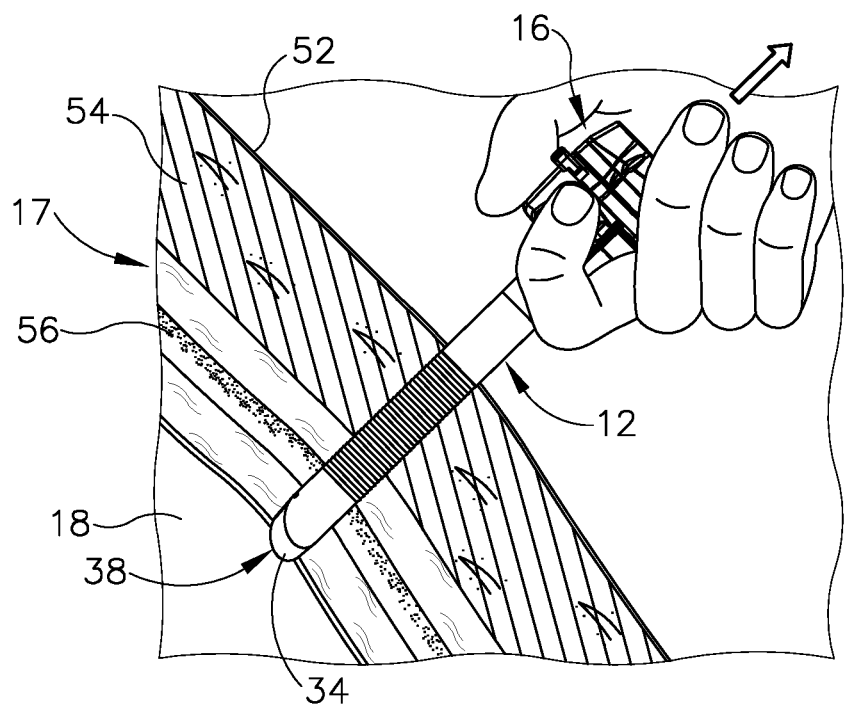
FIG. 3D depicts a sectional side view of the tissue and the trocar assembly of FIG. 3C, with the trocar housing and the trocar cannula being removed from the cavity and the tissue of the patient.
Figure 5:
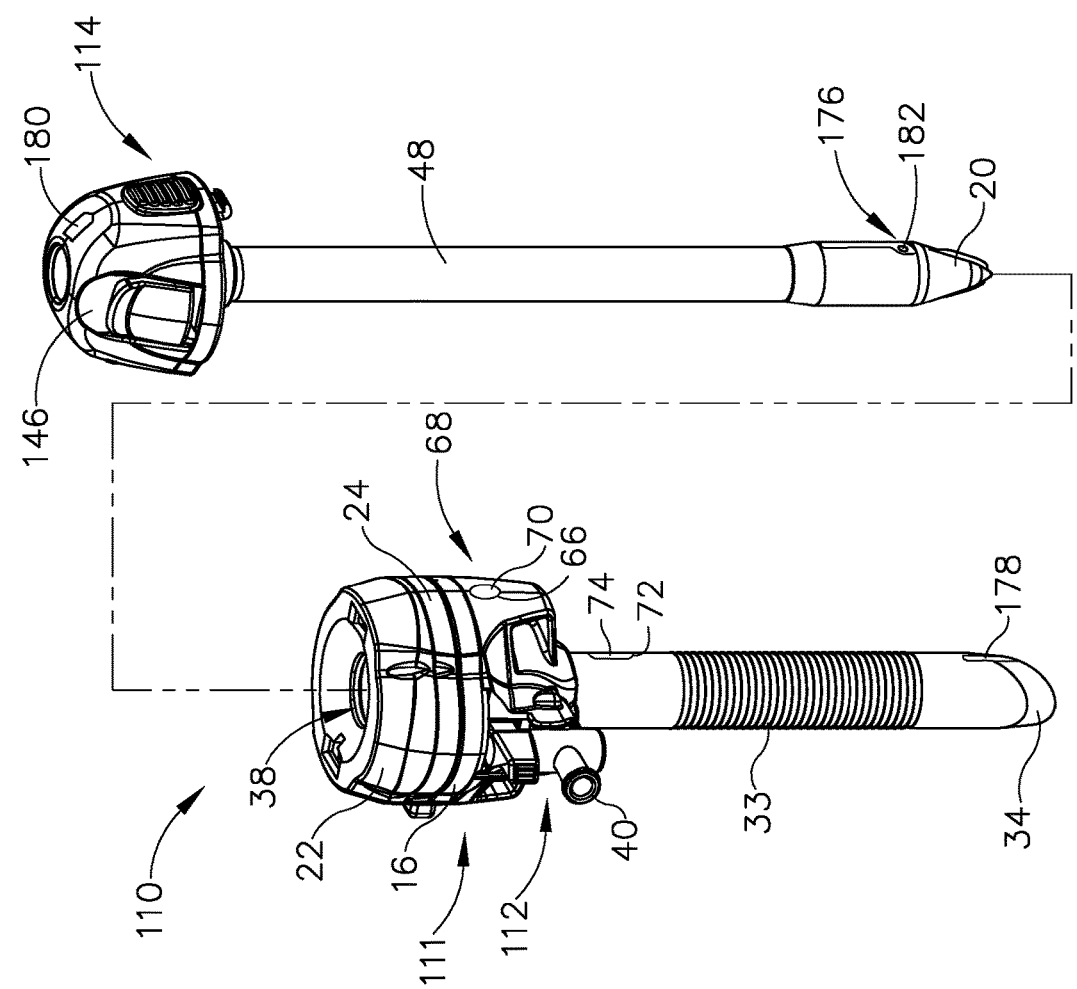
FIG. 5 depicts a perspective view of a first suturing trocar assembly having a cannula assembly and an obturator assembly with a first catch arm for releasably capturing a suture thread.
Figure 6:
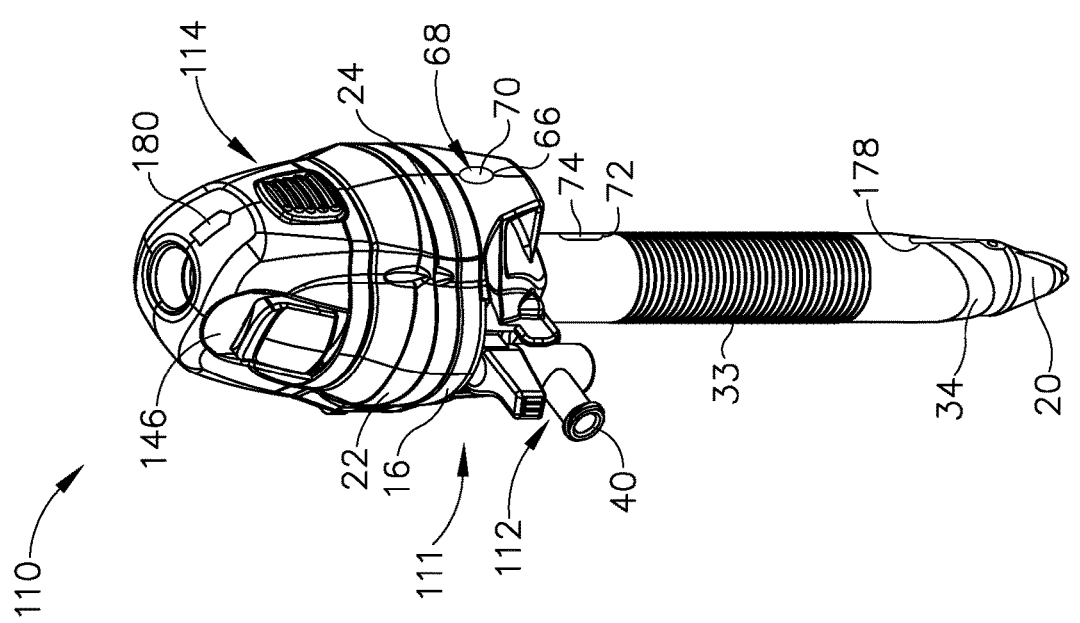
FIG. 6 depicts a partially exploded perspective view of the suturing trocar assembly of FIG. 5.

FIGS. 3A-3D illustrate accessing cavity (18) through tissue (17) with trocar assembly (10) discussed above. Tissue (17) of the present example more particularly has relatively outward superficial layers and relatively inward deep layers. Superficial layers generally include an outer layer of skin (52) and an inner layer of fat (54); whereas the deeper layers include layers of fascia (56), which are fibrous and flexible with relatively higher tensile strength than the superficial layers. As shown in FIG. 3A, with obturator (14) received within cannula (12) and connected to trocar housing (16), the clinician manipulates trocar assembly (10) to urge tip (20) of obturator (14) against skin (52) and inward toward cavity (18) while rotating trocar assembly (10) back and forth. Arrow (49) and arrow (50) respectively indicate this inward and rotatable movement. Continued inward urging of trocar assembly (10) further directs tip (20) and beveled end (34) of cannula (12) through the layers of fat (54) and fascia (56) and into cavity (18) as shown in FIG. 3B. The clinician then disconnects obturator (14) from trocar housing (16) and withdraws obturator (14) from cannula (12) to establish access from the exterior of tissue (17) into cavity (18) via working channel (38) as shown in FIG. 3C for achieving a diagnostic or therapeutic effect with another surgical instrument (not shown). Once the diagnostic or therapeutic effect is complete, clinician withdraws cannula (12) and trocar housing (16) outwardly for removal from tissue (17) as shown in FIG. 3D.

As shown in FIG. 4A, removal of cannula (12) from tissue (17) generally results in a tissue opening (58), which may also be referred to as a tissue port or tissue wound, that clinician closes to encourage healing of tissue (17). While some tissue openings may sufficiently close as tissue (17) comes together, other openings, such as tissue opening (58), are sutured closed with a suture thread (60). In one example shown in FIGS. 4A-4D, suture thread (60) is removably coupled with a needle (62) for guiding suture thread (62) through tissue (17) as the clinician manipulates needle (62). More particularly, as shown in FIG. 4B, the clinician directs needle (62) downwardly through fascia (56) on one side of tissue opening (58) and then upwardly through fascia (56) on the other side of tissue opening (58) as needle (62) clears tissue (17). Notably, the clinician threads needle (62) though fascia (56) a desirable distance distally from tissue opening (58) in order to provide a relatively close proximity to tissue opening (58); but also at a sufficient distance to provide ample fascia (56) for anchoring suture thread (60) therein. Additionally, the clinician angles a tip of needle (62) obliquely away from a central axis of opening (58) at a suitable angle in order to achieve sufficient "bite" when anchoring suture thread (60) within fascia (56). As shown in FIG. 4C, suture thread (60) from respective sides of tissue opening (58) are brought together and pulled to similarly pull tissue (17) together and at least partially close tissue opening (58). The clinician then knots suture thread (60) to secure tissue (17) together and sufficiently close tissue opening (58) with a formed suture (64) as shown in FIG. 4D. Additional sutures (64) may be placed along tissue (17) to further close tissue opening (58) and encourage healing of tissue (17).

While the above described suturing technique shown in FIGS. 4A-4D is one exemplary procedure for closing tissue opening (58) with suture thread (60) following use of trocar assembly (10) (see FIG. 1), other exemplary procedures and devices may be alternatively used for closing such tissue openings. By way of example, U.S. patent application Ser. No. 15/088,723, entitled "Surgical Access Devices with Integrated Wound Closure Features," filed on Apr. 1, 2016, issued as U.S. Pat. No. 10,299,785 on May 28, 2019, which is incorporated by reference herein in its entirety, describes an alternative trocar assembly and suturing technique. To this end, alternative trocar assemblies and suturing techniques may be used in any combination as desired by the clinician.

II. Various Suturing Trocar Assemblies with a Deployable Catch Arm

Generally, withdrawing trocar assembly (10) to reveal tissue opening (58) as shown with respect to FIGS. 1-3D may provide for sufficient space and visibility in many instances to thereby suture tissue opening (58) closed as shown in FIGS. 4A-4D. However, in some instances, it may be desirable to suture tissue opening (58) closed while trocar assembly (10) remains in tissue opening (58). To this end, trocar assembly (10) of FIGS. 1-2 has opposed openings (66) disposed in trocar housing (16) through which to suture tissue (17) while trocar assembly (10) is positioned within tissue opening (58). Openings (66) are formed in housing sidewall (24) and extend therethrough across a longitudinal axis along a channel (68). A seal (70) is disposed within channel (68) at opening (66), which serves as a proximal entrance port for a needle (490) (see FIG. 15A) to be introduced into channel (68). In the illustrated example, channel (68) extends through working channel (38) at an oblique angle with respect to the longitudinal axis such that channel (68) terminates to another opening (72) with a seal (74). Opening (72) is distal of the distal-most seal, such as the duckbill seal (not shown), and defines a suture path for needle (490) (see FIG. 15A) and suture thread (492) (see FIG. 15A) between an outside environment and a surgical site.

While such instances may provide for one or more diagnostic or therapeutic effects to the patient, the resulting suturing technique may become more complicated, difficult, or tedious in one or more aspects due to the limited space and visibility about tissue opening (58). For example, even in the event that the clinician inserts needle (490) (see FIG.

15A) with suture thread (492) (see FIG. 15A) into tissue (17), releasing suture thread (492) (see FIG. 15A), repositioning suture thread (492) (see FIG. 15A), and reattaching suture thread (492) (see FIG. 15A) to needle (490) (see FIG. 15A) for withdrawal from tissue (17) may be difficult with such limited visibility of suture thread (492) (see FIG. 15A) within the patient. The difficulty of visualizing suture thread (492) (see FIG. 15A) while suturing tissue (17) may thus result in additional suturing attempts, greater surgical time, and even an increased likelihood inadvertent tissue damage.

A suturing trocar assembly (110, 210, 310, 410, 610) with a deployable catch arm (176, 276, 376, 476, 676) as described below may thus be desirable in some instances. More particularly, catch arms (176, 276, 376, 476, 676) are configured to releasably capture suture thread (492) (see FIG. 15A) from needle (490) (see FIG. 15A) and reposition suture thread (492) (see FIG. 15A) for reattaching suture thread (492) (see FIG. 15A) for withdrawal from tissue (17) (see FIG. 15A). While direct visibility may still be helpful in such instances, catch arms (176, 276, 376, 476, 676) provide the clinician with greater predictability for placing suture thread (492) (see FIG. 15A) during suturing for enhanced patient outcomes.

The following description provides various examples of suturing trocar assemblies (110, 210, 310, 410, 610) including various deployable catch arms (176, 276, 376, 476, 676). Such catch arms (176, 276, 376, 476, 676) described below may be used with any trocar assembly described above and below and in any of the various procedures described in the various patent references cited herein. To this end, like numbers below indicated like features described above. Other suitable ways in which various trocar assemblies may be used will be apparent to those of ordinary skill in the art in view of the teachings herein.

A. First Suturing Trocar Assembly with a First Deployable Catch Arm Repositioned within a Patient Via Rotation of Trocar Obturator FIGS. 5-8B illustrate a first exemplary suturing trocar assembly (110) with a cannula assembly (111) and an obturator (114). With respect to FIGS. 5-6, obturator (114) has a distal end portion with shaft (48) distally extending to tip (20). In addition, the distal end portion of obturator (114) includes a catch arm (176) that is selectively movable from a retracted position to a deployed position. In the retracted position, catch arm (176) with the remainder of the distal end portion of obturator (114) is positioned relatively radially inward and thus configured to be inserted into the patient and removed from the patient, such as via cannula (112). In the deployed position, catch arm (176) extends relatively radially outward to align with channel (68) for receiving needle (490) (see FIG. 15A) thereagainst. Catch arm (176) in the deployed position is thereby configured to releasably capture suture thread (492) (see FIG. 15A) for suturing tissue (17) (see FIG. 15A).

Cannula assembly (111) has trocar housing (16) and cannula (112) similar to those discussed above, but, in addition, has a pair of longitudinally extending clearance channels (178) on opposing lateral sides of the distal end portion of cannula sidewall (33). Each clearance channel (178) extends through cannula sidewall (33) to beveled end (34) and aligns with catch arm (176) in respective deployed positions to provide clearance for catch arm (176) to pivot through selective movement. To this end, in the present example, one of the two clearance channels (178) receives catch arm (176) in a catch deployed position to releasably capture suture thread (492) (see FIG. 15A). Once captured, catch arm (176) returns to the retracted position and obturator (114) is rotated 180 degrees relative to cannula assembly (111) such that catch arm (176) aligns with the other clearance channel (178). Catch arm (176) is then extended to a release deployed position such that needle (490) (see FIG. 15A) reattaches with suture thread (492) (see FIG. 15A) to be withdrawn via another channel (68) through tissue (17) (see FIG. 15A) as generally discussed below in use with respect to FIGS. 15A-15D.

Figure 7A:
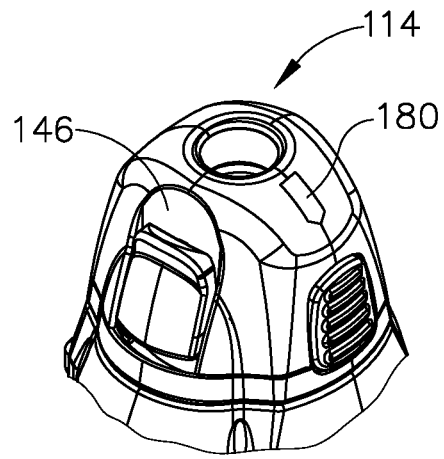
FIG. 7A depicts an enlarged perspective view of a proximal end portion of the suturing trocar assembly of FIG. 5 with an actuator in an unactuated position for extending the catch arm from a retracted position to a deployed position.
Figure 8A:
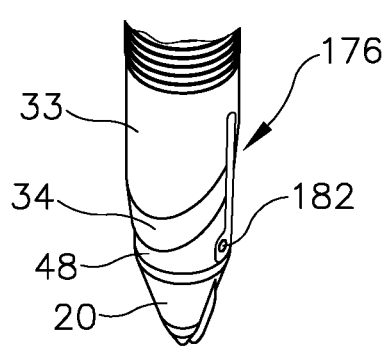
FIG. 8A depicts an enlarged perspective view of a distal end portion of the suturing trocar assembly of FIG. 5 with the catch arm in the retracted position.

FIGS. 7A and 8A show catch arm (176) in the retracted position in greater detail. A handle head (146) includes an actuator (180) operatively connected to catch arm (176) and configured to direct movement of catch arm (176). While not shown herein, actuator (180) is connected to catch arm (176) by a cable (not shown) for moving actuator (180). Of course, alternative mechanisms for operatively connecting actuator (180) to catch arm (176) will be appreciated by those of ordinary skill in the art. Actuator (180) in the unactuated position causes catch arm (176) to remain in the retracted position. In the present example, cannula sidewall (33) has an outer surface that defines a generally circular profile that is transverse to the longitudinal axis along which cannula (112) extends. Catch arm (176) in the retracted position is generally parallel with the longitudinal axis and within this transverse circular profile in order to inhibit catch arm (176) from engaging, or even catching, on tissue (17) (see FIG. 15A) and/or cannula (112) upon insertion. As the term "generally within" is used herein, catch arm (176) may also overlap with the transverse circular profile of cannula wall (33) and be considered generally within the transverse circular profile. In other words, catch arm (176) is at least generally flush with the outer surface of cannula sidewall (33), but may also be positioned radially inward of the outer surface of cannula sidewall (33).

Figure 7B:
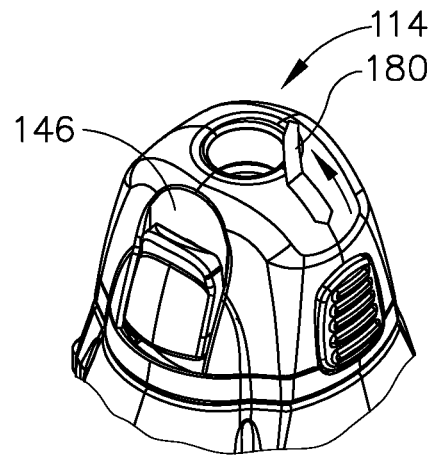
FIG. 7B depicts the enlarged perspective view of the proximal end portion of the suturing trocar assembly similar to FIG. 7A, but with the actuator manipulated to an actuated position.
Figure 8B:
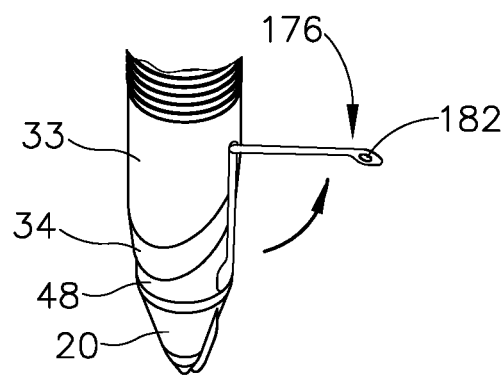
FIG. 8B depicts the enlarged perspective view of the distal end portion of the suturing trocar assembly similar to FIG. 8A, but with the catch arm in the deployed position.

Selectively manipulating actuator (180) in a proximal direction causes catch arm (176) to proximally pivot to the deployed position shown in FIGS. 7B and 8B. In the deployed position, catch arm (176) extends radially outward from shaft (48). More particularly, in the present example, catch arm (176) extends transversely relative to the longitudinal axis and radially outward to align with channel (68). Catch arm (176) further includes a catch hole (182) that extends transversely therethrough and aligns with channel (68) so that needle (490) (see FIG. 15A) may be simultaneously received within channel (68) and catch hole (182) in use. Catch arm (176) is configured to releasably capture suture thread (492) (see FIG. 15A) within catch hole (182) for suturing tissue (17) (see FIG. 15A) as described below in greater detail.

B. Second Suturing Trocar Assembly with a Second Deployable Catch Arm Repositioned within a Patient Via Pivoting Second Deployable Catch Arm FIGS. 9-10C illustrate a second exemplary suturing trocar assembly (210) with cannula assembly (111) discussed above and an obturator (214). With respect to FIG. 9, obturator (214) has a distal end portion with shaft (48) distally extending to a forked portion including a longitudinally and transversely extending slot (219a). The forked portion of obturator (114) receives a catch arm (276) pivotally mounted therein to be selectively movable from a retracted position to a deployed position. From a pivotal mounting (219b), catch arm (276) extends to a tip (220) configured to pierce tissue similar to those discussed above. Tip (220) is thus positioned on a distal end of catch arm (276) in the present example. In the retracted position, catch arm (176) with the remainder of the distal end portion of obturator (114) is positioned relatively radially inward and thus configured to be inserted into the patient and removed from the patient, such as via cannula (112). In the deployed position, catch arm (276) with tip (220) extends relatively radially outward to align tip (220) with channel (68) for receiving needle (490) (see FIG. 15A) thereagainst. Catch arm (276) in the deployed position is thereby configured to releasably capture suture thread (492) (see FIG. 15A) for suturing tissue (17) (see FIG. 15A).

Cannula assembly (111) has clearance channel (178) configured to receive catch arm (276) in a catch deployed position to releasably capture suture thread (492) (see FIG. 15A). Once captured, catch arm (276) pivots 180 degrees through the retracted position to a release deployed position transversely opposite from the catch deployed position such that catch arm (276) aligns with the other clearance channel (178). Catch arm (276) in the release deployed position is configured such that needle (490) (see FIG. 15A) reattaches with suture thread (492) (see FIG. 15A) to be withdrawn via another channel (68) through tissue (17) (see FIG. 15A) as generally discussed below in use with respect to FIGS. 15A-15D.

FIG. 10A shows catch arm (176) in the retracted position in greater detail. A handle head (246) includes a rotatable actuator (280) operatively connected to catch arm (276) and configured to direct movement of catch arm (276). Actuator (280) is resiliently depressed to proximally translate release actuator (280) for being gripped by the clinician. Actuator (280), once depressed, generally remains in the unactuated position as shown in FIG. 10A until rotated in a clockwise or a counterclockwise direction to actuated positions. In the present example, cannula sidewall (33) (see FIG. 9) has the outer surface that defines the generally circular profile that is transverse to the longitudinal axis along which cannula (112) extends. Catch arm (276) in the retracted position is generally parallel with the longitudinal axis and within this transverse circular profile. Tip (220) is configured to pierce tissue (17) (see FIG. 15A) and proximally widens in shape in order to gradually widen penetrated tissue (17) (see FIG. 15A) toward beveled end (34) upon insertion.

Figure 10B:
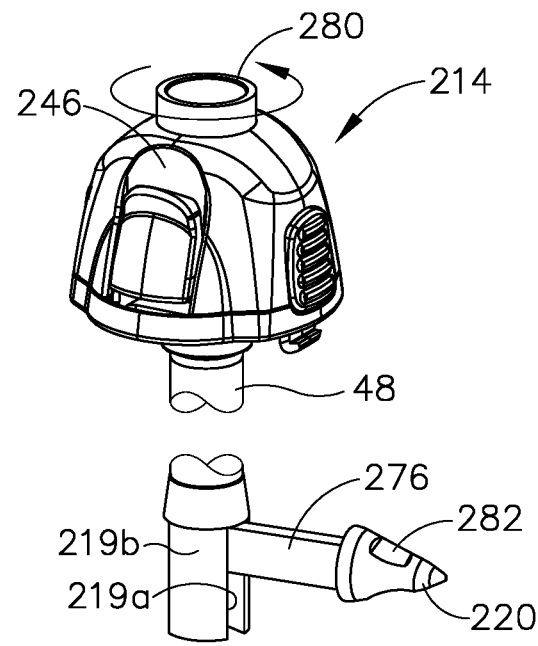
FIG. 10B depicts the perspective view of the suturing trocar assembly similar to FIG. 10A, but with the catch arm in a deployed position.
Figure 10C:
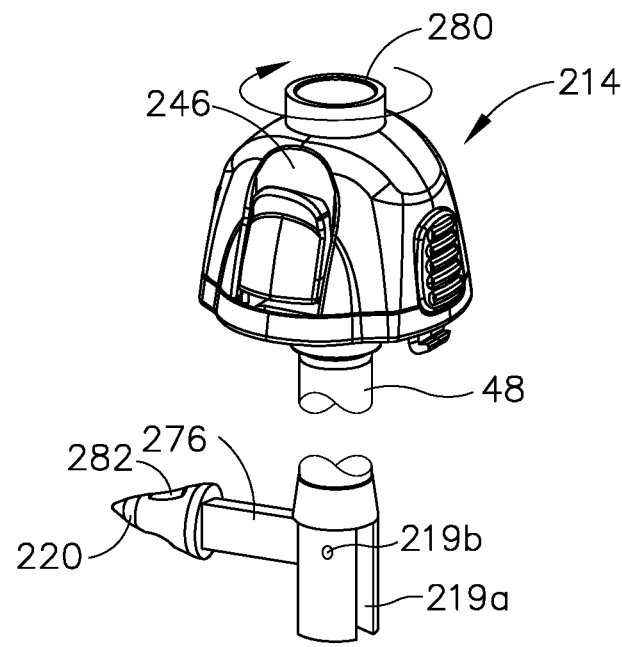
FIG. 10C depicts the perspective view of the suturing trocar assembly similar to FIG. 10B, but with the catch arm in another deployed position.

Selectively manipulating actuator (280) in a counterclockwise or clockwise directions as shown respectively in FIG. 10B and FIG. 10C causes catch arm (276) to pivot to the catch deployed position and the release deployed position. In each deployed position, catch arm (276) extends radially outward from shaft (48). More particularly, in the present example, catch arm (276) extends transversely relative to the longitudinal axis and radially outward to align with channel (68). Catch arm (276) further includes a catch hole (282) that extends transversely through tip (220) and aligns with channel (68) so that needle (490) (see FIG. 15A) may be simultaneously received within channel (68) and catch hole (282) in use. Catch arm (276) is configured to releasably capture suture thread (492) (see FIG. 15A) within catch hole (282) for suturing tissue (17) (see FIG. 15A) as described below in greater detail.

Figure 11:
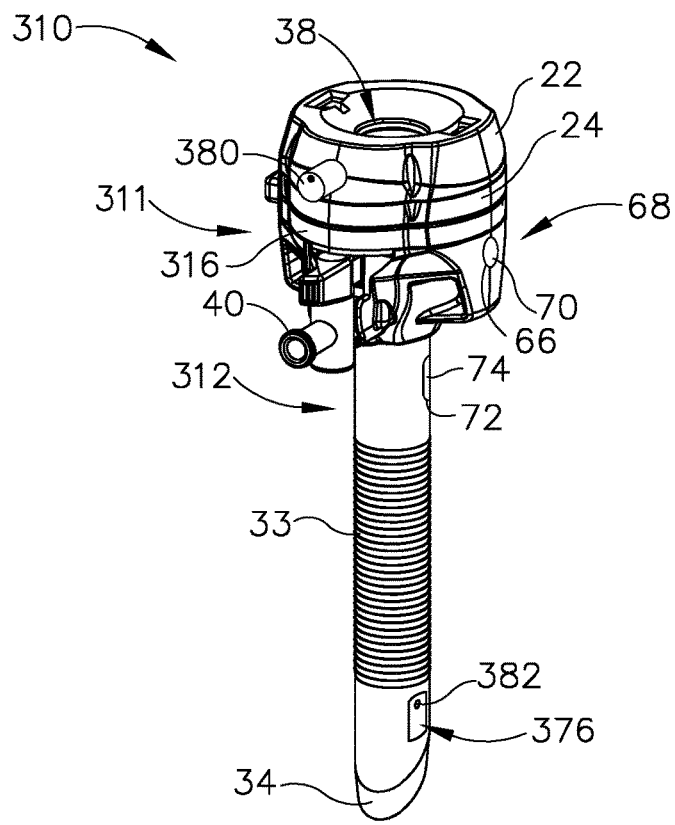
FIG. 11 depicts a perspective view of a third suturing trocar assembly having a cannula assembly with a third catch arm for releasably capturing a suture thread.

C. Third Suturing Trocar Assembly with a Third Deployable Catch Arm Repositioned within a Patient Via Rotation of Trocar Assembly FIGS. 11-12B illustrate a third exemplary suturing trocar assembly (310) with a cannula assembly (311) having a cannula (312) and obturator (14). With respect to FIG. 11, cannula assembly (311) has a distal end portion with cannula sidewall (33) distally extending to beveled end (34). In addition, the distal end portion of cannula assembly (311) includes a catch arm (376) positioned in cannula sidewall (33) that is selectively movable from a retracted position to a deployed position. In the retracted position, catch arm (376) with the remainder of the distal end portion of cannula sidewall (33) is positioned relatively radially inward and thus configured to be inserted into the patient and removed from the patient. In the deployed position, catch arm (376) extends relatively radially outward to align with channel (68) for receiving needle (490) (see FIG. 15A) thereagainst. Catch arm (376) in the deployed position, such as a catch deployed position, is thereby configured to releasably capture suture thread (492) (see FIG. 15A) for suturing tissue (17) (see FIG. 15A). Once captured, cannula assembly (311) is rotated 180 degrees relative to the patient such that catch arm (176) is in a release deployed position for reattaching suture thread (492) (see FIG. 15A) to needle (490) (see FIG. 15A) to be withdrawn via another channel (68) through tissue (17) (see FIG. 15A) as generally discussed below in use with respect to FIGS. 15A-15D.

Figure 12A:
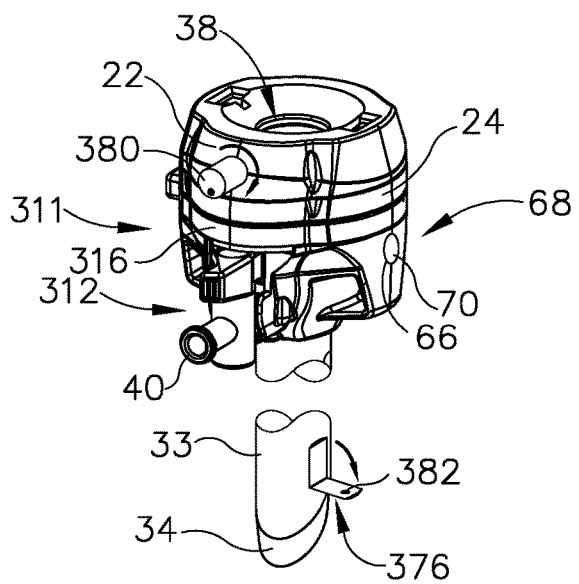
FIG. 12A depicts a perspective view of the suturing trocar assembly of FIG. 11 with the catch arm in a deployed position.
Figure 12B:
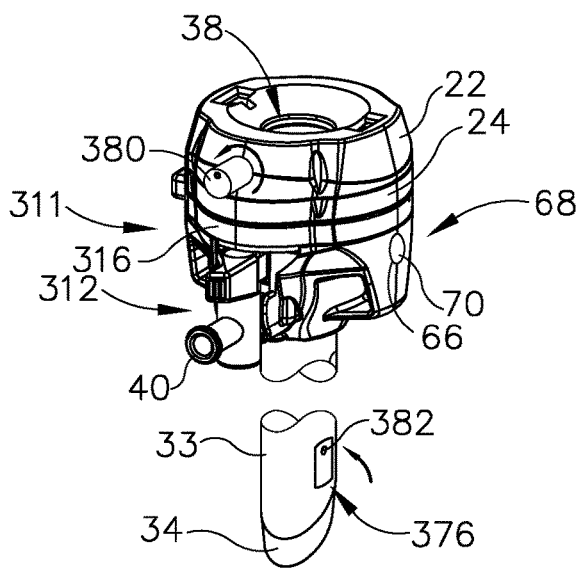
FIG. 12B depicts the perspective view of the suturing trocar assembly similar to FIG. 12A, but with the catch arm in a retracted position.

FIGS. 12A and 12B show catch arm (376) in the deployed and retracted positions, respectively. A trocar housing (316) includes an actuator (380) operatively connected to catch arm (376) and configured to direct movement of catch arm (376). Actuator (380) in the unactuated position (see FIG. 11) causes catch arm (376) to remain in the retracted position. In the present example, cannula sidewall (33) has an outer surface that defines the generally circular profile that is transverse to the longitudinal axis along which cannula (312) extends. Catch arm (376) in the retracted position is generally parallel with the longitudinal axis and within this transverse circular profile in order to inhibit catch arm (376) from engaging, or evening catching, on tissue (17) (see FIG. 15A) upon insertion.

Selectively manipulating actuator (380) in a clockwise direction causes catch arm (376) to proximally pivot to the deployed position shown in FIG. 12A. In the deployed position, catch arm (376) extends radially outward from cannula sidewall (33). More particularly, in the present example, catch arm (376) extends transversely relative to the longitudinal axis and radially outward to align with channel (68). Catch arm (376) further includes a catch hole (382) that extends transversely therethrough and aligns with channel (68) so that needle (490) (see FIG. 15A) may be simultaneously received within channel (68) and catch hole (382) in use. Catch arm (376) is configured to releasably capture suture thread (492) (see FIG. 15A) within catch hole (382) for suturing tissue (17) (see FIG. 15A) as described below in greater detail.

D. Fourth Suturing Trocar Assembly with a Fourth Deployable Catch Arm Repositioned within a Patient Via Rotation of Trocar Assembly FIGS. 13A-14C illustrate a fourth exemplary suturing trocar assembly (410) with a cannula assembly (411), which has a cannula (412), and an obturator (414) that operate similar to those discussed above with respective features for performing a surgical procedure. Suturing trocar assembly (410) also includes a pair of openings (466, 472) with respective seals (470, 474) and a channel (468) for suturing tissue (17) (see FIG. 15A) without removing suturing trocar assembly (410) from the patient. With respect to FIG. 13A, obturator (414) has a distal end portion with a shaft (448) distally extending to a tip (420). In addition, the distal end portion of obturator (414) includes a catch arm (476) that is selectively movable from a retracted position to a deployed position. In the retracted position, catch arm (476) with the remainder of the distal end portion of obturator (414) is positioned relatively radially inward and thus configured to be inserted into the patient and removed from the patient, such as via cannula (412). In the deployed position, catch arm (476) extends relatively radially outward to align with channel (468) for receiving needle (492) (see FIG. 15A)

thereagainst. Catch arm (476) in the deployed position, such as a catch deployed position, is thereby configured to releasably capture suture thread (492) (see FIG. 15A) for suturing tissue (17) (see FIG. 15A). Once captured, cannula assembly (411) is rotated 180 degrees relative to the patient such that catch arm (476) is in a release deployed position for reattaching suture thread (492) (see FIG. 15A) to needle (492) (see FIG. 15A) to be withdrawn via channel (468) through tissue (17) (see FIG. 15A) as generally discussed below in use with respect to FIGS. 15A-15D.

Figures 13A, 13B, 13C:
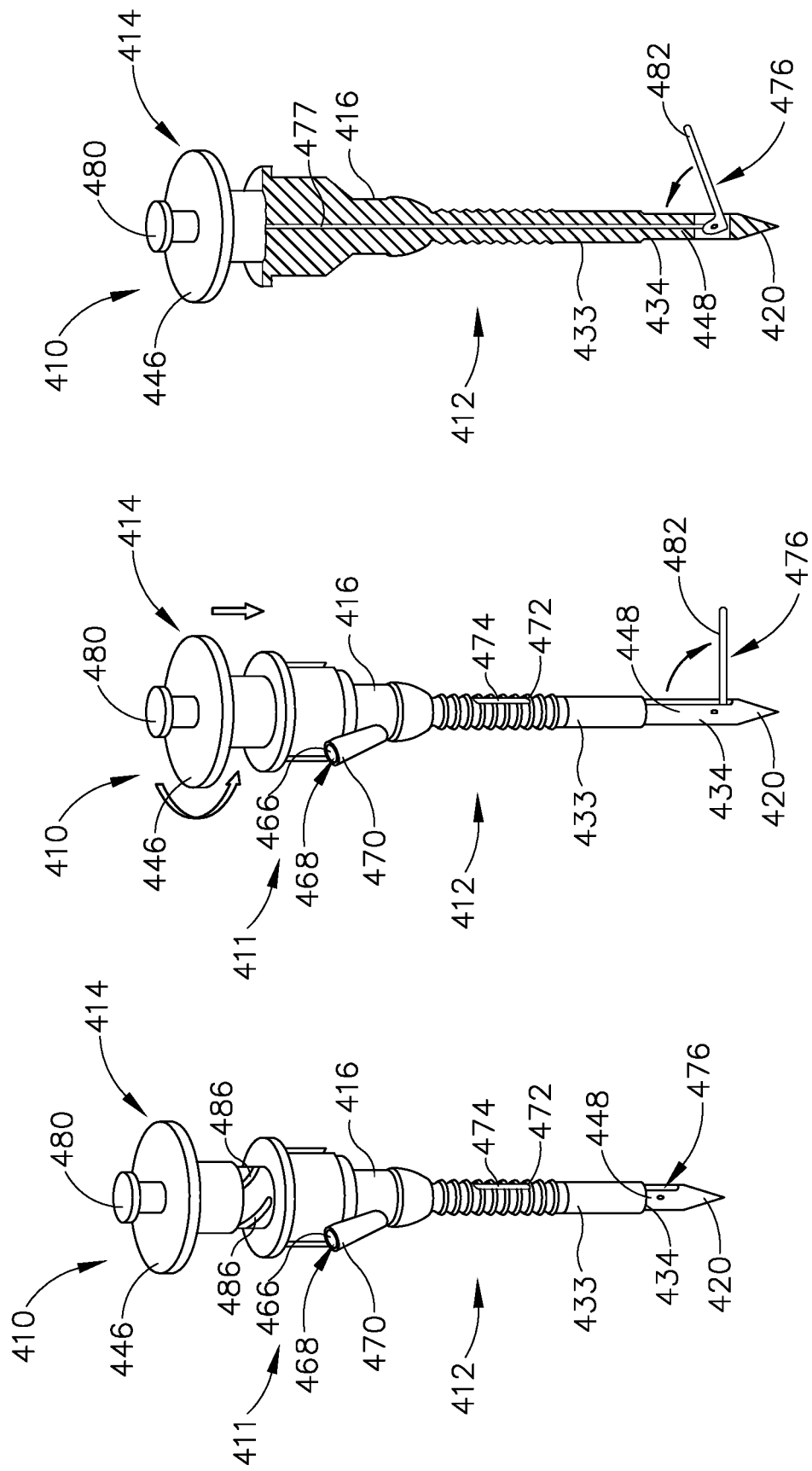
FIG. 13A depicts a perspective view of a fourth suturing trocar assembly having a cannula assembly with a fourth catch arm for releasably capturing a suture thread in a retracted state.
FIG. 13B depicts the perspective view of the suturing trocar assembly similar to FIG. 13A, but with the catch arm extended from the retracted position to a deployed position.
FIG. 13C depicts a cross-sectional perspective view of the suturing trocar assembly similar to FIG. 13B, but with the catch arm being returned from the deployed position to the retracted position.

While suturing trocar assembly (410) has similar features to those discussed herein, at least one difference of a proximal end portion of suturing trocar assembly (410) is a rotatably movable interface between a handle head (446) of obturator (414) and a trocar housing (416). To this end, FIGS. 13A and 14A illustrate handle head (446) with a plurality of radially inward extending tabs (484) received respectively within a plurality of spiral slots (486). Spiral slots (486) longitudinally extend and angularly spiral about trocar housing (416) and are configured to movably receive respective tabs (484) therein. Tabs (484) within spiral slots (486) cooperate similar to a threaded engagement such that rotating obturator (414) counterclockwise causes obturator (414) to also distally move relative to cannula assembly (411) as shown in FIGS. 13B and 14B. Such distal movement causes catch arm (476), to distally extend from a distal end (434) of a cannula sidewall (434) for deployment. Otherwise, in the present example, cannula sidewall (433) prevents deployment of catch arm (476) prior to such distal extension.

FIGS. 13B and 14B show catch arm (376) being extend from the retracted position to the deployed position, whereas FIGS. 13C and 14C show catch arm (376) being returned from the deployed position to the retracted position. Handle head (446) of obturator (414) includes an actuator (480) operatively connected to catch arm (476) via a push-pull cable (477) and configured to direct movement of catch arm (476). Actuator (480) in the unactuated position (see FIG. 14A) causes catch arm (476) to remain in the retracted position. In the present example, cannula sidewall (433) has an outer surface that defines the generally circular profile that is transverse to the longitudinal axis along which cannula (412) extends. Catch arm (476) in the retracted position is generally parallel with the longitudinal axis and within this transverse circular profile in order to inhibit catch arm (476) from engaging, or even catching, on tissue (17) (see FIG. 15A) upon insertion.

Selectively manipulating actuator (480) in a distal direction causes catch arm (476) to distally pivot to the deployed position. In the deployed position, catch arm (476) extends radially outward from shaft (448). More particularly, in the present example, catch arm (476) extends transversely relative to the longitudinal axis and radially outward to align with channel (468). Catch arm (476) further includes a catch hole (482) that extends transversely therethrough and aligns with channel (468) so that needle (490) (see FIG. 15A) may be simultaneously received within channel (468) and catch hole (482) in use. Catch arm (476) is configured to releasably capture suture thread (492) (see FIG. 15A) within catch hole (482) for suturing tissue (17) (see FIG. 15A).

E. Method of Suturing a Tissue with a Deployable Catch Arm and Suture Thread

In use, as shown in FIGS. 15A-15D, a needle (490) and a suture thread (492) in conjunction with suturing trocar assembly (410) are configured to suture tissue (17). With suturing trocar assembly (410) positioned within tissue opening (58) and catch arm (476) in the catch deployed position, clinician inserts needle (490) through channel (468) along the suture path with a distal suture thread end (494) removably attached to a distal needle end (496). Distally along the suture path from opening (472), distal needle end (496) and distal suture thread end (494) pass through fascia (56) on one side of tissue opening (58). Continuing distally along the suture path from fascia (56), distal needle end (496) and distal suture thread end (494) are received within catch hole (482) of catch arm (476). Clinician manipulates needle (490) such that distal suture thread end (494) attaches to catch arm (476), but releases from distal needle end (496). Once detached from suture thread (492), clinician withdraws needle (490) from fascia (56) and channel (468), but suture thread (492) remains within fascia (56) on the one side of tissue opening (58) as shown in FIG. 15B.

FIG. 15C shows clinician manipulating suturing trocar assembly (410) to move catch arm (476) from the catch deployed position to the release deployed position a predetermined distance for repositioning distal suture thread end (494) to the other, opposing side of tissue opening (58). More particularly, in the present example, clinician rotates an entirety of suturing trocar assembly (410) with catch arm (476) extended to the deployed position such that catch arm (467) similarly rotates from the catch deployed position to the release deployed position. Distal suture thread end (494) remains attached to catch arm (476) throughout this movement and is thereby repositioned relative to tissue (17) for continued suturing.

With respect to FIG. 15D, clinician again inserts needle (490) through channel (468) along the suture path through fascia (56), but on the opposing side of tissue opening (58). Distal needle end (496) is received within catch hole (482) in the release deployed position and reattaches to distal suture thread end (494) as distal suture thread end (494) is also released from catch arm (476). Once distal needle end (496) is reattached to distal suture thread end (494), clinician proximally withdraws needle (490) and suture thread (492) such that distal suture thread end (494) is inserted and withdrawn through fascia (56) as shown in FIGS. 15E-15F. Needle (490) followed by suturing trocar assembly (410) are then removed by clinician such that suture thread (492) forms a loop through fascia (56) on opposing sides of tissue opening (58). As shown in FIG. 15D, clinician tightens and ties suture thread (492) to suture close tissue opening (58) at fascia (56). Additional suturing may be performed by the clinician as desired to further close tissue opening (58).

The above method of suturing tissue opening (58) closed with suturing trocar assembly (410) may be similarly performed with other suturing trocar assemblies (110, 210, 310) described above. It will be appreciated that similarly described features performed similar functions to that shown and described with respect to FIGS. 15A-15D. In contrast, it will be further appreciated that various distinguishing features operate as discussed above for each respective suturing trocar assembly (110, 210, 310), particularly with respect to transitioning catch arms (176, 276, 376) from catch deployed positions to release deployed positions. The invention is thus not intended to be unnecessarily limited to use with suturing trocar assembly (410).

III. Barbed Suture Thread and Related Methods of Suturing Tissue

While suture thread (492) is knotted to effectively secure suture thread (492) and close tissue opening (58), it may be beneficial in some instances for suture thread (492) to include a securement to affix one portion of suture thread (492) to another portion of suture thread (492) without knotting. FIGS. 16-19C shows a unidirectional barbed suture thread (510) with such a securement in the form of a plurality of barbs (512) extending along a thread body (514) to a pledget end (516). For purposes of reference with respect to suture thread (510), pledget end (516) is at a distal end of thread body (514) with the opposing end being a proximal end. Each barb (512) extends longitudinally and radially outward in a direction toward pledget end (516) such that barbs (512) are at an oblique angle relative to thread body (514). Barbs (512) are configured to be proximally inserted into tissue (17) (see FIG. 19A) such that barbs (512) are inhibited from catching tissue (17). In contrast, barbs (512) are configured to grip tissue in the distal direction to inhibit unidirectional barbed suture thread (510) from backing out in the distal direction. Additionally, pledget end (516) is configured to catch tissue (17) (see FIG. 19A) in a direction opposite to that of barbs (512) to thereby secure unidirectional barbed suture thread (510) in tissue (17) (see FIG. 19A).

Figure 16:
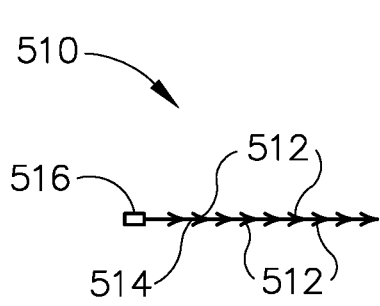
FIG. 16 depicts a side elevational view of a unidirectional barbed suture thread.
Figure 17:
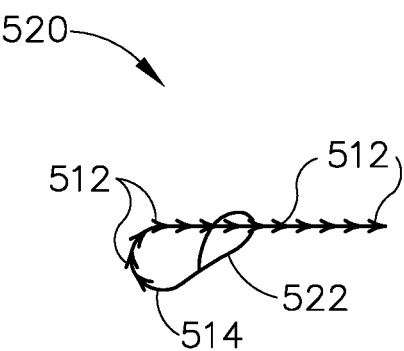
FIG. 17 depicts a side elevational view of an alternative unidirectional barbed suture thread.

FIG. 17 shows an alternative unidirectional barbed suture (520) similar to unidirectional barb suture (510) (see FIG. 16), but having a looped end (522) rather than pledget end (516) (see FIG. 16). Upon insertion through tissue (17) (see FIG. 19A), clinician inserts the proximal end portion of unidirectional barbed suture (520) through distal looped end (522) for noosing unidirectional barbed suture (520) tight and closing tissue opening (58) (see FIG. 19A). Barbs (512) thereby catch on looped end (522) when tightened to inhibit loosening of unidirectional barbed suture (520) similar to a ratchet mechanism.

Figure 18:
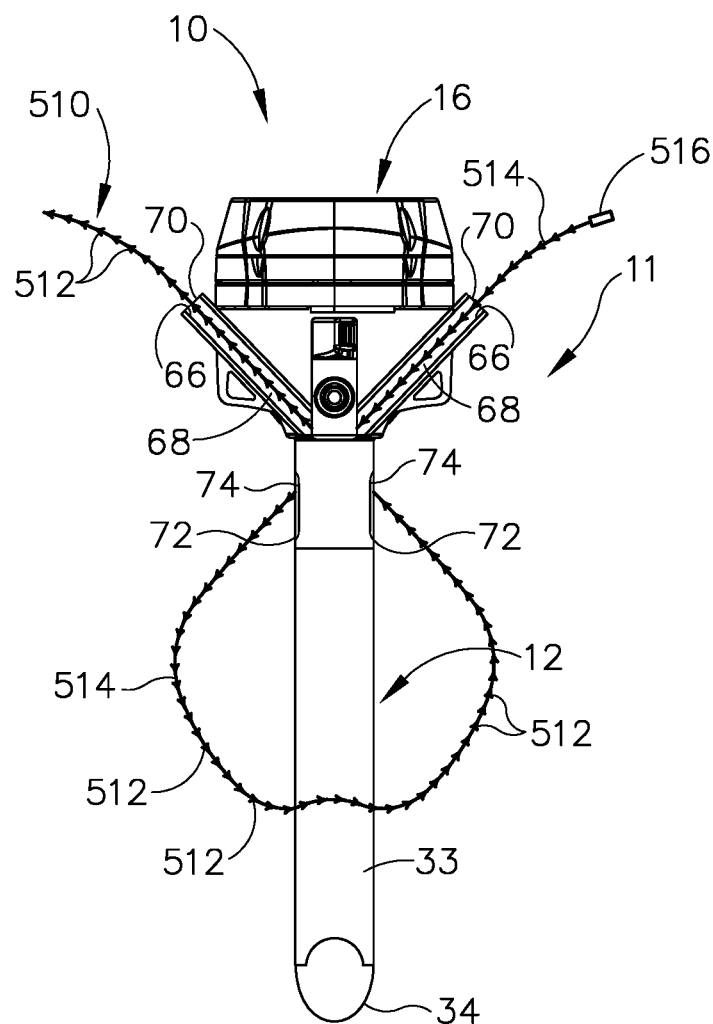
FIG. 18 depicts a side elevational view of the trocar assembly of FIG. 1 with the unidirectional barbed suture thread of FIG. 16 having various components removed for clarity.
Figure 20:
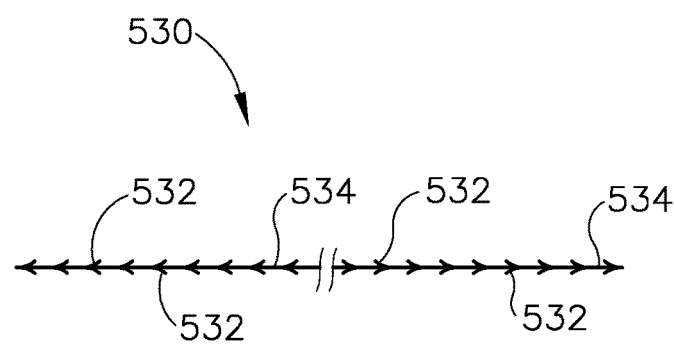
FIG. 20 depicts a side elevational view of a bidirectional barbed suture thread.
Figure 21A:
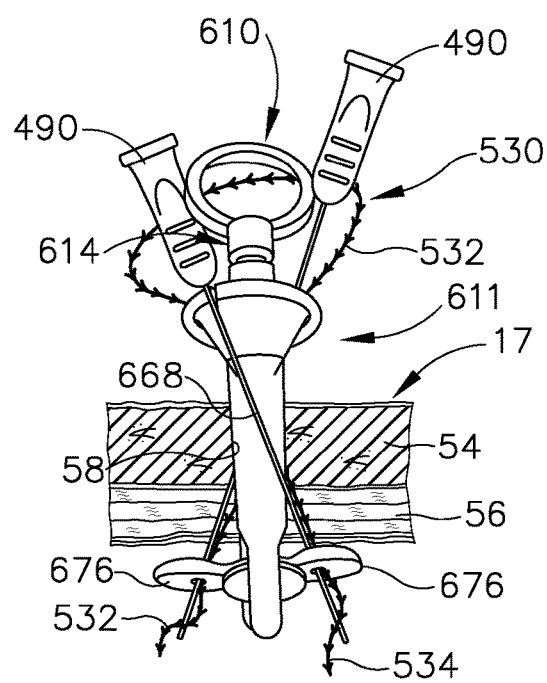
FIG. 21A depicts a perspective sectional view of a fifth exemplary suturing trocar assembly inserted into a tissue with the bidirectional barbed suture thread of FIG. 20.
Figure 21B:
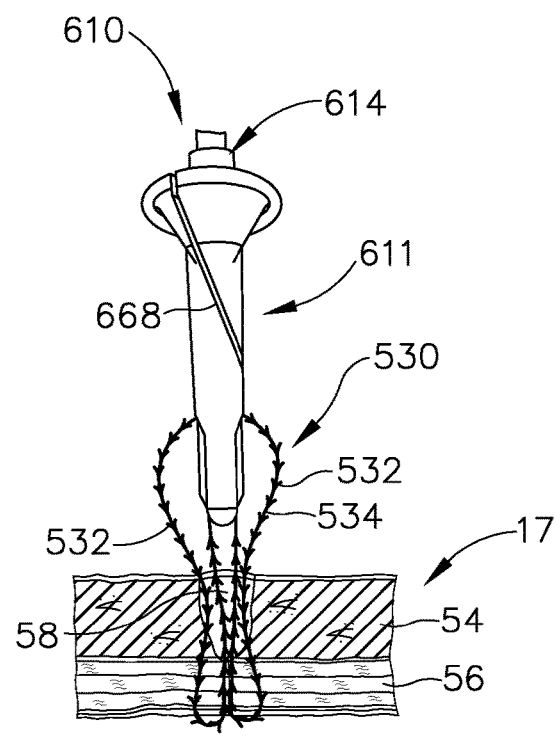
FIG. 21B depicts the perspective sectional view of the suturing trocar assembly similar to FIG. 21A, but with the suturing trocar assembly being removed from the tissue.

In use, FIG. 18-19C show unidirectional barbed suture (510) following the suture path through channels (68) of trocar assembly (10) as discussed herein, although alternative suturing trocar assemblies may be similarly used. As briefly discussed above, unidirectional barbed suture (510) is proximally inserted through fascia (56) on opposing sides of tissue opening (58) as shown in FIG. 19A. Clinician pulls on proximal end portion of thread body (514) out from tissue opening (58) to similarly pull pledget end (516) into tissue opening (58) to catch on fascia (56). Further pulling on the proximal end portion of thread body (514) tightens unidirectional barbed suture (510) as shown in FIGS. 19B-19C and closes tissue opening (58) between barbs (512) and pledget end (516).

Figure 22A:
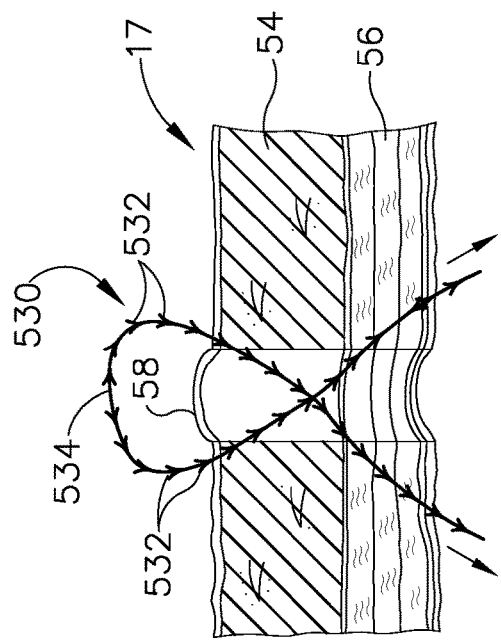
FIG. 22A depicts a cross-sectional view of the tissue and the bidirectional barbed suture of FIG. 21B in the tissue opening.
Figure 22C:
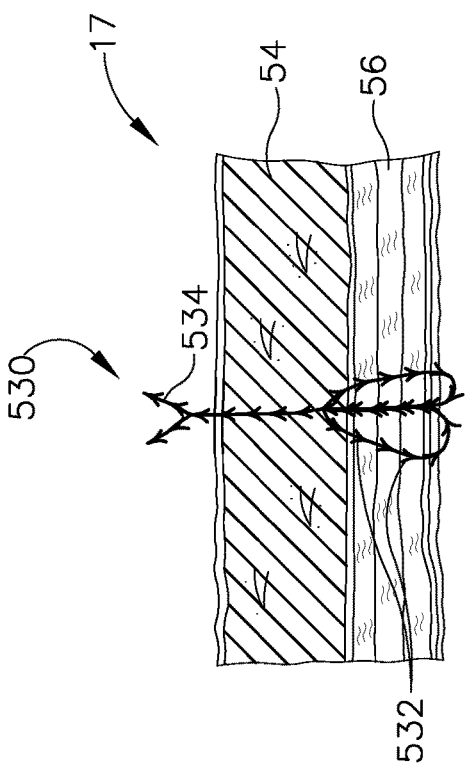
FIG. 22C depicts the cross-sectional view of the tissue and the bidirectional barbed suture similar to FIG. 22B, but showing the bidirectional barbed suture having closed the tissue opening.
Figure 22B:
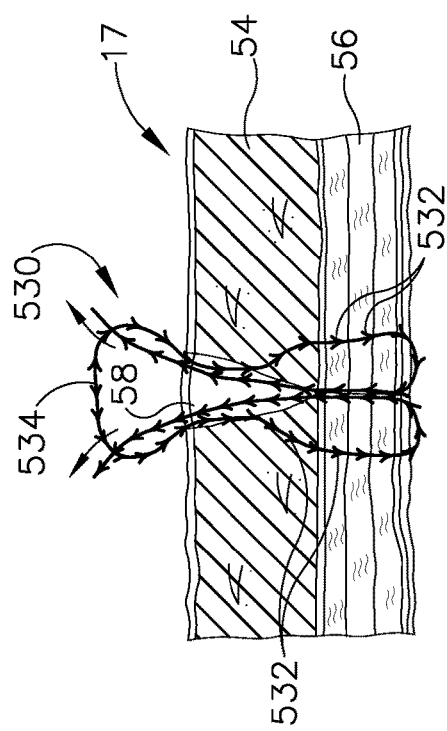
FIG. 22B depicts the cross-sectional view of the tissue and the bidirectional barbed suture similar to FIG. 21A, but showing the bidirectional barbed suture closing the tissue opening.

FIGS. 22A-22C show a bidirectional barbed suture (530) for an alternative suture path of an alternative trocar assembly (610) having a cannula assembly (611), an obturator (614), and a pair of opposing catch arms (676). Bidirectional barbed suture (530) has a first plurality of barbs (532) extending longitudinally and radially outward and in a first direction from a thread body (534). In addition, bidirectional barbed suture (530) also has a second plurality of barbs (532) extending longitudinally and radially outward and in a second direction from thread body (534) opposite from first direction. End portions of thread body (534) are each inserted through respective channels (668) and inserted into fascia (56) as shown in FIGS. 21A-22A. End portions of thread body (534) are then pulled out from tissue opening (58) to be looped and tightened as shown in FIGS. 22B-22C such that barbs (532) catch tissue (17) and other looped barbs (532) to suture tissue opening (58) closed.

IV. Pledget Surgical Instrument for Suturing Tissue

Figure 23:
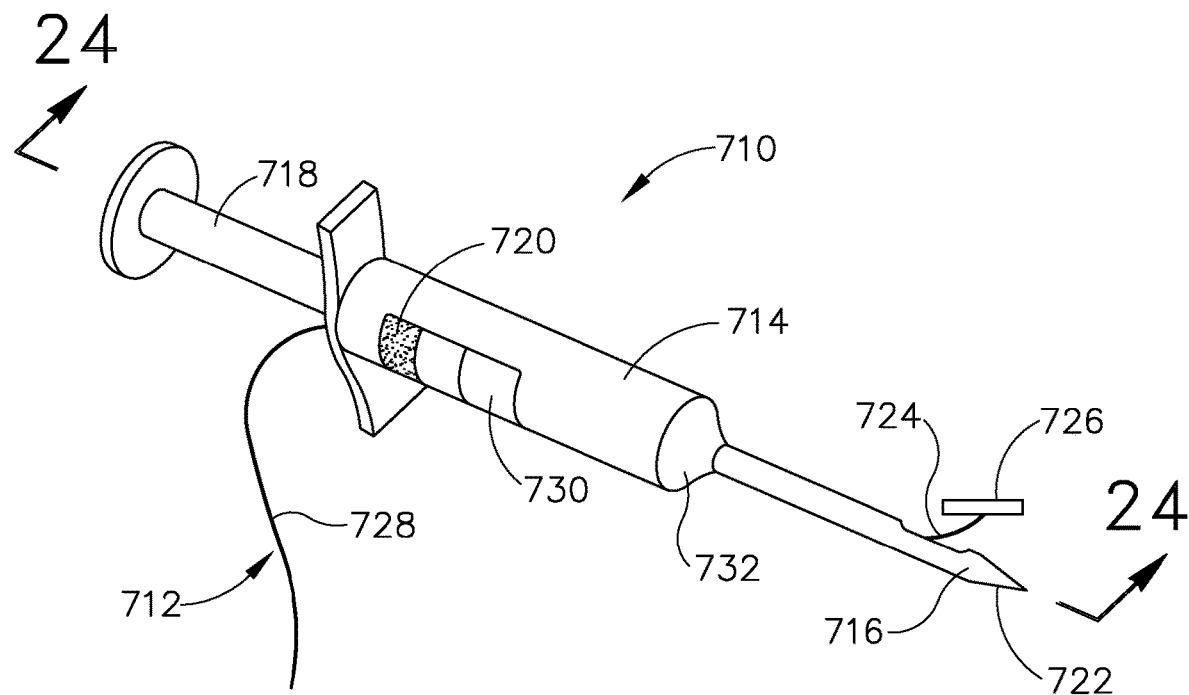
FIG. 23 depicts a perspective view of a suturing surgical instrument with a slip pledget suture thread.
Figure 24:
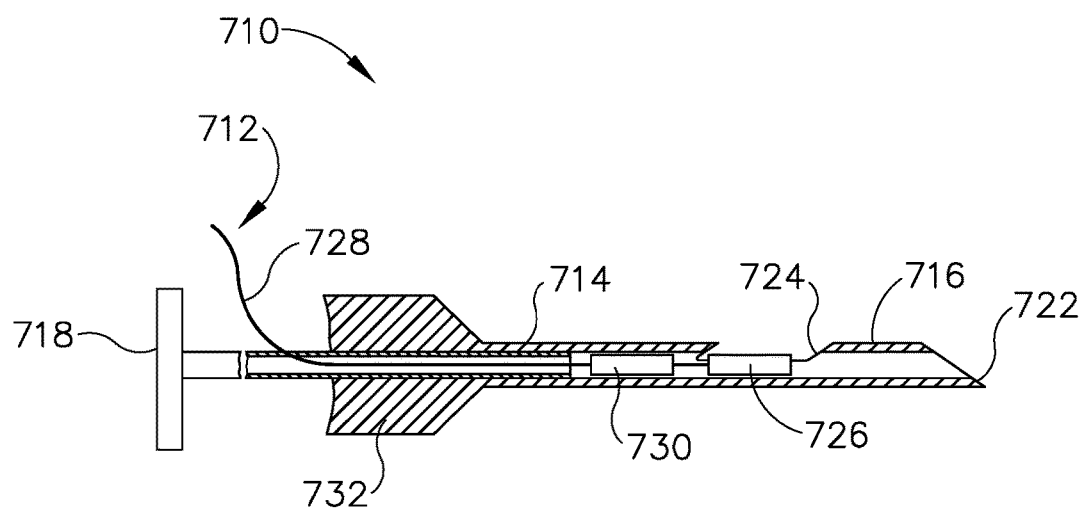
FIG. 24 depicts an enlarged cross-sectional view of the suturing surgical instrument of FIG. 23 taken along section line 24-24 of FIG. 23.

FIGS. 23-24 show a pledget surgical instrument (710) configured to position a slip pledget suture thread (712) into tissue (17) (see FIG. 28A) for suturing tissue (17) (see FIG. 28A). Pledget surgical instrument (710) includes a barrel body (714) with a distally extending needle introducer (716) as well as a plunger (718) slidably received within barrel body (714). Barrel body (714) is configured to receive slip pledget suture thread (712) for being inserted into tissue (17) (see FIG. 28A) via needle introducer (716). Barrel body (714) of the present example also includes a window (720) for viewing slip pledget suture thread (712) within barrel body (714). Needle introducer (716) has a distal beveled end (722) configured to penetrate tissue (17) (see FIG. 28A) and a discharge slot (724) extending longitudinally through a sidewall of needle introducer (716) between beveled end (722) and barrel body (714). Slip pledget suture thread (712) is configured to be ejected from discharge slot (724) for positioning slip pledget suture thread (712) in tissue (17) (see FIG. 28A) as discussed below in greater detail.

Plunger (718) is configured to be selectively translated by the clinician into barrel body (714) and against slip pledget suture thread (712) contained therein. Thereby, plunger (718) urges a distal pledget end (726) from discharge slot (724) followed by at least a portion of thread body (728). Further selective translation of plunger (718) into barrel body (714) urges a proximal pledget end (728) from discharge slot (724) followed by a remaining portion of thread boy (728). In one example, pledget surgical instrument (710) also includes a plug body (732) between barrel body (714) and needle introducer (716) that is configured to at least partially plug tissue opening (58) (see FIG. 28A) in use to inhibit fluid, such as insufflation fluid, from tissue opening (58) (see FIG. 28A).

Figure 25:
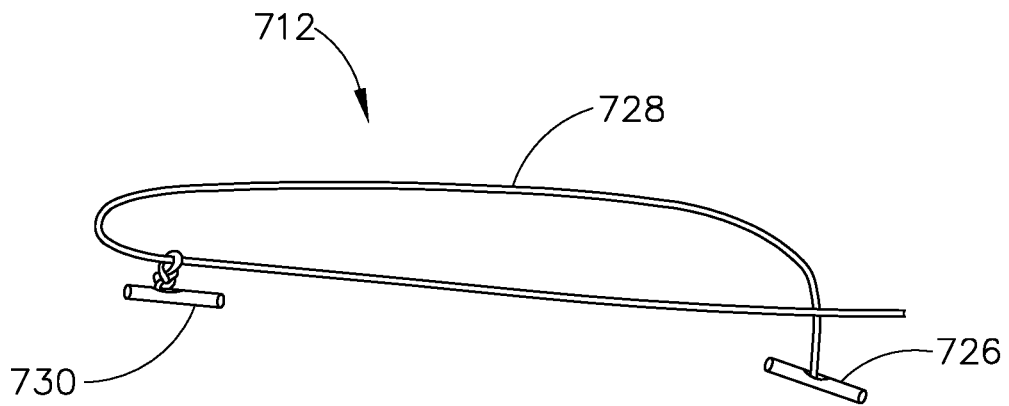
FIG. 25 depicts a perspective view of the slip pledget suture thread of FIG. 23.
Figure 26A:
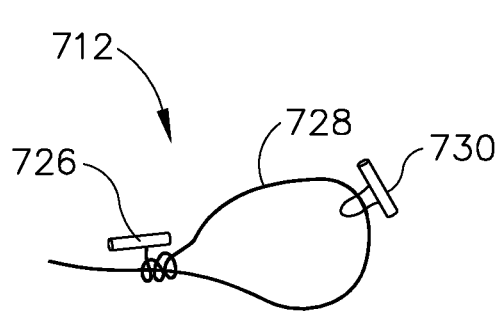
FIG. 26A depicts a perspective view of the slip pledget suture thread of FIG. 25 in a looped opened configuration.
Figure 26B:
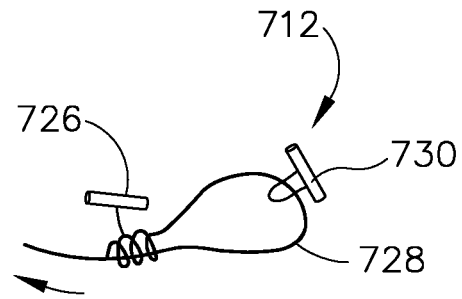
FIG. 26B depicts the perspective view of the slip pledget suture thread similar to FIG. 26A, but showing the slip pledget suture thread being closed from the looped open configuration to a looped closed configuration.

FIG. 25-26B show slip pledget suture thread (712) having thread body (728) as well as distal and proximal pledget ends (726, 730). FIGS. 26A-26B respectively show distal pledget end (726) and a distal portion of thread body (728) looped around a proximal portion of thread body (728) with proximal pledget (730) slidably connected on thread body (728) therebetween. Selectively pulling on thread body (728) thereby nooses slip pledget suture thread (712) tighter.

Figure 27A:
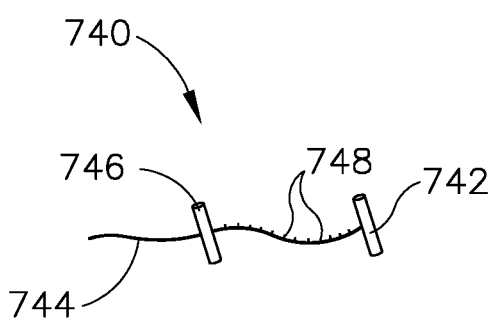
FIG. 27A depicts a perspective view of a barbed pledget suture thread in an extended opened configuration.
Figure 27B:
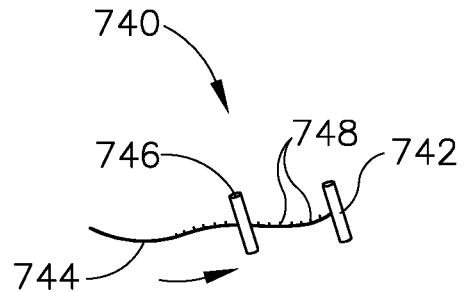
FIG. 27B depicts the perspective view of the barbed pledget suture thread similar to FIG. 27A, but showing the barbed pledget suture thread being closed from the extended open configuration to a contracted closed configuration.

An alternative barbed pledget suture thread (740) is shown in FIGS. 27A-27B. Barbed pledget suture thread (740) include a distal end pledget (742) connected to a thread body (744) as well as a slidable proximal end pledget (746). Rather than looping thread body (744) as discussed above with respect to thread body (728) (see FIG. 26A), barbed pledget suture thread (740) further includes a plurality of barbs (748) configured to allow distal translation of proximal end pledget (746) toward distal end pledget (742), but inhibit proximal translation of proximal end pledget (746) away from distal end pledget (742). In other words, proximal end pledget (746) and barbs (748) cooperate similar to a ratchet mechanism for securing tightened barbed pledget suture thread (740) in tissue (17) (see FIG. 28A) for closing tissue opening (58) (see FIG. 28A).

Figure 28D:
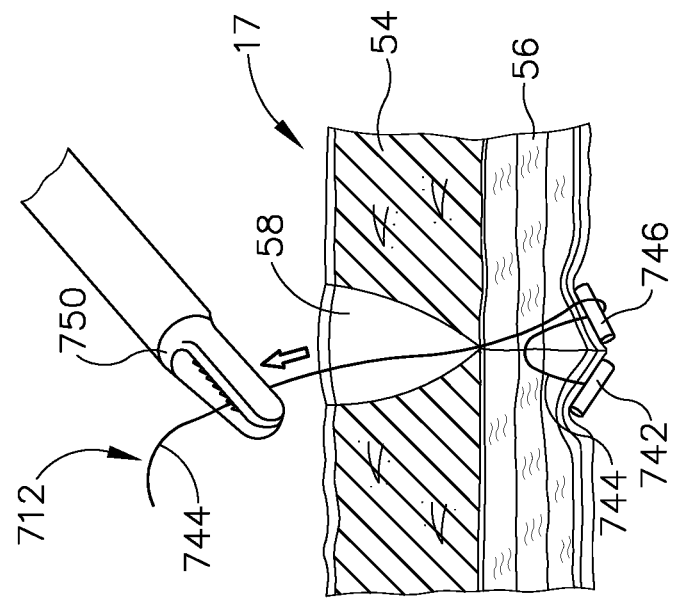
FIG. 28D depicts the perspective sectional view of the suturing surgical instrument and the slip pledget suture thread similar to FIG. 28C, but with the suturing surgical instrument removed from the tissue opening and a clamp jaw tightening the slip pledget suture thread to the looped closed configuration for closing the tissue opening.

In use, with respect to FIGS. 28A-28D, pledget surgical instrument (710) contains slip pledget suture thread (712) and needle introducer (716) is inserted into fascia (56) on one side of tissue opening (58). More particularly, needle introducer (716) is distally inserted such that discharge slot (724) also slides through and distal of fascia (56) within the patient as shown in FIG. 28A. The clinician then selectively distally translates plunger (718) to urge distal pledget end (726) from discharge slot (724) and position distal pledget end (726) in fascia (56). Pledget surgical instrument (710) is further manipulated such that needle introducer (716) is again inserted into fascia (56) on another, opposing side of tissue opening (58) as shown in FIG. 28B. The clinician then again selectively distally translates plunger (718) to urge proximal pledget end (730) from discharge slot (724) and position proximal pledget end (730) in fascia (56).

Figure 28C:
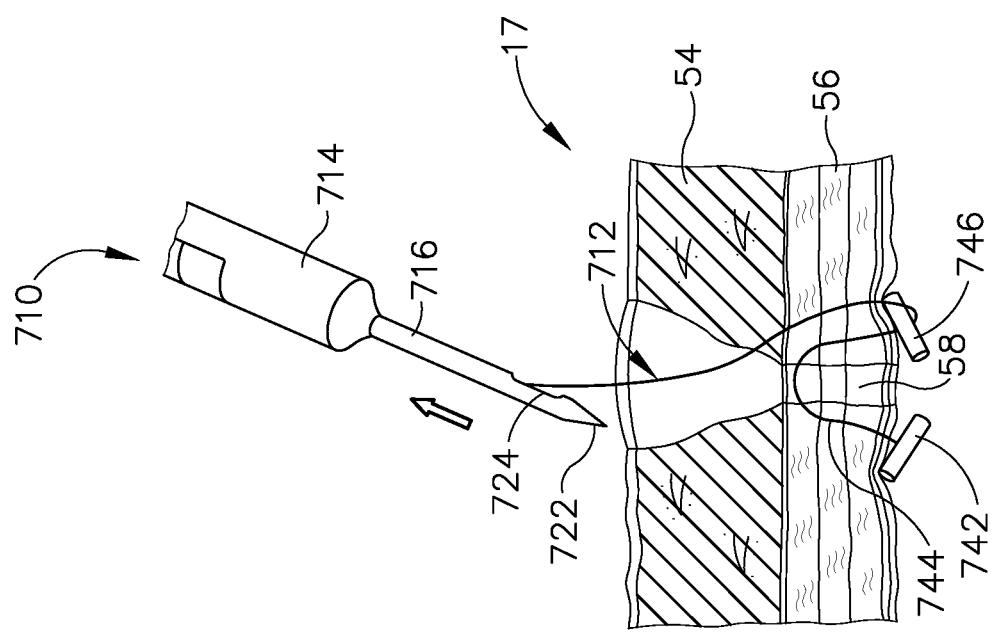
FIG. 28C depicts the perspective sectional view of the suturing surgical instrument and the slip pledget suture thread similar to FIG. 28B, but with the suturing surgical instrument being removed from the tissue opening.

FIGS. 28C-28D show pledget surgical instrument (710) being withdrawn from tissue opening (58) and the remainder of thread body (728) being pulled from within surgical instrument (710). In the present example, thread body (728) is looped as discussed above. A clamp jaw (750) is then manipulated by clinician in order to grip and pull the remainder of thread body (728) to tighten pledget suture thread (712) for closing tissue opening (58).

V. Exemplary Suture Passer

Figure 29:
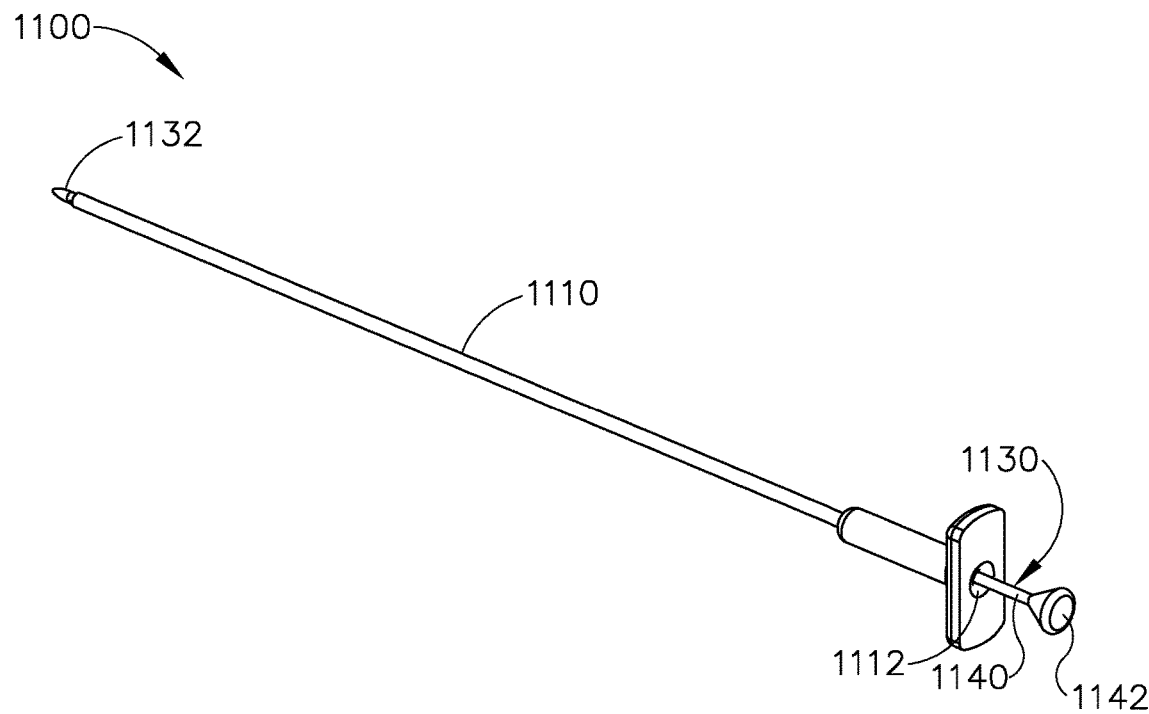
FIG. 29 depicts a perspective view of an exemplary suture passer having a first needle head.

Gripping suture thread (60) to manipulate suture thread (60) for closing tissue opening (58) may be difficult in some instances, particularly given limited access within tissue opening (58) and the relatively small size of suture thread (60). It may be thus beneficial to use a suture passer, such as a suture passer (1100) as shown in FIG. 29, that is configured to catch and release suture thread (60) to facilitate closure of tissue opening (58) following removal of trocar assembly (10). For example, after suture thread (60) has been inserted through fascia (56) on one side of tissue opening (58), suture passer (1100) catches suture thread (60) to facilitate redirection and selective repositioning of suture thread (60) upward toward fascia (56) on the other side of tissue opening (58) as discussed below in greater detail.

The following description provides various examples of suture passer (1100) with various needle heads (1132, 1232, 1332, 1432) in FIGS. 29-39C configured to catch and securely hold suture thread (60) within a patient. Each needle head (1132, 1232, 1332, 1432) is configured to enable catching and releasing suture thread (60). Furthermore, suture passer (1100) also includes various actuation mechanisms for covering and uncovering needle heads (1132, 1232, 1332, 1432) in use. Suture passer (1100) and needle heads (1132, 1232, 1332, 1432) described below may be used with any of the various trocar assemblies (10) described above and in any of the various procedures described in the various references described herein. While the following examples are provided in the context of trocar assembly (10) described above, the teachings below may be readily incorporated into any other surgical access devices and instruments. Other suitable ways in which the below-described suture passer (1100) may be used will be apparent to those of ordinary skill in the art in view of the teachings herein.

A. Exemplary Suture Passer with Biasing Member

Figure 30:
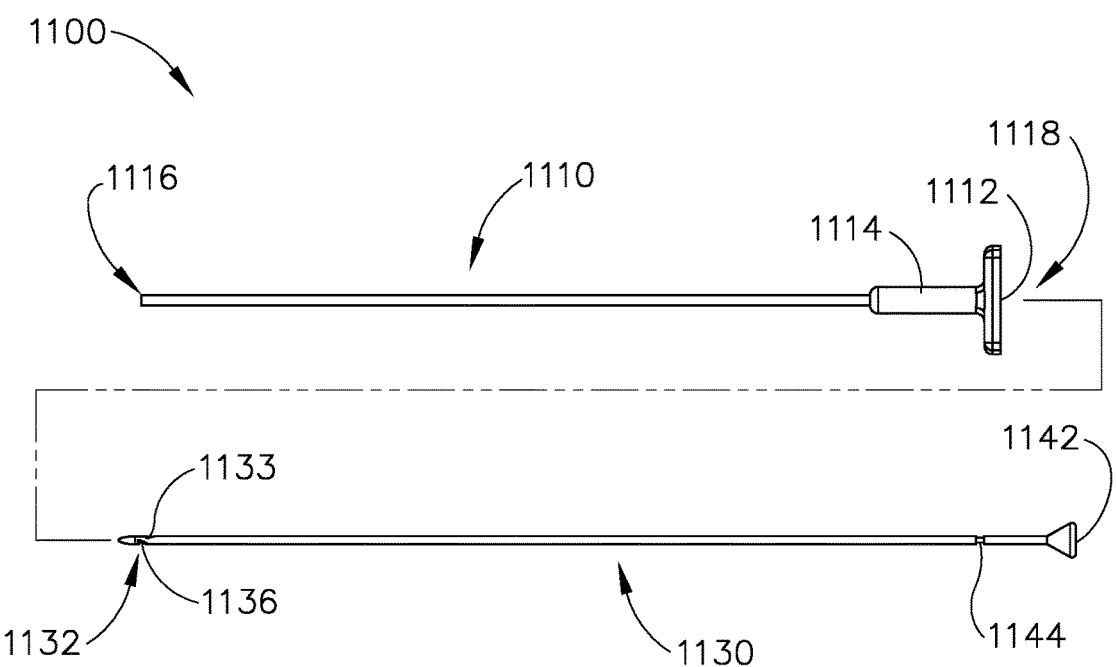
FIG. 30 depicts a partially exploded side elevational view of the suture passer of FIG. 29.

As shown in FIGS. 29-30, an exemplary suture passer (1100) includes an outer sheath (1110) and an inner needle (1130). Inner needle (1130) is substantially enclosed within outer sheath (1110) such that the longitudinal length of inner needle (1130) extends within a bore (1112) of outer sheath (1110). Inner needle (1130) comprises a first needle head (1132), a longitudinal shaft (1140), and a driver (1142). Longitudinal shaft (1140) has a longitudinal length that separates needle head (1132), positioned on a distal end of longitudinal shaft (1140), from driver (1142), positioned on an opposite, proximal end of longitudinal shaft (1140). Needle head (1132) of inner needle (1130) comprises a proximal notch (1133) and a distal notch (1136). Outer sheath (1110) comprises bore (1112), a housing (1114), a radial wall (1115) (see FIG. 32) with a distal opening (1116) (see FIG. 31A), and a proximal opening (1118) (see FIG. 31A). Bore (1112) has a longitudinal length that separates distal opening (1116) (see FIG. 31A) from housing (1114) and proximal opening (1118) (see FIG. 31A). Openings (1116, 1118) (see FIG. 31A) are in communication with bore (1112) and in axial alignment with the longitudinal length of bore (1112). Inner needle (1130) inserts into outer sheath (1110) by directing needle head (1132) into proximal opening (1118) and slidably advancing inner needle (1130) through bore (1112). As further seen in FIG. 30, inner needle (1130) further comprises a latch (1144) configured to engage a biasing member (1120) of outer sheath (1110) and contained within housing (1114).

As a merely illustrative example, inner needle (1130) is formed of a hardened stainless steel while the molded features on inner needle (1130), particularly driver (1142) and latch (1144), are formed of plastic, such as polycarbonate. Notches (1133, 1136) are machined into inner needle (1130) in the present example, but may alternatively be molded with inner needle (1130), such as by injection molding. In another example, inner needle (1130) may be form of a plastic material and metal coated for additional surface hardness similar to stainless steel with a bending strength similar to aluminum. Inner needle (1130) has a diameter smaller than a diameter of outer sheath (1110) such that inner needle (1130) is slidably received within outer sheath (1110). For example, inner needle (1130) has a diameter ranging from approximately 2 millimeters to approximately 3 millimeters and outer sheath (1110) has a corresponding larger diameter with ample clearance configured to receive a United States Pharmacopeia (U.S.P.) designation 2 sized suture thread (60). Furthermore, outer sheath (1110) is formed of a seamless stainless steel tubing. As will be apparent to those of ordinary skill in the art, outer sheath (1110) and inner needle (1130) may be formed of other, various suitable materials that will maintain durability when inserted into the cavity of a patient.

FIGS. 31A-31B show suture passer (1100) transitioning respectively from a retracted position to an extended position when a clinician exerts a distal force on driver (1142). In particular, FIG. 31A illustrates suture passer (1100) in the initial, retracted position where inner needle (1130) is slidably inserted into bore (1112) of outer sheath (1110). Due to the natural expanded state of biasing member (1120) being captured in compression, suture passer (1100) generally remains in the retracted position unless manipulated toward the extended position by the clinician. While in the retracted position, needle head (1132) of inner needle (1130) is substantially contained within bore (1112) at distal opening (1116). Furthermore, proximal notch (1133) and distal notch (1136) are fully covered within bore (1112) by outer sheath (1110) in the retracted position, and driver (1142) is fully extended from proximal opening (1118). With suture passer (1100) in the retracted position, the potential for notches (1133, 1136) to contact tissue opening (58) or other portion of the patient's body in use is reduced as notches (1133, 1136) remain covered within outer sheath (1110). Biasing member (1120) within housing (1114) is similarly in a fully extended state and securely engaged with latch (1144) of inner needle (1130). Latch (1144) is configured to movably secure inner needle (1130) to outer sheath (1110) such that inner needle (1130) has limited translational movement that does not distally slide out of outer sheath (1110) from distal opening (1116).

In the present example, the clinician grasps suture passer (1100) at housing (1114) to selectively position needle head (1132) adjacent to suture thread (60) (see FIG. 4A) within a cavity of the patient. Upon exertion by the clinician on driver (1142) of the predetermined force to overcome the resilient bias created by biasing member (1120), inner needle (1130) slidably translates within bore (1112) in the distal direction, as seen in FIG. 31B. Biasing member (1120) compresses to a compressed state while suture passer (1100) is in the extended position and driver (1142) is held distally towards housing (1114). As a merely illustrative example, biasing member (1120) has a spring rate ranging from approximately 2.3 lbs./inch to approximately 2.8 lbs./inch, although other spring rates configured to provide for a relatively smooth translation of inner needle (1130) within outer sheath (1110) may be similarly used. With suture passer (1100) in the extended position, needle head (1132) of inner needle (1130) extends distally through distal opening (1116) such that notches (1133, 1136) extend beyond bore (1112) of outer sheath (1110). In this instance, inner needle (1130) and notches (1133, 1136) are configured to be physically maneuvered within tissue opening (58) to catch and subsequently release suture thread (60) (see FIG. 4A).

Figure 32:
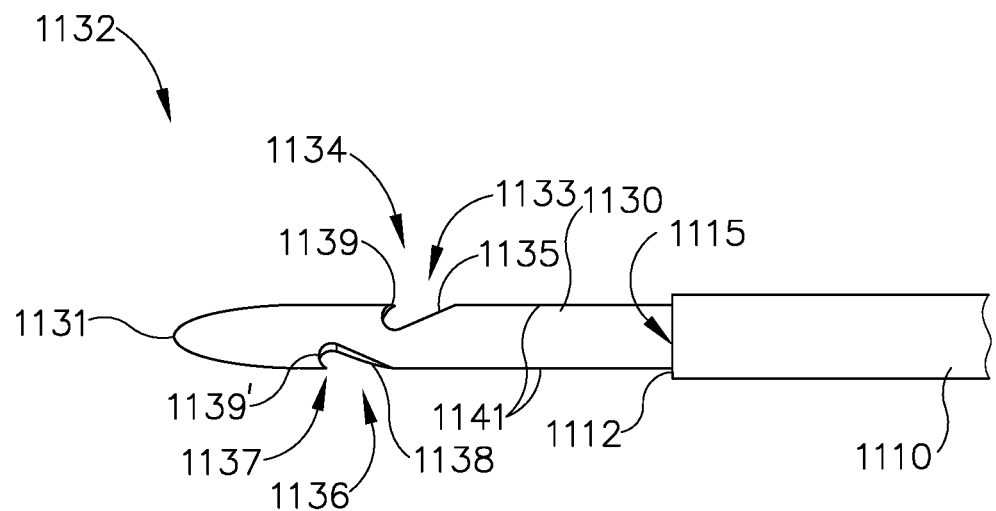
FIG. 32 depicts a side elevational view of the first needle head of the suture passer of FIG. 29.

FIG. 32 shows needle head (1132) of inner needle (1130) exposed beyond bore (1112) of outer sheath (1110) when suture passer (1100) is in the extended position. In addition to notches (1133, 1136), needle head (1132) further comprises a domed pointer (1131) geometrically configured to provide inner needle (1130) with a smooth, low force impact when inner needle (1130) is inserted into tissue opening (58) (see FIG. 4A). With this unsharpened point, domed pointer (1131) is configured to inhibit inadvertent damage to tissue when inserting suture passer (1100) within the patient.

Proximal notch (1133) extends through inner needle (1130) and comprises a proximal catch undercut (1134) and a proximal release cam surface (1135). Proximal catch undercut (1134) has a hooked surface (1139) and is configured to receive and hold suture thread (60) (see FIG. 4A) radially inwardly toward inner needle (1130) when inner needle (1130) is selectively maneuvered to catch suture thread (60) (see FIG. 4A). Proximal release cam surface (1135) is positioned between proximal catch undercut (1134) and an outer radial surface (1141) of inner needle (1130). Proximal release cam surface (1135) extends proximally and radially outwardly from hooked surface (1139) of proximal catch undercut (1134) until flush with outer radial surface (1141) of inner needle (1130). Proximal release cam surface (1135) is configured to urge suture thread (60) (see FIG. 4A) radially outwardly from proximal catch undercut (1134) to thereby remove suture thread (60) (see FIG. 4A) from proximal notch (1133) when inner needle (1130) is selectively maneuvered to release suture thread (60) (see FIG. 4A).

Similarly, distal notch (1136) extends through inner needle (1130) and comprises a distal catch undercut (1137) and a distal release cam surface (1138). Distal catch undercut (1137) has a hooked surface (1139') and is configured to receive and hold suture thread (60) (see FIG. 4A) radially inwardly towards inner needle (1130) when inner needle (1130) is selectively maneuvered in a catch direction to catch suture thread (60) (see FIG. 4A). Distal release cam surface (1138) is positioned between distal catch undercut (1137) and outer radial surface (1141) of inner needle (1130). Distal release cam surface (1138) extends distally and radially outwardly from hooked surface (1139') of distal catch undercut (1137) until becoming level with outer radial surface (1141) of inner needle (1130). Distal release cam surface (1138) is configured to urge suture thread (60) (see FIG. 4A) radially outwardly from distal catch undercut (1137) to thereby remove suture thread (60) (see FIG. 4A) from distal notch (1136) when inner needle (1130) is selectively maneuvered in a release direction to release suture thread (60) (see FIG. 4A).

As best seen in FIG. 32, notches (1133, 1136) are positioned along inner needle (1130) at varying angular positions about a longitudinal axis (1129) such that proximal notch (1133) is angularly positioned on inner needle (1130) opposite of distal notch (1136). Notwithstanding the relative positioning of notches (1133, 1136) relative to each other along inner needle (1130), catch undercuts (1134, 1137) are distally oriented on inner needle (1130) relative to release cam surfaces (1135, 1138), respectively. Although not shown, it should be understood that proximal notch (1133) and/or distal notch (1136) may be orientated along inner needle (1130) in an opposite position than that depicted in FIG. 32. In this instance, catch undercuts (1134, 1137) are proximally oriented on inner needle (130) relative to release cam surfaces (1135, 1138), respectively.

Figure 33:
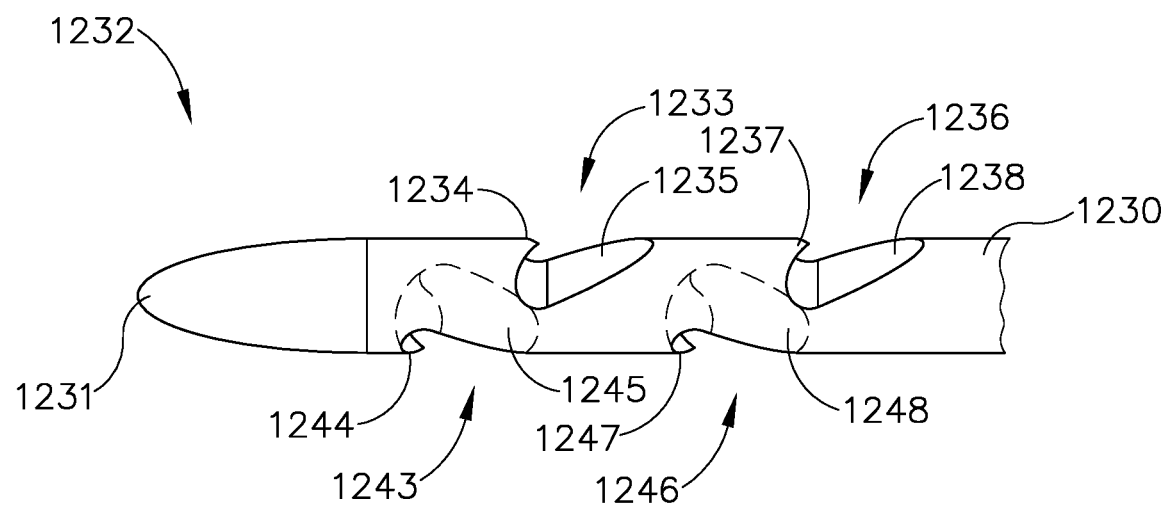
FIG. 33 depicts a side elevational view of a second needle head.

FIG. 33 depicts a second needle head (1232) of an inner needle (1230). Needle head (1232) comprises first-side notches (1233, 1236), second-side notches (1243, 1246), and a domed pointer (1231). Like domed pointer (1131) (see FIG. 31A), domed pointer (1231) is geometrically configured to provide inner needle (1230) with a smooth, low force impact when inner needle (1230) is inserted into tissue opening (58) (see FIG. 4A) to reduce the likelihood of damaging the tissue upon insertion of suture passer (1100) into the patient. First-side notches (1233, 1236) extend through inner needle (1230) and are positioned angularly opposite from second-side notches (1243, 1246) about a longitudinal axis (1229) of inner needle (1230). Like notches (1133, 1136) (see FIG. 31A) of inner needle (1130) (see FIG. 31A), first-side notches (1233, 1236) and second-side notches (1243, 1246) respectively include catch undercuts (1234, 1237, 1244, 1247) and release cam surfaces (1235, 1238, 1245, 1248) configured to similarly perform as described above with respect to catch undercuts (1134, 1137) (see FIG. 31A) and release cam surfaces (1135, 1138) (see FIG. 31A).

Figure 34:
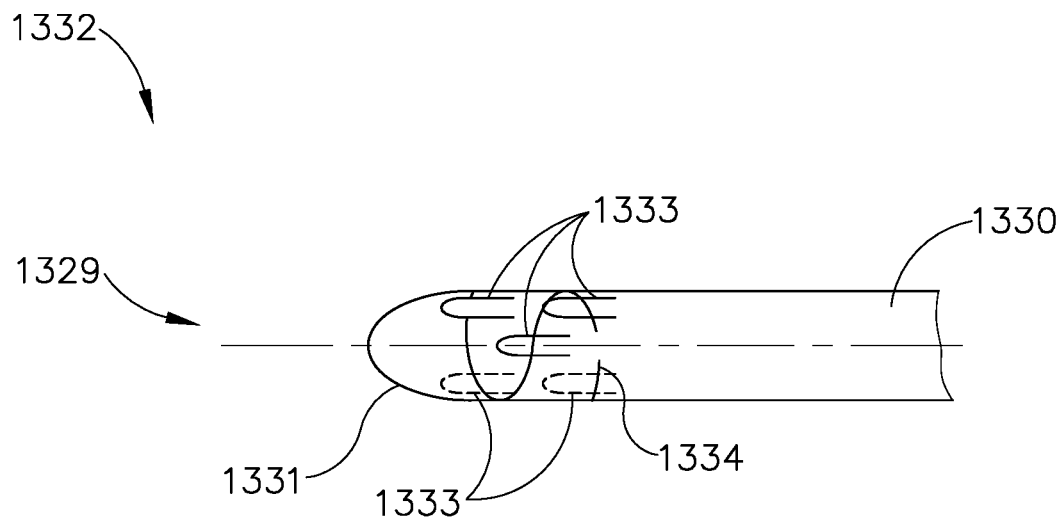
FIG. 34 depicts a side elevational view of a third needle head of the suture passer of FIG. 29.
Figure 35:
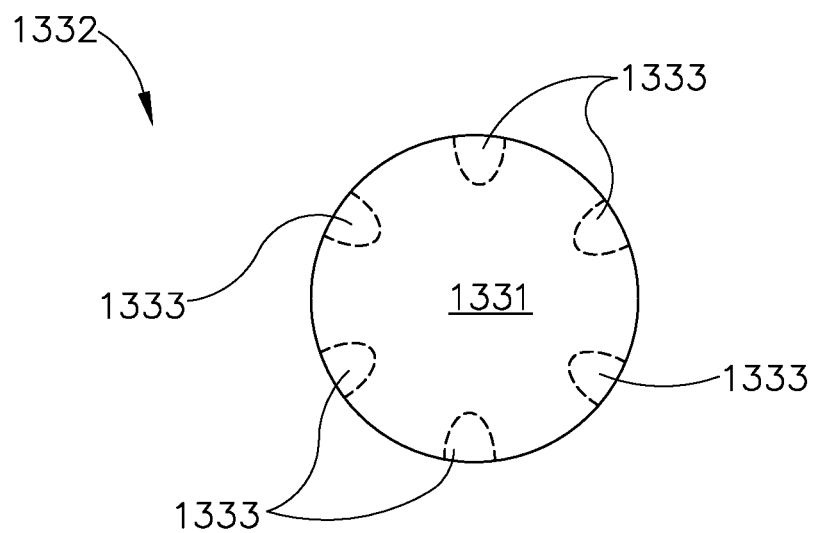
FIG. 35 depicts a distal end view of the needle head of FIG. 34.

FIGS. 34-35 illustrate a third needle head (1332) of an inner needle (1330). In the present example, needle head (1332) comprises a plurality of notches (1333) along inner needle (1330) and a domed pointer (1331). Plurality of notches (1333) are angularly positioned along needle head (1332) about a longitudinal axis (1329) of inner needle (1330) in a helical arrangement, as indicated by reference numeral (1334). Although six notches (1333) are depicted, it will be apparent to those of ordinary skill in the art that more or fewer notches (1333) may be positioned along needle head (1332).

B. Exemplary Suture Passer with Rotation Member

Figure 36:
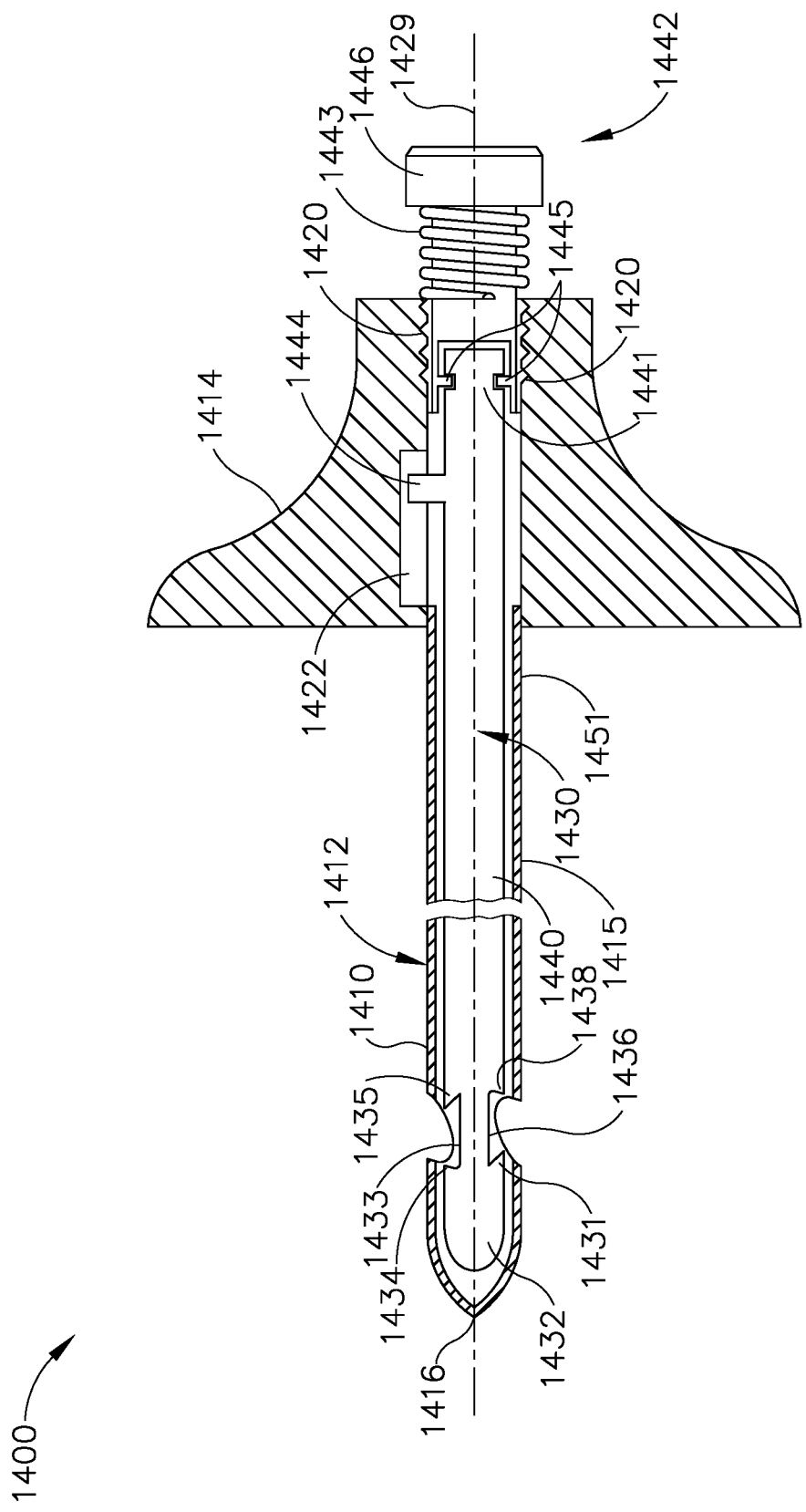
FIG. 36 depicts a cross-sectional side view of another exemplary suture passer with a rotating driver and a fourth needle head.

FIG. 36 depicts another exemplary suture passer (1400) comprising an outer sheath (1410) and an inner needle (1430) with a fourth needle head (1432). Inner needle (1430) is substantially enclosed within outer sheath (1410) such that the longitudinal length of inner needle (1430) extends within a bore (1412) of outer sheath (1410). Inner needle (1430) comprises needle head (1432), a longitudinal shaft (1440), and a driver (1442). Longitudinal shaft (1440) has a longitudinal length that separates needle head (1432), positioned on a distal end of longitudinal shaft (1440), from driver (1442), positioned on an opposite, proximal end of longitudinal shaft (1440). Driver (1442) includes a knob (1446), an external threaded portion (1443), and an engagement mechanism (1445). Longitudinal shaft (1440) further includes an engagement coupling (1441) configured to movably attach inner needle (1430) to driver (1442) by mating with the corresponding engagement mechanism (1445) of driver (1442).

Needle head (1432) of inner needle (1430) has an upper notch (1433) and a lower notch (1436) positioned angularly opposite of each other along inner needle (1430). Upper notch (1433) comprises an upper curved surface (1434) and an upper hooked surface (1435). Upper surfaces (1434, 1435) are positioned longitudinally opposite each other such that upper surfaces (1434, 1435) face each other along inner needle (1430). Upper curved surface (1434) is positioned distally relative to upper hooked surface (1435). As will be described in greater detail below, upper curved surface (1434) is configured to direct suture thread (60) (see FIG. 38A) toward an upper release cam surface (1455) (see FIG. 37A) such that upper curved surface (1434) pushes suture thread (60) (see FIG. 38A) out of upper notch (1433), whereas upper hooked surface (1435) is configured to catch and hold suture thread (60) (see FIG. 38A) against an upper catch undercut (1454) (see FIG. 37A). Similarly, lower notch (1436) comprises a lower hooked surface (1437) and a lower curved surface (1438). Lower surfaces (1437, 1438) are positioned longitudinally opposite each other such that lower surfaces (1437, 1438) face each other along inner needle (1430). Lower hooked surface (1437) is positioned distally relative to lower curved surface (1438). As will be further described below, lower curved surface (1438) is configured to direct suture thread (60) (see FIG. 39A) towards a lower release cam surface (1458) (see FIG. 37A) such that lower curved surface (1438) pushes suture thread (60) (see FIG. 39A) out of lower notch (1436), whereas lower hooked surface (1437) is configured to catch and hold suture thread (60) (see FIG. 39A) against a lower catch undercut (1457) (see FIG. 37A). Although not shown, it should be understood that needle head (1432) may comprise more or fewer notches (1433, 1436) along inner needle (1430) than that depicted.

Outer sheath (1410) comprises bore (1412), a housing (1414), a radial wall (1415), and a distal end (1416). Distal end (1416) is angular with a cutting edge configured to pierce tissue (117). Bore (1412) has a longitudinal length that separates distal end (1416) from housing (1414), which is positioned on a proximal end thereof. Inner needle (1430) is configured to slidably translate within bore (1412) of outer sheath (1410) through the rotation of driver (1442). In other words, inner needle (1430) and driver (1442) are translatably coupled at engagement mechanism (1445), but rotatably decoupled such that rotation and translation of driver (1442) will only translate inner needle (1430) without rotating inner needle (1430). To this end, housing (1414) includes an internal threaded portion (1420) and a slot (1422) to allow inner needle (1430) to slidably translate within bore (1412).

Internal threaded portion (1420) is configured to engage external threaded portion (1443) of driver (1442) such that the rotation of driver (1442) in a clockwise direction, when viewed from the proximal end, translates inner needle (1430) in a distal direction. Conversely, a counter rotation of driver (1442) in the counterclockwise direction, when viewed from the proximal end, translates inner needle (1430) in a proximal direction. As further seen in FIG. 36, slot (1422) extends inwardly into housing (1414) and has a longitudinal length parallel to a longitudinal axis (1429) of inner needle (1430). Inner needle (1430) further comprises a latch (1444) protruding laterally from shaft (1440) along a portion of inner needle (1430) contained within housing (1414). Latch (1444) is configured to engage slot (1422), which is configured to inhibit rotation of inner needle (1430) as well as constrain the longitudinal translation inner needle (1430) to the longitudinal length of slot (1422).

Figure 37A:
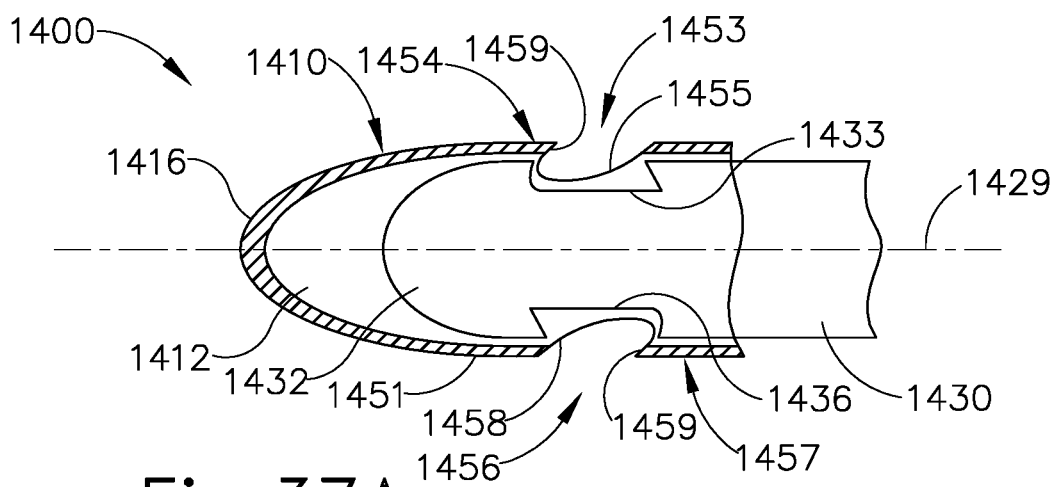
FIG. 37A depicts an enlarged cross-sectional side view of the needle head of FIG. 36 taken along a centerline thereof with the needle head in a retracted position.
Figure 37B:
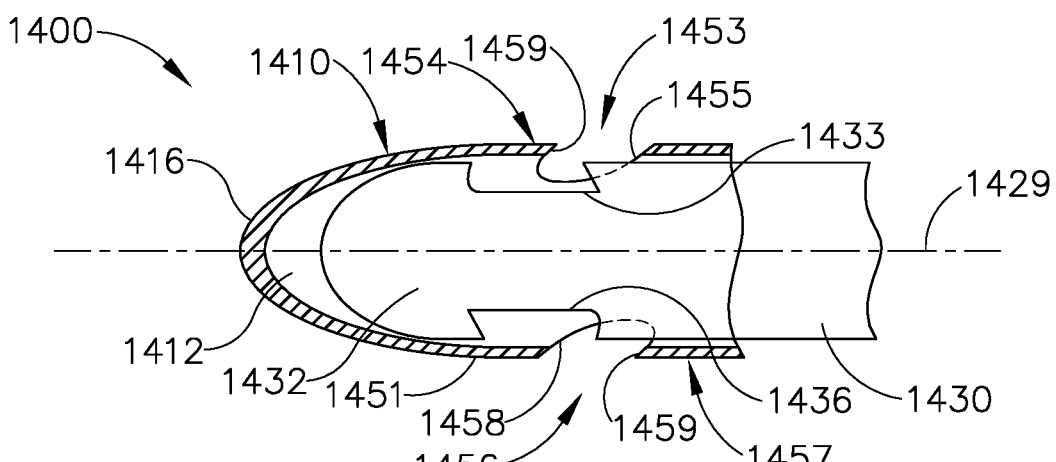
FIG. 37B depicts the enlarged cross-sectional side view of the needle head similar to FIG. 37A, but with the needle head in an extended position.
Figure 37C:
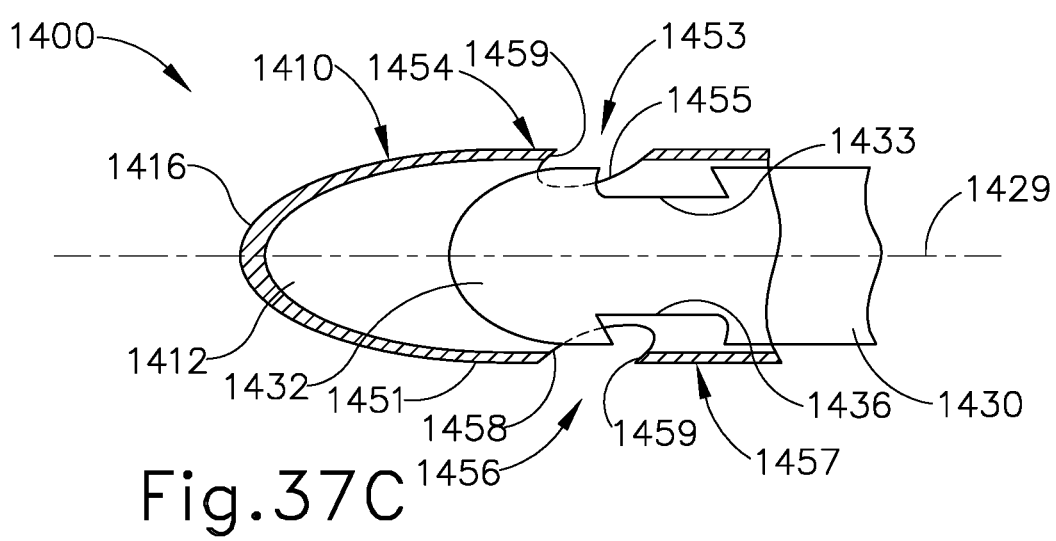
FIG. 37C depicts the enlarged cross-sectional side view of the needle head similar to FIG. 37B, but with the needle head in a third position.

As best seen in FIGS. 37A-37C, outer sheath (1410) further includes an upper aperture (1453) and a lower aperture (1456) proximal to end (1416). Apertures (1453, 1456) are configured to provide communication between an outer radial surface (1451) of outer sheath (1410) and bore (1412) such that apertures (1453, 1456) expose needle head (1432) when inner needle (1430) is slidably inserted within bore (1412). In particular, upper aperture (1453) is positioned along outer sheath (1410) to correspond with upper notch (1433) on needle head (1432) and lower aperture (1456) is positioned along outer sheath (1410) to correspond with lower notch (1436). Apertures (1453, 1456) extend through outer sheath (1410) and comprise catch undercuts (1454, 1457) and release cam surfaces (1455, 1458). Catch undercuts (1454, 1457) have a hooked surface (1459) and are configured to receive and hold suture thread (60) (see FIG. 38A) radially inwardly toward outer sheath (1410) when suture passer (1400) is selectively maneuvered in a catch direction to catch suture thread (60).

Release cam surfaces (1455, 1458) are positioned respectively between catch undercuts (1454, 1457) and outer radial surface (1451) of outer sheath (1410). Release cam surfaces (1455, 1458) extend distally and radially outwardly from the hooked surfaces (1459) of catch undercuts (1454, 1457) until becoming flush with outer radial surface (1451) of outer sheath (1410). Release cam surfaces (1455, 1458) are configured to urge suture thread (60) radially outwardly from catch undercuts (1454, 1457) to thereby remove suture thread (60) from notches (1433, 1436) when suture passer (1400) is selectively maneuvered in a release direction to release suture thread (60).

Upper aperture (1453) is positioned along outer sheath (1410) angularly opposite of lower aperture (1456) about a longitudinal axis (1429) of outer sheath (1410). Upper catch undercut (1454) is distally oriented on outer sheath (1410) relative to upper release cam surface (1455) such that upper catch undercut (1454) is positioned proximal to distal end (1416) and upper release cam surface (1455) is positioned distal to distal end (1416). In contrast, lower catch undercut (1457) is proximally oriented on outer sheath (1410) relative to lower release cam surface (1458) such that lower catch undercut (1457) is positioned distal to distal end (1416) and lower release cam surface (1458) is positioned proximal to distal end (1416).

In the present example, suture passer (1400) transitions to a series of positions when a clinician rotates driver (1442). In particular, rotation of driver (1442) slidably advances inner needle (1430) within bore (1412) through the threaded engagement of internal threaded portion (1420) and external threaded portion (1443) to the extent until latch (1444) encounters the confined limits of slot (1422). As seen in FIG. 37A, driver (1442) is rotated until notches (1433, 1436) are substantially aligned with apertures (1453, 1456). FIG. 37B shows inner needle (1430) in a distally translated position with notches (1433, 1436) not substantially aligned with apertures (1453, 1456) but instead substantially covered by bore (1412) in a position proximal to distal end (1416). Lastly, as seen in FIG. 37C, driver (1442) is oppositely rotated until inner needle (1430) is in a proximally translated position with notches (1433, 1436) not substantially aligned with apertures (1453, 1456) but instead substantially covered by bore (1412) in a position distal to distal end (1416).

Figure 38A:
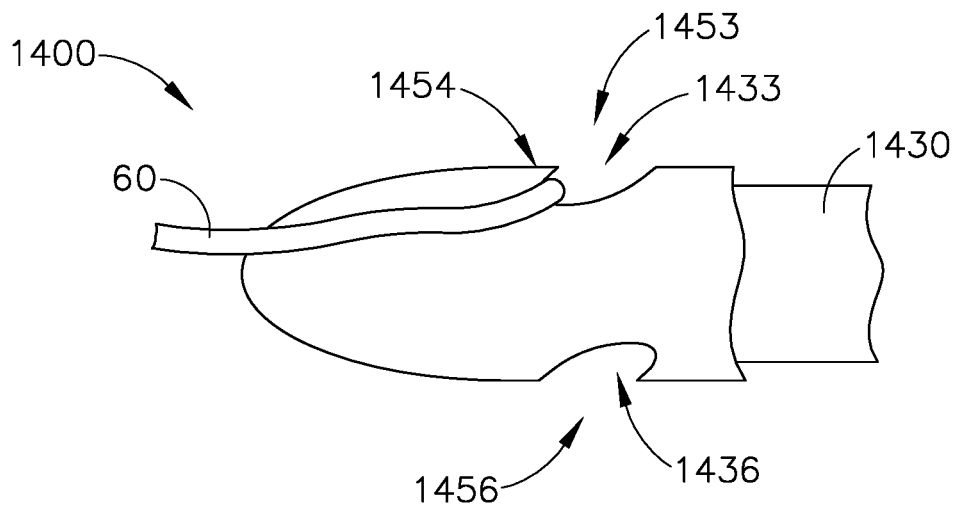
FIG. 38A depicts an enlarged side elevational view of the needle head of FIG. 37A with the needle head in the retracted position and grasping a suture thread within a suture notch.
Figure 38B:
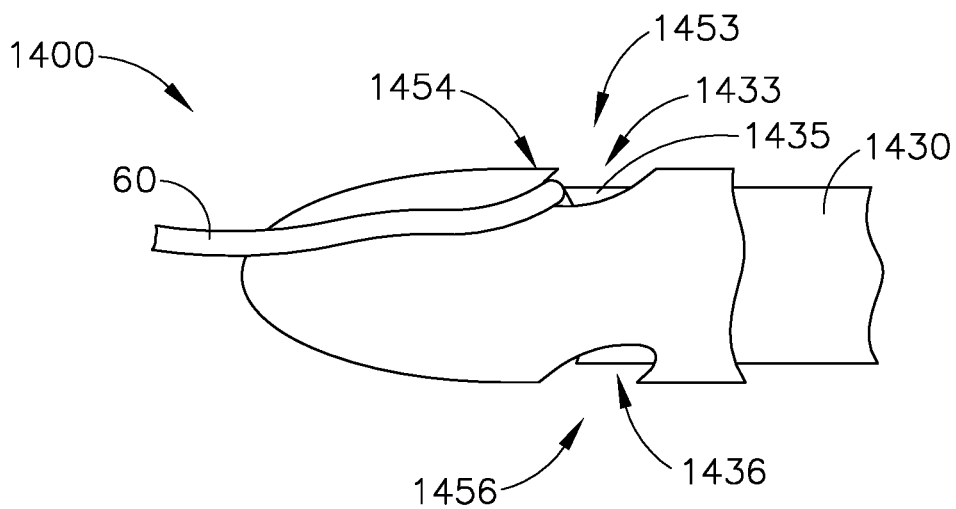
FIG. 38B depicts an enlarged side elevational view of the needle head of FIG. 37B with the needle head in the extended position and securing the suture thread within the suture notch.
Figure 38C:
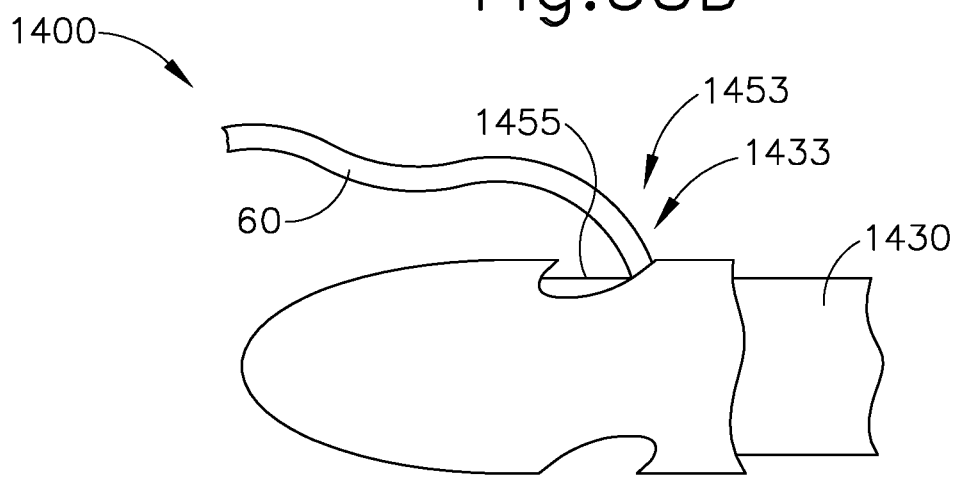
FIG. 38C depicts an enlarged side elevational view of the needle head of FIG. 37C with the needle head returned to the retracted position and releasing the suture thread from within the suture notch.

FIGS. 38A-38C illustrate suture passer (1400) capturing and releasing suture thread (60) within upper aperture (1453) and upper notch (1433). In particular, FIG. 38A depicts notches (1433, 1436) substantially aligned with apertures (1453, 1456) (in the position previously illustrated in FIG. 37A) and suture thread (60) releasably secured at upper catch undercut (1454) of upper aperture (1453). By rotating driver (1442), inner needle (1430) translates distally within bore (1412) of outer sheath (1410) thus causing notches (1433, 1436) to distally translate. In this instance, as seen in FIG. 38B, upper hooked surface (1435) of upper notch (1433) securely captures suture thread (60) against upper catch undercut (1454), thereby preventing suture thread (60) from slipping out from the grasp of suture passer (1400). The clinician may then selectively maneuver suture passer (1400), with suture thread (60) securely seized, to a preferred position for placement. By rotating driver (1442) in a direction opposite of that represented in FIG. 38B, upper notch (1433) translates proximally and simultaneously releases suture thread (60) from upper catch undercut (1454), as seen in FIG. 38C. As upper notch (1433) translates proximally, upper curved surface (1434) directs suture thread (60) proximally along upper release cam surface (1455) until suture thread (60) is freely released from upper aperture (1453).

Figure 39A:
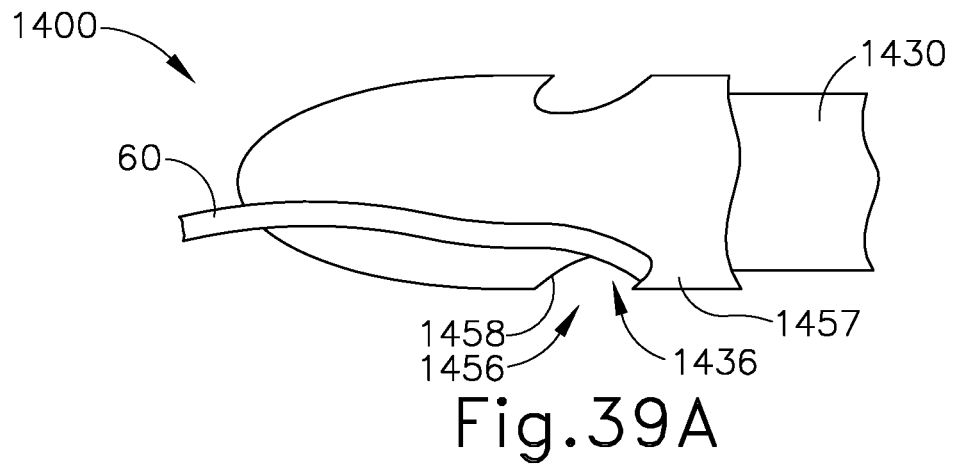
FIG. 39A depicts an enlarged side elevational view of the needle head of FIG. 37A with the needle head in the retracted position and grasping the suture thread within another suture notch.
Figure 39B:
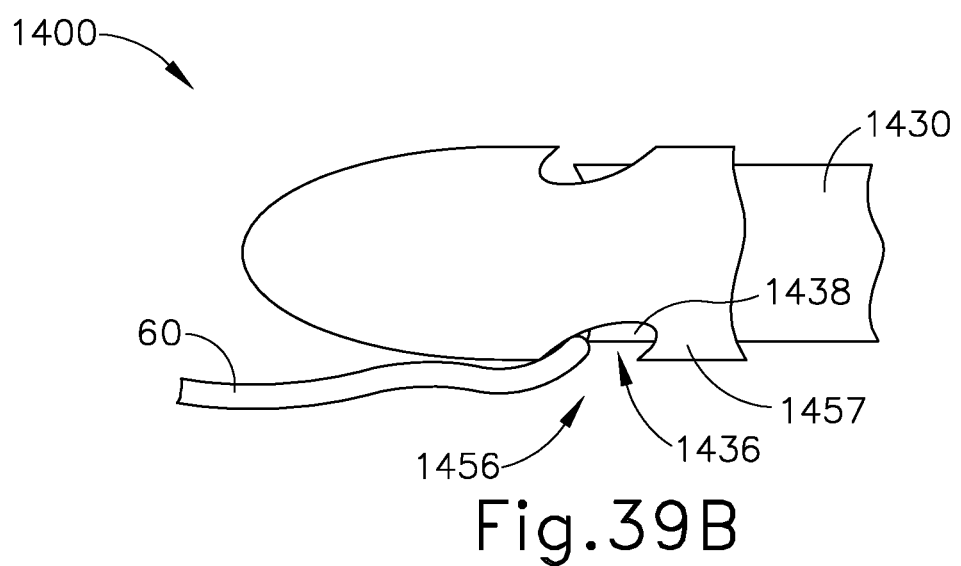
FIG. 39B depicts an enlarged side elevational view of the needle head of FIG. 37B with the needle head in the extended position and releasing the suture thread from within the other suture notch.
Figure 39C:
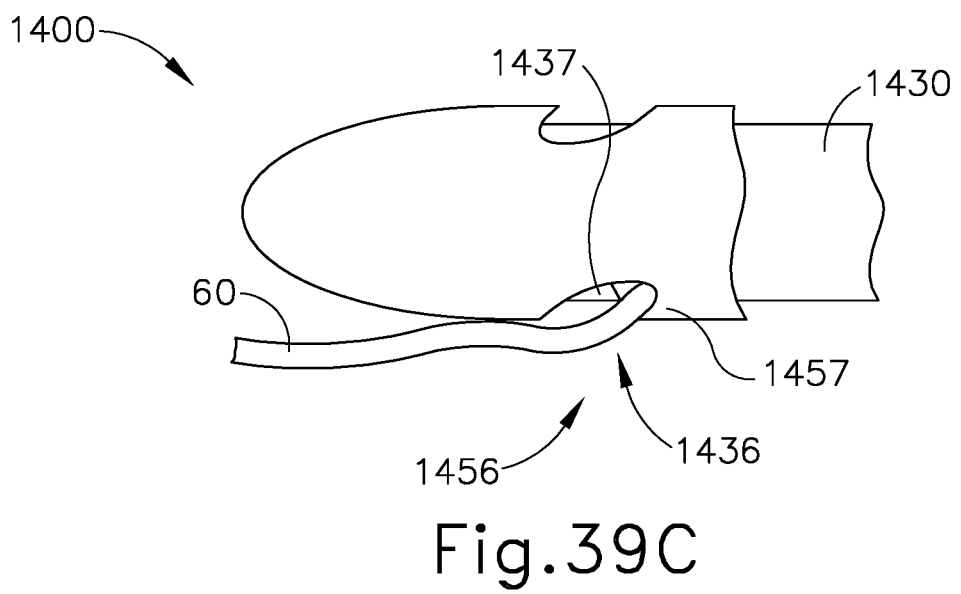
FIG. 39C depicts an enlarged side elevational view of the needle head of FIG. 37C with the needle head returned to the retracted position and securing the suture thread within the other suture notch.

As seen in FIGS. 39A-39C, suture passer (1400) may similarly capture and release suture thread (60) within lower aperture (1456) and lower notch (1436). However, due to the opposite orientation of lower aperture (1456), and particularly lower catch undercut (1457) and lower release cam surface (1458), the identical rotations of driver (1442) may generate different interactions between suture passer (1400) and suture thread (60). For instance, by rotating driver (1442) in a direction like that represented in FIG. 38B, lower curved surface (1438) serves to release suture thread (60) from lower catch undercut (1457), as seen in FIG. 39B. Thus, the identical rotation of driver (1442) generates an opposite interaction between suture thread (60) and upper notch (1433) or lower notch (1436). In this instance, lower curved surface (1438) directs suture thread (60) distally along lower release cam surface (1458) until suture thread (60) is freely released from lower aperture (1456). Furthermore, by rotating driver (1442) in the direction represented in FIG. 38C, wherein lower notch (1436) translates in the proximal direction, upper hooked surface (1437) securely captures suture thread (60) against upper catch undercut (1457), as seen in FIG. 39C.

VI. Exemplary Surgical Access Device Having Wound Closure Features

Figure 40A:
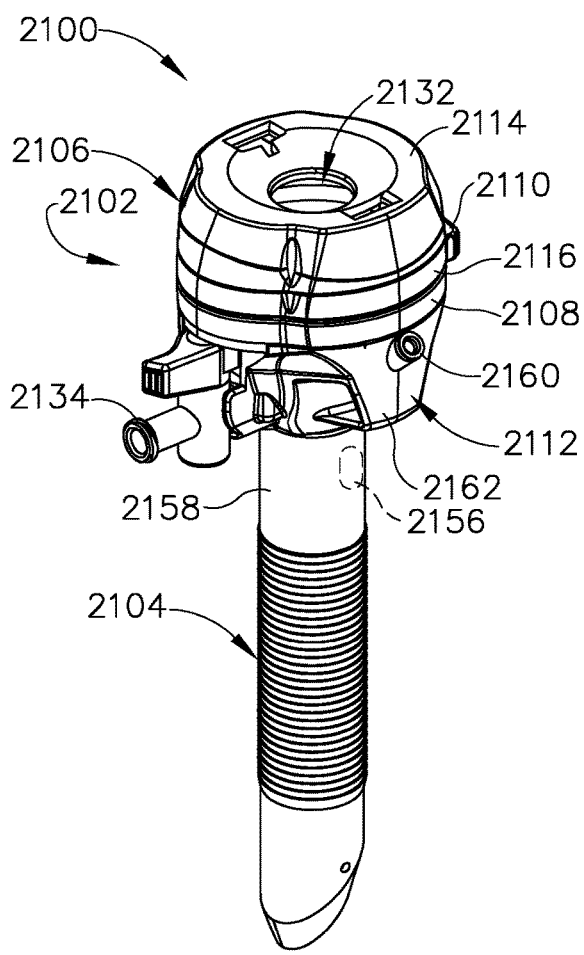
FIG. 40A depicts a front perspective view of an exemplary trocar having a housing and a cannula.
Figure 40B:
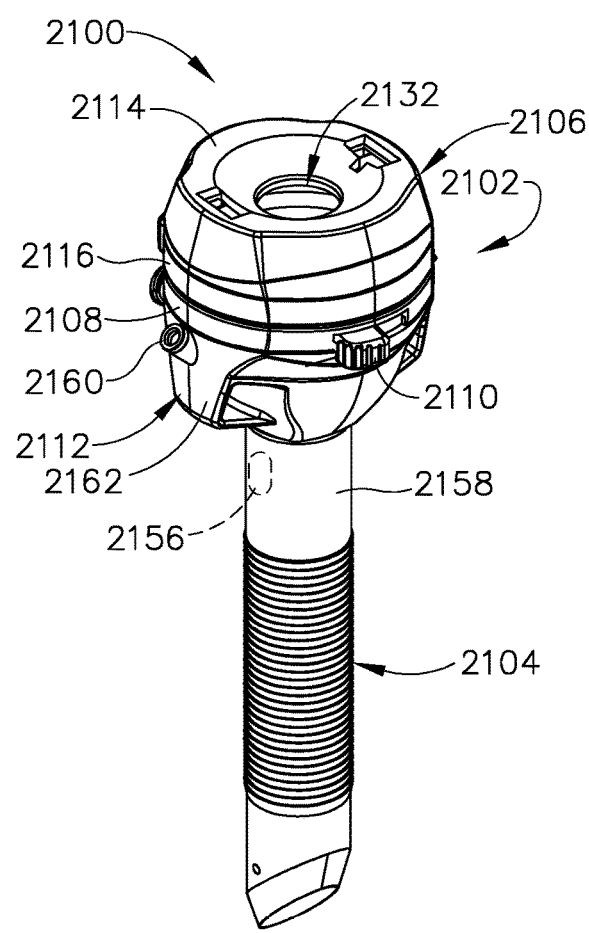
FIG. 40B depicts a rear perspective view of the trocar of FIG. 40A.
Figure 41:
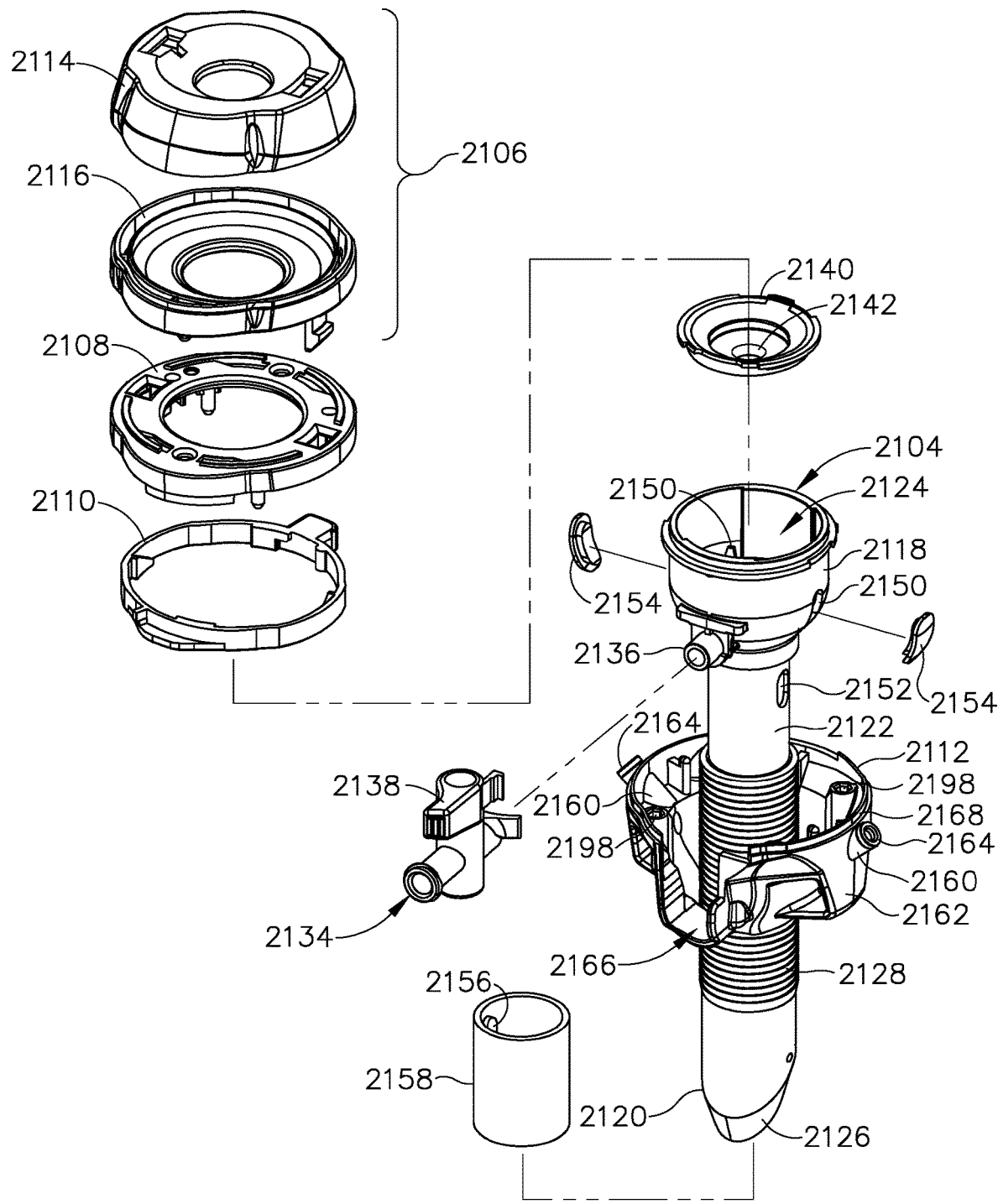
FIG. 41 depicts an exploded perspective view of the trocar of FIG. 40A.

A. Exemplary Trocar Having Latch Ring and Needle Ports Defining Oblique Suture Paths FIGS. 40A-41 show another exemplary surgical access device in the form of a trocar (2100). Though not shown, those of ordinary skill in the art will recognize that trocar (2100) may be used in combination with any suitable trocar obturator, such as obturator (14) described above, for example. Trocar (2100) generally includes a housing (2102) and a cannula (2104) coupled to and extending distally from housing (2102) along a central longitudinal axis of trocar (2100). Housing (2102) includes a proximal housing (2106), a housing cap plate (2108), a latch ring (2110), and a distal housing (2112). Proximal housing (2106) has a proximal housing head (2114) and a proximal housing base (2116). As described in greater detail below, proximal housing (2106) is coupled with and selectively releasable from the remainder of trocar (2100) via housing cap plate (2108) and latch ring (2110). In particular, distally extending protrusions of proximal housing (2106) are received through housing cap plate (2108) and are releasably engaged by latch ring (2110). Latch ring (2110) is rotatable about a central axis of trocar (2100) to selectively release the distally extending protrusions and thereby enable separation of proximal housing (2102) proximally from housing cap plate (2108). As described below, latch ring (2110) is suitably oriented to avoid obstructing needle ports and needle guide tubes that define suture paths extending obliquely through trocar (2100).

As shown in FIG. 41, cannula (2104) includes a proximal hub (2118), a distal tip (2120), and a cylindrical body (2122) extending therebetween along the central axis of trocar (2100). Proximal hub (2118) flares radially outwardly from cylindrical body (2122) in a proximal direction and defines a proximal opening to a cannula lumen (2124), while distal tip (2120) defines a distal opening to cannula lumen (2124). Distal tip (2120) itself is beveled and includes a chamfered edge (2126) to facilitate insertion of distal tip (2120) through tissue and into a patient body cavity during a surgical procedure. An outer surface of cylindrical body (2122) may be provided with a plurality of tissue engagement ribs (2128) or other similar features suitable to frictionally engage the inner wall of a tissue opening through which cannula (2104) is received into the body cavity.

Figure 45B:
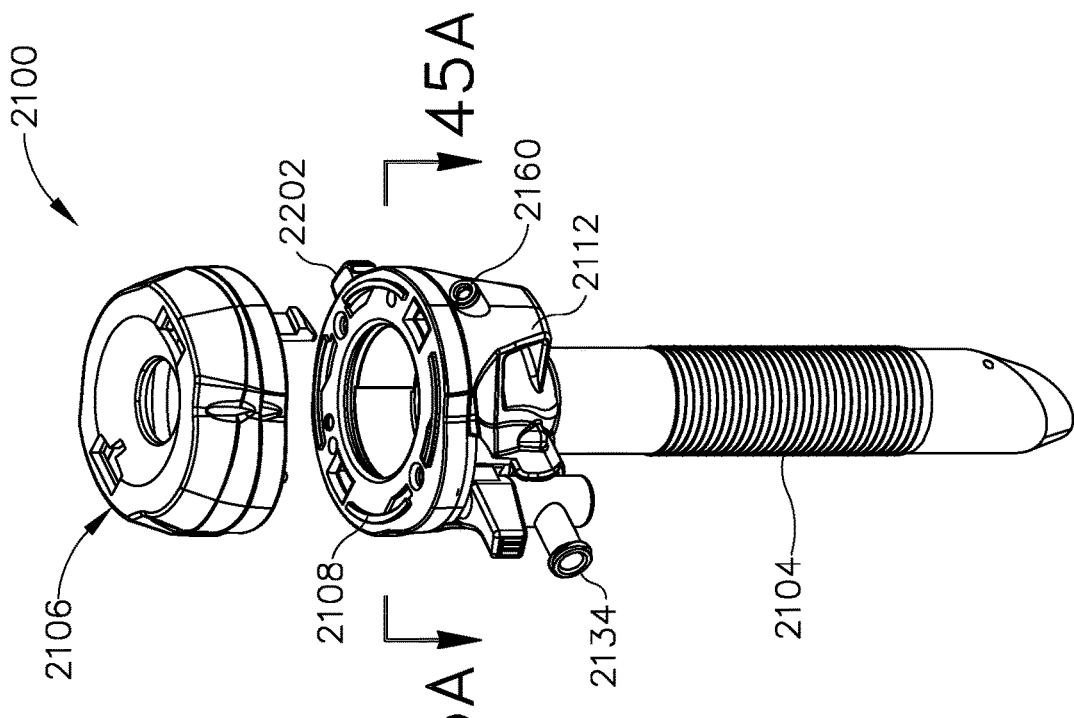
FIG. 45B depicts a front perspective view of the trocar of FIG. 40A, showing the proximal housing in a decoupled state corresponding to the latch ring rotational position of FIG. 44A.
Figure 46:
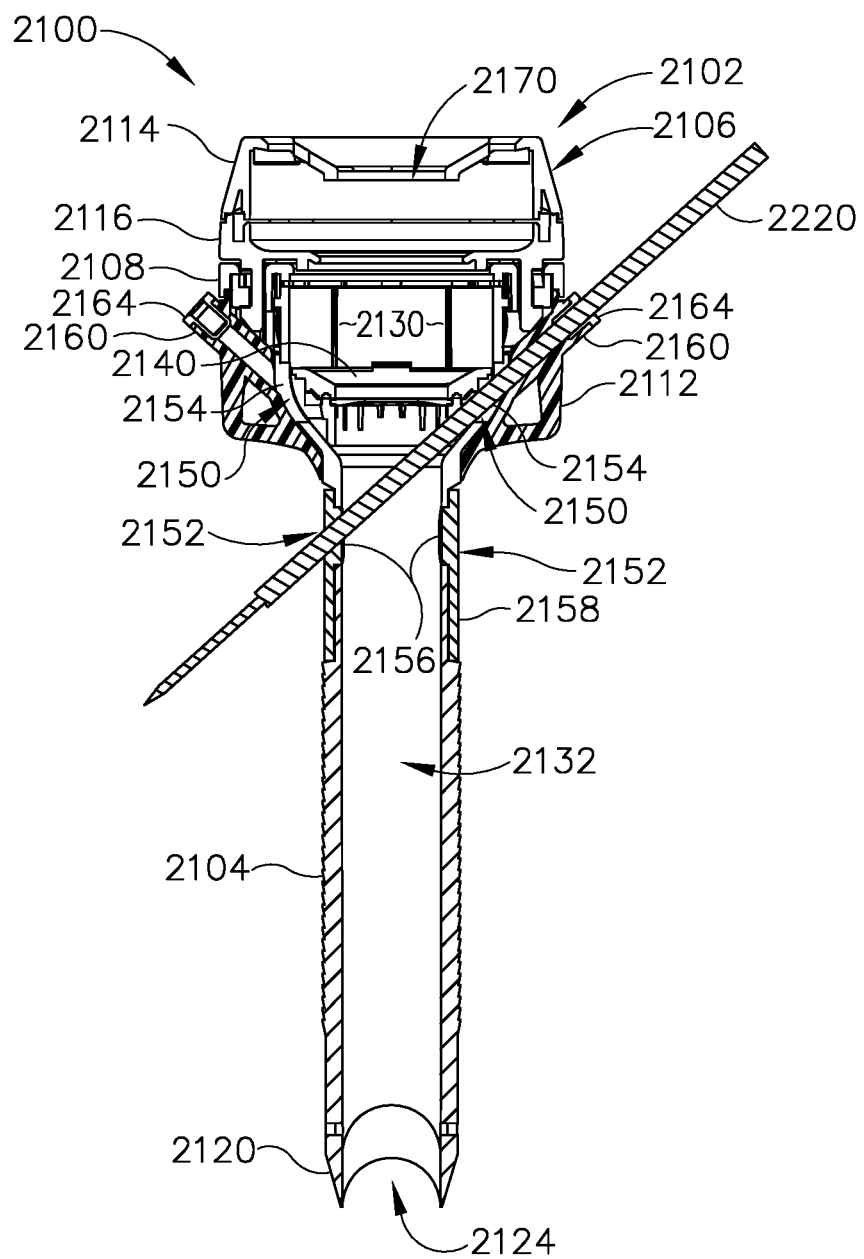
FIG. 46 depicts a side sectional view of the trocar of FIG. 40A, showing an exemplary suture needle passer extending through the trocar along a first suture path oriented obliquely relative to a central axis of the trocar.

Referring briefly to FIG. 46, cannula lumen (2124) fluidly communicates with an interior (2130) of housing (2102) to collectively define a working channel (2132) extending through trocar (2100) along the central axis thereof. A distal opening to working channel (2132) is defined by distal tip (2120) of cannula (2104), and a proximal opening to working channel (2132) is defined by proximal housing head (2114). In configurations in which proximal housing (2106) is decoupled from the remainder of trocar (2100), for example as described below with reference to FIG. 45B, the proximal opening to working channel (2132) is defined by housing cap plate (2108). Working channel (2132) is configured to receive one or more surgical instruments therethrough, such as a variety of endoscopic surgical instruments for example, for accessing the patient body cavity and observing and/or treating tissue accessible therein.

As shown in FIG. 41, an insufflation port (2134) (or "stopcock") is operatively connected to proximal hub (2118) of cannula (2104) at fitting (2136), and includes an internal valve (not shown) similar to valve (42) and a valve lever (2138). Insufflation port (2134) may be formed integrally with fitting (2136), or alternatively coupled to fitting (2136) during assembly of trocar (2100). Insufflation tubing (not shown) is coupled to an inlet of insufflation port (2134) and directs insufflation fluid, such as carbon monoxide, from a fluid source into insufflation port (2134), which directs the fluid distally through working channel (2132) into the patient body cavity. Valve lever (2138) is configured to rotate the internal valve (not shown) between open and closed positions to control the flow of insufflation fluid through insufflation port (2134).

Similar to trocar assembly (10), trocar (2100) may include a proximal (or "outer") seal assembly and/or a distal (or "inner") seal assembly each arranged within working channel (2132). In the present example, trocar (2100) includes a distal seal assembly in the form of an instrument seal (2140) arranged within a distal tapered portion of proximal hub (2118). Distal instrument seal (2140) includes a central opening (2142) configured to receive a surgical instrument therethrough, and is configured to sealingly engage an outer surface of a surgical instrument extending through central opening (2142) to prevent proximal advancement of bodily fluids and/or tissue into interior (2130) of housing (2102). In exemplary configurations, instrument seal (2140) may be configured to absorb or otherwise remove bodily fluids from the outer surface of the surgical instrument as the surgical instrument is retracted proximally through instrument seal (2140). Though not shown, trocar (2100) may further include a proximal seal assembly arranged within proximal housing (2106).

Those of ordinary skill in the art will recognize that trocar (2100) may include proximal and/or distal seal assemblies of various alternative configurations, such as those disclosed in U.S. patent application Ser. No. 15/088,723, issued as U.S. Pat. No. 10,299,785 on May 25, 2019, incorporated by reference above. For instance, though not shown, trocar (2100) may include a proximal seal assembly in the form of an instrument seal arranged within proximal housing (2106), and a distal seal assembly in the form of a zero-closure seal, such as a duckbill seal, arranged within proximal hub (2118) of cannula (2104). As described above with reference to trocar assembly (10), such a zero-closure seal is generally configured to form a fluid-tight seal in working channel (2132) and thereby maintain insufflation even when no surgical instrument is present in working channel (2132). Furthermore, the distal zero-closure seal may be manipulated to provide an opening to a distal portion of working channel (2132) (e.g., cannula lumen (2124)) that is large enough to enable extraction of tissue proximally therethrough, particularly when proximal housing (2106) is removed from trocar (2100) to provide access to the distal zero-closure seal.

As shown in FIG. 41, trocar (2100) further includes a plurality of needle ports formed in select side portions of cannula (2104). As described in greater detail below, each needle port is configured to direct a suture passer needle (or simply "suture passer") across working channel (2132) of trocar (2100) at an oblique angle relative to the central axis of trocar (2100) (see FIG. 46) to thereby establish an oblique suture path extending through trocar (2100) and adjacent tissue. As used herein, the term "oblique" means neither parallel nor perpendicular to the referenced axis, such as the central axis of trocar (2100).

In the present example, trocar (2100) includes a pair of needle entrance ports (2150) and a corresponding pair of needle exit ports (2152) arranged distally of needle entrance ports (2150). Needle entrance ports (2150) extend through respective side portions of proximal hub (2118) of cannula (2104) at diametrically opposed positions, and open to cannula lumen (2124). Needle exit ports (2152) extend through respective side portions of cylindrical body (2122) of cannula (2104) at diametrically opposed positions, and open to cannula lumen (2124). Each needle port (2150, 2152) is generally elongate along the central axis of trocar (100), though needle ports (2150, 2152) may be formed with various other shapes in alternative configurations.

Each needle entrance port (2150) is configured to cooperate with an opposing needle exit port (2152) to direct a suture passer needle along a respective oblique suture path. In particular, a needle entrance port (2150) on a first side of cannula (2104) cooperates with a needle exit port (2152) on an opposing second side of cannula (2104) to define a first oblique suture path. Similarly, a needle entrance port (2152) on the second side of cannula (2104) cooperates with a needle exit port (2152) on the opposing first side of cannula (2104) to define a second oblique suture path. In the present example, each needle exit port (2152) is positioned in circumferential alignment with the adjacent needle entrance port (2150), such that the resulting oblique suture paths define an X-shaped pattern in a single suture plane extending along the central axis of trocar (2100). In other examples, needle entrance ports (2150) and/or needle exit ports (2152) may be arranged in a non-diametrically opposed configuration, and/or needle exit ports (2152) may be circumferentially offset from needle entrance ports (2150), such that the resulting oblique suture paths lie in separate suture planes.

Each needle exit port (2152) may be spaced distally from its respective needle entrance port (2150) by a distance suitable to achieve a desired suture path angle (or "tissue bite angle") measured between the resulting suture path and the central axis of trocar (2100). In the present example, each needle exit port (2152) is spaced distally from its respective needle entrance port (2150) by the same axial distance, such that the resulting suture paths exhibit the same suture path angles. In other examples, however, needle exit ports (2152) may be spaced distally at different distances to achieve different suture path angles. Moreover, in various other examples, any suitable quantity and arrangement of needle entrance ports (2150) and needle exit ports (2152) may be provided.

Each needle port (2150, 2152) is provided with a pierceable seal configured to aid in maintaining insufflation when a suture passer needle is directed through trocar (2100) along the suture paths, and/or when the suture passer needle is withdrawn from trocar (2100). In the present example, each needle entrance port (2150) is provided with an entrance seal shown in the form of an elongate plug (2154), and each needle exit port (2152) is provided with an exit seal shown in the form of an elongate protrusion (2156) projecting radially inwardly from an inner surface of a cannula sleeve (2158). Each seal (2154, 2156) is shaped to sealingly engage its respective needle port (2150, 2152). As shown in FIGS. 40A-41, cannula sleeve (2158) is received over a narrowed region of cylindrical body (2122) of cannula (2104), and has an outer diameter similar to an outer diameter of a distal region of cylindrical body (2122) located distally of tissue engagement ribs (2128). In exemplary configurations, plugs (2154) and cannula sleeve (2158), including protrusions (2156), and may be formed of an elastomeric material. Additionally, cannula sleeve (2158) may be overmolded over cannula (2104) during manufacture.

Trocar (2100) further includes a pair of needle guide structures shown in the form of guide tubes (2160), each configured to guide a suture passer needle along the oblique suture path defined by the respective pair of needle entrance and exit ports (2150, 2152), described above. In the present example, needle guide tubes (2160) are formed integrally with distal housing (2112) and extend angularly through side wings (2162) of distal housing (2112). Each needle guide tube (2160) includes a proximal opening through which a suture passer needle is introduced, and a distal opening that confronts seal plug (2154) of a respective needle entrance port (2150), as shown in FIG. 46. Additionally, the entrance opening of each needle guide tube (2160) includes a seal cap (2164). As described in greater detail below with reference to FIGS. 47A and 47B, seal caps (2164) are pierceable by a suture passer needle and function in a manner similar to seal plugs (2154) to assist in maintaining insufflation during a surgical procedure. While the needle guide structures of the present example are shown in the form of needle guide tubes (2160), it will be appreciated that in alternative examples various other structures suitable to guide a suture passer needle along the oblique suture paths of trocar (2100) may be employed instead. In other examples, such needle guide structures may be omitted from trocar (2100).

As shown in FIGS. 40A-41, distal housing (2112) is in the form of a generally annular shell shaped to receive and encircle proximal hub (2118) of cannula (2104). A sidewall of distal housing (2112) includes a cutout (2166) that accommodates insufflation port (2134), which extends radially outwardly from proximal hub (2118). As described above, distal housing (2112) includes a pair of diametrically opposed side wings (2162) that support needle guide tubes (2160). During a surgical procedure, side wings (2162) may be gripped by a surgeon when introducing trocar (2100) through patient tissue. An upper edge (2168) of distal housing (2112) supports housing cap plate (2108) and latch ring (2110).

Figure 42A:
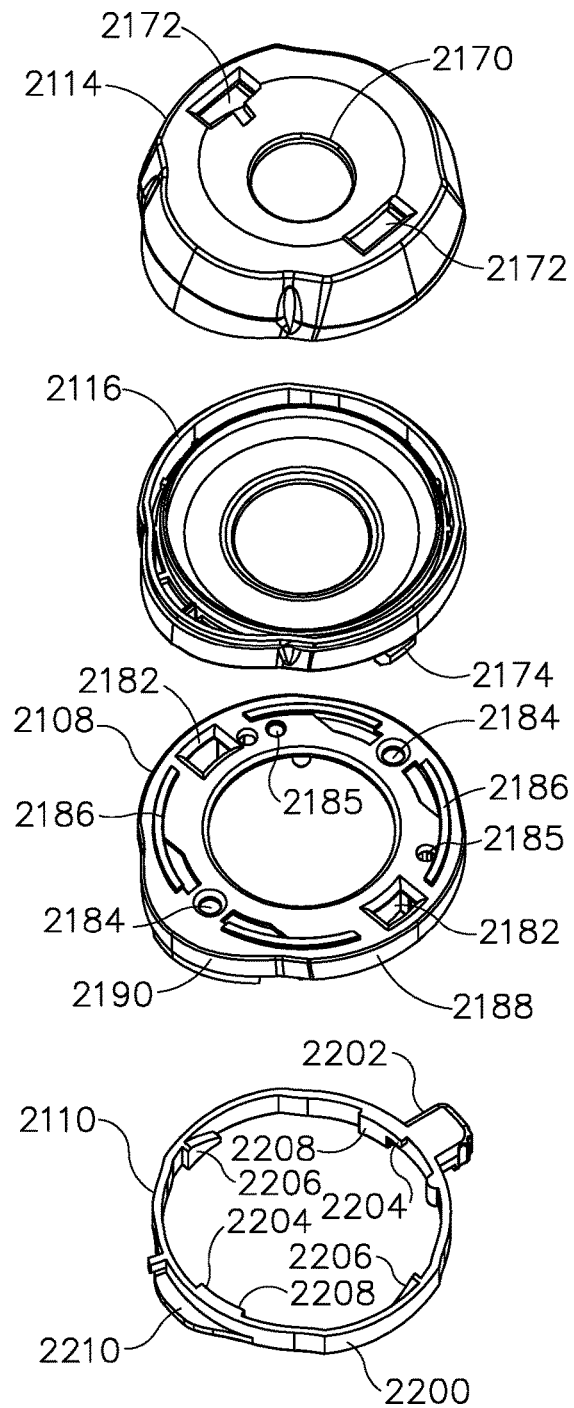
FIG. 42A depicts an exploded top perspective view of a portion of the trocar housing of FIG. 40A.
Figure 42B:
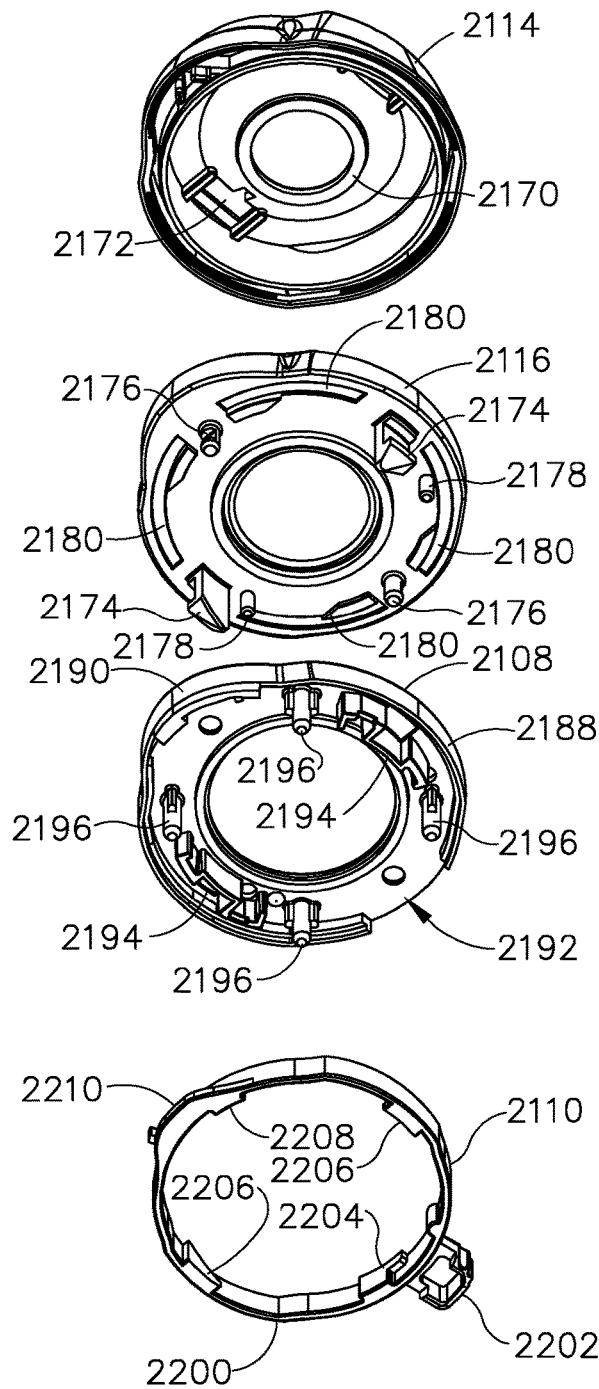
FIG. 42B depicts an exploded bottom perspective view of the housing portion of FIG. 42A.
Figure 43:
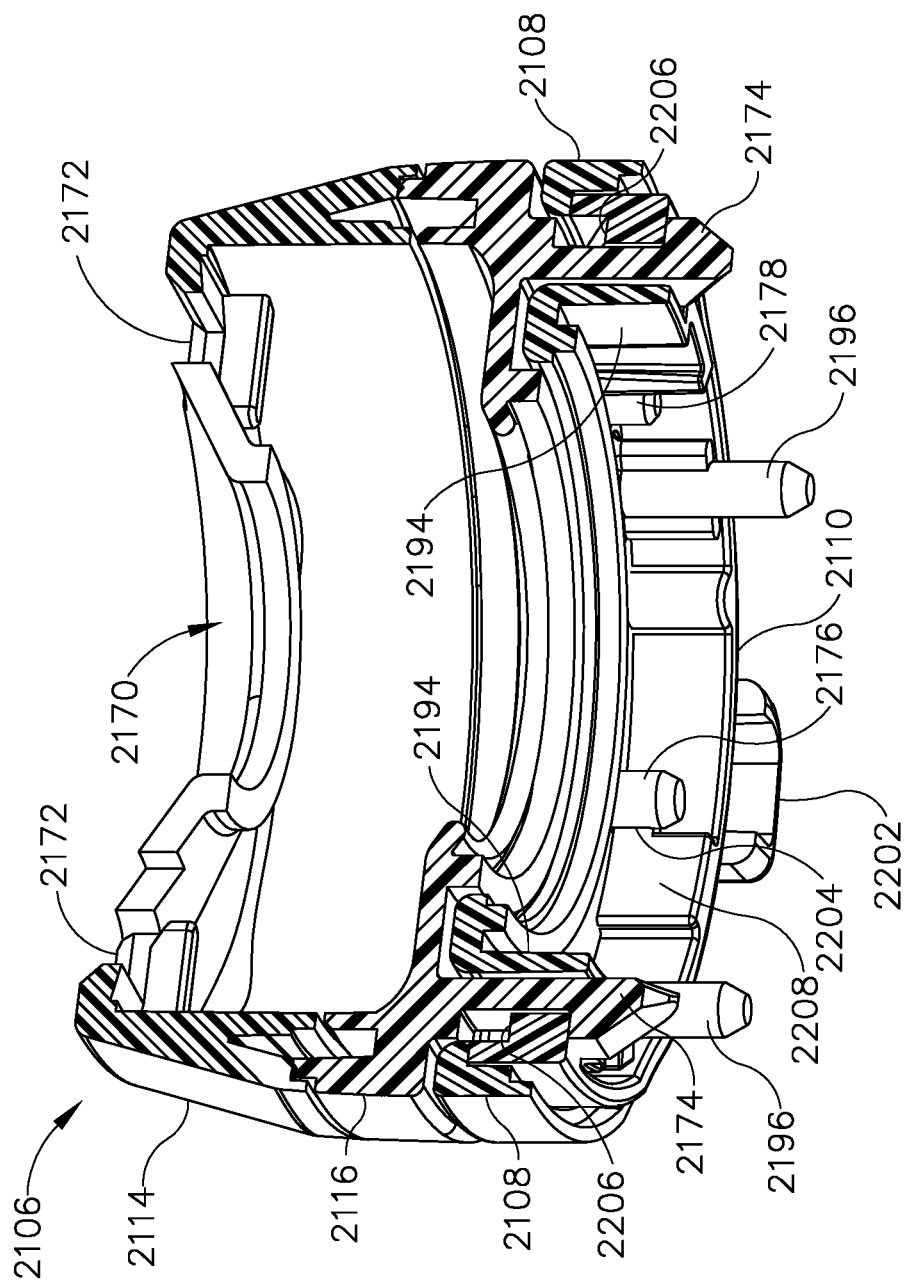
FIG. 43 depicts an assembled side sectional perspective view of the housing portion of FIG. 42A.

FIGS. 42A-43 show additional details of proximal housing head (2114), proximal housing base (2116), housing cap plate (2108), and latch ring (2110). Proximal housing head (2114) includes a central opening (2170) that defines a proximal end of working channel (2132) of trocar (2100). Proximal housing head (2114) further includes a pair of slots (2172) configured to receive a corresponding pair of tabs extending distally from the proximal head of an obturator, such as tabs (32) of obturator (14), for releasably connecting the obturator to trocar (2100). Proximal housing head (2114) is supported by and coupled to proximal housing base (2116), for example by a snap-fit connection. Though not shown, a proximal seal assembly, such as an instrument seal, may be arranged between proximal housing head and proximal housing base (2116). Such a proximal seal assembly may cooperate with distal seal assembly (2140), described above, to ensure a sealing engagement between trocar (2100) and a surgical instrument inserted through trocar (2100) while maintaining insufflation.

As described below, proximal housing (2106), defined by proximal housing head (2114) and proximal housing base (2116), is configured to couple with and selectively decouple from the remaining distal portion of trocar (2100) via operation of latch ring (2110) in combination with housing cap plate (2108). In that regard, proximal housing base (2116) further includes a plurality of distally extending mating features configured to facilitate attachment and release of proximal housing (2106) from housing cap plate (2108) and latch ring (2110). In particular, an underside of proximal housing base (2116) includes a pair of latching tabs (2174), a pair of latching posts (2176), a pair of guide pins (2178), and a plurality circumferentially extending arcuate recesses (2180). In the present example, four arcuate recesses (2180) are provided in respective quadrants of the underside of proximal housing base (2116). Additionally, latching tabs (2174) are arranged at diametrically opposed positions along a first transverse axis, and latching tabs (2174) are arranged at diametrically opposed positions along a second transverse axis that is perpendicular to the first transverse axis. Each guide pin (2178) is positioned circumferentially between a latching tab (2174) and an adjacent latching post (2176). In other examples, various alternative quantities and arrangements of latching tabs (2174), latching posts (2176), guide pins (2178), arcuate recesses (2180), and/or other like mating features, and corresponding mating features of housing cap plate (2108) and latch ring (2110) described below, may be provided.

As shown in FIG. 42A, housing cap plate (2108) includes a plurality of mating features configured and positioned to receive the above-described features of proximal housing base (2116) to promote coupling and rotational alignment of proximal housing (2106) with housing cap plate (2108) and latch ring (2110). In particular, housing cap plate (2108) includes a pair of tab slots (2182) configured to receive latching tabs (2174) therethrough, a pair of post bores (2184) configured to receive latching posts (2176) therethrough, a pair of pin bores (2185) configured to receive guide pins (2178) therethrough, and a plurality of circumferentially extending arcuate ribs (2186) configured to seat within arcuate recesses (2180). As described above, various alternative quantities and arrangements of these mating features may be provided in other examples.

Housing cap plate (2108) further includes a downwardly depending sidewall (2188) extending about an outer perimeter of housing cap plate (2108). A section of sidewall (2188) bulges radially outwardly to define a nose portion (2190) of housing cap plate (2108) that is centered on the axis along which post bores (2184) and latching posts (2176) are arranged. As shown in FIG. 40A, nose portion (2190) aligns with and overhangs a portion of insufflation port (2134). As shown in FIG. 42B, housing cap plate (2108) further includes a circumferentially extending slot (2192) formed in sidewall (2188) at a location opposite of nose portion (2190). Slot (2192) is configured to expose a user engagement feature projecting radially outwardly from latch ring (2110), as described below.

As shown in FIGS. 42B and 43, an underside of housing cap plate (2108) includes a pair of distally extending tab retaining walls (2194) aligned with tab slots (2182) and configured to abut and circumferentially constrain latching tabs (2174) when tabs (2174) are inserted through tab slots (2182). The underside of housing cap plate (2108) additionally includes a plurality of distally extending coupling posts (2196) configured to be received by a corresponding plurality of coupling bores (2198) formed on distal housing (2112), as shown in FIG. 41, for coupling housing cap plate (2108) with distal housing (2112). In exemplary configurations, coupling posts (2196) and coupling bores (2198) may be suitably shaped and sized respectively to couple with a press-fit or a snap-fit engagement.

As shown in FIGS. 42A-43, latch ring (2110) includes an annular body (2200) and a user engagement feature in the form of a knob (2202) projecting radially outwardly from annular body (2200). Latch ring (2110) further includes a plurality of latching features projecting radially inwardly from annular body (2200). In particular, latch ring (2110) includes a pair of latching arms (2204) arranged at diametrically opposed positions along a first transverse axis, and a pair of cam ramps (2206) arranged at diametrically opposed positions along a second transverse axis that is generally perpendicular to the first transverse axis. Each latching arm (2204) extends circumferentially from an adjoining base (2208) that may function as a secondary rotational stop for latch ring (2110), as described below. Latch ring (2110) additionally includes an arcuate fin (2210) configured to be received and move circumferentially within nose portion (2190) of housing cap plate (2108). Knob (2202) and arcuate fin (2210) are generally diametrically opposed from one another across annular body (2200).

Latch ring (2110) is arranged distally of housing cap plate (2108) and is housed radially inwardly of housing cap plate sidewall (2188) at a proximal end, as best shown in FIG. 43, and radially inwardly of distal housing (2112) at a distal end, as shown in FIG. 46. Latch ring (2110) is rotatable about the central axis of trocar (2100) between a latched position (see FIG. 44A) in which the latching features of latch ring (2110) capture the distally extending features of proximal housing base (2116), and an unlatched position (see FIG. 45A) in which the latching features of latch ring (2110) release the distally extending features of proximal housing base (2116) to thereby allow proximal detachment of proximal housing (2106). Latch ring (2110) is movable between the latched and unlatched positions by knob (2202), which projects radially through circumferential slot (2192) of housing cap plate (2108) and is movable circumferentially therein as latch ring (2110) rotates about the trocar central axis. In particular, circumferential slot (2192) may define the rotational range of latch ring (2110) such that a first end of slot (2192) defines the latched position and a second end of slot (2192) defines the unlatched position. In various configurations, proximal housing base (2116), housing cap plate (2108), and latch ring (2110) may be suitably configured to define any desired rotational range of latch ring (2110) relative to proximal housing base (2116) and housing cap plate (2108), which remain rotationally fixed.

FIG. 43 shows latch ring (2110) in an exemplary latched position. As latch ring (2110) is rotated into this latched position, from an unlatched position, each cam ramp (2206) is received within an outwardly facing notch of a respective latching tab (2174) of proximal housing base (2116). Simultaneously, each latching arm (2204) is received within an outwardly facing notch (see FIG. 42B) of a respective latching post (2176) of proximal housing base (2116). As latch ring (2110) is rotated further toward the latched position, the sloped surface of each cam ramp (2206) engages a proximal notch wall of the respective latching tab (2174), and the latching arms (2204) advance further within the notches of their respective latching posts (2176), thereby securing proximal housing (2106) axially against housing cap plate (2108). Latch ring (2110) may be rotated in the opposite direction to disengage cam ramps (2206) from latching tabs (2174) and latching arms (2204) from latching posts (2176), to thereby enable proximal detachment of proximal housing (2106) from the remaining distal portion of trocar (2100).

Rotation of latch ring (2110) between the latched and unlatched positions is limited by direct contact of latch ring knob (2202) with the ends of circumferential slot (2192) formed in housing cap plate (2108), which serves as a primary rotational stop. One or more secondary rotational stops may also be provided. For example, a side surface of each latching arm base (2208) is configured to abut a respective latching post (2176) of proximal housing base (2116), and a first end of fin (2210) is configured to abut a corresponding first inner surface of distal housing (2112) (see FIG. 44A), to prevent rotation of latch ring (2110) beyond the latched position. A second end of fin (2210) may be configured to abut a corresponding second inner surface of distal housing (2112) (see FIG. 45A) to prevent rotation of latch ring (2110) beyond the unlatched position. Though not shown, latch ring (2110) may be coupled with a resilient member configured to bias latch ring (2110) toward the latched position.

Figure 45A:
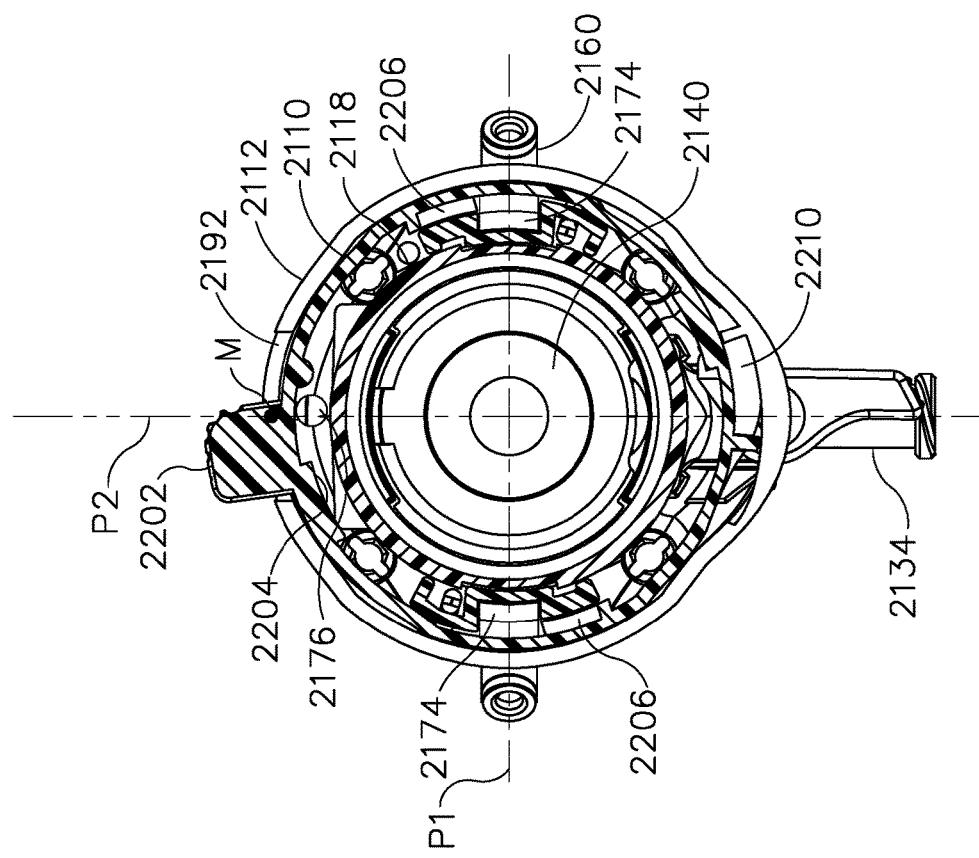
FIG. 45A depicts a top sectional view of the trocar of FIG. 40A, taken along section line 45A-45A shown in FIG. 45B, showing the latch ring in a second exemplary rotational position.

FIGS. 44A-45B show rotation of latch ring (2110) relative to the remainder of trocar (2100), including proximal housing base (2116) and housing cap plate (2108), between the latched position (FIGS. 44A-44B) and the unlatched position (FIGS. 45A-45B). FIG. 44A shows latch ring (2110) in the latched position in which cam ramps (2206) and latching arms (2204) engage latching tabs (2174) and latching posts (2176), respectively, of proximal housing base (2116). As shown in FIG. 44B, this position of latch ring (2110) maintains proximal housing (2106) in axial engagement with the remaining distal portion of trocar (2100). FIG. 45A, by comparison, shows latch ring (2110) after having been rotated to the unlatched position such that cam ramps (2206) and latching arms (2204) disengage latching tabs (2174) and latching posts (2176), respectively. As shown in FIG. 45B, this position of latch ring (2110) enables proximal housing (2106) to be removed proximally from the remaining distal portion of trocar (2100).

As shown in FIGS. 44A and 45A, needle guide tubes (2160) are oriented at diametrically opposed positions along a first axial plane (P1) extending along and through (i.e., containing) the central axis of trocar (2100). Additionally, latch ring (2110) is oriented such that knob (2202) is movable within circumferential slot (2192) along a circumferential path having a midpoint (M) that is diametrically opposed from insufflation port (2134) along a second axial plane (P2) extending along and through the central axis of trocar (2100). In the present example, first axial plane (P1) and second axial plane (P2) are perpendicular to one another. Accordingly, path midpoint (M) is spaced circumferentially equidistantly between needle guide tubes (2160) and their respective needle ports (2150, 2152); specifically, at approximately 90 degrees in the present example. Consequently, latch ring knob (2202) remains circumferentially spaced (or "offset") from needle guide tubes (2160) and needle ports (2150, 2152) throughout the full range of permissible rotation of latch ring (2110). Advantageously, this configuration prevents undesirable interference between knob (2202) and a suture passer needle being directed through needle guide tubes (2160) and needle ports (2150, 2152), as shown in FIG. 46.

As used herein with reference to various first and second structures or reference points, such as path midpoint (M) and insufflation port (2134) described above, the term "diametrically opposed" encompasses but is not limiting to a configuration in which the referenced structures or reference points are located at the same longitudinal location along the central axis of trocar (2100). Indeed, in the present example shown throughout FIGS. 40A-45B, path midpoint (M) for latch ring knob (2202) is spaced proximally from insufflation port (2134), though midpoint (M) and port (2134) are still understood to be diametrically opposed from one another along axial plane (P2), shown in FIGS. 9A and 10A.

Those of ordinary skill in the art will recognize that various other configurations of housing (2102) and cannula (2104) as described above may be provided such that latch ring knob (2202) remains circumferentially spaced (or "offset") from needle guide tubes (2160) and needle entrance ports (2150) throughout the full range of permissible rotation of latch ring (2110). In such alternative configurations, midpoint (M) of the circumferential path along which knob (2202) travels may or may not be spaced circumferentially equidistantly between needle guide tubes (2160) and needle entrance ports (2150). In various examples, path midpoint (M) may be circumferentially spaced from one or more of needle guide tubes (2160) and the respective needle entrance port (2150) by less than, greater than, or equal to 90 degrees. Furthermore, in other examples as described above, needle guide tubes (2160) and their respective needle entrance ports (2150), and/or needle exit ports (2152), may be positioned in non-diametrically opposed arrangements.

FIG. 46 shows a side sectional view of trocar (2100) with an exemplary suture passer needle (2220) inserted therethrough along an oblique suture path extending through needle guide tube (2160), needle entrance port (2150), across working channel (2132), and through needle exit port (2152). As described above, each oblique suture path passing through trocar (2100) includes a plurality of pierceable seals, including a guide tube entrance seal (2164), a needle entrance port seal (2154), and a needle exit port seal (2156). Each seal (2154, 2156, 2164) is configured to assist in maintaining insufflation when suture passer needle (2220) is inserted through trocar (2100) along the suture path, and/or when suture passer needle (2220) is withdrawn from trocar (2100).

Figure 47A:
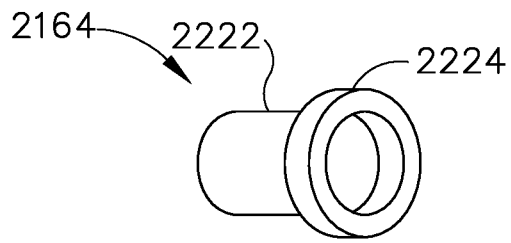
FIG. 47A depicts a perspective view of an exemplary pierceable seal provided at the entrance ends of first and second needle guide tubes of the trocar of FIG. 40A.

As described above, the guide tube entrance seals of the present example are shown in the form of seal caps (2164). FIG. 47A shows additional details of seal cap (2164), which includes a cylindrical body (2222) and a proximal rim (2224) defining a proximal opening to seal cap (2164). Cylindrical body (2222) is formed with an outer diameter sized to be received within a proximal end of a needle guide tube (2160), and includes a closed distal end that is pierceable by suture passer needle (2200), as shown in FIG. 46. Cylindrical body (2222) and proximal rim (2224) define an inner dimeter sized to sealingly engage an outer surface of suture needle passer (2220) upon insertion through trocar (2100).

Figure 47B:
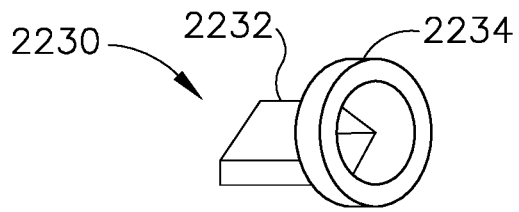
FIG. 47B depicts a perspective view of another exemplary pierceable seal provided at the entrance ends of first and second needle guide tubes of the trocar of FIG. 40A.

FIG. 47B shows another exemplary seal cap (2230) having a body (2232) and a proximal rim (2234) defining a proximal opening to seal cap (2230). Body (2232) may be in the form of a duckbill seal or a tab having a closed distal end, for example. Proximal rim (2234) defines a first inner dimension of seal cap, and body (2232) defines a second smaller inner dimension of seal cap (2230). In some variations, the second inner dimension defined by body (2232) may taper distally. Seal caps (2164, 2230) described above may be formed separately from housing (2102) and cannula (2104) and assembled with needle guide tubes (2160) during manufacture of trocar (2100). In other examples, seal caps (2164, 2230) may be co-molded with needle guide tubes (2160) in a single operation.

B. Exemplary Needle Guide Tubes

Figure 48:
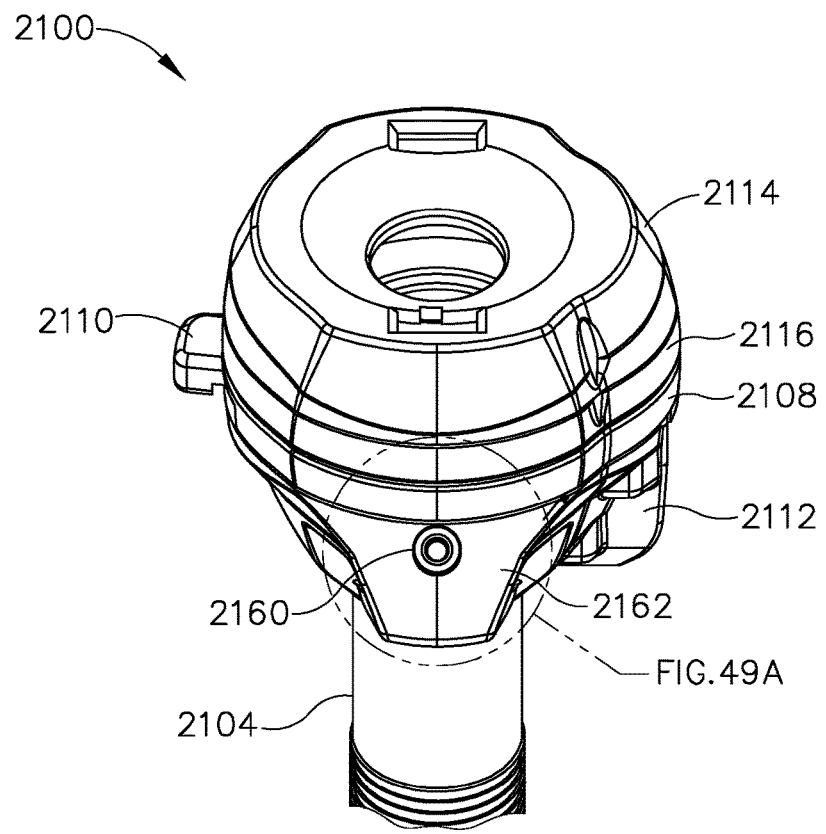
FIG. 48 depicts a side perspective view of the trocar of FIG. 40A.
Figures 49A, 49B, 49C:
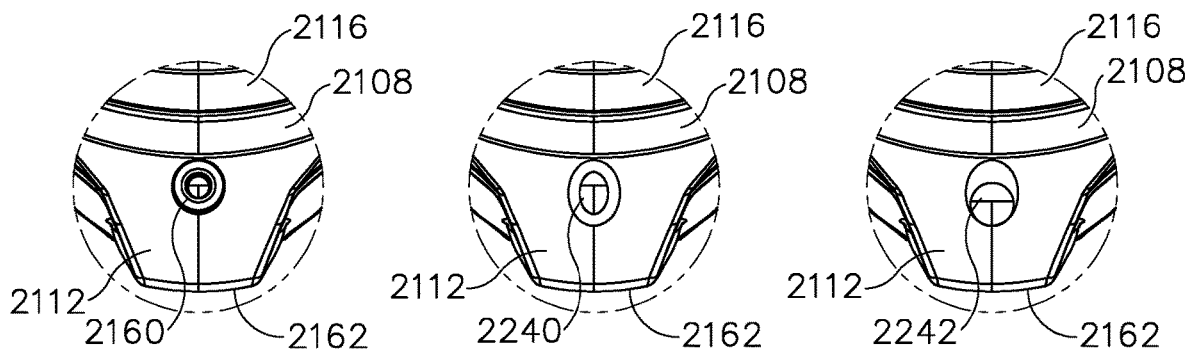
FIG. 49A depicts an enlarged perspective view of a region indicated in FIG. 48, showing details of a needle guide tube of the trocar.
FIG. 49B depicts an enlarged perspective view showing details of a needle guide tube shaped according to an exemplary variation of the needle guide tube of FIG. 49A.
FIG. 49C depicts an enlarged perspective view showing details of a needle guide tube shaped according to another exemplary variation of the needle guide tube of FIG. 49A.

FIGS. 48 and 49A show additional details of needle guide tubes (2160) of trocar (2100). In the present example, needle guide tubes (2160) are formed with a generally circular cross-section. In other examples, needle guide tubes (2160) may be formed with various alternatively shaped cross-sections to facilitate insertion of suture passer needles. For example, FIG. 49B shows an exemplary alternative configuration in which distal housing (2112) is provided with needle guide tubes (2240) having a generally oval cross-section. FIG. 49C shows another exemplary configuration in which distal housing (2112) is provided with needle guide tubes (2242) having entrance ends that are recessed inwardly within an outer surface of side wings (2162), which may also serve to ease insertion of suture passer needles. Guide tubes (2242) may be provided with any suitably shaped cross-section, such as a circular cross-section, for example.

C. Exemplary Suturing Procedure Using Trocar Having Needle Ports

FIGS. 50A-50E schematically illustrate steps of an exemplary procedure for suturing closed an opening (258) (see FIG. 50D) formed in tissue (217) by trocar (2100) during insertion for accessing body cavity (18). Advantageously, the features of trocar (2100) described above enable a surgeon to leave trocar (2100) in place within opening (258) and use trocar (2100) as a needle guide mechanism for directing suture thread (2250) distally through tissue (17) and into cavity (18) at desired suture angles to achieve an appropriate degree of "tissue bite" in lower fascia layers (56) of tissue (17). As used herein, the term "tissue bite" refers to the amount of tissue (17) captured by a suture thread. In the present context, tissue bite is defined by a distance (X) (see FIG. 50E) measured perpendicularly from the inner wall of tissue opening (58), which may coincide with the outer surface of cannula (2104), to the point at which a suture passer needle and thus suture thread (2250) exits distally from fascia (56) into body cavity (18).

FIG. 50A shows trocar cannula (2104) extending distally through a portion of upper fat layers (54) and through a full thickness of lower fascia layers (56) of patient tissue (17), and into body cavity (18). All surgical instruments (not shown) have been withdrawn from trocar (2100) such that working channel (2132) is clear. FIG. 50B shows insertion of an exemplary suture passer needle (2252) distally through a needle guide tube (2160) and along the respective first suture path as generally described above. A distal tip (2254) of suture passer needle (2252) carries an end (2256) of suture thread (2250) along the suture path, through fascia (56) and into body cavity (18). As described above, needle guide tubes (2160) and needle ports (2150, 2152) are positioned such that the resulting suture paths are angled obliquely relative to the central axis of trocar (2100).

Once suture thread end (2256) has been delivered into cavity (18), suture passer needle (2252) releases suture thread end (2256) and is withdrawn proximally from trocar (2100). As shown in FIG. 50C, suture passer needle (2252) is then re-inserted distally through the opposing needle guide tube (2160) and along the respective second suture path into cavity (18). Suture passer needle (2252) is then manipulated by a surgeon to recapture suture thread end (2256) with needle tip (2254). Once captured, thread end (2256) and needle are withdrawn proximally through trocar (2100) along the second suture path.

FIG. 50D shows trocar (2100) and suture thread (2250) following proximal removal of suture passer needle (2252) along the second suture path. In the present configuration, suture thread (2250) includes a first thread leg (2258) passing distally along the first suture path and through a first captured portion of fascia (56) located on a first side of tissue opening (58); a second thread leg (2260) passing distally along the second suture path and through a second captured portion of fascia (56) located on a second side of tissue opening; and an anchoring loop (2262) extending through cavity (18) between the first and second captured portions of fascia (56). As shown in FIG. 50D, trocar (2100) is withdrawn proximally from tissue opening (58) to allow thread legs (2258, 2260) to advance distally through needle guide tubes (2160) and along their respective suture paths, thereby releasing suture thread (2250) from trocar (2100).

As shown in FIG. 50E, once trocar (2100) has been fully disengaged from suture thread (2250), thread legs (2258, 2260) may be pulled tight to draw together fascia (56) on either side of tissue opening (58), and then tied to form a suture knot (2264) at a location just proximally of fascia layers (56). Optionally, the remaining portions of thread legs (2258, 2260) may be directed through fat layers (54) and skin (52) using suture needles, for example as shown in FIG. 4D using needles (62), to create an additional "superficial" suture knot to fully close tissue opening (58) and promote healing.

Figures 51A, 51B:
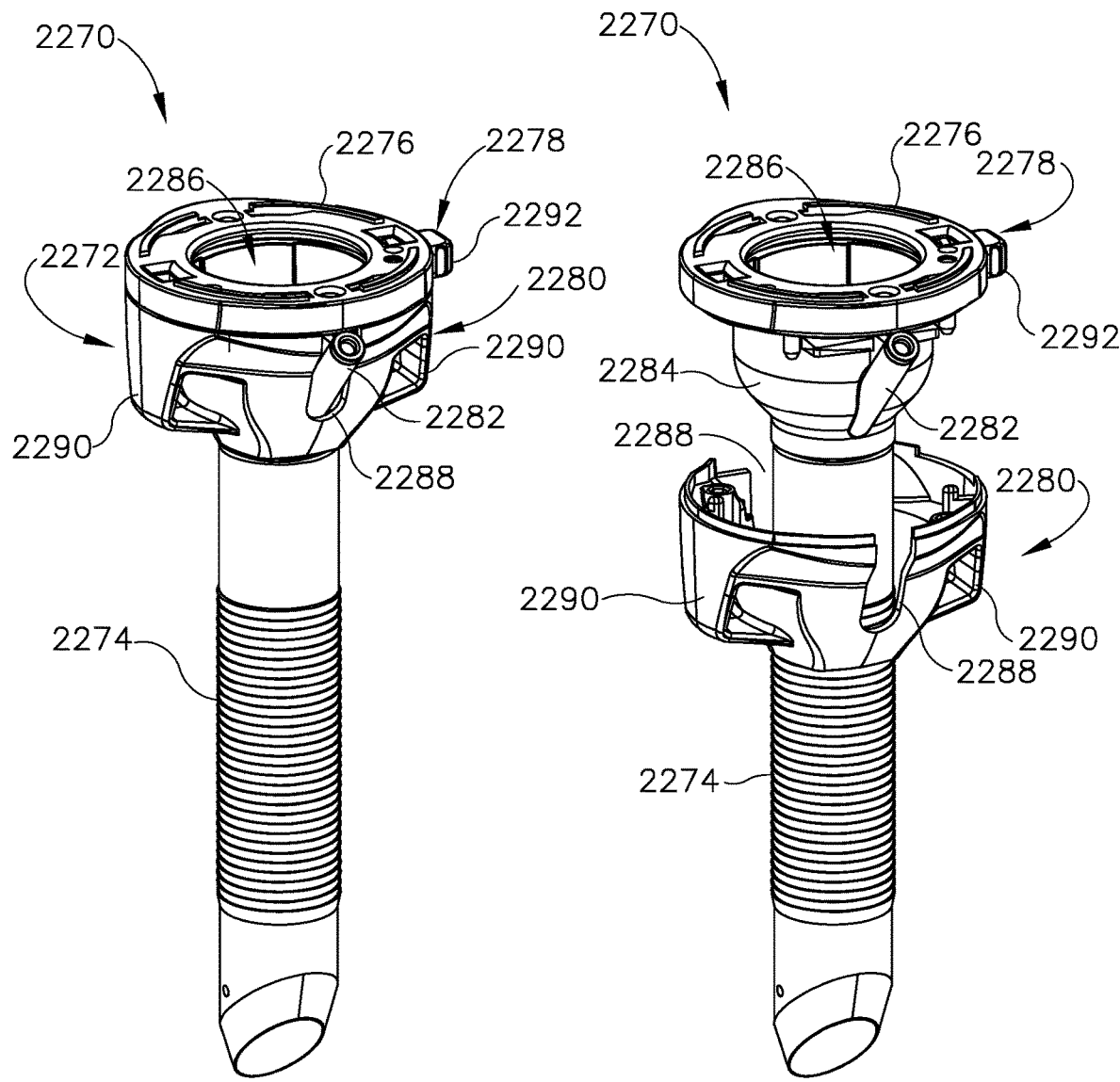
FIG. 51A depicts a perspective view of another exemplary trocar having needle guide tubes that are integrally molded with the cannula.
FIG. 51B depicts a partially disassembled perspective view of the trocar of FIG. 51A.

VII. Exemplary Trocar Having Distal Housing with Integrally Formed Needle Guide Tubes FIGS. 51A and 51B show another exemplary trocar (2270). Trocar (2270) is similar to trocar (2100) in that trocar (2270) includes a housing (2272) and a cannula (2274) coupled to and extending distally from housing (2272) along a central axis of trocar (2270). Housing (2272) includes a proximal housing (2 not shown), a housing cap plate (2276), a latch ring (2278), and a distal housing (2280). These components are substantially similar in structure and function to the corresponding components of trocar (2100) described above, except as otherwise described below. In particular, trocar (2270) includes first and second needle guide tubes (2282) that are formed integrally with proximal hub (2284) of cannula (2274), rather than with distal housing (2280). Distal ends of needle guide tubes (2282) open directly to a working channel (2286) of trocar (2270), and thus needle guide tubes (2282) define the needle entrance ports to working channel (2286). Plug seals (2154) received within needle entrance ports (2150) of trocar (2100) may be omitted from trocar (2270).

Distal housing (2280) of trocar (2270) includes a pair of axially extending slots (2288) sized and shaped to accommodate needle guide tubes (2282) therethrough when distal housing (2280) is connected to housing cap plate (2276) during device assembly. In the present example, distal housing (2280) is oriented such that slots (2288) are arranged in sidewalls of distal housing (2280) extending between side wings (2290) of distal housing (2280). In alternative configurations, slots (2288) may be arranged in side wings (2290) or in various other portions of distal housing (2280). Similar to trocar (2100) described above, trocar (2270) is configured such that a knob (2292) of latch ring (2278) remains circumferentially spaced from each of needle guide tubes (2282) throughout a full range of permissible rotation of latch ring (2278) relative to housing cap plate (2276). As described above in connection with trocar (2100), such a configuration ensures unobstructed access to needle guide tubes (2282) during use.

Figure 52:
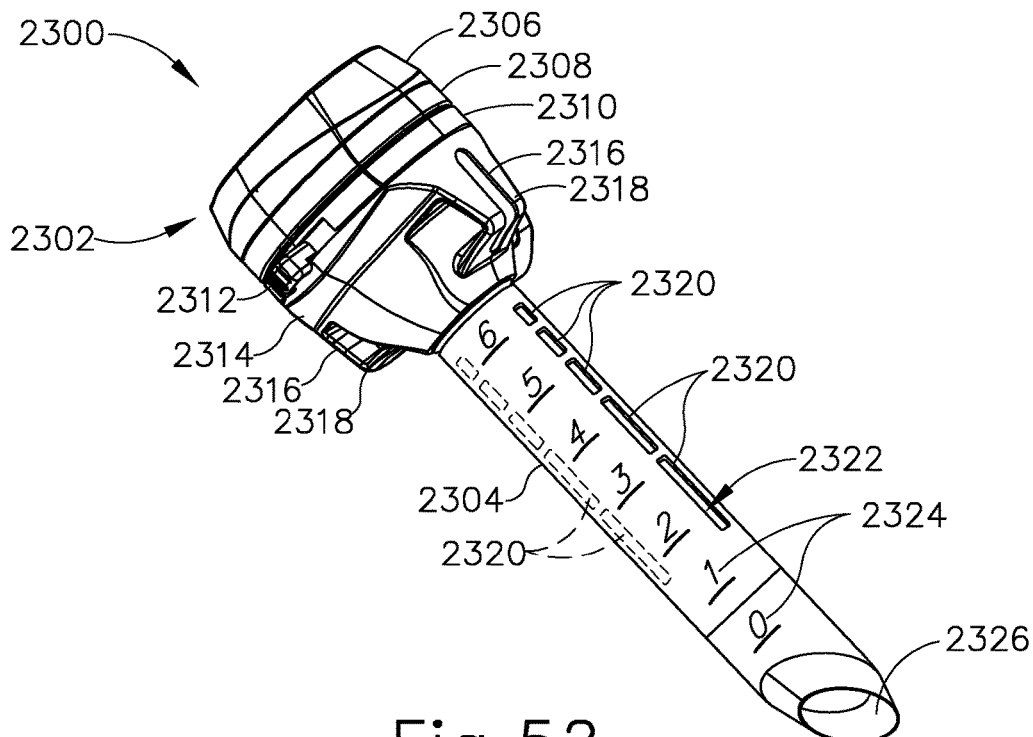
FIG. 52 depicts a perspective view of another exemplary trocar including a housing and a cannula having a plurality of axially spaced needle ports and corresponding indicia.

VIII. Exemplary Trocar Having Suturing Features for Use with Various Tissue Thicknesses FIG. 52 shows another exemplary trocar (2300) configured for use with patient tissue of various thicknesses. Trocar (2300) is similar to trocar (2100) in that trocar (2300) includes a housing (2302) and a cannula (2304) coupled to and extending distally from housing (2302) along a central axis of trocar (2300). Housing (2302) includes a proximal housing having a proximal housing head (2306) and a proximal housing base (2308), a housing cap plate (2310), a latch ring (2312), and a distal housing (2314). These components are substantially similar in structure and function to the corresponding components of trocar (2100) described above, except as otherwise described below. In particular, distal housing (2314) includes needle guide structures in the form of slots (2316) formed in side wings (2318). Additionally, cannula (2304) includes a plurality of elongate needle ports (2320) spaced axially along opposing sides of cannula (2304). Each needle port (2320) is provided with a pierceable seal (2322), which may include an axial slit (not shown) to ease passage of a suture passer needle through seal (2322).

Cannula (2304) of trocar (2300) further includes visual indicia shown in the form of tissue depth graduation marks (2324) spaced axially along a length of cannula (2304). Marks (2324) may indicate any suitable distance increments, such as inches or centimeters for example, and subdivisions of each increment. Marks (2324) are configured to communicate to a surgeon a depth, measured from cannula tip (2326), to which cannula (2304) has been inserted within patient tissue. For example, during or after insertion of cannula (2304) into tissue, a surgeon may observe a distalmost mark (2324) that is visible extracorporeally to determine a depth to which cannula (2304) has been inserted into the tissue, which may indicate a thickness of the tissue. Those of ordinary skill in the art will appreciate that any one or more of the features of trocar (2300) may be incorporated into any of the other exemplary trocars described herein.

Figure 53A:
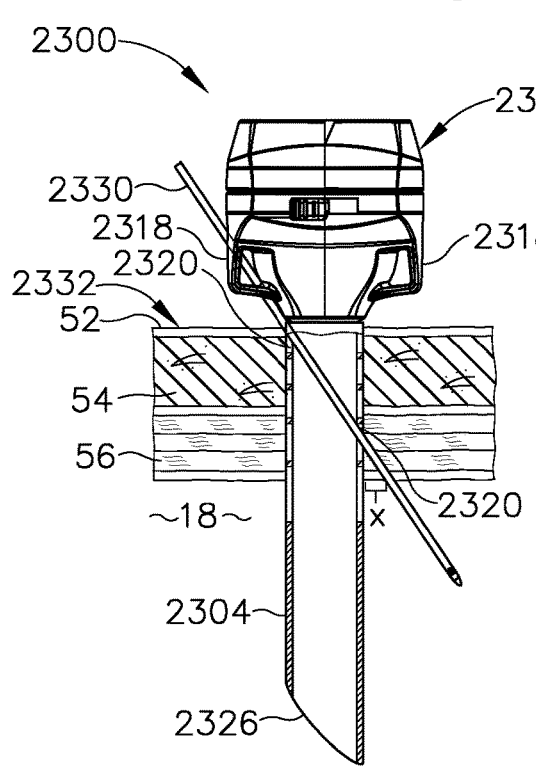
FIG. 53A depicts a schematic side sectional view of the trocar of FIG. 52 positioned within tissue of a first thickness, showing a suture passer device extending distally through the trocar and tissue along a first exemplary suture path defining a first oblique angle relative to a central axis of the trocar.
Figure 53B:
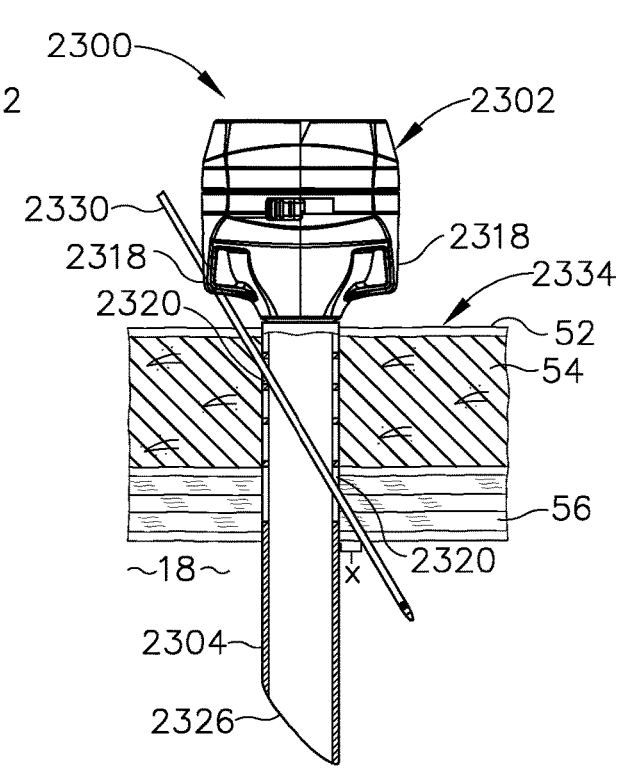
FIG. 53B depicts a schematic side sectional view of the trocar of FIG. 52 positioned within tissue of a second thickness, showing the suture passer device extending distally through the trocar and tissue along a second exemplary suture path defining a second oblique angle relative to the central axis of the trocar.

As shown in FIGS. 52-53B, elongate needle ports (2320) increase in length along cannula (2304) to allow a suture passer needle (2330) to be directed through trocar (2300) at a selected suture path angle, measured relative to a central axis of trocar (2300), of a plurality of available suture path angles. This enables trocar (2300) to be used as a suturing guide mechanism with tissues exhibiting a range of tissue thicknesses, while maintaining a consistent tissue bite distance (X) across the range of tissue thickness. FIG. 53A shows trocar (2300) inserted through tissue (2332) of a first thickness. Suture needle passer (2330) is inserted through a first pair of needle ports (2320) to define a first suture path angle and a tissue bite distance (X). FIG. 53B shows trocar (2300) inserted through tissue (2334) of a greater thickness than tissue (2332). Suture needle passer (2330) is inserted through a second pair of needle ports (2320) to define a second suture path angle while maintaining substantially the same tissue bite distance (X) shown in FIG. 53A.

IX. Exemplary Trocar for Applying Multiple Sutures at Same Surgical Site

In some instances, it may be desirable to apply multiple suture threads for closing an opening formed in patient tissue by a trocar cannula. For example, in instances in which the tissue opening is formed by a trocar cannula having a diameter of approximately 15 mm or greater, application of multiple suture threads may ensure effective closing of the tissue opening to promote complete and proper healing of the tissue. Accordingly, it may be desirable to provide one or more variations of any of the above-described trocars that includes suture features of suitable quantity and arrangement to facilitate application of multiple suture threads for closing a tissue opening.

FIGS. 54-56 show an exemplary variation of trocar (2100) in the form of trocar (2340), having suture features configured to facilitate application of first and second suture threads for closing a single tissue opening formed by trocar (2340). Trocar (2340) is similar to trocar (2100) in that trocar (2340) includes a housing (2342) and a cannula (2344) coupled to and extending distally from housing (2342) along a central axis of trocar (2340). Housing (2342) includes a proximal housing (2346), a housing cap plate (2348), a latch ring (2350) having a user engagement feature (2352), and a distal housing (2354). Cannula (2344) and housing together define a working channel (2356) extending through trocar (2340) along the central axis thereof. These components of trocar (2340) are substantially similar in structure and function to the corresponding components of trocar (2100) described above, except as otherwise described below. For example, like trocar (2100), trocar (2340) includes a distal seal assembly (2358), shown in FIG. 54, that separates a lumen of cannula (2344) from an interior of housing (2342). However, unlike distal seal assembly (2140) of trocar (2100), distal seal assembly (2358) is shown in the form of a duckbill seal. Further, trocar (2340) includes a proximal seal assembly (2360) in the form of an instrument seal supported within proximal housing (2346), as shown in FIG. 55.

Distal housing (2354) of trocar (2340) includes four needle guide tubes (2362) defining respective needle entrance ports, and four needle exit ports (2364) arranged on cannula (2344), each needle exit port (2364) corresponding to a respective needle guide tube (2362). Each needle guide tube (2362) and its respective needle exit port (2364) defines a suture path, indicated by axes (A1, A2, A3, A4) in FIG. 56, extending distally through and obliquely relative to the central axis of trocar (2340). Each needle port (2362, 2364) opens to working channel (2356) and is sealed by a respective pierceable seal. Specifically, an entrance end of each needle guide tube (2362) is sealed by a respective pierceable seal cap (2366), which may be similar to seal caps (2164, 2230) described above. Each needle exit port (2364) is sealed by a respective pierceable seal protrusion (2368) projecting radially inwardly from an inner surface of a cannula sleeve (2370), which may be similar to cannula sleeve (2158) described above.

In the present example, latch ring (2350) is oriented rotationally about the central axis of trocar (2340) such that its user engagement feature (2352) is generally diametrically opposed from an insufflation port (2372). Additionally, needle guide tubes (2362) and their respective needle exit ports (2364) are arranged circumferentially about the central axis such that each needle guide tube (2362) is circumferentially spaced from user engagement feature (2352) and from insufflation port (2372). As shown best in FIG. 55, user engagement feature (2352) is spaced circumferentially equidistantly between a first pair of needle guide tubes (2362), and insufflation port (2372) is spaced circumferentially equidistantly between a second pair of needle guide tubes (2362). Each needle exit port (2364) is positioned to align with a respective needle guide tube (2362) arranged along the corresponding suture path. In alternative examples, various other quantities and arrangements of needle guide tubes (2362) and their respective needle exit ports (2364) may be provided.

In use, each needle guide tube (2362) and its respective needle exit port (2364) cooperate with an opposed needle guide tube (2362) and its needle exit port (2364) to guide application of a suture thread (not shown) to tissue. Application of each of the first and second suture threads may be performed using the exemplary procedure described above in connection with FIGS. 50A-50D, for example. As is evident in FIG. 55, needle guide tubes (2362) and needle exit ports (2364) are circumferentially arranged such that the applied first and second suture threads cross over one another to define an X-shaped pattern in the tissue when viewed from above. It will be appreciated that any suitable circumferential spacing between needle guide tubes (2362), and between needle exit ports (2364), may be provided to achieve a desired suture pattern and resulting closure effect on the tissue opening.

Though not shown, the needle guide structures of any of the examples disclosed herein may be coupled to one or more rotatable structures configured to rotate about the central axis of the respective trocar. Examples of such a configuration are disclosed in U.S. application Ser. No. 15/637,688, entitled "Trocar with Oblique Needle Insertion Port and Coplanar Stopcock," filed on Jun. 29, 2017, issued as U.S. Pat. No. 10,485,580 on Nov. 26, 2019, the disclosure of which is incorporated by reference herein. This rotating configuration enables the suture path corresponding to each needle guide structure to be selectively rotationally positioned about the trocar central axis during use. Further, such a configuration may include one or more detents or other rotational limiting mechanisms suitably positioned to define various predetermined rotational positions of the one or more rotatable structures. The trocar cannula may be provided with a plurality of needle ports arranged circumferentially about the central axis to account for the various rotational positions of the needle guide structures. In various examples, the one or more rotatable structures may be incorporated within or coupled to the cannula or any portion of the housing, for instance.

X. Exemplary Surgical Access Devices Having Wound Closure Features

Figure 57:
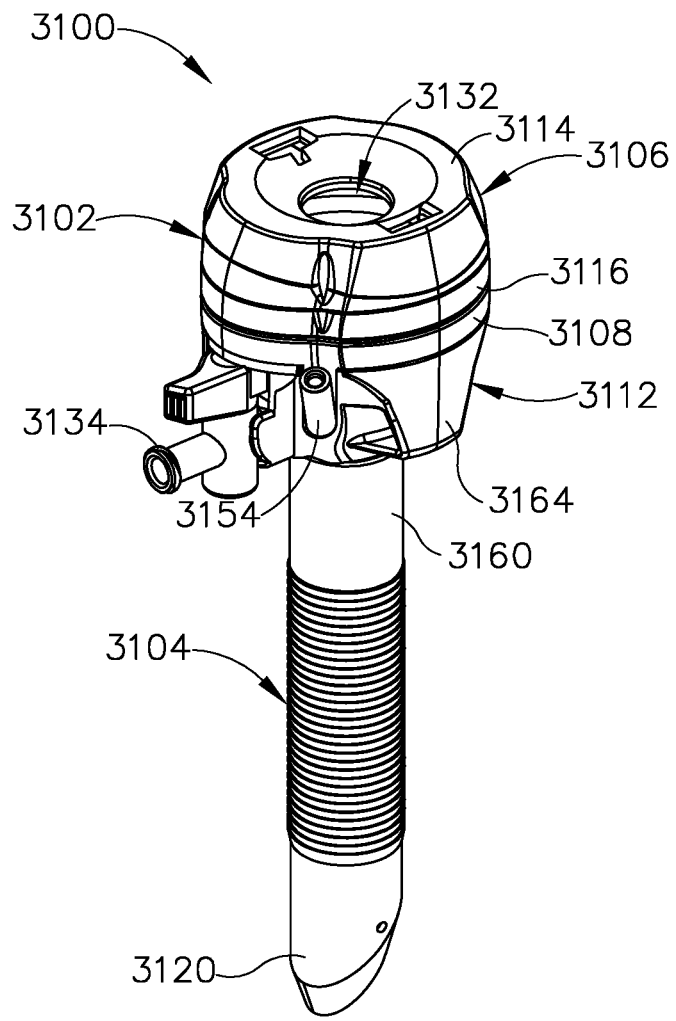
FIG. 57 depicts a perspective view of an exemplary trocar having a housing assembly, cannula, and needle ports.
Figure 58:
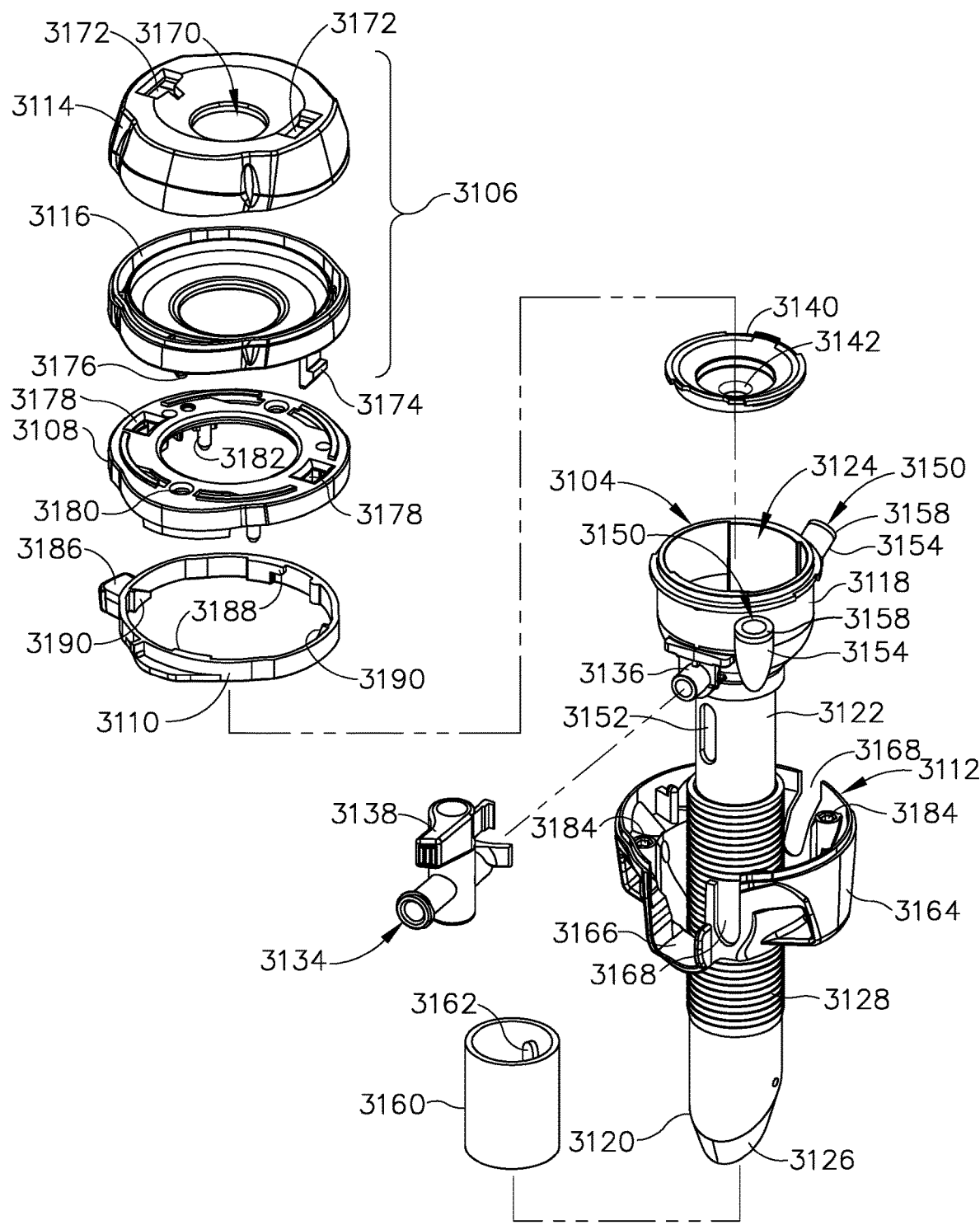
FIG. 58 depicts an exploded perspective view of the trocar of FIG. 57.
Figure 59:
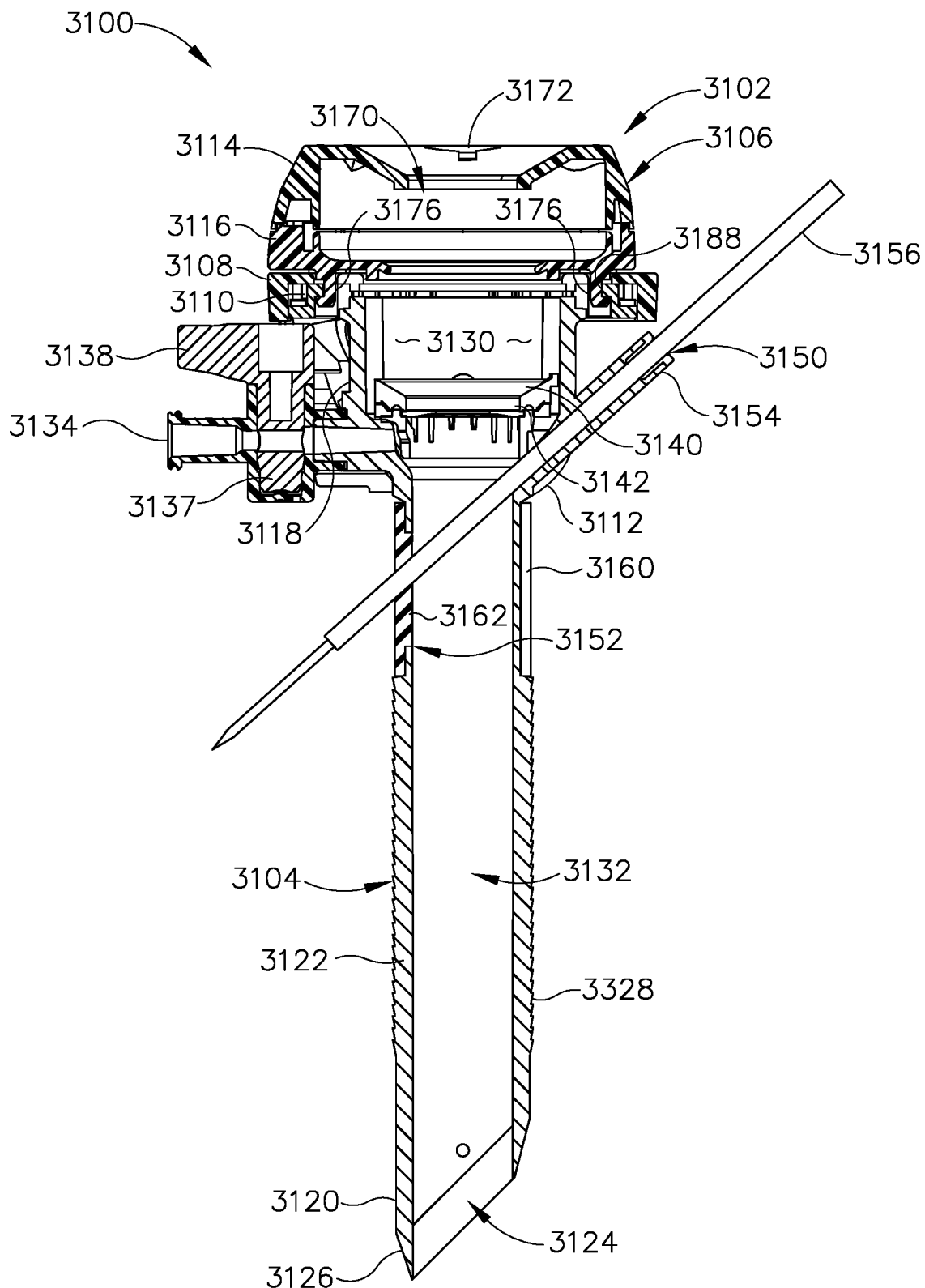
FIG. 59 depicts a side sectional view of the trocar of FIG. 57, showing an exemplary suture needle passer extending through the trocar along an exemplary first suture path oriented obliquely relative to a central axis of the trocar.

A. Exemplary Trocar Having Needle Ports and Insufflation Port in First Arrangement FIGS. 57-59 show another exemplary surgical access device in the form of a trocar (3100). Though not shown, those of ordinary skill in the art will recognize that trocar (3100) may be used in combination with any suitable trocar obturator, such as obturator (14) described above, for example. Trocar (3100) generally includes a housing assembly (3102) and a cannula (3104) coupled to and extending distally from housing assembly (3102) along a central longitudinal axis of trocar (3100). Housing assembly (3102) includes a proximal housing (3106), a housing cap plate (3108), a latch ring (3110), and a distal housing (3112). Proximal housing (3106) has a proximal housing head (3114) and a proximal housing base (3116). Proximal housing (3106) is coupled with and selectively releasable from the remainder of trocar (3100) via housing cap plate (3108) and latch ring (3110). As described in greater detail below, trocar (3100) further includes a plurality of needle entrance ports (3150) and needle exit ports (3152) defining a corresponding plurality of suture paths extending obliquely through trocar (3100) across its central axis. In the present example, at least one of the needle entrance ports (3150), and a corresponding needle guide structure (3154), is positioned in diametric opposition to an insufflation port (3134) of trocar (3100), in a coplanar relationship.

As shown in FIG. 58, cannula (3104) includes a proximal hub (3118), a distal tip (3120), and a cylindrical body (3122) extending therebetween along the central axis of trocar (3100). Proximal hub (3118) flares radially outwardly from cylindrical body (3122) in a proximal direction and defines a proximal opening to a cannula lumen (3124), while distal tip (3120) defines a distal opening to cannula lumen (3124). Distal tip (3120) itself is beveled and includes a chamfered edge (3126) configured to facilitate insertion of distal tip (3120) through tissue and into a patient body cavity during a surgical procedure. An outer surface of cylindrical body (3122) may be provided with a plurality of tissue engagement ribs (3128) or other similar features suitable to frictionally engage the inner wall of a tissue opening through which cannula (3104) is received into the body cavity.

As shown in FIG. 59, cannula lumen (3124) fluidly communicates with an interior (3130) of housing assembly (3102) to collectively define a working channel (3132) extending through trocar (3100) along the central axis thereof. A distal opening to working channel (3132) is defined by distal tip (3120) of cannula (3104), and a proximal opening to working channel (3132) is defined by proximal housing head (3114). When proximal housing (3106) is decoupled from the remainder of trocar (3100), the proximal opening to working channel (3132) is defined by housing cap plate (3108). Working channel (3132) is configured to receive one or more surgical instruments therethrough, such as a variety of endoscopic surgical instruments, for example, for accessing the patient body cavity and observing and/or treating tissue accessible therein.

As shown in FIGS. 58 and 59, an insufflation port (3134) (or "stopcock") is operatively connected to proximal hub (3118) of cannula (3104) at fitting (3136). Insufflation port (3134) includes an internal valve (3137) and a valve lever (3138), and may be formed integrally with fitting (3136), or alternatively coupled to fitting (3136) during assembly of trocar (3100). Insufflation tubing (3 not shown) is coupled to an inlet of insufflation port (3134) and directs insufflation fluid, such as carbon monoxide, from a fluid source into insufflation port (3134), which directs the fluid distally through working channel (3132) into the patient body cavity. Valve lever (3138) is configured to rotate the internal valve (3137) between open and closed positions to control the flow of insufflation fluid through insufflation port (3134).

Similar to trocar assembly (10), trocar (3100) may include a proximal (or "outer") seal assembly and/or a distal (or "inner") seal assembly, each arranged within working channel (3132). In the present example, trocar (3100) includes a distal seal assembly in the form of an instrument seal (3140) arranged within a tapered portion of proximal hub (3118). Distal instrument seal (3140) includes a central opening (3142) configured to receive a surgical instrument therethrough, and is configured to sealingly engage an outer surface of the surgical instrument to prevent proximal advancement of bodily fluids and/or tissue into housing assembly interior (3130). In exemplary configurations, instrument seal (3140) may be configured to absorb or otherwise remove bodily fluids from the outer surface of the surgical instrument as the surgical instrument is retracted proximally through instrument seal (3140).

Those of ordinary skill in the art will recognize that trocar (3100) may include proximal and/or distal seal assemblies of various suitable configurations, such as those disclosed in U.S. patent application Ser. No. 15/088,723, issued as U.S. Pat. No. 10,299,785 on May 28, 2019, incorporated by reference above. For instance, though not shown, trocar (3100) may include a proximal seal assembly in the form of an instrument seal arranged within proximal housing (3106), and/or a distal seal assembly in the form of a zero-closure seal, such as a duckbill seal, arranged within proximal hub (3118) of cannula (3104). As described above with reference to trocar assembly (10), such a zero-closure seal is generally configured to form a fluid-tight seal in working channel (3132) and thereby maintain insufflation even when no surgical instrument is present in working channel (3132). Furthermore, the distal zero-closure seal may be manipulated to provide an opening to a distal portion of working channel (3132) (e.g., cannula lumen (3124)) that is large enough to enable extraction of tissue proximally therethrough, particularly when proximal housing (3106) is separated from trocar (3100) to provide access to the distal zero-closure seal.

As shown in FIG. 58, trocar (3100) further includes a plurality of needle ports formed in select side portions of cannula (3104). As described in greater detail below, each needle port is configured to direct a suture passer needle (or simply "suture passer") across working channel (3132) of trocar (3100) at an oblique angle relative to the central axis of trocar (3100) to thereby establish an oblique suture path extending through trocar (3100) and adjacent tissue. As used herein, the term "oblique" means neither parallel nor perpendicular to the referenced axis, such as the central axis of trocar (3100).

In the present example, trocar (3100) includes a pair of needle entrance ports (3150) and a corresponding pair of needle exit ports (3152) arranged distally of needle entrance ports (3150). Each needle entrance port (3150) is defined by a respective needle guide structure shown in the form of a needle guide tube (3154) formed integrally with and projecting obliquely outwardly from proximal hub (3118) at a respective side portion of cannula (3104). Needle entrance ports (3150) extend through proximal hub (3118) and open to cannula lumen (3124), as best shown in FIG. 59. As best shown in FIGS. 55-59, each needle exit port (3152) extends through cylindrical body (3122) of cannula (3104) and opens to cannula lumen (3124) at a position generally diametrically opposed from a respective one of needle entrance ports (3150) and its corresponding needle guide tube (3154). In the present example, each needle exit port (3152) is generally elongate along the central axis of trocar (3100), though needle exit ports (3152) may be formed with various other shapes in alternative examples.

As used herein with reference to various first and second structures or reference points, the term "diametrically opposed" encompasses but is not limiting to a configuration in which the referenced structures or reference points are located at the same longitudinal position along the central axis of trocar (3100). For instance, in the present example each needle entrance port (3150) is spaced proximally from its respective needle exit port (3152), though ports (3150, 3152) are still understood to be diametrically opposed from one another along the same axially extending plane containing the central axis of trocar (3100). Of course, in alternative versions of trocar (3100), a needle entrance port (3150) may lie in a first plane containing the trocar central axis while the corresponding needle exit port (3152) lies in a second plane containing the central trocar axis and being offset from the first plane, such that the needle entrance and exit ports (3150, 3152) are not diametrically opposed from one another.

As best shown in FIG. 59, each needle entrance port (3150) and its respective needle guide tube (3154) is configured to cooperate with an opposing needle exit port (3152) to direct a suture passer needle (3156) along a respective suture path that extends obliquely relative to the central axis of trocar (3100). In particular, a needle entrance port (3150) and its respective needle guide tube (3154) on a first side portion of cannula (3104) cooperate with a needle exit port (3152) on a second side portion of cannula (3104) to define a first oblique suture path. Additionally, a needle entrance port (3152) and its respective needle guide tube (3154) on the second side portion of cannula (3104) cooperate with a needle exit port (3152) on the first side portion of cannula (3104) to define a second oblique suture path.

Each needle exit port (3152) is spaced distally from its respective needle entrance port (3150) by a distance suitable to achieve a desired suture path angle (or "tissue bite angle") measured between the resulting suture path and the central axis of trocar (3100). In the present example, each needle exit port (3152) is spaced distally from its respective needle entrance port (3150) by the same axial distance, such that the resulting suture paths exhibit the same suture path angles. In other examples, however, needle exit ports (3152) may be spaced distally from their respective needle entrance ports (3150) by different axial distances to achieve different suture path angles.

While the needle guide structures of the present example are shown in the form of needle guide tubes (3154) formed integrally with cannula (3104), those of ordinary skill in the art will recognize that various other configurations and structures suitable to guide a suture passer needle (3156) along the oblique suture paths of trocar (3100) may be implemented. For instance, trocar (3100) may be provided with needle guide tubes that are formed integrally with or otherwise defined by distal housing (3112), for example as disclosed in U.S. application Ser. No. 15/637,683, entitled "Trocar with Oblique Needle Insertion Port and Perpendicular Seal Latch," filed on Jun. 29, 2017, issued as U.S. Pat. No. 10,639,068 on May 5, 2020, the disclosure of which is incorporated by reference herein. In other examples, such externally-projecting needle guide structures may be omitted from trocar (3100).

As shown in FIGS. 58 and 59, each needle port (3150, 3152) of trocar (3100) is provided with a pierceable seal configured to aid in maintaining insufflation when a suture passer needle (3156) is directed through trocar (3100) along the suture paths, and/or when the suture passer needle (3156) is withdrawn from trocar (3100). In the present example, each needle entrance port (3150) is provided with an entrance seal shown in the form of a seal cap (3158) received within an entrance end of the respective needle guide tube (3154). Further, each needle exit port (3152) is provided with an exit seal shown in the form of an elongate protrusion (3162) projecting radially inwardly from an inner surface of a cannula sleeve (3160). As shown in FIGS. 57 and 58, cannula sleeve (3160) is received over a narrowed region of cylindrical body (3122) of cannula (3104), and has an outer diameter similar to an outer diameter of a distal portion of cylindrical body (3122) located distally of tissue engagement ribs (3128). In exemplary configurations, seal caps (3158) and cannula sleeve (3160), including protrusions (3162), may be formed of an elastomeric material. Additionally, cannula sleeve (3160) and/or seal caps (3158) may be formed through an overmolding process, for example.

As shown in FIGS. 57-59 distal housing (3112) is in the form of a generally annular shell shaped to receive and encircle proximal hub (3118) of cannula (3104). Distal housing (3112) includes a pair of diametrically opposed side wings (3164), which may be gripped by a surgeon when introducing trocar (3100) through patient tissue. Distal housing (3112) further includes a cutout (3166) sized and shaped to accommodate insufflation port (3134) therethrough, and a pair of axially extending slots (3168) sized and shaped to accommodate needle guide tubes (3154) therethrough. In the present example, distal housing (3112) is oriented relative to cannula (3104) and needle guide tubes (3154) such that slots (3168) are arranged in respective sidewall portions extending between side wings (3164). In alternative configurations, distal housing (3112) may be oriented such that slots (3168) are arranged in side wings (3164) or in various other portions of distal housing (3112).

Proximal housing (3106), defined by proximal housing head (3114) in combination with proximal housing base (3116), is configured to couple with and selectively decouple from the remaining distal portion of trocar (3100) via operation of latch ring (3110) relative to housing cap plate (3108). As shown in FIGS. 58 and 59, proximal housing head (3114) includes a central opening (3170) that defines a proximal end of working channel (3132) of trocar (3100) when proximal housing (3106) is coupled with cannula (3104). Proximal housing head (3114) further includes a pair of slots (3172) configured to receive a corresponding pair of tabs extending distally from the proximal head of an obturator, such as tabs (32) of obturator (14) shown in FIG. 2, for releasably connecting the obturator to trocar (3100). Proximal housing head (3114) is supported by and coupled to proximal housing base (3116), for example by a snap-fit connection. Though not shown, a proximal seal assembly, such as an instrument seal, may be arranged between proximal housing head (3114) and proximal housing base (3116). Such a proximal seal assembly may cooperate with distal seal assembly (3140), described above, to ensure a sealing engagement between trocar (3100) and a surgical instrument inserted through trocar (3100).

Proximal housing base (3116) includes a plurality of distally extending mating features configured to facilitate attachment and release of proximal housing (3106) from housing cap plate (3108) and latch ring (3110). In particular, as shown in FIG. 58, an underside of proximal housing base (3116) includes a pair of distally extending latching tabs (3174) and a pair of distally extending latching posts (3176). Housing cap plate (3108) includes a pair of tab slots (3178) configured to receive latching tabs (3174) therethrough, and a pair of post bores (3180) configured to receive latching posts (3176) therethrough. Housing cap plate (3108) further includes a plurality of distally extending coupling posts (3182) configured to be received by a corresponding plurality of coupling bores (3184) formed on distal housing (3112) for coupling housing cap plate (3108) with distal housing (3112), for example with a press-fit or snap-fit engagement.

Latch ring (3110) is arranged distally of housing cap plate (3108) and is housed radially inwardly of a sidewall of housing cap plate (3108) at an upper proximal end of latch ring (3110), and radially inwardly of distal housing (3112) at a lower distal end of latch ring (3110). As shown in FIG. 58, latch ring (3110) includes a user engagement feature in the form of an outwardly projecting knob (3186). Latch ring (3110) further includes a plurality of inwardly projecting latching features in the form of a pair of latching arms (3188) and a pair of cam ramps (3190) spaced circumferentially between latching arms (3188).

Latch ring (3110) is rotatable about the central axis of trocar (3100) between a latched position in which the latching features of latch ring (3110) capture the distally extending features of proximal housing base (3116), and an unlatched position in which the latching features of latch ring (3110) release the distally extending features of proximal housing base (3116) to thereby allow proximal detachment of proximal housing (3106). More specifically, in the latched position, latching arms (3188) engage latching posts (3176), and cam ramps (3190) engage latching tabs (3174). In the unlatched position, latching arms (3188) disengage latching posts (3176), and cam ramps (3190) disengage latching tabs (3174), to thereby release proximal housing (3106) from the remaining distal portion of trocar (3100). Latch ring (3110) is rotatable between the latched and unlatched positions by knob (3186), which projects radially through a circumferential slot (not shown) formed in a sidewall of housing cap plate (3108).

The components of housing assembly (3102), including proximal housing (3106), housing cap plate (3108), and latch ring (3110) may be further configured and operable in accordance with one or more teachings of U.S. application Ser. No. 15/637,683, issued as U.S. Pat. No. 10,639,068 on May 5, 2020, incorporated by reference above. For instance, in various examples, trocar (3100) may be configured such that latch ring knob (3186) remains circumferentially spaced (or "offset") from each of needle guide tubes (3154) throughout a full range of permissible rotation of latch ring (3110) relative to housing cap plate (3108), thereby ensuring unobstructed access to needle guide tubes (3154) during a suturing procedure performed with trocar (3100).

Figure 60:
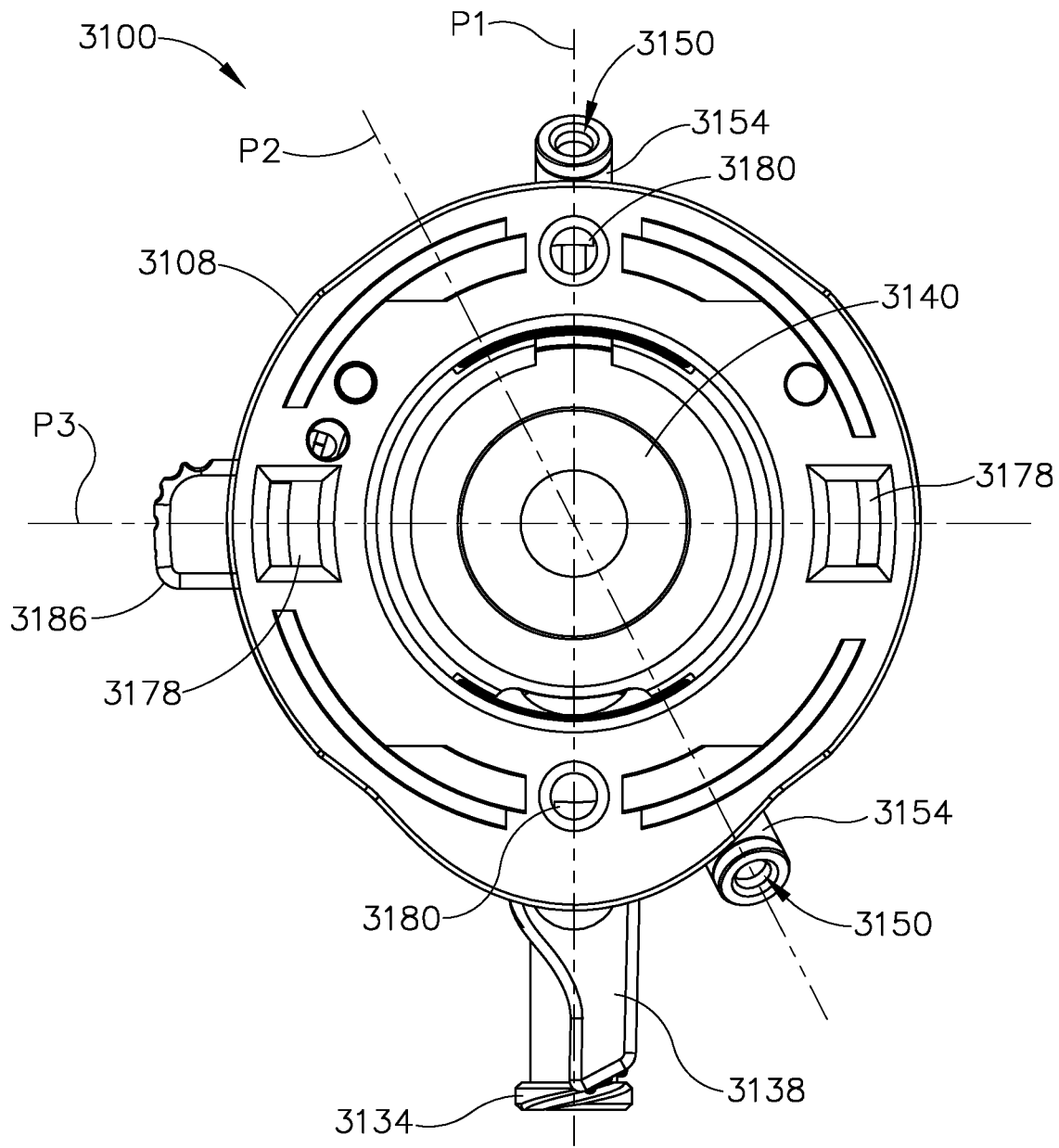
FIG. 60 depicts a top elevational view of the trocar of FIG. 57, with a proximal housing of the housing assembly being omitted.

As shown best FIG. 60, in the present example a first needle guide tube (3154) and its needle entrance port (3150) are arranged in diametric opposition to insufflation port (3134). Accordingly, the first needle guide tube (3154), its needle entrance port (3150), the corresponding needle exit port (3152), and insufflation port (3134) are arranged in a first plane (P1) extending axially along and through (i.e., containing) the central axis of trocar (3100). A second needle guide tube (3154) and its needle entrance and exit ports (3150, 3152) are arranged in a second axially extending plane (P2) containing the central axis of trocar (3100). Accordingly, the first and second suture paths defined by needle ports (3150, 3152) and needle guide tubes (3154)

intersect at the central axis. Knob (3186) of latch ring (3110) is arranged in a third axially extending plane (P3) containing the central axis. It will be understood that third plane (P3) may correspond to a midpoint of the circumferential path along which knob (3186) travels when latch ring (3110) rotates relative to the remainder of trocar (3100).

In the present example, second plane (P2) is offset from first plane (P1) such that the first and second needle tubes (3154) are positioned in a non-diametrically opposed relationship, and the resulting first and second suture paths lie in different planes. More specifically, in some examples second plane (P2) may be offset from first plane (P1) by approximately 17 degrees. Furthermore, in the present example third plane (P3) extends perpendicularly to first plane (P1) such that knob (3186) is circumferentially offset from each of first needle guide tube (3154) and insufflation port (3134) by approximately 90 degrees. Accordingly, needle guide tubes (3154), insufflation port (3134), and latch ring knob (3186) are circumferentially offset from one another in the present example. Additionally, knob (3186) remains circumferentially offset from each needle guide tube (3154) and insufflation port (3134) throughout a full range of permissible rotation of latch ring (3110) about the central axis of trocar (3100). Such a configuration ensures unobstructed access to needle guide tubes (3154) during use of trocar (3100).

It will be appreciated that in other examples, axially extending planes (P1, P2, P3) may be arranged in various other configurations. In that regard, second plane (P2) containing second needle guide tube (3154) and its needle entrance port (3150) may be offset from first plane (P1) by greater than or less than 17 degrees. Additionally, third plane (P3) containing latch ring knob (3186) may be non-perpendicular to first plane (P1). For instance, third plane (P3) may be oriented such that knob (3186) is circumferentially offset from insufflation port (3134) or first needle guide tube (3154) by greater than or less than 90 degrees. Furthermore, while trocar (3100) of the present example is shown and described as providing two suture paths oriented in a particular arrangement, each suture path being defined by a respective needle entrance port (3150) and needle exit port (3152), other versions of trocar (3100) may be suitably configured to provide alternative quantities and arrangements of suture paths. For example, trocar (3100) may be configured to provide three or more suture paths.

Figure 61:
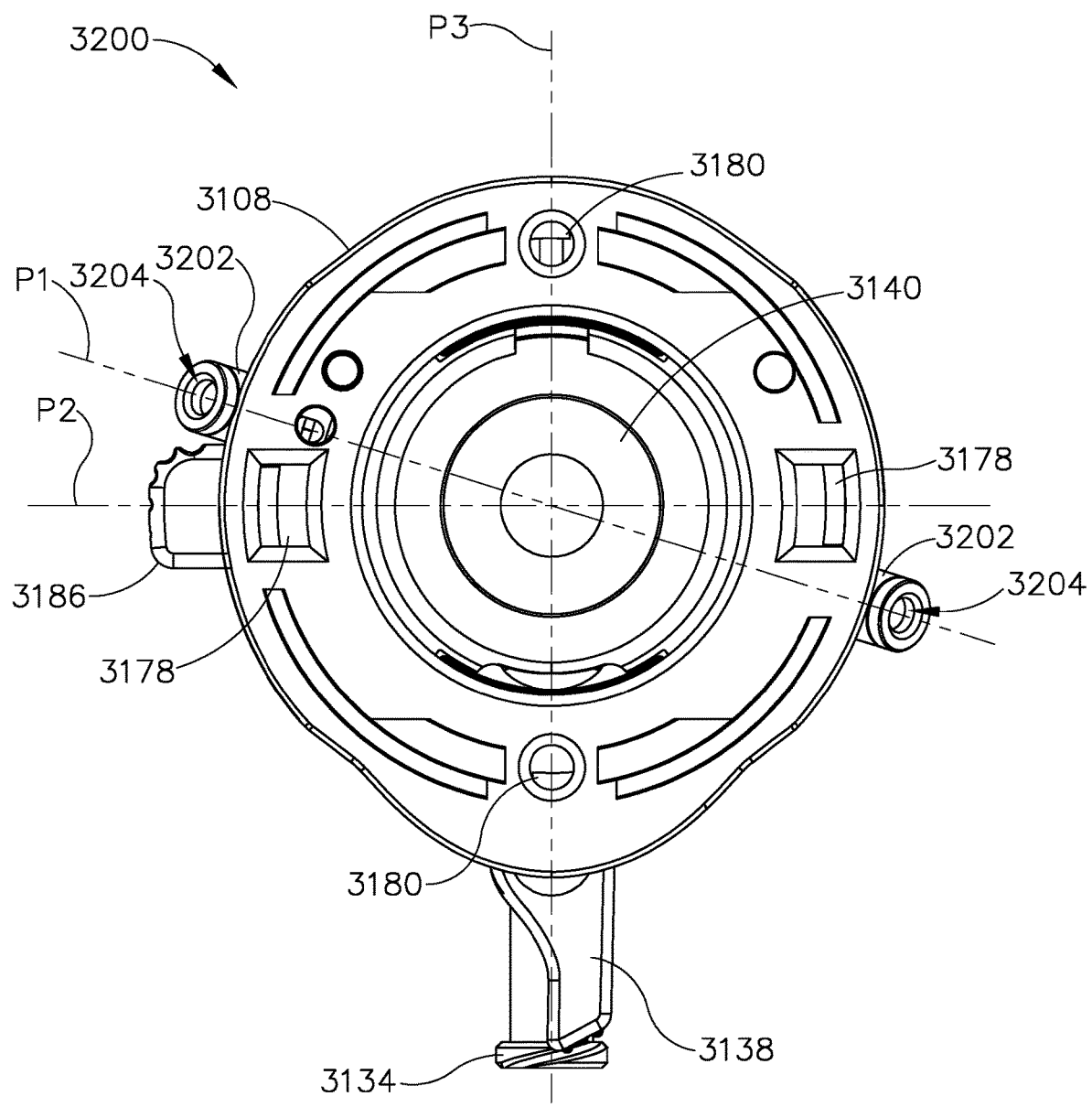
FIG. 61 depicts a top elevational view of another exemplary trocar.

B. Exemplary Trocar Having Needle Ports and Insufflation Port in Second Arrangement FIG. 61 shows another exemplary surgical access device in the form of trocar (3200), for which like reference numerals refer to like features described above in connection with trocar (3100). Trocar (3200) is substantially similar to trocar (3100) except as otherwise described below. In particular, trocar (3200) includes a pair of needle guide tubes (3202) and corresponding needle entrance ports (3204) that are arranged in a diametrically opposing relationship along a first axially extending plane (P1) containing the central axis of trocar (3200). A second axially extending plane (P2) extends through the central trocar axis and latch ring knob (3186), and a third axially extending plane (P3) extends through the central trocar axis and insufflation port (3134). In various examples, second plane (P2) may extend through a path endpoint or a path midpoint of knob (3186).

In the present example, second plane (P2) extends perpendicularly to third plane (P3) such that latch ring knob (3186) is circumferentially offset from insufflation port (3134) by 90 degrees. Additionally, first plane (P1) is angularly offset from second plane (P2) and third plane (P3) such that needle guide tubes (3202) and needle entrance ports (3204) are circumferentially offset from knob (3186) and insufflation port (3134). In the present example, first plane (P1) is angularly offset from second plane (P2) by approximately 17 degrees. Alternative versions of trocar (3200) may present angular offsets of first plane (P1) relative to second plane (P2) of greater than or less than 17 degrees.

C. Exemplary Trocar Having Needle Ports Arranged on Rotary Collar

During a suturing procedure for closing a tissue opening using a trocar having needle entrance and exit ports defining one or more suture paths, such as one or both of trocars (3100, 3200) described above, it may be desirable to adjust the rotational position of one or more of the suture paths about the trocar central axis in situ, without rotating the trocar as a whole relative to the patient. Such adjustment may be desirable, for example, to better accommodate certain anatomy of the patient and achieve a better "bite" of the tissue fascia being sutured. Exemplary trocar features described below enable such adjustment.

Figure 62:
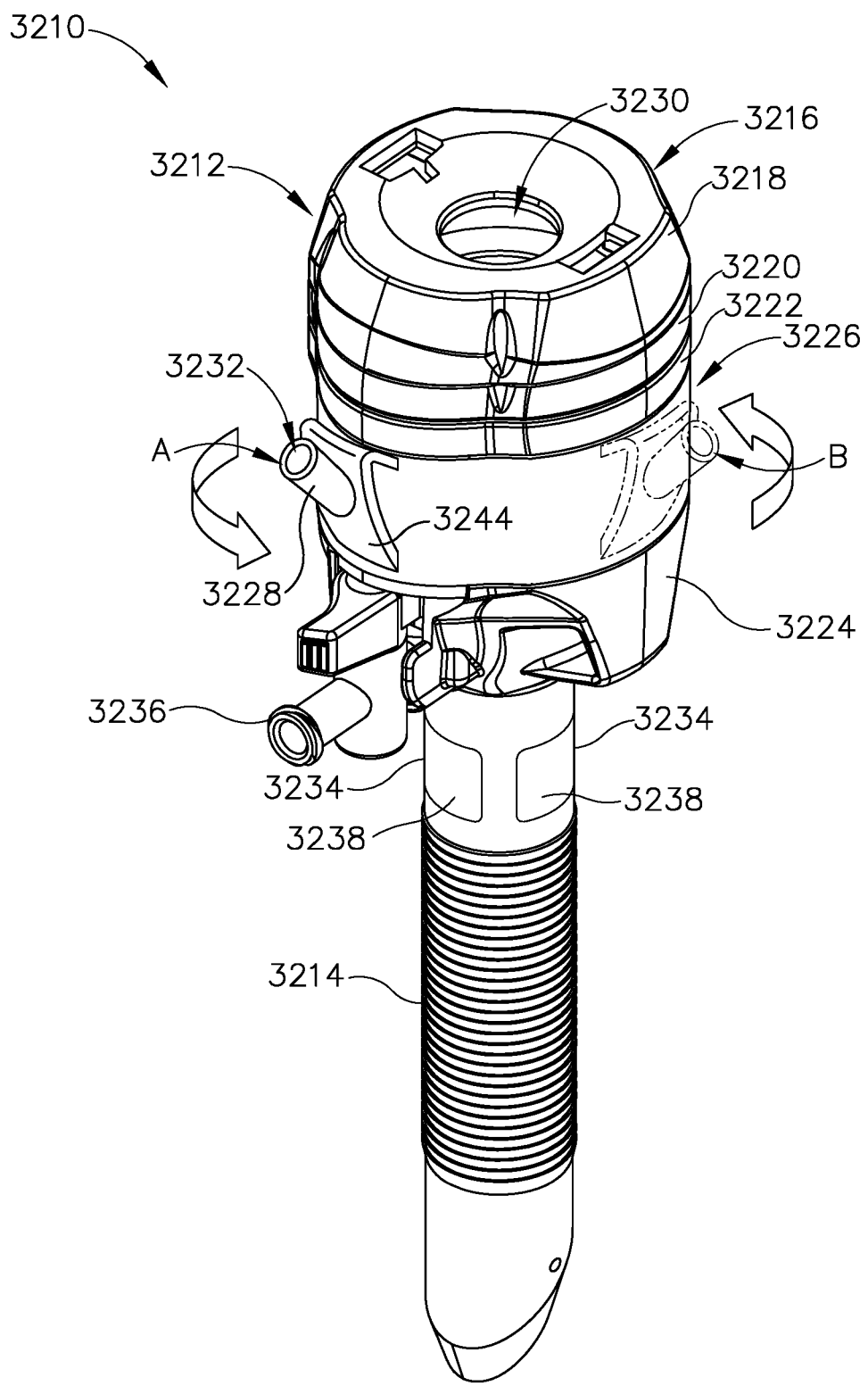
FIG. 62 depicts a perspective view of another exemplary trocar having a rotary collar.

FIG. 62 shows an exemplary trocar (3210) configured to enable selective rotational adjustment of its suture paths about a central axis of trocar (3210). Trocar (3210) is similar to trocar (3100) in that trocar (3210) includes a housing assembly (3212) and a cannula (3214) coupled to and extending distally from housing assembly (3212) along a trocar central axis. Housing assembly (3212) includes a proximal housing (3216) having a proximal housing head (3218) and a proximal housing base (3220), a housing cap plate (3222), a latch ring (not shown) similar to latch ring (3110), and a distal housing (3224). The components of trocar (3210) are substantially similar in structure and function to the corresponding components of trocar (3100) described above, except as otherwise described below.

Unlike housing assembly (3102) of trocar (3100), housing assembly (3212) of trocar (3210) includes a rotary collar (3226) arranged between housing cap plate (3222) and distal housing (3224). Rotary collar (3226) supports a pair of needle guide tubes (3228), each guide tube (3228) defining a needle entrance port (3232) that communicates with a working channel (3230) of trocar (3210). Rotary collar (3226) is configured to enable selective rotational adjustment of one or both of needle guide tubes (3228) and their respective suture paths about the trocar central axis relative to rotationally-fixed components of trocar (3210), including a pair of needle exit ports (3234) formed in cannula (3214). For instance, in the present example needle guide tubes (3228) are fixed relative to rotary collar (3226), and rotary collar (3226) is configured to rotate about the trocar central axis. Consequently, first and second needle guide tubes (3228) rotate together about trocar central axis. In other examples, rotary collar (3226) may be fixed relative to cannula (3214) while first and second needle guide tubes (3228), or other needle guide structures, are configured to rotate independently or dependently of one another about trocar central axis, for example along one or more circumferentially extending tracks (not shown) formed in rotary collar (3226).

Rotary collar (3226) is configured to rotate relative to cannula (3214) between first and second end positions, as indicated by reference numerals (A, B) in FIG. 62. First and second end positions (A, B) are circumferentially offset from one another by any suitable degree, such as approximately 30-45 degrees, for example. Additionally, rotary collar (3226) is mounted to trocar (3210) such that when rotary collar (3226) is in its first end position (A) a first needle guide tube (3228) is circumferentially offset from insufflation port (3236) by a selected degree, such as approximately 17 degrees. Accordingly, in an exemplary configuration in which rotary collar (3226) rotates through a range of 45 degrees between first and second end positions (A, B), first needle guide tube (3228) is movable from a first end position in which guide tube (3228) is offset from insufflation port by 17 degrees, to a second end position in which needle guide tube (3228) is offset from insufflation port (3236) by 57 degrees. In various examples, trocar (3210) may include one or more detent mechanisms or other rotation limiting mechanisms (not shown) configured to releasably retain rotary collar (3226) in one or more predetermined rotational positions relative to cannula (3214).

As shown in FIG. 62, needle exit ports (3234) are formed in a proximal cylindrical portion of cannula (3214). Each exit port (3234) extends circumferentially about trocar central axis with a circumferential dimension sufficient to enable a corresponding needle guide tube (3228) to align with needle exit port (3234) throughout a full range of rotation of rotary collar (3226) between its first and second end positions (A, B). Additionally, each needle exit port (3234) is formed with an axial dimension sufficient to accommodate suture paths therethrough of various different suture path angles. In alternative examples, trocar (3210) may include a plurality of needle exit ports arranged circumferentially about trocar central axis at locations corresponding to predetermined rotational positions of rotary collar (3226). Each needle exit port (3234) includes a pierceable seal (3238) configured to assist in maintaining insufflation during a surgical procedure, similar to seals (3162) of trocar (3100). Each needle guide tube (3228) may also include a pierceable seal (not shown), such as a seal cap (not shown) similar to seal caps (3158) of trocar (3100).

Figure 63:
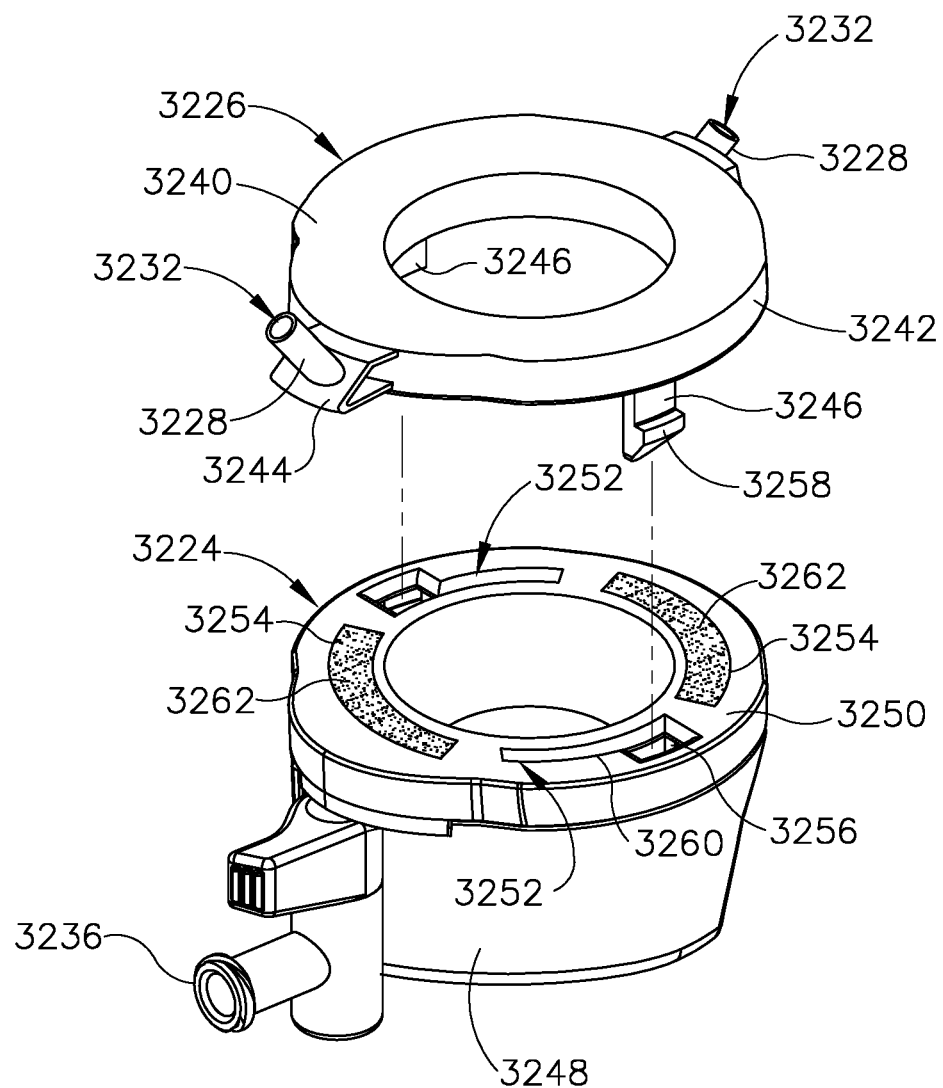
FIG. 63 depicts a disassembled perspective view of the rotary collar and a distal housing of the trocar of FIG. 62.

FIG. 63 shows additional details of exemplary features of rotary collar (3226) and distal housing (3224). Rotary collar (3226) includes a generally annular body (3240) and an outer sidewall (3242) that supports needle guide tubes (3228). Each needle guide tube (3228) is supported by a shoulder element (3244) projecting radially outwardly from annular body (3240), and needle guide tubes (3228) are arranged at diametrically opposed positions on annular body (3240). In other examples, needle guide tubes (3228) may be arranged in various other configurations, such as those described above in connection with trocars (3100, 3200). Additionally, needle guide tubes (3228) and/or shoulder elements (3244) may be omitted and replaced with needle guide structures of various other forms, such as structures integrated within annular body (3240) of rotary collar (3226). Rotary collar (3226) further includes a pair of downwardly depending L-shaped legs (3246) configured to couple rotary collar (3226) with distal housing (3224) and guide rotation of rotary collar (3226) relative to distal housing (3224), as described below. In the present example, legs (3246) are diametrically opposed from one another and are spaced circumferentially equidistantly between needle guide tubes (3228).

Distal housing (3224) of the present example includes a generally annular body (3248) having an upper wall (3250). A pair of circumferentially extending slots (3252) are arranged in upper wall (3250) and are configured to receive downwardly depending legs (3246) of rotary collar (3226). A pair of circumferentially extending sealed openings (3254) are also arranged in upper wall (3250) and are configured to receive a suture passer needle (not shown) therethrough. Slots (3252) and sealed openings (3254) are arranged in a circumferentially alternating manner, such that each slot (3252) is configured to align with a respective leg (3246) and each sealed opening (3254) is configured to align with the distal end of a respective needle guide tube (3228). Each slot (3252) has a radially enlarged opening (3256) configured to receive a radially projecting distal foot (3258) of the respective leg (3246) when rotary collar (3226) is assembled with distal housing (3224). Each slot (3252) further includes an elongate channel (3260) extending circumferentially from enlarged opening (3256) and configured to retain and guide legs (3246) along a circumferential path as rotary collar (3226) rotates relative to distal housing (3224). A circumferential length of slot (3252) defines the permissible rotational range of rotary collar (3226) relative to distal housing (3224), and may be suitably sized to provide any desired rotational range.

Each circumferentially extending sealed opening (3254) is formed with a circumferential length sufficient to enable alignment of the distal end of a respective needle guide tube (3228) with sealed opening (3254) throughout the entire permissible range of rotation of rotary collar (3226) relative to distal housing (3224). Each sealed opening (3254) is provided with a pierceable seal (3262) configured to be pierced by a suture passer needle directed distally through the respective needle guide tube (3228). In various examples, each pierceable seal (3262) may include a circumferentially extending slit (not shown) configured to facilitate insertion of a suture passer needle distally through pierceable seal (3262), and rotation of rotary collar (3226) relative to distal housing (3224) while suture passer needle extends through pierceable seal (3262). Each sealed opening (3254) is configured to direct a suture passer needle into working channel (3230) and toward a respective needle exit port (3234) on cannula (3214). Additionally, each sealed opening (3254) is formed with a radial dimension sufficient to accommodate suture paths therethrough of various different suture path angles.

Each of the exemplary trocars (3100, 3200, 3210) described above is configured to be implemented as a suture guide mechanism for directing suture guide needles, and suture thread carried by the suture guide needles, distally therethrough and into tissue at predetermined suture path angles for suturing closed an opening formed in a patient by the trocar cannula. Any of trocars (3100, 3200, 3210) may be implemented in connection with the general steps of the exemplary suturing procedure disclosed in U.S. application Ser. No. 15/637,683, issued as U.S. Pat. No. 10,639,068 on May 5, 2020, incorporated by reference above, for example.

XI. Exemplary Suture Passer with Puncture Site Identification Feature

Identifying the proper location to puncture through a patient's tissue to access an internal target site may be difficult in some instances, particularly when it is not readily apparent from the patient's outer skin layer where the internal target site is located. For example, the clinician may determine the location for puncturing a patient's tissue by utilizing their professional judgment with the expectation that the probability of accurately designating a desirable puncture site is measured. In instances where the determined location was not the desirable puncture site, the clinician may need to repair the patient's damaged tissue where the puncture had occurred and then subsequently identify an alternative site for puncturing through the patient's tissue. This occurrence may not only be detrimental to the patient's health and well-being but it may also be time consuming. It may thus be beneficial in such instances for a surgical instrument, such as any of suture passers (4100, 4200, 4300)

discussed below, to be capable of indicating where a potential puncture may occur within a patient's body based on the current positioning of the instrument while also inhibiting damage to the tissue during use.

The following description provides various exemplary suture passers (4100, 4200, 4300) with respective needle heads (4132, 4232, 4332) that are configured to designate a potential puncture site while inhibiting damage to the patient's tissue and subsequently puncturing the tissue upon confirmation of the desired location. Providing the capability to designate and puncture the tissue may thereby reduce the likelihood of the clinician misidentifying the location of the desirable puncture site. Suture passers (4100, 4200, 4300) and needle heads (4132, 4232, 4332) described below may be readily incorporated into any of the various surgical instruments described above and in any of the various surgical procedures described in the various references provided herein. Other suitable ways in which the below-described suture passers (4100, 4200, 4300) and puncture site identification features may be used will be apparent to those of ordinary skill in the art in view of the teachings herein.

Figure 64:
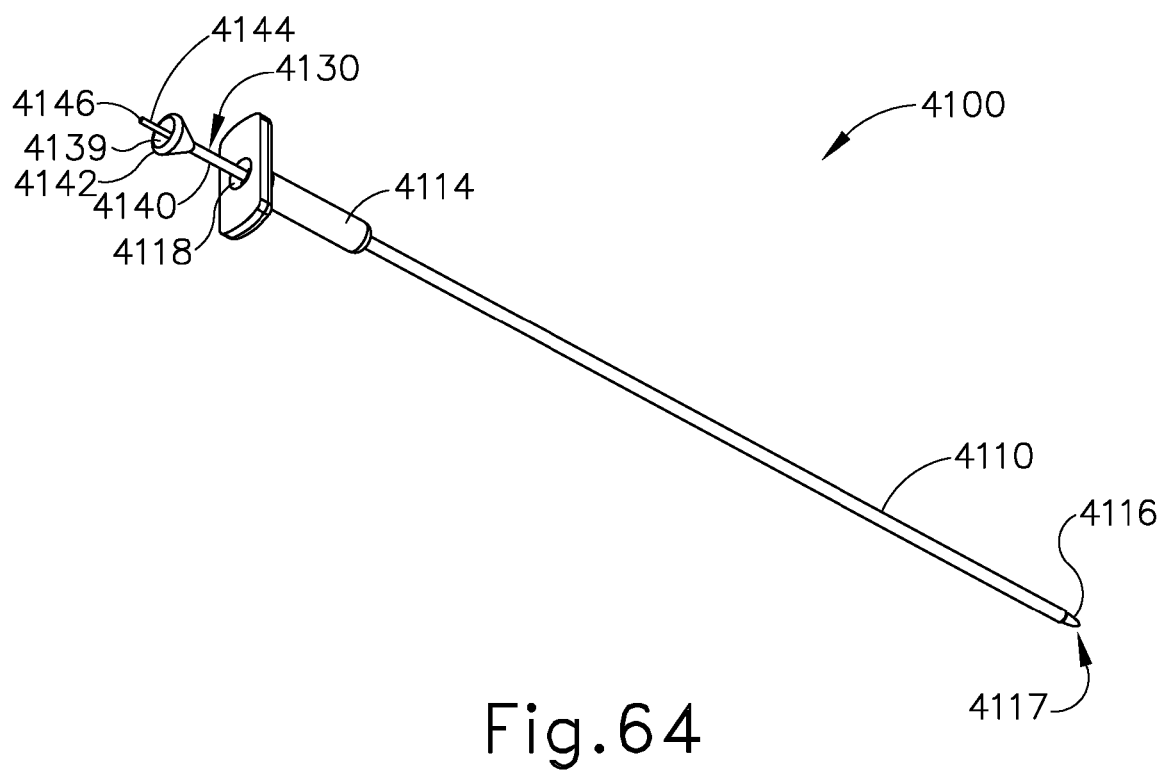
FIG. 64 depicts a perspective view of a first exemplary suture passer having an inner needle slidably received within an outer needle.

A. Exemplary Suture Passer with Deformable Head i. Exemplary Outer Needle with Pointed Tip FIGS. 64-65G show a first exemplary suture passer (4100) comprising an outer sheath (4110) and an inner needle (4130). Inner needle (4130) is substantially enclosed within outer sheath (4110) such that the longitudinal length of inner needle (4130) extends within an outer lumen (4112) of outer sheath (4110). Inner needle (4130) comprises a needle head (4132), a longitudinal shaft (4140), and a driver (4142). Longitudinal shaft (4140) has a longitudinal length that separates needle head (4132), which is positioned on a distal end of longitudinal shaft (4140), from driver (4142), which is positioned on an opposite, proximal end of longitudinal shaft (4140). Driver (4142) is in the form of a plunger that is configured to slidably translate inner needle (4130) within outer lumen (4112) of outer sheath (4110). To this end, outer sheath (4110), which may also be referred to herein as outer needle (4110), comprises outer lumen (4112), a housing (4114), a distal tip (4116) and a proximal opening (4118). Distal tip (4116) has a sharp point configured to puncture tissue (17) and includes a distal opening (4117). Outer lumen (4112) has a longitudinal length that separates opening (4117) of distal tip (4116) from housing (4114) and proximal opening (4118). Openings (4117, 4118) are in communication with outer lumen (4112) and in axial alignment with the longitudinal length of outer lumen (4112).

Inner needle (4130) is inserted into outer sheath (4110) by directing needle head (4132) into proximal opening (4118) and slidably advancing inner needle (4130) through outer lumen (4112) and toward distal opening (4117). Inner needle (4130) further comprises a cable (4144) extending through an inner lumen (4139) of inner needle (4130). Cable (4144) is securely attached on a distal end to needle head (4132) and on a proximal end to an actuator (4146). Actuator (4146) extends out from inner lumen (4139) through driver (4142) and is operatively connected to needle head (4132). Needle head (4132) of inner needle (4130) is formed of deflectable material, such as an elastomer, and may be flexible and/or elastic, and further configured to expand from a contracted state to an expanded state as shown respectively in FIG. 65A and FIG. 65D. In the present example, needle head (4132) also is an atraumatic, blunt needle head (4132) that is configured to not puncture tissue (17) and thus reduce the likelihood of damage to tissue (17) when extended beyond distal tip (4116) in use. Of course, alternative examples of atraumatic ends may be so used, and the invention is not intended to be unnecessarily limited to blunt needle head (4132) as shown.

Figure 65A:
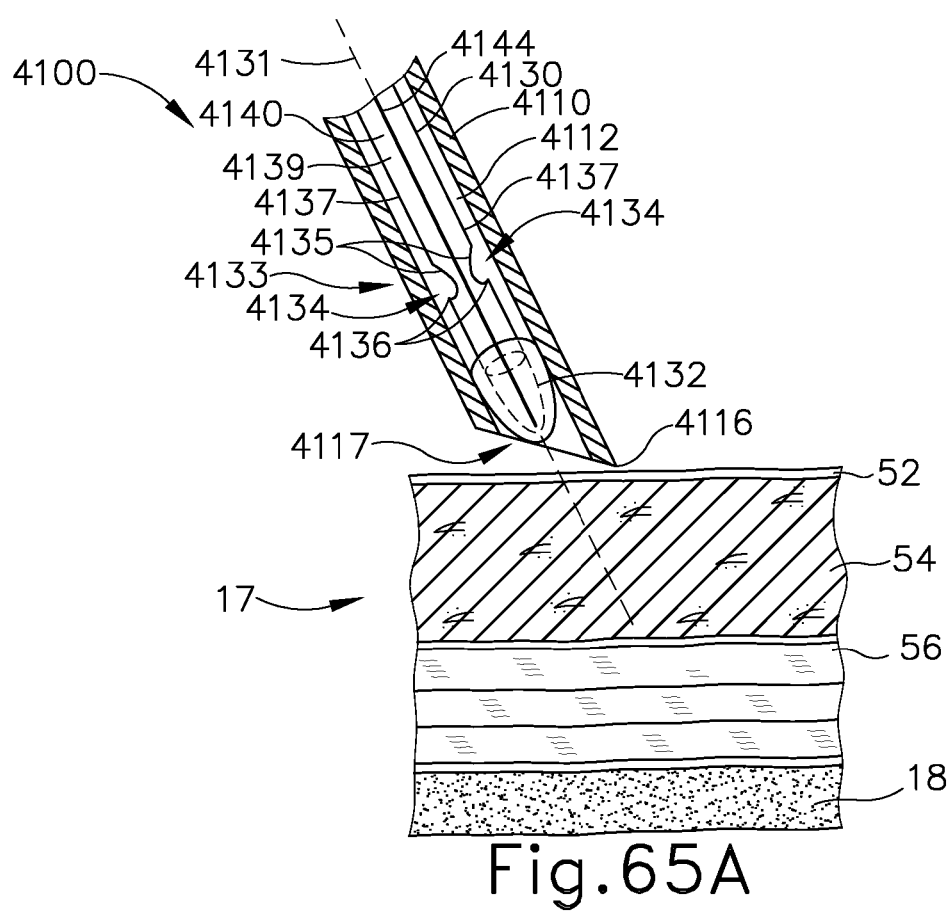
FIG. 65A depicts a partial cross-sectional view of the suture passer of FIG. 1, taken generally along a centerline thereof, with the suture passer positioned along a patient's outer layer of skin and the inner needle in a retracted position contained within the outer needle.

With respect to FIG. 65A, needle head (4132) is configured to resiliently expand from the contracted state to the expanded state upon actuation of cable (4144) by actuator (4146). In the present example, proximal actuation of cable (4144) pulls a distal portion of needle head (4132) proximally toward a distal end of longitudinal shaft (4140). A proximal portion of needle head (4132) simultaneously abuts against the distal end of longitudinal shaft (4140) thereby causing needle head (4132) to umbrella radially outwardly to the expanded state (see FIG. 65D) relative to a longitudinal axis (4131) of inner needle (4130).

Inner needle (4130) of the present example is resiliently biased toward a proximal, retracted position within outer lumen (4112), such as by a coil spring or other kind of biasing member (not shown) operatively connected between inner needle (4130) and outer sheath (4110). To transition inner needle (4130) from the retracted position (see FIG. 64) to a distal, extended position, the clinician exerts a distal force on driver (4142) to thereby slidably advance inner needle (4130) through outer lumen (4112). The natural state of biasing member (not shown) generally positions suture passer (4100) in the retracted position with needle head (4132) confined within distal tip (4116).

As a merely illustrative example, inner needle (4130) is formed of a hardened stainless steel, such as a thick wall stainless steel tube stock, while the molded features on inner needle (4130), particularly driver (4142), are formed of plastic, such as polycarbonate. In another example, inner needle (4130) may be form of a plastic material and metal coated for additional surface hardness similar to stainless steel with a bending strength similar to aluminum. Inner needle (4130) has a diameter smaller than a diameter of outer sheath (4110) such that inner needle (4130) is slidably received within outer sheath (4110). For example, inner needle (4130) may have a diameter ranging from approximately 2 millimeters to approximately 3 millimeters and outer sheath (4110) may have a corresponding larger diameter with ample clearance configured to receive a United States Pharmacopeia (U.S.P.) designation 2 sized suture thread (60). Furthermore, outer sheath (4110) is formed of a seamless stainless steel tubing, such as a thin wall hypodermic stainless steel stock, in the present example. As will be apparent to those of ordinary skill in the art, outer sheath (4110) and inner needle (4130) may be formed of various suitable materials that will maintain durability when inserted into the cavity of a patient.

As seen in FIG. 65A, inner needle (4130) includes a pair of notches (4133). Notches (4133) extend through inner needle (4130) and comprise a catch undercut (4134) and a release cam surface (4135), respectively. Catch undercuts (4134) have a hooked surface (4136) and are configured to receive and hold suture thread (460) (see FIG. 4A) radially inwardly toward inner needle (4130) when inner needle (4130) is selectively maneuvered to catch suture thread (60) (see FIG. 4A). Release cam surfaces (4135) are positioned between catch undercuts (4134) and an outer radial surface (4137) of inner needle (4130). Release cam surfaces (4135) extend proximally and radially outwardly from hooked surfaces (4136) of catch undercuts (4134) until becoming flush with outer radial surface (4137) of inner needle (4130). Release cam surfaces (4135) are configured to urge suture thread (460) (see FIG. 4A) radially outwardly from catch undercuts (4134) to thereby remove suture thread (60) (see FIG. 4A) from notches (4133) when inner needle (4130) is selectively maneuvered to release suture thread (60) (see FIG. 4A). Although not shown, it should be understood that inner needle (4130) may comprise more or fewer notches (4133) along inner needle (4130) than that depicted in the present example.

Notches (4133) are positioned along inner needle (4130) at varying angular positions about longitudinal axis (4131) such that notches (4133) are oppositely positioned along inner needle (4130). Notwithstanding the relative positioning of notches (4133) relative to each other along inner needle (4130), catch undercuts (4134) are distally oriented on inner needle (4130) relative to release cam surfaces (4135). Although not shown, it should be understood that notches (4133) may be positioned along inner needle (4130) in an opposite orientation than that depicted in FIG. 65A. In this instance, catch undercuts (4134) are proximally oriented on inner needle (4130) relative to release cam surfaces (4135). FIG. 65A shows suture passer (4100) in the retracted position and needle head (4132) contained within distal tip (4116). With suture passer (4100) in the retracted position, notches (4133) remain covered within outer sheath (4110) such that inserting suture passer (4100) against tissue (17) will inhibit injury to the patient from the potential encounter of notches (4133) against tissue (17) or any other portion of the patient's body.

Figure 65B:
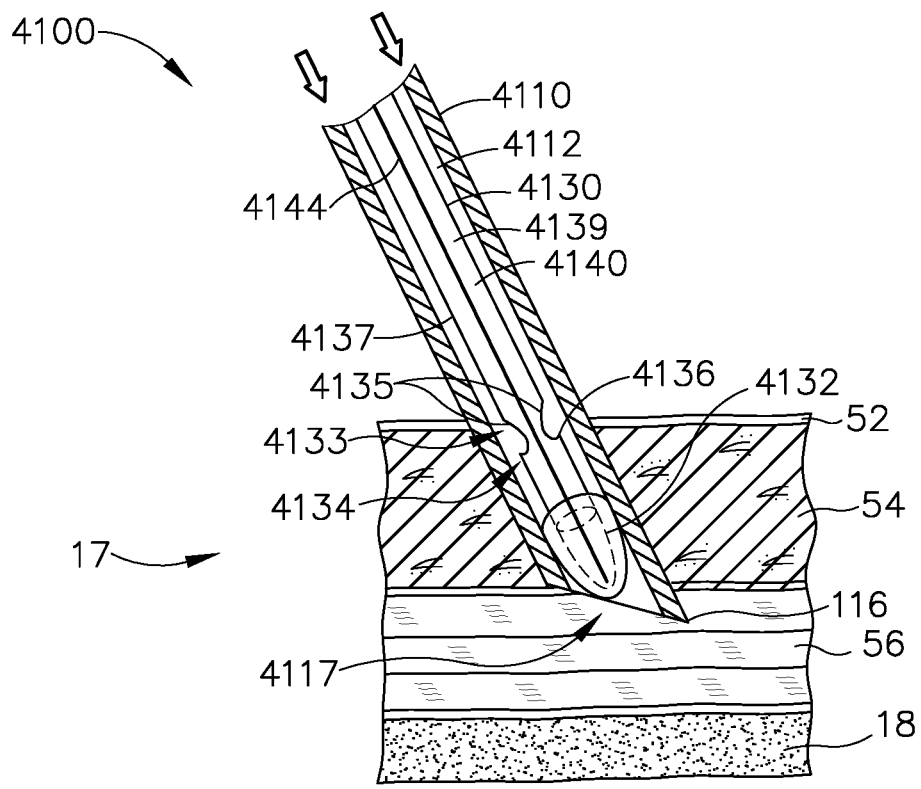
FIG. 65B depicts the partial sectional view of the suture passer similar to FIG. 65A, but with the suture passer inserted through the patient's outer layer of skin.
Figure 65C:
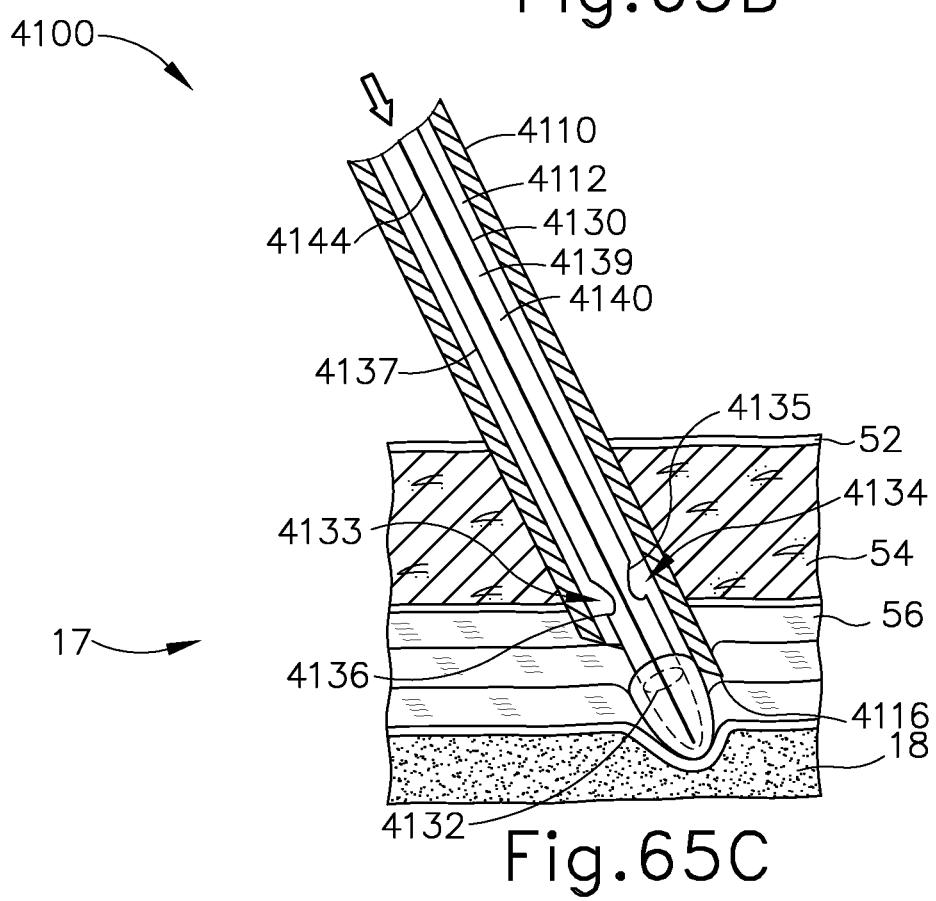
FIG. 65C depicts the partial sectional view of the suture passer similar to FIG. 65B, but with the inner needle in an extended position and a needle head of the inner needle in a contracted state.

In the present example, the clinician grasps housing (4114) (see FIG. 64) to selectively position distal tip (4117) against outer layer of skin (52). The exertion of force by the clinician on housing (4114) results in distal tip (4116) puncturing outer layer of skin (52) and inner layer of fat (54), as seen in FIG. 65B. Once positioned adjacent to tissue (17), the clinician exerts sufficient force upon driver (4142) (see FIG. 64) to overcome the resilient bias created by the biasing member (not shown) to slidably translate inner needle (4130) within outer lumen (4112) in the distal direction, as seen in FIG. 65C. The biasing member (not shown) is forced into a compressed state while suture passer (4100) is in the extended position and driver (4142) is distally held towards housing (4114) (see FIG. 64). As a merely illustrative example, the biasing member (not shown) may provide a spring rate ranging between approximately 2.3 lbs./inch to approximately 2.8 lbs./inch. Alternatively, the biasing member may include other various suitable spring rates that will allow for the translation of inner needle (4130) within outer sheath (4110) upon exertion of sufficient force. With suture passer (4100) now being in the extended position, needle head (4132) of inner needle (4130) is distally extended through distal opening (4117). As shown in FIG. 65C, this causes the tissue layers of fascia (56) to protrude or "tent" to some degree in cavity (18).

Figure 65D:
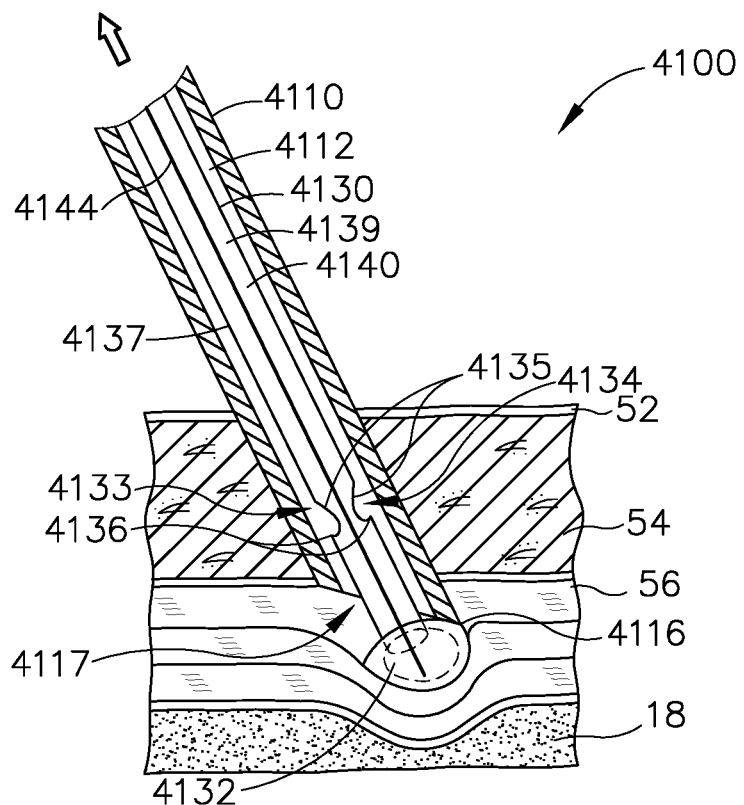

FIG. 65D shows needle head (4132) of inner needle (4130) exposed beyond outer lumen (4112) of outer sheath (4110) at distal opening (4117) when suture passer (4100) is in the extended position, with head (4132) expanded to the expanded state. In this instance, needle head (4132) assumes a widened geometric shape configured to produce a low force impact against tissue (417) to emphasize a tenting effect on tissue (417). Needle head (4132) is configured to transition to this enlarged geometric shape when cable (4144) is moved proximally within inner lumen (4139) to thereby pull needle head (4132) in the proximal direction as discussed above in greater detail. The tenting effect created on tissue (17) provides the clinician with greater visibility, particularly when viewed through an endoscopic camera that is positioned within cavity (18) at an orientation viewing generally upwardly toward the insertion site of outer sheath (4110) and inner needle (4130). In this instance, the clinician is then able to determine whether the current location of suture passer (4100), as indicated by the tenting of tissue (17) into cavity (18), is the desirable position for puncturing tissue (17).

In other words, by observing the location of the tenting effect on the layers of fascia (56) as shown in FIG. 65D, before outer sheath (4110) and inner needle (4130) pierce and penetrate the layers of fascia (56), the clinician may verify that the tenting effect is located at a desired position for outer sheath (4110) and inner needle (4130) to enter cavity (18) via the layers of fascia (56). If the clinician is not satisfied with the location of the observed tenting effect on the layers of fascia (56) as shown in FIG. 65D, the clinician may fully remove suture passer (4100) from tissue (17) and then re-insert suture passer (4100) at a different location and/or orientation. Thus, the clinician may repeat and reverse the steps shown in FIGS. 65A-65D, repositioning and/or reorienting suture passer (4100) between each iteration of these steps, until the clinician is satisfied with the location of the observed tenting effect on the layers of fascia (56) as shown in FIG. 65D.

Figure 65E:
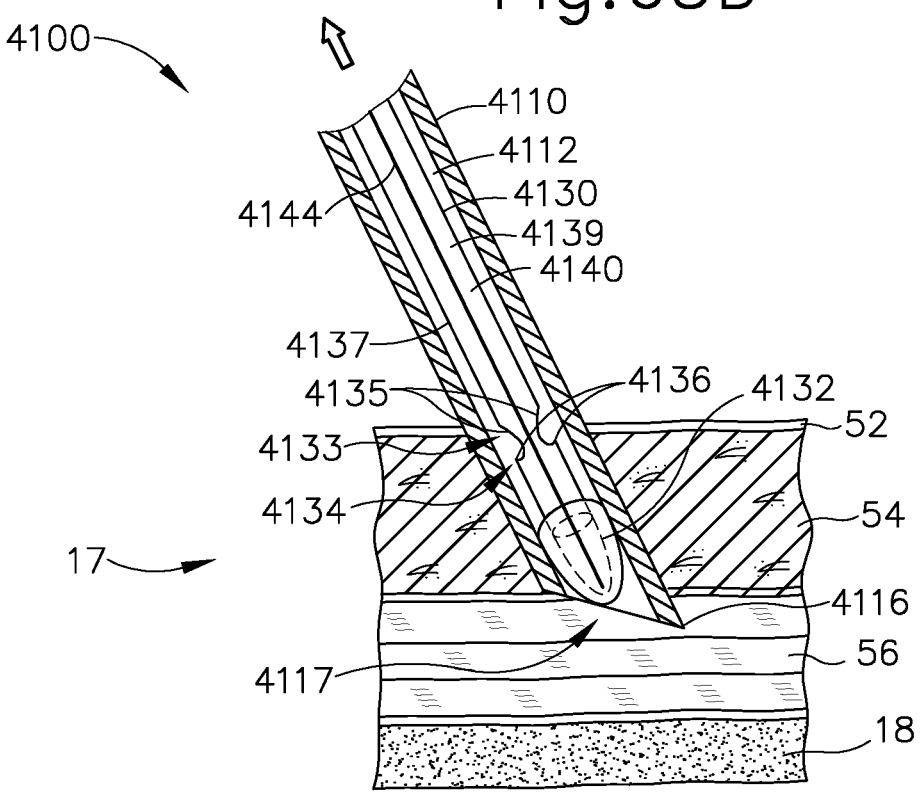
Figure 65F:
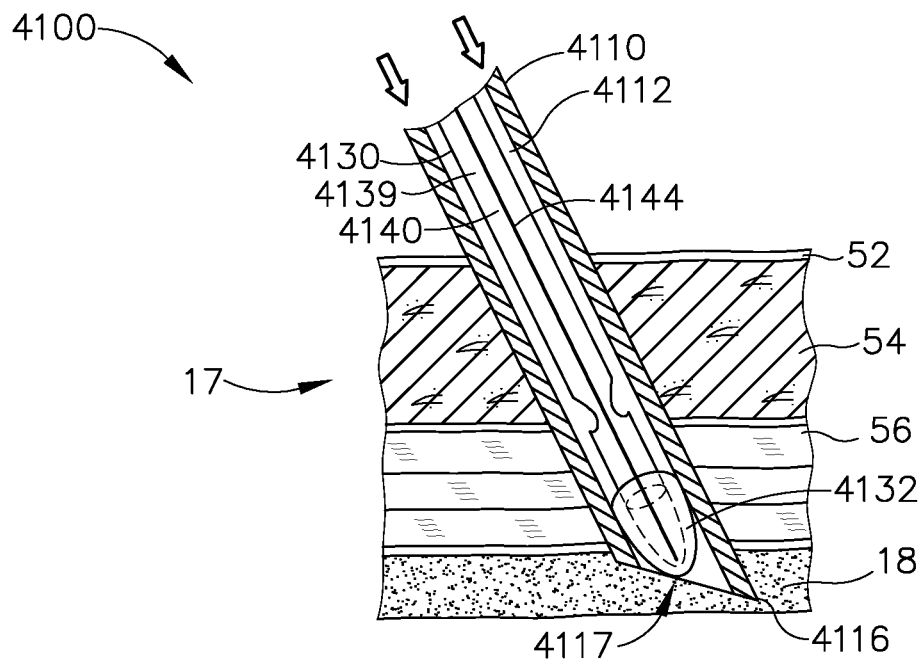
Figure 65G:
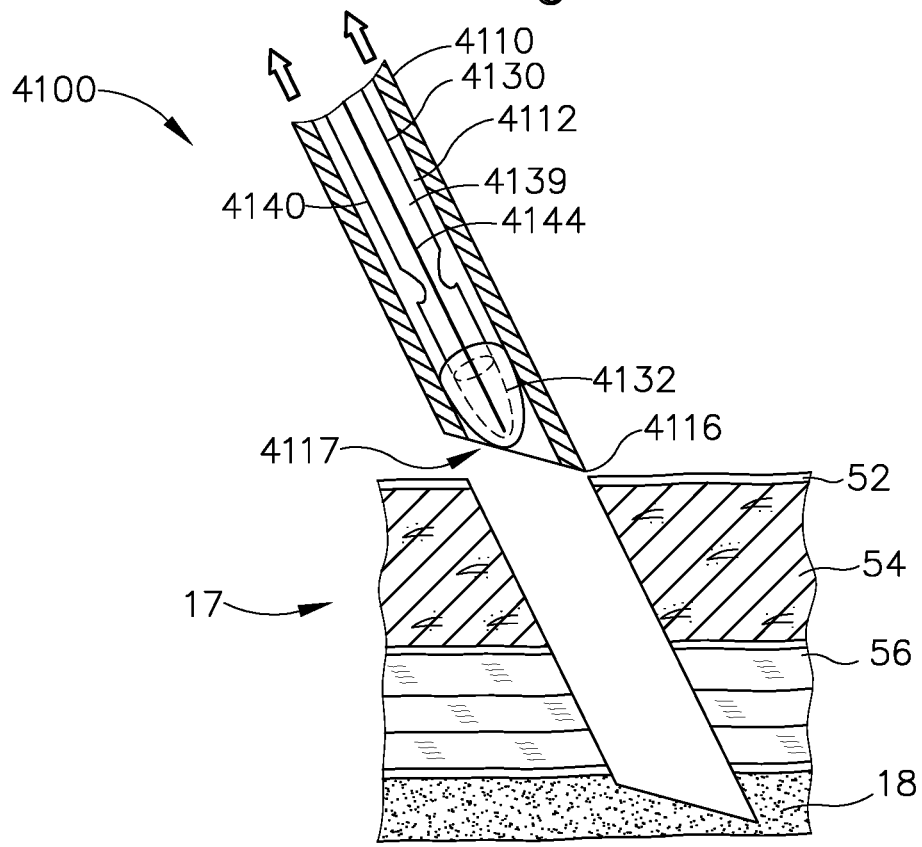

Once the clinician has confirmed that the current location of suture passer (4100) is the desirable site for puncturing the layers of fascia (56), cable (4144) is released to move distally through inner lumen (4139) to thereby allow needle head (4132) to return to the contracted state. Needle head (4132) and inner needle (4130) are then retracted into outer lumen (4112) through distal opening (4117) as seen in FIG. 65E. In addition, tissue (17) also reassumes its original characteristics and no longer extends into cavity (18) once needle head (4132) and inner needle (4130) are retracted into outer lumen (4112). As shown in FIG. 65F, suture passer (4100) is further advanced into the patient's body to puncture tissue (17) with distal tip (4116) since needle head (4132) and inner needle (4130) are contained within outer sheath (4110). Since suture passer (4100) is capable of performing both functions of identifying the penetration site and subsequently puncturing tissue (17), it is more likely that clinician will puncture tissue (17) at the desired location.

After reaching the state shown in FIG. 65F, inner needle (4130) may be advanced distally and then retracted proximally to capture a suture thread (60) within a notch (4133). For instance, an additional exertion of force on driver (4142) extends notches (4133) beyond outer lumen (4112) of outer sheath (4110). In this instance, inner needle (4130) and notches (4133) are configured to be physically maneuvered within the patient's body to catch and subsequently release suture thread (60) (see FIG. 4A). After suture passer (4100) captures suture thread (60) within cavity (18), suture passer (4100) may then be retracted proximally from tissue (17) to pull the captured suture thread (60) through tissue (17). Suture passer (4100) may then release suture thread (60) for subsequent manipulation of suture thread (60). After suture passer (4100) has been retracted from and reinserted through tissue (17) to reach cavity (18) a desired number of times, suture passer (4100) may be finally removed from tissue (17) as shown in FIG. 65G. In some instances, this may leave a passageway through tissue (17) that needs to be closed using a suture, staple, adhesive, and/or any other suitable devices or techniques. In some other instances, the passageway left in tissue (17) may be small enough to be self-sealing, such that a suture, staple, adhesive, and/or any other device or technique is not needed in order to close the passageway left by suture passer (4100) in tissue (17).

ii. Exemplary Outer Needle with Circular Sharpened Edge Tip

Figure 66:
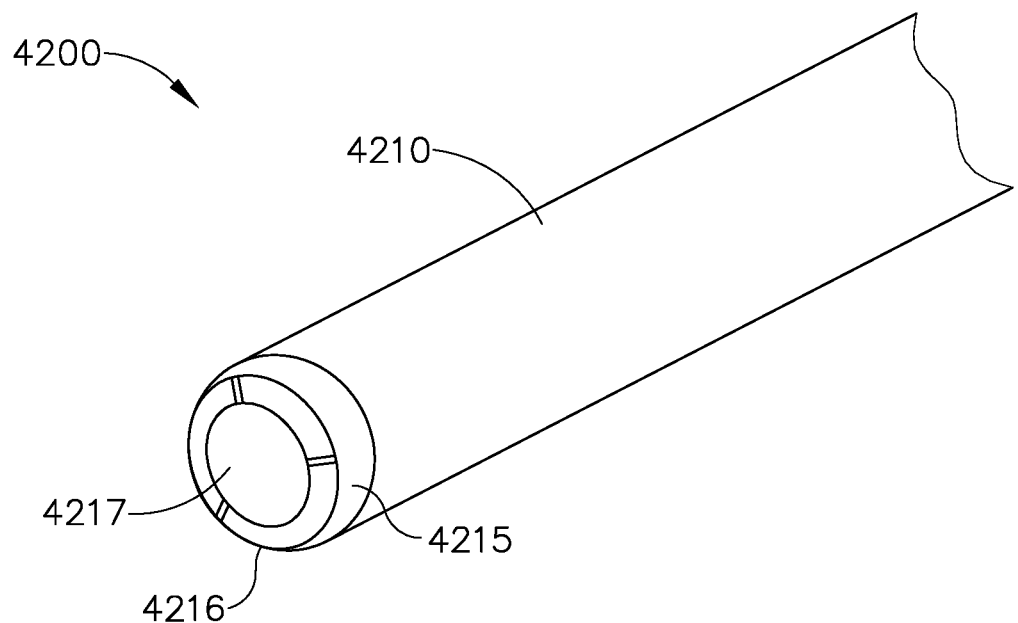
Figure 67:
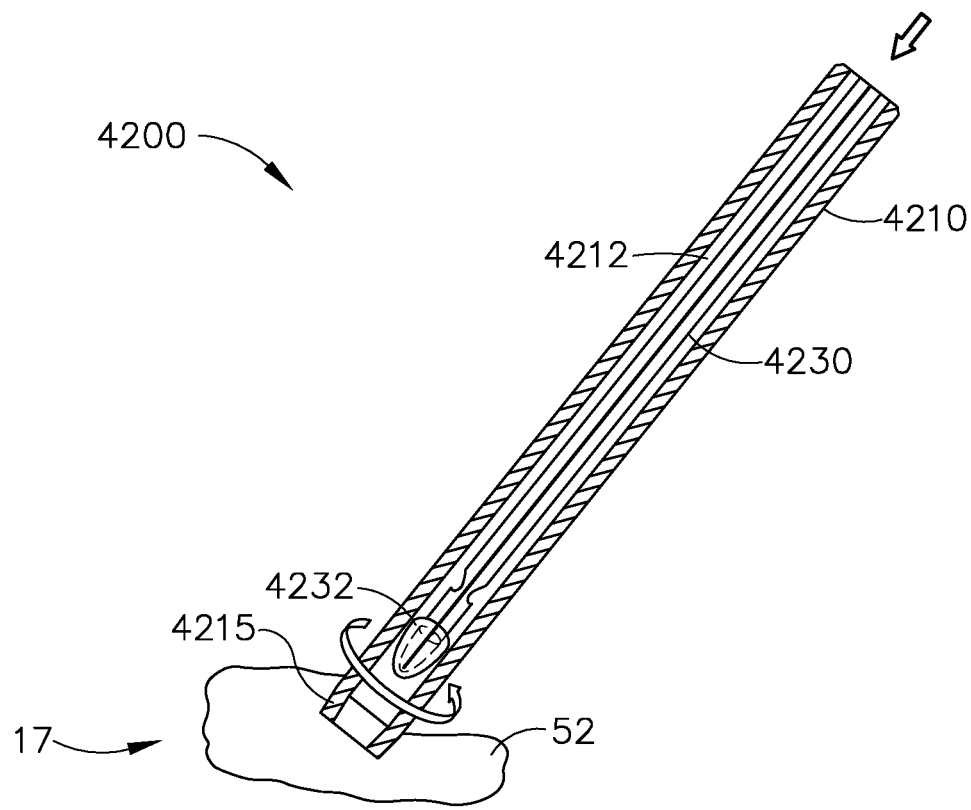

FIGS. 66-67 illustrate a second exemplary suture passer (4200) comprising an outer sheath (4210) and inner needle (4130) contained therein. Except as otherwise described below, outer sheath (4210) is operable similar to outer sheath (4110) (see FIG. 64) described above. Outer sheath (4210) includes a distal tip (4216) that has a distal end with a circular sharped edge tip (4215) about a longitudinal axis (not shown). Sharpened edge tip (4215) is configured to puncture tissue (17) when outer sheath (4210) is rotated and driven distally against tissue (17). Distal tip (4216) further includes a distal opening (4217) coaxially positioned inward of sharpened edge tip (4215) such that sharpened edge tip (4215) surrounds distal opening (4217). Inner needle (4130) is slidably contained within an outer lumen (4212) of outer sheath (4210) for use against tissue (17) as discussed above. Suture passer (4200) of this example is thus operable in the same way as suture passer (4100) described above. The difference between suture passers (4100, 4200) lies in the fact that distal tip (4116) of outer sheath (4110) is obliquely oriented along the longitudinal axis of outer sheath (4110); while distal tip (4216) of outer sheath (4210) is perpendicular to the longitudinal axis of outer sheath (4210).

B. Exemplary Suture Passer with a Resiliently Pointed Tip

Figure 68:
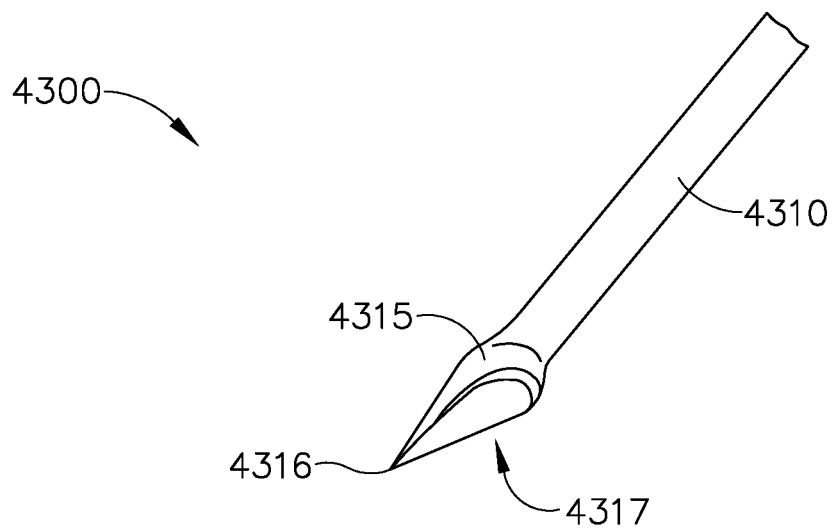
Figure 69A:
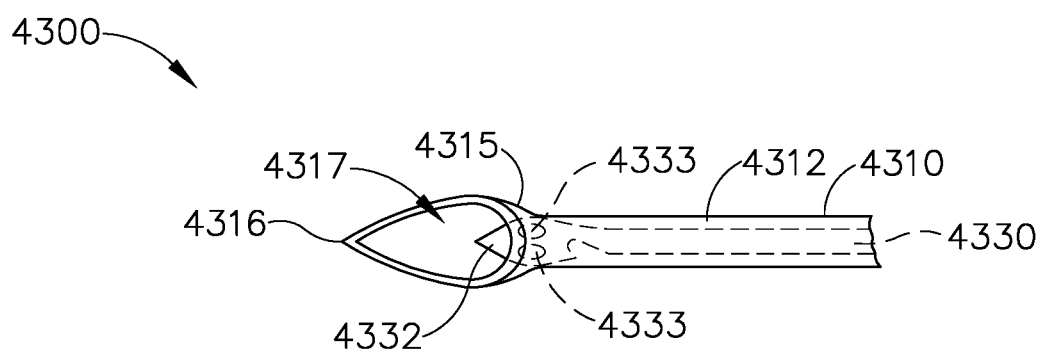
Figure 69B:
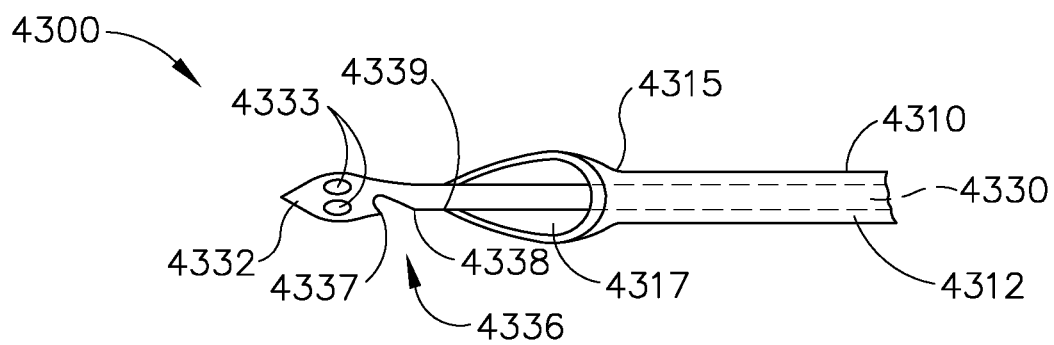

FIGS. 68-69B depict a third exemplary suture passer (4300) comprising an outer sheath (4310) and an inner needle (4330) contained therein. Except as otherwise described below, outer sheath (4310) and inner needle (4330) are respectively similar to outer sheath (4110) (see FIG. 64) and inner needle (4130) (see FIG. 64) described above. A distal portion of outer sheath (4310) includes a distal tip (4316), a bulbous neck (4315), and a distal opening (4317). Distal tip (4316) has a pointed end positioned distally along outer sheath (4310) relative to bulbous neck (4315) and distal opening (4317). Distal tip (4316) is also configured to puncture tissue (17) (see FIG. 65A) when outer sheath (4310) is driven against tissue (17) (see FIG. 65A).

As seen in FIG. 69A, inner needle (4330) includes a distal end having a head (4332) that is resiliently biased to an expanded state. However, with head (4332) positioned in outer lumen (4312), head (4332) is laterally constrained to a contracted state within outer sheath (4310). Head (4332) includes a pair of flex apertures (4333) that are configured to facilitate the resilient contraction of head (4332) when in the contracted state. Any other suitable number of flex apertures (4333) may be provided. Bulbous neck (4315) has a wider diameter than outer lumen (4312) along the longitudinal length of outer sheath (4310) such that bulbous neck (4315) allows head (4332), including flex apertures (4333), to resiliently expand from the contracted state to the expanded state as inner needle (4330) distally translates from a retracted position shown in FIG. 69A toward an extended position shown in FIG. 69B.

In the present example, flex apertures (4333) are configured to provide for compressible deformation of head (4332) to thereby reduce the frictional resistance between head (4332) and outer lumen (4312) during translation of inner needle (4330) between extended and retracted positions. Upon inner needle (4330) distally translating to the extended position, where head (4332) extends beyond distal opening (4317), flex apertures (4333) become enlarged and thereby cause head (4332) to transition to the expanded state, as seen in FIG. 69B.

In the present example, head (4332) further includes a notch (4336) that is configured to receive and hold suture thread (60) (see FIG. 4A) radially inwardly toward inner needle (4330) when inner needle (4330) is selectively maneuvered to catch suture thread (60). Notch (4336) may be further configured to urge suture thread (60) (see FIG. 4A) radially outwardly to thereby release suture thread (60) (see FIG. 4A) from notch (4336) when inner needle (4130) is selectively maneuvered to release suture thread (see FIG. 4A). Similar to notches (4133) (see FIG. 65A), notch (4336) includes a catch undercut (4337) and a release cam surface (4338) positioned between catch undercut (4337) and an outer radial surface (4339) of inner needle (4330).

Figure 70:
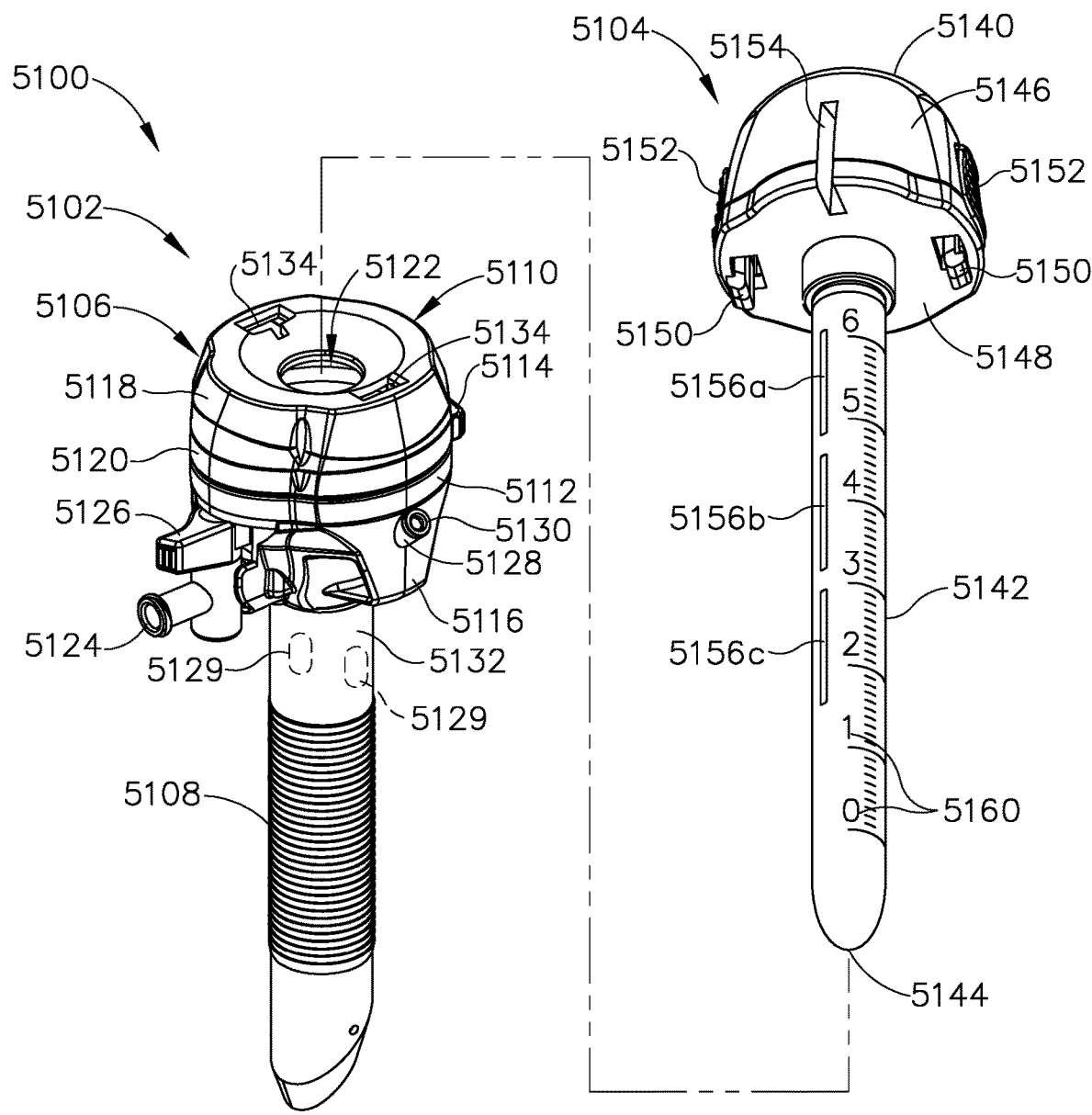

XII. Exemplary Surgical Access Device Having Obturator Configured as Wound Closure Device FIG. 70 shows another exemplary surgical access device in the form of trocar assembly (5100), which includes a trocar (5102) and an obturator (5104) configured to releasably couple with trocar (5102). Trocar (5102) includes a housing assembly (5106) and a cannula (5108) coupled to and extending distally from housing assembly (5106) along a central axis of trocar (5102), which coincides with a central axis of trocar assembly (5100). Housing assembly (5106) includes a proximal housing (5110), a housing cap plate (5112), a latch ring (5114), and a distal housing (5116). Proximal housing (5110) has a proximal housing head (5118) and a proximal housing base (5120), and is selectively detachable from the remainder of trocar (5102) via actuation (e.g., rotation) of latch ring (5114) relative to housing cap plate (5112). A central lumen of cannula (5108) communicates with an interior of housing assembly (5106) to define a working channel (5122) extending through trocar (5102) along the central axis thereof. Trocar (5102) further includes an insufflation port (5124) (or "stopcock") having an internal valve (not shown) that is movable between open and closed positions by a valve lever (5126). Insufflation tubing (not shown) is coupled to an inlet of insufflation port (5124) and directs insufflation fluid, such as carbon monoxide, from a fluid source into insufflation port (5124), which directs the fluid distally through working channel (5122) into a patient body cavity.

In the present example, trocar (5102) is constructed as a wound closure device configured to facilitate suturing of a tissue opening created by trocar (5102) during initial insertion through tissue, described above. In that regard, trocar (5102) includes a pair of needle guide structures shown in the form of needle guide tubes (5128) projecting outwardly from respective side portions of housing assembly (5106). Each needle guide tube (5128) is configured to direct a suture passer needle (or simply "suture passer") through trocar (5102), across working channel (5122), at an oblique angle relative to the central axis of trocar (5102) to thereby establish an oblique suture path extending through trocar (5102) and adjacent tissue to be sutured. Each needle guide tube (5128) defines or otherwise communicates with a needle entrance port that opens to working channel (5122) through a first side portion of trocar (5102) at a proximal location. Each needle guide tube (5128) further communicates with a needle exit port (5129) that opens to working channel (5122) through an opposed second side portion of trocar (5102) at a distal location. Each pair of needle entrance and exit ports and their respective needle guide tube (5128) cooperate to define a corresponding suture path extending across working channel (5122) and through the trocar central axis at an oblique angle relative to the trocar central axis. As used herein, the term "oblique" and variations thereof means neither parallel nor perpendicular to the referenced axis, such as the central axis of trocar (5102).

Each needle entrance port and needle exit port (5129) of trocar (5102) may be provided with a pierceable seal configured to maintain insufflation while a suture passer needle extends through the port, and/or following proximal withdrawal of the suture passer needle from the port. In the present example, trocar (5102) includes a seal cap (5130) arranged within the entrance end of each needle guide tube (5128) and which serves to seal the corresponding needle entrance port. Trocar (5102) further includes a cannula sleeve (5132) received over a narrowed proximal portion of cannula (5108), and which includes a pair of seal protrusions (not shown) projecting radially inwardly from an inner surface of cannula sleeve (5132) and into needle exit ports (5129) to thereby seal needle exit ports (5129). Each seal is configured to be pierced by a suture passer needle directed through trocar (5102) along the oblique suture paths.

Trocar (5102) may be further configured and operable in accordance with any one or more of the exemplary teachings disclosed in U.S. application Ser. No. 15/637,683, entitled "Trocar with Oblique Needle Insertion Port and Perpendicular Seal Latch," filed on Jun. 29, 2017; issued as U.S. Pat. No. 10,639,068 on May 5, 2020; and U.S. application Ser. No. 15/637,688, entitled "Trocar with Oblique Needle Insertion Port and Coplanar Stopcock," filed on Jun. 29, 2017, issued as U.S. Pat. No. 10,485,580 on Nov. 26, 2019. The disclosures of these references are incorporated by reference herein.

A. Exemplary Obturator Wound Closure Device Configured to Define Various Suture Path Angles In some instances, it may be desirable to provide suture guide features on an obturator to enable the obturator to function as a wound closure device independently from or in combination with a trocar. In the present example, as described in greater detail below, obturator (5104) of trocar assembly (5100) is provided with various suture guide features that enable obturator (5104) to function as a wound closure device independently from a trocar (5102). Advantageously, obturator (5104) may be employed to facilitate closure of a tissue opening created by trocar (5102) or by various other trocars not having suture guide features.

As best shown in FIG. 71, obturator (5104) of the present example includes a head (5140) and a shaft (5142) extending distally from head (5140) and terminating at a distal tip (5144). Shaft (5142) is formed with an outer diameter smaller than that of obturator head (5140), and is configured to be received within working channel (5122) of trocar (5102) through a proximal opening formed in proximal housing head (5118). Obturator head (5140) is configured to function as a handle by which an operator may grasp and manipulate obturator (5104). Head (5140) includes a circumferentially extending sidewall (5146) that tapers proximally, and a distal wall (5148) extending generally transverse to a central axis of obturator (5104). A pair of tabs (5150) depends downwardly from distal wall (5148) and is configured to be received within a corresponding pair of slots (5134) formed in a proximal face of proximal housing head (5118) of trocar (5102). Tabs (5150) are configured to releasably engage slots (5134) to thereby releasably couple obturator (5104) with trocar (5102). Buttons (5152) arranged on sidewall (5146) are selectively operable, for example by squeezing, to actuate tabs (5150) radially and thereby release tabs (5150) from slots (5134) so obturator (5104) may be separated from trocar (5102).

Distal tip (5144) of obturator (5104) tapers distally to a rounded point configured to puncture tissue. Accordingly, when coupled with trocar (5102) via engagement of tabs (5150) with slots (5134), obturator (5104) is configured to facilitate insertion of trocar cannula (5108) distally through tissue to thereby establish an opening in the tissue. During insertion, trocar assembly (5100) may be grasped and manipulated by obturator head (5140). As described above in connection with trocar assembly (510), following insertion of cannula (5108) through tissue into a body cavity, obturator (5104) is removed from trocar (5102) and one or more surgical procedures is performed by inserting a surgical instrument distally through trocar (5102) along working channel (5122). Following completion of the one or more surgical procedures, trocar (5102) is removed from the tissue opening and the tissue opening may be sutured closed using suture guide features provided on obturator (5104), as described below. Accordingly, obturator (5104) of the present example is operable as both a trocar insertion device and a wound closure device.

As shown best in FIG. 71, obturator (5104) includes suture guide features in the form of a pair of needle entrance ports (5154) arranged on obturator head (5140), and a plurality of needle exit ports (5156a, 5156b, 5156c) arranged on obturator shaft (5142). Each needle port (5154, 5156a, 5156b, 5156c) opens to an interior of obturator (5104), defined by head (5140) and shaft (5142) in combination, and is configured to guide a suture passer needle distally through the obturator interior along a suture path that defines an angle relative to a central axis of obturator (5104) (referred to herein as a "suture path angle") that is oblique, as described in greater detail below.

In the present example, each needle entrance port (5154) of obturator (5104) is in the form of an elongate slot that extends axially along head sidewall (5146) and into a radially outer portion of head distal wall (5148). Needle entrance ports (5154) are arranged at diametrically opposed positions on obturator head (5140), and are spaced circumferentially equidistantly between tabs (5150). In other examples, needle entrance ports (5154) may be arranged in various other configurations. For instance, needle entrance ports (5154) may be arranged in a non-diametrically opposing configuration. Additionally, obturator (5104) may include three or more needle entrance ports (5154) arranged with uniform or non-uniform circumferential spacing such that no entrance ports (5154), or alternatively one or more pairs of needle entrance ports (5154), are arranged in a diametrically opposed configuration.

Needle exit ports (5156a, 5156b, 5156c) are in the form of elongate slots that extend axially along obturator shaft (5142). In the present example, shaft (5142) includes first and second sets of three needle exit ports, arranged on opposing sides shaft (5142): a proximal exit port (5156a), a medial exit port (5156b), and a distal exit port (5156c). Needle exit ports (5156a, 5156b, 5156c) of each set are aligned axially with one another parallel to the obturator central axis, and the first and second sets are arranged at diametrically opposed positions on shaft (5142). Each needle entrance port (5154) on obturator head (5140) cooperates with a respective set of needle exit ports (5156a, 5156b, 5156c) arranged on an opposing side of obturator shaft (5142) to guide a suture passer needle along a respective suture path. In the present example, each needle entrance port (5154) is diametrically opposed from its respective set of needle exit ports (5156a, 5156b, 5156c). Accordingly, the first and second suture paths defined by needle ports (5154, 5156a, 5156b, 5156c) of the present example lie in the same axially extending plane, and intersect to define an X-shaped pattern. In configurations in which the first and second suture paths define the same suture path angle relative to the central axis of obturator (5104), the suture paths may intersect generally at the central axis.

Each suture path defined by a needle entrance port (5154) and its respective set of needle exit ports (5156a, 5156b, 5156c) may define a variety of oblique suture path angles relative to the obturator central axis, depending on the particular needle exit port (5156a, 5156b, 5156c) through which a suture passer needle exits obturator (5104). For instance, a suture passer needle may be directed to exit obturator (5104) through: (i) a proximal exit port (5156a), to define a first oblique suture path angle suitable for use with tissue of a first thickness; (ii) a medial exit port (5156b), to define a second, steeper (i.e., smaller) oblique suture path angle suitable for use with tissue of a second, greater thickness; or (iii) a distal exit port (5156c), to define a third, even steeper oblique suture path angle suitable for use with tissue of a third, even greater thickness. Advantageously, the axially elongate shape of each needle exit port (5156a, 5156b, 5156c) enables a suture passer needle to be directed through a selected portion of the needle exit port (5156a, 5156b, 5156c), selected in a proximal-distal direction, to achieve a variety of different suture path angles within the same needle exit port (5156a, 5156b, 5156c).

In the present example, each set of needle exit ports (5156a, 5156b, 5156c) is diametrically opposed from its respective needle entrance port (5154) along an axially extending plane containing the central axis of obturator (5104). In that regard, as used herein with reference to various first and second structures or reference points, the term "diametrically opposed" and variations thereof is intended to encompass configurations in which the referenced structures are arranged at different longitudinal locations along a referenced axis, such as central axis of obturator (5104). For instance, in the present example each needle entrance port (5154) is spaced proximally from its respective needle exit ports (5156a, 5156b, 5156c), though the entrance port (5154) and its needle exit ports (5156a, 5156b, 5156c) are still understood to be diametrically opposed from one another along the same axially extending plane, as described above. In alternative versions of obturator (5104), a needle entrance port (5154) may lie in a first plane containing the obturator central axis while the corresponding needle exit ports (5156a, 5156b, 5156c) lie in a second plane containing the obturator central axis. In such versions, the first and second planes may be angularly offset from one another such that the needle entrance port (5154) and its respective needle exit ports (5156a, 5156b, 5156c) are not diametrically opposed from one another.

As shown in FIG. 71, each needle exit port (5156a, 5156b, 5156c) is provided with a pierceable seal (5158) configured to be pierced by a suture passer needle upon insertion through obturator (5104) during a wound closure procedure. Each pierceable seal (5158) is configured to support a suture passer needle and suture thread directed therethrough, as well as prevent advancement of tissue and bodily fluids into the obturator interior, and also maintain any remaining insufflation of the patient body cavity. Though not shown, each needle entrance port (5154) may be provided with a pierceable seal as well. Further, it will be appreciated that one or more of the needle ports of the additional exemplary obturators (5210, 5260, 5330) described below may be provided with a pierceable seal or other sealing element that provides similar functional benefits. In various examples, such sealing elements may ensure that each of the suture paths extending through the respective obturator (5210, 5260, 5330) remains in a generally sealed state while a suture passer needle is received along the suture path, as well as following proximal withdrawal of the suture passer needle from the obturator (5210, 5260, 5330).

In the present example, obturator shaft (5142) further includes visual indicia in the form of tissue depth graduation marks (5160) spaced axially along a length of shaft (5142). Marks (5160) may indicate any suitable distance increments, such as inches or centimeters for example, and subdivisions of each increment. Marks (5160) are configured to communicate to a surgeon a depth, measured from a distal end portion of shaft (5142), to which shaft (5142) has been inserted within patient tissue. For example, during or after insertion of shaft (5142) into tissue through a tissue opening, a surgeon may observe a distal-most mark (5160) that is visible extracorporeally to determine a depth to which shaft (5142) has been inserted into the tissue, which may indicate a thickness of the tissue. The surgeon may account for this depth when determining which needle exit port (5156a, 5156b, 5156c) through which to direct the suture passer needles during a wound closure procedure.

B. Exemplary Wound Closure Procedure Using Obturator Wound Closure Device Configured to Define Various Suture Path Angles FIGS. 72A-72I show steps of an exemplary wound closure procedure (also referred to as a "suturing procedure") for suturing closed a tissue opening (5172) formed in tissue (5170) of an exemplary thickness, using obturator (5104) of trocar assembly (5100) as a wound closure device. Like tissue (17) described above, tissue (5170) includes outward superficial layers and inward deeper layers. Superficial layers generally include an outer layer of skin (5174) and an inner layer of fat (5176). The deeper layers include layers of fascia (5178), which are fibrous and flexible with relatively higher tensile strength than the superficial layers.

FIG. 72A shows trocar (5102) of trocar assembly (5100) following completion of one or more surgical procedures in which one or more endoscopic surgical instruments are directed distally through trocar (5102), via working channel (5122), into body cavity (5180) to access tissue therein. FIG. 72B shows proximal removal of trocar from tissue opening (5172). FIG. 72C shows insertion of obturator shaft (5142) distally through tissue opening (5172) so that obturator tip (5144) resides within body cavity (5180).

FIG. 72D shows an exemplary suture passer needle (5182) and a suture thread (5184) having a thread end (5186) directed distally through obturator (5104) along an exemplary first suture path. The first suture path extends through a first needle entrance port (5154), an interior of obturator (5104), an opposed proximal needle exit port (5156a), and an adjacent first portion of tissue fascia (5178) into body cavity (5180). The suture path defines a corresponding first suture path angle relative to the central axis of obturator (5104). The suture path and the resulting suture path angle are chosen by a surgeon based on a thickness of tissue (5170) and a desired amount of tissue fascia (5178) to be captured by suture thread (5184) on each side of obturator (5104), referred to as "tissue bite." In the present context, tissue bite is defined by a distance (X) measured perpendicularly from the inner wall of tissue opening (5172), which may coincide with the outer surface of obturator shaft (5142), to the point at which suture passer needle (5182) and thus suture thread (5184) exits distally from tissue fascia (5178) into body cavity (5180). In some examples, tissue bite distance (X) may be approximately 1 centimeter.

FIG. 72E shows an exemplary alternative arrangement in which obturator (5104) is positioned within a tissue opening (5192) formed in tissue (5190) of an exemplary second thickness that is greater than the thickness of tissue (5170). Like tissue (5170), tissue (5190) includes an outer layer of skin (5194), an upper layer of fat (5196), and deeper layers of fascia (5198) above body cavity (5200). To achieve the same tissue bite distance (X) in tissue (5190) as in tissue (5170), suture passer needle (5182) is directed along a suture path having a steeper suture path angle measured relative to the obturator central axis. In the present example, suture passer needle (5182) extends along the suture path through a proximal portion of needle entrance port (5154), through an interior of obturator head (5140), and exiting from a distal portion of needle entrance port (5154). The suture passer needle (5182) reenters obturator (5104) through a proximal needle port (5156a) on a first side of obturator shaft (5142), and exits through a medial needle port (5156b) on an opposed second side of obturator shaft (5142). Accordingly, it will be appreciated that proximal and medial needle exit ports (5156a, 5156b) on shaft (5142) may also function as needle entrance ports when defining suture paths of relatively steeper angles relative to obturator central axis.

Following the steps shown in FIGS. 72D and 72E, suture passer needle (5182) is manipulated by a surgeon to release thread end (5186) of suture thread (5184) within body cavity (5180, 5200), and suture passer needle is withdrawn proximally from obturator (5104). FIG. 72F shows obturator (5104) positioned within tissue (5170), and suture passer needle (5182) being directed distally through obturator (5104) along a second suture path extending through a second needle entrance port (5154), an opposed proximal needle exit port (5156a), and an adjacent second portion of tissue fascia (5178), into body cavity (5180). Suture passer needle (5182) and/or obturator (5104), via head (5140), are suitably manipulated by a surgeon to capture thread end (5186) with a distal tip of suture passer needle (5182). Suture passer needle (5182) and thread end (5186) are then withdrawn proximally along the second suture path.

As shown in FIG. 72G, a first thread leg (5202) of suture thread (5184) extends through obturator (5104) and tissue fascia (5178) along the first suture path; a second thread leg (5204) extends through obturator (5104) and tissue fascia (5178) along the second suture path; and an anchoring loop (5206) extends through body cavity (5180) between first and second captured portions of tissue fascia (5178). In the present example, the second suture path defines a suture path angle similar to that of the first suture path, shown in FIG. 72D. In alternative examples, however, suture passer needle (5182) may be directed through obturator (5104) along first and second suture paths having different suture path angles, for example to accommodate nonuniformities in the structure of tissue (5170).

As shown in FIG. 72H, once suture thread (5184) has been threaded through tissue (5170) along the first and second suture paths, obturator (5104) is withdrawn proximally from tissue opening (5172) to allow thread legs (5202, 5204) to advance distally through needle ports (5154, 5156a), thereby releasing suture thread (5184) from obturator (5104). Thread legs (5202, 5204) may then be pulled tight to draw together the captured portions of fascia (5178) on either side of tissue opening (5172), and tied to form a suture knot (5208) at a location just proximally of fascia layers (5178), as shown in FIG. 72I. Optionally, the remaining portions of thread legs (5202, 5204) may be directed through fat (5176) and skin (5174) using suture needles, for example as shown in FIG. 4D, to create an additional "superficial" suture knot to fully close tissue opening (5172) and promote optimal healing.

XIII. Exemplary Obturator Wound Closure Device Having Deployable Needle Guide Arms

A. Exemplary Obturator Wound Closure Device

FIGS. 73A and 73B show another exemplary obturator (5210) configured for use as a wound closure device. Though not shown, it will be understood that obturator (5210) may also be used as a trocar insertion device in combination with any suitable trocar, such as trocar (5102) described above. Like obturator (5104) described above, obturator (5210) is provided with suture guide features that enable obturator (5104) to function as a wound closure device independently from a trocar, as described in greater detail below.

Obturator (5210) is similar to obturator (5104) in that obturator (5210) includes a head (5212) and a shaft (5214) extending distally from head (5212) and terminating at a distal tip (5216) configured to puncture tissue. Shaft (5214) is formed with an outer diameter smaller than that of head (5212), and is configured to be received within a working channel of any suitable trocar, such as trocar (5102) described above. Head (5212) is configured to function as a handle by which an operator may grasp and manipulate obturator (5210). Head (5212) includes a circumferentially extending sidewall (5218) that tapers proximally, and a distal wall (5220) extending generally transverse to a central axis of obturator (5210). A pair of tabs (5222) depends downwardly from distal wall (5220) and is configured to be received within a corresponding pair of slots formed in a proximal face of a trocar (not shown), such as slots (5134) of trocar (5102). Tabs (5222) are configured to releasably engage trocar slots to thereby releasably couple obturator (5210) with the trocar. Buttons (5224) arranged on sidewall (5218) are selectively operable, for example by squeezing, to actuate tabs (5222) radially and thereby release tabs (5222) from the trocar slots so obturator (5210) may be separated from the trocar.

As shown in FIG. 73A, obturator (5210) includes suture guide features in the form of a pair of needle entrance ports (5226) arranged on obturator head (5212), a pair of needle exit ports (5228) arranged on a proximal portion of shaft (5214), and a pair of deployable needle guide arms (5230) arranged distally of needle exit ports (5228) on shaft (5214). Each needle entrance port (5226) cooperates with a needle exit port (5228) arranged on an opposing side of obturator (5210) to guide a suture passer needle along a respective suture path extending obliquely relative to a central axis of obturator (5210). As described below, a corresponding needle guide arm (5230) guides a distal portion of a suture passer needle along the respective suture path.

Each needle entrance port (5226) communicates with its respective needle exit port (5228) via an internal pathway or interior (not shown) of obturator (5210). In the present example, each needle entrance port (5226) is defined by a needle guide tube (5232) projecting angularly outwardly from head (5212), and needle exit ports (5228) are in the form of elongate slots. The elongate configuration of each needle exit port (5228) enables the location at which a suture passer needle passes through needle exit port (5228) to be adjusted proximally or distally to thereby alter the resulting suture path angle. In other examples, needle guide tubes (5232) may be omitted from obturator (5210), and/or needle exit ports (5228) may be formed with various other shapes. In some examples, each needle entrance port (5226) and/or its respective needle exit port (5228) may include a sealing element, such as a pierceable seal, configured to maintain the corresponding suture path in a generally sealed state during use of obturator (5210) as a wound closure device.

In the present example, needle entrance ports (5226) are diametrically opposed relative to one another, and each needle entrance port (5226) is diametrically opposed from a respective needle exit port (5228) along an axially extending plane containing the obturator central axis. Accordingly, the first and second suture paths defined by needle ports (5226, 5228) of the present example lie in the same plane, and intersect to define an X-shaped pattern. In configurations in which the first and second suture paths define the same suture path angle, the sutures paths may intersect generally at the central axis of obturator (5210). In other examples, needle entrance and exit ports (5226, 5228) may be arranged in various other configurations and quantities to define corresponding suture paths of various suture path angles.

As shown in FIGS. 73A and 73B, deployable needle guide arms (5230) are coupled to obturator shaft (5214) distally of needle exit ports (5228), on a medial portion of shaft (5214) in the present example. Needle guide arms (5230) are diametrically opposed to one another in the same axial plane in which needle entrance and exit ports (5226, 5228) are arranged. Each needle guide arm (5230) is configured to pivot about a proximal end (5234) thereof between a deployed position (see FIG. 73A) and a retracted position (see FIG. 74D). In the retracted position, each needle guide arm (5230) is received within a respective elongate recess (5236) formed in a side of the medial portion of obturator shaft (5214). Each recess (5236) is formed with a depth sufficient to enable its guide arm (5230) to lie flush with, or recessed slightly beneath, an outer surface of shaft (5214) when guide arm (5230) is retracted. Advantageously, this enables shaft (5214) to pass freely through a working channel of a trocar when obturator (5210) is coupled to the trocar. In the deployed position, each needle guide arm (5230) extends radially outwardly from shaft (5214) and generally perpendicular to the central axis of obturator (5210), as shown in FIG. 73A. When in the deployed position, each needle guide arm (5230) is configured to receive and guide the distal end of a suture passer needle, as well as anchor obturator (5210) within a tissue opening, as described in greater detail below.

Needle guide arms (5230) are selectively movable between their retracted and deployed positions by an actuator element (not shown), which may be arranged on obturator head (5212), for example. Persons of ordinary skill in the art will recognize that the actuator element may be in the form of a button, switch, knob, wheel, or any other suitable element operatively coupled with needle guide arms (5230) and movable between two or more positions to effect deployment and retraction of needle guide arms (5230) relative to shaft (5214). Additionally, the actuator element may be configured to maintain needle guide arms (5230) at one or more intermediate positions between the retracted and deployed positions shown herein.

As shown in FIG. 73B, each needle guide arm (5230) includes an elongate sealed aperture (5238) configured to be pierced by a distal tip of a suture passer needle. An opening (5240) extends from a lateral side of sealed aperture (5238) to a corresponding lateral side of needle guide arm (5230). Opening (5240) is configured to allow a suture thread directed through sealed aperture (5238) to be released laterally from needle guide arm (5230), for example by applying a lateral pulling force to the suture thread. The elongate configuration of each sealed aperture (5238) enables it to receive therethrough a suture passer needle oriented at various suture path angles relative to the central axis of obturator (5210).

While obturator (5210) of the present example includes distal needle guide structures in the form of pivoting needle guide arms (5230), other variations of obturator (5210) may include distal needle guide structures of various other forms configured to project radially outwardly from shaft (5214) and guide distal portions of suture passer needles along first and second suture paths extending through obturator (5210). Additionally, while obturator (5210) of the present example is shown having suture guide features defining first and second suture paths, in other examples obturator (5210) may have suture guide features arranged in various configurations to define a single suture path or three or more suture paths.

B. Exemplary Wound Closure Procedure Using Obturator Wound Closure Device Having Deployable Needle Guide Arms FIGS. 74A-74E show steps of an exemplary procedure for suturing closed a tissue opening (5172) formed in tissue (5170) by a trocar (not shown), such as trocar (5102), using obturator (5210) as wound closure device. Following completion of one or more surgical procedures using the trocar, the trocar is removed from tissue opening (5172) and obturator shaft (5214) is inserted distally through tissue opening (5172), with needle guide arms (5230) in their retracted positions. Once obturator (5210) is positioned such that its head (5212) generally confronts skin (5174), needle guide arms (5230) are deployed so that they confront a distal surface of tissue fascia (5178), as shown in FIG. 74A. In that regard, pivoting proximal ends (5234) of needle guide arms (5230) are spaced distally from obturator head (5212) by a distance generally corresponding to the anticipated thickness of tissue (5170). Such a configuration enables needle guide arms (5230) to abut a distal surface of a lower-most layer of fascia (5178) when deployed, and thereby function as anchor elements configured to limit axial movement of obturator (5210) relative to tissue (5170) during a suturing procedure.

As shown in FIG. 74A, a suture passer needle (5242) and a thread end (5246) of a suture thread (5244) are directed distally through obturator (5210) along a first oblique suture path extending through a first needle entrance port (5226), an opposed first needle exit port (5228), an adjacent first portion of tissue fascia (5178), and a corresponding first needle guide arm (5230) via its sealed aperture (5238), into body cavity (5180). Suture passer needle (5242) is then manipulated to release thread end (5246) within body cavity (5180), and is withdrawn proximally along first suture path.

As shown in FIG. 74B, suture passer needle (5242) is then directed distally along a second oblique suture path extending through a second needle entrance port (5226), an opposed second needle exit port (5228), an adjacent second portion of tissue fascia (5178), and a corresponding second needle guide arm (5230) via its sealed aperture (5238), into body cavity (5180). Suture passer needle (5242) and/or obturator (5210) are then manipulated as needed to recapture thread end (5246) with suture passer needle (5242). Suture passer needle (5242) and thread end (5246) are then withdrawn proximally along the second suture path, yielding the configuration shown in FIG. 74C. As shown in FIG. 74C, a first thread leg (5248) of suture thread (5244) extends along the first suture path and captures a first portion of tissue fascia (5178), a second thread leg (5250) extends along the second suture path and captures an opposed second portion of tissue fascia (5178), and an anchoring loop (5252) extends between first and second thread legs (5248, 5250) within body cavity (5180).

As shown in FIG. 74D, needle guide arms (5230) are moved to their retracted positions to capture anchoring loop (5252) of suture thread (5244) between guide arms (5230), and obturator (5210) is withdrawn proximally from tissue opening (5240). This enables first and second thread legs (5248, 5250) to slide distally through needle ports (5226, 5228) and release from obturator (5210). As shown in FIG. 74E, needle guide arms (5230) are then moved back to their deployed positions to facilitate release of anchoring loop (5252) from guide arms (5230) through lateral openings (5240) (see FIG. 73B), thereby completely freeing suture thread (5244) from obturator (5210). Thread legs (5248, 5250) may then be pulled tight to draw together the captured portions of fascia (5178) on either side of tissue opening (5172), and then tied to form a suture knot (5254) at a location just proximally of fascia (5178), as shown in FIG. 74E. Optionally, the remaining portions of thread legs (5248, 5250) may be directed through fat (5176) and skin (5174) using suture needles, for example as shown in FIG. 4D, to create an additional "superficial" suture knot to fully close tissue opening (5172) and promote optimal healing.

XIV. Exemplary Obturator Wound Closure Device Having Deployable Anchor Feet

A. Exemplary Obturator Wound Closure Device

FIGS. 75-76B show another exemplary obturator (5260) configured for use as a wound closure device as well as a trocar insertion device. In the present example, obturator (5260) is provided with suture guide features that enable obturator (5260) to function as a wound closure device in combination with a trocar, such as trocar (5102) as described below in connection with FIGS. 77A-77E. Obturator (5260) includes a head (5262) and a shaft assembly (5264) extending distally from head (5262) along a central axis. Head (5262) includes a movable latch (5266) configured to releasably couple head (5262) with shaft assembly (5264). Shaft assembly (5264) includes a shaft (5270) having a proximal shaft portion (5272), a distal shaft portion (5274), and a flange (5276) arranged at a proximal end of proximal shaft portion (5272). In the present example, distal shaft portion (5274) is formed with a larger diameter than proximal shaft portion (5272). Shaft assembly (5264) terminates at a distal tip (5278) configured to puncture tissue during a trocar insertion procedure.

Distal tip (5278) is operatively coupled with distal shaft portion (5274) by a pair of deployable anchor feet (5280) extending therebetween. In the present example, each anchor foot (5280) includes a proximal link (5282), a distal link (5284), and medial joint (5286) hingedly coupling links (5282, 5284) to one another. Proximal links (5282) are hingedly coupled to a distal end of distal shaft portion (5274), and distal links (5284) are hingedly coupled to a proximal end of distal tip (5278). Anchor feet (5280) are movable together between a retracted position (see FIGS. 75 and 76A) in which anchor feet links (5282, 5284) extend axially and generally flush with outer surfaces of distal shaft portion (5274) and distal tip (5278), and a deployed position (see FIG. 76B) in which anchor feet links (5282, 5284) project radially outwardly from distal shaft portion (5274) and distal tip (5278). Each anchor foot link (5282, 5284) includes a chamfered end (5288) adjacent to medial joint (5286). Chamfered ends (5288) better enable proximal and distal links (5282, 5284) to hinge relative to one another when moving toward the deployed position, and are configured to contact one another in the deployed position to provide enhanced structural support to anchor feet links (5282, 5284) when deployed.

Shaft assembly (5264) of obturator (5260) further includes a plunger (5290) slidably arranged within a central lumen of shaft (5270). A proximal end of plunger (5290) extends proximally of proximal shaft portion (5272) and includes an actuation knob (5292). A distal end of plunger (5290) extends distally of distal shaft portion (5274), through a gap defined between anchor feet (5280), and couples to distal tip (5278). Plunger (5290) is slidable within the shaft lumen between a distal position in which anchor feet (5280) are retracted, as shown in FIGS. 75 and 76A, and a proximal position in which anchor feet (5280) are deployed, as shown in FIG. 76B. When plunger (5290) is arranged in its distal position, its distal end pushes distal tip (5278) axially away from distal shaft portion (5274), thereby drawing anchor feet (5280) radially inwardly toward plunger (5290). When plunger (5290) is arranged in its proximal position, its distal end pulls distal tip (5278) axially toward distal shaft portion (5274), thereby causing anchor feet (5280) to expand radially outwardly away from plunger (5290). In the present example, proximal movement of plunger (5290) causes anchor feet (5280) to deploy to a triangular configuration in which proximal links (5282) extend perpendicularly relative to the obturator central axis and distal links (5284) extend obliquely relative to the central axis. In various examples, plunger (5290) may be resiliently biased toward one of its proximal or distal positions.

Shaft assembly (5264) further includes suture guide features in the form of a pair of needle entrance ports (5294) and a pair of needle exit ports (5296) arranged distally of needle entrance ports (5294). In the present example, needle entrance and exit ports (5294, 5296) are arranged on proximal shaft portion (5272). Additionally, needle entrance ports (5294) are diametrically opposed from one another, needle exit ports (5296) are diametrically opposed from one another, and needle ports (5294, 5296) are arranged in a single axially extending plane containing the obturator central axis. Each needle entrance port (5294) communicates with a respective needle exit port (5296) arranged on an opposing side of obturator shaft (5270), via an internal pathway (not shown) or interior of shaft (5270), to define a respective suture path extending through obturator (5260) at an oblique angle relative to the obturator central axis. In the present example, the suture path angles defined by the suture paths relative to the central axis are equal to one another. In other examples, needle entrance and exit ports (5294, 5296) may be arranged in various other quantities and configurations to define corresponding suture paths of various quantities, arrangements, and suture path angles. In some examples, each needle entrance port (5294) and/or its respective needle exit port (5296) may include a sealing element, such as a pierceable seal, configured to maintain the corresponding suture path in a generally sealed state during use of obturator (5260) as a wound closure device.

As shown best in FIG. 75, obturator head (5262) is releasably coupled to proximal shaft portion (5272) and is configured to selectively decouple from proximal shaft portion (5272) during use. Head (5262) includes a proximally tapering sidewall (5300) defining an interior cavity (5302). Interior cavity (5302) is configured to receive a proximal end of the shaft assembly (5264), including a proximal end of proximal shaft portion (5272), shaft flange (5276), and plunger knob (5292). As shown in FIG. 77C, head (5262) may include a pair of downwardly depending tabs (5304) configured to releasably engage slots formed on a trocar, such as slots (5134) of trocar (5102), to thereby releasably couple obturator (5260) with trocar (5102). Buttons (5306) on head (5262) are operable to actuate tabs (5304) to selectively release obturator head (5262) from trocar (5102), for example after a trocar insertion procedure.

As shown in FIG. 75, latch (5266) of obturator head (5262) is operable to translate between an inward latched position and an outward unlatched position. In the inward latched position, latch (5266) engages an underside of shaft flange (5276) to thereby secure head (5262) to shaft assembly (5264), as well as restrain plunger (5290) in its distal position to maintain anchor feet (5280) in their retracted position. In configurations in which plunger (5290) is resiliently biased proximally, latch (5266) is configured to overcome the bias force and compress plunger knob (5292) toward flange (5276) to maintain plunger (5290) in its distal position. In the outward unlatched position, latch (5266) releases shaft flange (5276) to thereby enable head (5262) to be separated from shaft assembly (5264). In the present example, latch (5266) includes a first projection (5308) arranged at an outward end thereof to facilitate manual actuation of latch (5266), and a second projection (5310) arranged at an inward end thereof to prevent latch (5266) from decoupling from head (5262) when in its outward unlatched position. Those of ordinary skill in the art will recognize that latch (5266) make take various alternative forms in other variations of obturator (5260).

B. Exemplary Wound Closure Procedure Using Obturator Wound Closure Device Having Deployable Anchor Feet FIGS. 77A-77F show steps of an exemplary procedure for suturing closed a tissue opening (5172) formed in tissue (5170) by trocar (5102), using obturator (5260) as a wound closure device. Following completion of one or more surgical procedures using trocar (5102), all surgical instruments are withdrawn from working channel (5122) of trocar (5102). Obturator (5260) is manipulated by a surgeon, with latch (5266) in its latched position, to insert shaft assembly (5264) distally through working channel (5122). In this state, as shown in FIG. 77A, proximal shaft portion (5272) of obturator (5260) resides within trocar housing assembly (5106), distal shaft portion (5274) resides within trocar cannula (5108), and distal tip (5278) projects through the distal opening of cannula (5108) into body cavity (5180). Additionally, anchor feet (5280) remain in their retracted positions.

As indicated by directional arrows shown in FIGS. 77B and 77C, latch (5266) is moved to its outward unlatched position to enable proximal separation of obturator head (5262) from obturator shaft assembly (5264) and thereby expose plunger knob (5292). Additionally, head buttons (5306) are actuated to decouple head tabs (5304) from proximal housing head (5118) of trocar (5102). As shown in FIG. 77C, shaft assembly (5264) is advanced distally until shaft flange (5276) abuts proximal housing head (5118) of trocar (5102). In that regard, flange (5276) is formed with a diameter larger than the diameter of a proximal opening to trocar working channel (5122) formed in proximal housing head (5118). Accordingly, flange (5276) abuts proximal housing head (5118) to thereby limit distal axial movement of obturator shaft assembly (5264) relative to trocar (5102). In this position, anchor feet (5280) clear the distal end of trocar cannula (5108), and the oblique suture paths defined by obturator (5260) align with the oblique suture paths defined by trocar (5102), described above. Plunger (5290) is then moved to its proximal position to deploy anchor feet (5280). Plunger (5290) may be actuated either manually or automatically by a bias force exerted by a resilient member (Snot shown). Once deployed, anchor feet (5280) are configured to abut the distal end of cannula (5108) to thereby restrict proximal axial movement of obturator shaft assembly (5264) relative to trocar (5102). In this configuration, trocar (5102) and obturator (5260) are configured to be used in combination to guide placement of a suture thread in tissue (5170), as described below.

As shown in FIG. 77D, a suture passer needle (5314) of a suture passer device (5312) has been manipulated by an operator to direct a thread end (5318) of a suture thread (5316) distally along a first suture path extending through a first needle guide tube (5128) of trocar (5102), a first needle entrance port (5294) of obturator (5260), an opposed first needle exit port (5296) of obturator (5260), a corresponding first needle exit port (5129) of trocar (5102), and an adjacent first portion of tissue fascia (5178), into body cavity (5180). Thread end (5318) was then released by suture passer needle (5314) within body cavity (5180). As shown in FIG. 77D, suture passer needle (5314) is now directed distally along a second suture path extending through a second needle guide tube (5128) of trocar (5102), a second needle entrance port (5294) of obturator (5260), an opposed second needle exit port (5296) of obturator (5260), a corresponding second needle exit port (5129) of trocar (5102), and an adjacent second portion of tissue fascia (5178), into body cavity (5180). Suture passer needle (5314) and/or trocar (5102) and obturator (5260) are manipulated as needed to recapture suture thread end (5318) with suture passer needle (5314). Suture passer needle (5314) and thread end (5318) are then withdrawn proximally along the second suture path, yielding the suture thread configuration shown in FIG. 77E. In particular, a first thread leg (5320) of suture thread (5316) extends along the first suture path to capture a first portion of fascia (5178), a second thread leg (5322) of suture thread (5316) extends along the second suture path to capture an opposed second portion of fascia (5178), and an anchoring loop (5324) extends between first and second thread legs (5320, 5322) within body cavity (5180).

As indicated by directional arrows shown in FIG. 77E, plunger (5290) is actuated distally to thereby retract anchor feet (5280) inwardly. Trocar (5102) and obturator shaft assembly (5264) are then withdrawn distally together from tissue opening (5172), thereby releasing suture thread legs (5320, 5322) from trocar (5102) and obturator (5260). Thread legs (5320, 5322) may then be pulled tight to draw together the captured portions of fascia (5178) on either side of tissue opening (5172), and then tied to form a suture knot (5326) at a location just proximally of fascia (5178), as shown in FIG. 77F. Optionally, the remaining portions of thread legs (5320, 5322) may be directed through fat (5176) and skin (5174) using suture needles, for example as shown in FIG. 4D, to create an additional "superficial" suture knot to fully close tissue opening (5172) and promote optimal healing. Though not shown, it will be appreciated that in some variations of the exemplary wound closure procedure described above, obturator (5260) may be employed as a wound closure device independently of trocar (5102).

XV. Alternative Exemplary Obturator Wound Closure Device Having Deployable Anchor Feet A. Exemplary Obturator Wound Closure Device FIGS. 78-79B show another exemplary obturator (5330) configured for use as a wound closure device as well as a trocar insertion device. Obturator (5330) is provided with suture guide features that enable obturator (5330) to function as a wound closure device independently of a trocar. In that regard, obturator (5330) is generally similar to obturator (5260) described above, except as otherwise described below. Similar to obturator (5260), obturator (5330) includes a head (5332) and a shaft assembly (5334) extending distally from head (5332) along a central axis. Head (5332) includes a movable latch (5336) configured to releasably couple head (5332) with shaft assembly (5334). Shaft assembly (5334) includes a shaft (5338) having a proximal shaft portion (5340), a distal shaft portion (5342), and a flange (5344) arranged at a proximal end of proximal shaft portion (5340). Shaft assembly (5334) terminates at a distal tip (5346) configured to puncture tissue during a trocar insertion procedure. As described below, the components of shaft assembly (5334), including flange (5344), are formed with diameters smaller than the diameter of the working channel of the trocar with which obturator (5330) is used.

Distal tip (5346) is operatively coupled with distal shaft portion (5342) by a pair of deployable anchor feet (5348) extending therebetween. Anchor feet (5348) are similar to anchor feet (5348) described above in that each anchor foot (5348) includes a proximal link (5350), a distal link (5352), and medial joint (5354) hingedly coupling links (5352, 5354) to one another. Proximal links (5352) are hingedly coupled to a distal end of distal shaft portion (5342), and distal links (5354) are hingedly coupled to a proximal end of distal tip (5346). Anchor feet (5348) are movable together between a retracted position (see FIGS. 78 and 79A) in which anchor feet links (5352, 5354) are angled and biased inwardly towards the central axis of shaft assembly (5334), and a deployed position (see FIG. 79B) in which anchor feet links (5352, 5354) project radially outwardly from distal shaft portion (5342) and distal tip (5346). As shown best in FIG. 79B, anchor feet links (5352, 5354) may include chamfered ends adjacent to medial joint (5354) configured to contact one another in the deployed position to provide mutual structural support to anchor feet links (5352, 5354) in the deployed position.

Shaft assembly (5334) of obturator (5330) further includes a plunger (5356) slidably arranged within a central lumen of shaft (5338). Plunger (5356) includes a proximal knob (5358) and is functionally similar to plunger (5290) described above in that plunger (5356) is movable between proximal and distal positions for deploying and retracting anchor feet (5348). In various examples, plunger (5356) may be resiliently biased toward one of its proximal or distal positions.

Shaft assembly (5334) further includes suture guide features in the form of a pair of needle entrance ports (5360) and a pair of needle exit ports (5362) arranged distally of needle entrance ports (5360). In the present example, needle entrance and exit ports (5360, 5362) are arranged on distal shaft portion (5342). Additionally, needle entrance ports (5360) are diametrically opposed from one another, needle exit ports (5362) are diametrically opposed from one another, and needle ports (5294, 5296) are arranged in a single axially extending plane containing the obturator central axis. Each needle entrance port (5360) communicates with a respective needle exit port (5362) arranged on an opposed side of obturator shaft (5338) to define a respective suture path extending through obturator (5330) at an oblique angle relative to the obturator central axis. In the present example, the suture path angles defined by the suture paths relative to the central axis are equal to one another. In other examples, needle entrance and exit ports (5360, 5362) may be arranged in various other quantities and configurations to define corresponding suture paths of various quantities, arrangements, and suture path angles. In some examples, each needle entrance port (5360) and/or its respective needle exit port (5362) may include a sealing element, such as a pierceable seal, configured to maintain the corresponding suture path in a generally sealed state during use of obturator (5330) as a wound closure device.

Similar to head (5262) of obturator (5260), head (5332) of obturator (5330) is releasably coupled to proximal shaft portion (5340) of obturator shaft assembly (5334), and is configured to selectively decouple from proximal shaft portion (5340) during use. Head (5332) includes a proximally tapering sidewall (5364) defining an interior cavity (5366). As shown in FIG. 78, interior cavity (5366) is configured to receive a proximal end of the shaft assembly (5334), including a proximal end of proximal shaft portion (5340), shaft flange (5344), and plunger knob (5358). As shown in FIG. 80C, head (5332) may include a pair of downwardly depending tabs (5368) configured to releasably engage slots formed on a trocar, such as slots (5134) of trocar (5102), to thereby releasably couple obturator (5330) with trocar (5380). Buttons (5370) on head (5332) are operable to actuate tabs (5368) to selectively separate obturator head (5332) from trocar (5380), for example after a trocar insertion procedure.

Similar to latch (5266) of obturator (5260), latch (5336) of obturator (5330) is movable between latched position and unlatched positions to selectively couple and decouple obturator head (5332) with obturator shaft assembly (5334). As shown in FIG. 78, latch (5336) is pivotally coupled to head (5332) at a pivot joint (5372) and is configured to pivot relative to head (5332) between the latched and unlatched positions. In the present example, latch (5336) is generally L-shaped and includes a first latch leg (5374) having a user engagement feature, and a second latch leg (5376) having a shaft engagement feature.

In the latched position, shown in FIGS. 78 and 79A, second latch leg (5376) extends generally perpendicularly to shaft (5338) to engage proximal shaft portion (5340) and thereby secure head (5332) to shaft assembly (5334), as well as restrain plunger (5356) in its distal position to maintain anchor feet (5348) in their retracted position. When moved to the latched position, second latch leg (5376) may be received within a groove or recess (5not shown) formed on proximal shaft portion (5340), or otherwise frictionally engage proximal shaft portion (5340). In the unlatched position, shown in FIGS. 78 and 79B, second latch leg (5376) is angled obliquely relative to shaft (5338) to thereby disengage proximal shaft portion (5340) and permit separation of head (5332) from shaft assembly (5334).

B. Exemplary Wound Closure Procedure Using Alternative Obturator Wound Closure Device Having Deployable Anchor Feet FIGS. 80A-80F show steps of an exemplary procedure for suturing closed a tissue opening (5172) formed in tissue (5170) by a trocar (5380), using obturator (5330) as a wound closure device independently from a trocar (5380). Trocar (5380) is generally similar in structure to trocar (5102) described above, as indicated by like reference numerals. Because obturator (5330) is employed as a wound closure device independently of trocar (5380) in the present example, suture guide features are omitted from trocar (5380). It will be understood, however, that in some variations obturator (5330) may be used in combination with a trocar that includes suture guide features, such as trocar (5102). Following completion of one or more surgical procedures using trocar (5380), all surgical instruments are withdrawn from working channel (5122) of trocar (5380). Obturator (5330) is manipulated by a surgeon, with latch (5336) in its latched position, to insert shaft assembly (5334) distally through working channel (5122). In this state, as shown in FIG. 80A, proximal shaft portion (5340) of obturator (5330) resides within trocar housing assembly (5106), distal shaft portion (5342) resides within trocar cannula (5108), and distal tip (5346) extends through the distal opening of cannula (5108). Additionally, anchor feet (5348) remain in their retracted position.

As indicated by directional arrows shown in FIGS. 80B and 80C, latch (5336) is pivoted to its unlatched position to enable proximal separation of obturator head (5332) from obturator shaft assembly (5334) and thereby expose plunger knob (5358). Additionally, head buttons (5370) are actuated to decouple head tabs (5368) from proximal housing head (5118) of trocar (5380). As shown in FIG. 80C, trocar (5380) is raised proximally while shaft assembly (5334) is pushed distally through trocar (5380) so anchor feet (5348) clear the distal end of trocar cannula (5108).

As shown in FIG. 80D, plunger (5290) is moved to its proximal position to deploy anchor feet (5280) radially outwardly. Plunger (5290) may be actuated either manually, or automatically by a bias force exerted by a resilient member (Snot shown), for example. Once deployed, anchor feet (5280) are configured to abut a distal surface of tissue fascia (5178) and thereby restrict proximal movement of obturator shaft assembly (5334) relative to tissue (5170). Consequently, trocar (5380) may be withdrawn proximally from tissue opening (5172) while obturator shaft assembly (5334) remains, as shown in FIG. 80E. As described above, and as shown in FIG. 80E, obturator shaft flange (5344) is formed with a diameter smaller than that of working channel (5122) of trocar (5380), thereby enabling obturator shaft assembly (5334) to pass distally through working channel (5122).

As shown in FIG. 80F, trocar (5380) has been fully removed leaving only obturator shaft assembly (5334) within tissue opening (5172). A suture passer needle (5382) and suture thread (5384) is then directed through obturator shaft assembly (5334) and tissue fascia (5178) along first and second oblique suture paths defined by respective pairs of needle entrance and exit ports (5360, 5362), to thereby capture first and second portions of fascia (5178). Once suture thread (5384) has been fully threaded through fascia (5178), plunger (5356) is actuated distally to retract anchor feet (5348), similar to the step shown in FIG. 77E in connection with the wound closure procedure described above. Obturator shaft assembly (5334) is then withdrawn proximally from tissue opening (5172), thereby releasing suture thread (5384) from shaft assembly (5334). As described above in connection with other wound closure methods described herein, suture thread (5384) is then manipulated to form a suture knot securing together the first and second captured portions of fascia (5178). Optionally, a second, "superficial" knot may be formed proximally of the first knot to secure together fat (5176) and skin (5174) and promote optimal healing of tissue opening (5172).

XVI. Exemplary Single-Incision Surgical Access Devices Having Integrated Suture Guide Features In various laparoscopic surgical procedures, and particularly those conducted in the abdominal cavity, a surgeon may need to direct two or more surgical instruments into the cavity simultaneously in order to access and provide effective treatment to tissue. It is generally desirable, however, to minimize the quantity of surgical openings formed in the abdominal wall to thereby mitigate tissue trauma, cosmetic damage, and post-operation recovery time for the patient. Accordingly, in some procedures a single surgical access device having multiple instrument channels may be utilized, and inserted through a single opening (e.g., formed by incision) in the abdominal wall tissue. Such devices are commonly referred to as "single-incision" or "single-site" surgical access devices (or "ports"). In some examples, one or more of the instrument channels and the corresponding surgical instruments inserted therethrough may be of a generally smaller diameter, such as approximately 5 millimeters or less, for example. Laparoscopic procedures employing such devices may be referred to as "mini-laparoscopy."

The single tissue opening formed for a single-incision surgical access device is often arranged in the patient umbilicus (or navel). Advantageously, the umbilicus is generally well-hidden, of lesser thickness, and less vascularized than surrounding regions of the abdominal wall. Accordingly, an umbilical incision can be easily enlarged without significantly compromising cosmesis, and without increasing the risk of wound complications. Nevertheless, the incision created for a single-incision surgical access device remains substantially larger in diameter than an incision created for any one of the surgical instruments directed through the surgical access device. For example, in some cases the single incision may be up to 20-25 millimeters in diameter.

Each of the exemplary single-incision surgical access devices described below includes integrated suture guide features that enable the surgical access device to be implemented as a wound closure device configured to effectively close the tissue opening in which the device is inserted. In particular, the exemplary suture guide features described below are configured to guide the application of multiple sutures along respective suture paths extending distally through the access device and adjacent tissue, obliquely relative to a central axis of the access device. As used herein, the term "oblique" and variations thereof means neither parallel nor perpendicular to the referenced axis, such as the central axis of a surgical access device. The resulting effective closure of the tissue opening promotes swift healing and minimizes tissue scarring. Advantageously, the exemplary single-incision surgical access devices described below are further configured to release suture threads directed therethrough and thereby promote easy removal of the surgical access devices from tissue openings following application of suture threads.

A. Exemplary Single-Incision Surgical Access Device Having Insert with Needle Entry Guide Members FIGS. 81-83 show an exemplary single-incision surgical access device (6100) having integrated suture guide features configured to facilitate closure of a tissue opening (or wound) in which access device (6100) is positioned for a surgical procedure. Surgical access device (6100) generally includes a tissue retractor (6102) and an insert (6104) arranged within a central region of tissue retractor (6102). Tissue retractor (6102) includes a flexible annular body having a proximal flange (6106), a distal flange (6108), a medial body portion (6110) extending axially between proximal and distal flanges (6106, 6108), and a central passage (6112) (also referred to as a "working channel") extending axially through the annular body.

One or more portions of tissue retractor (6102), including distal flange (6108), are formed of a suitably resilient material, such as silicone for example. Accordingly, tissue retractor (6102) is configured to elastically deform while being inserted into a tissue opening, as shown in FIG. 84A, and then resiliently return to or toward its original shape once fully positioned within the opening. In particular, as shown in FIGS. 84B-84D, proximal and distal flanges (6106, 6108) are configured to exert inwardly directed axial bias forces on proximal and distal tissue surfaces, respectively, and medial body portion (6110) is configured to simultaneously exert an outwardly directed radial bias force on an inner tissue wall. Consequently, tissue retractor (6102) is configured to resiliently clamp tissue arranged between proximal and distal flanges (6106, 6108) when access device (6100) is positioned within a tissue opening, thereby releasably securing access device (6100) positionally relative to tissue. As shown best in FIG. 83, an outer lip of proximal flange (6106) houses a proximal resilient ring (6114), and an outer lip of distal flange (6108) houses a distal resilient ring (6116). Resilient rings (6114, 6116) may be formed of any suitably resilient material, such as nitinol, and are configured to aid tissue retractor (6102) in resiliently maintaining its annular shape when positioned within a tissue opening.

Insert (6104) is supported concentrically within central passage (6112) of tissue retractor (6102) and may be configured as a rigid assembly defining a generally cylindrical body having a proximal face (6118), a distal face (6120), a sidewall (6122), and a plurality of surgical instrument channels (6124) extending axially through the cylindrical body and opening to proximal and distal faces (6118, 6120). As shown in FIG. 83, proximal face (6118) of insert (6104) is oriented toward proximal flange (6106) of tissue retractor (6102), and distal face (6120) is oriented toward distal flange (6108). Each surgical instrument channel (6124) has an entrance end at proximal face (6118) and an exit end at distal face (6120), and is configured to guide a surgical instrument (not shown) distally through access device (6100) and into a body cavity. Such surgical instruments may include various endoscopic instruments such as endoscopes, grasping instruments, and cutting instruments, for example. Proximal face (6118) of insert (6104) includes a plurality of instrument entry guide members (6126), shown in the form of ring structures, configured to guide insertion of surgical instruments into the entrance ends of instrument channels (6124). In the present example, four instrument channels (6124) of equal diameter are provided and are arranged with uniform circumferential spacing about the central axis of insert (6104). In other examples, various other quantities, sizes, and arrangements of surgical instrument channels (6124) may be provided.

In some versions of surgical access device (6100), insert (6104) is releasably coupled to tissue retractor (6102) and may be selectively decoupled from retractor (6102), for example by pushing insert (6104) proximally or distally relative to tissue retractor (6102). In other versions, insert (6104) may be permanently coupled to tissue retractor (6102). Insert (6104) and/or tissue retractor (6102) may be further configured in accordance with one or more teachings of U.S. Pat. No. 8,226,553, entitled "Access Device with Insert," issued Jul. 24, 2012, the disclosure of which is incorporated by reference herein.

Single-incision surgical access device (6100) further includes a plurality of suture guide features that enable access device (6100) to facilitate closure of the tissue opening in which access device (6100) is positioned for one or more surgical procedures. Specifically, as shown best in FIG. 83, access device (6100) includes a plurality of circumferentially arranged needle channels (6128) extending distally through access device (6100) and obliquely relative to the central axis of access device (6100). As shown best in FIGS. 81 and 82, each needle channel (6128) is defined by a needle entrance port (6130) arranged on a proximal portion of access device (6100), and a corresponding needle exit port (6134) that communicates with and is arranged distally of its respective needle entrance port (6130). As shown in FIGS. 82 and 84B-84D, described below, each needle channel (6128) is configured to guide a suture passer needle (6136) and a suture thread carried by suture passer needle (6136) through surgical access device (6100) and adjacent tissue along a respective suture path. Each needle channel (6128) and its respective suture path extends at an oblique angle relative to the central axis of access device (6100) (referred to herein as a "suture path angle").

In the present example, each needle entrance port (6130) is defined by a corresponding needle entry guide member (6132) that protrudes radially outwardly from an outer perimeter of proximal face (6118) of insert (6104) and joins with sidewall (6122). Additionally, each needle exit port (6134) is arranged on a distal portion of medial body portion (6110) of tissue retractor (6102). Further, surgical access device (6100) includes four needle entrance ports (6130) and four needle exit ports (6134), collectively defining four needle channels (6128). As described below, each needle channel (6128) is configured to cooperate with one of the other needle channels (6128) to guide application of a corresponding suture thread to tissue along a respective pair of suture paths. Accordingly, the access device (6100) of the present example is configured to guide application of two suture threads to tissue. However, persons skilled in the art will recognize that access device (6100) may be provided with suture guide features of various other quantities to guide application of three or more suture threads.

As shown best in FIGS. 81 and 82, a first pair of needle entrance ports (6130) and corresponding needle exit ports (6134) are arranged in a first axial plane extending through the central axis of access device (6100). A second pair of needle entrance ports (6130) and corresponding needle exit ports (6134) are arranged in a second axial plane extending through the central axis, perpendicularly to the first axial plane. Accordingly, needle ports (6130, 6134) are arranged with uniform circumferential spacing about the central axis, and each needle entrance port (6130) is diametrically opposed from its respective needle exit port (6134) as well as from another needle entrance port (6130). Additionally, in the present example needle entrance ports (6130) and needle exit ports (6134) are aligned circumferentially with surgical instrument channels (6124), such that each needle channel (6128) extends obliquely through a pair of instrument channels (6124), as shown in FIG. 83. In other versions of surgical access device (6100), needle ports (6130, 6134) may be circumferentially offset from instrument channels (6124) such that each needle channel (6128) extends between instrument channels (6124) without passing through instrument channels (6124).

As used herein, the term "diametrically opposed" and variations thereof is intended to encompass configurations in which the referenced structures are arranged at different longitudinal locations along a referenced axis, such as central axis of surgical access device (6100). For instance, in the present example each needle entrance port (6130) is spaced proximally from its respective needle exit port (6134), though needle ports (6130, 6134) are still understood to be diametrically opposed from one another along the same axially extending plane, as described above. Of course, in alternative versions of access device (6100), one or more needle entrance ports (6130) and their respective needle exit ports (6134) may be arranged in different axial planes such that the needle ports (6130, 6134) are not diametrically opposed to one another. It will be further understood that needle entrance and exit ports (6130, 632) may be circumferentially arranged about the central axis of access device (6100) in various other suitable configurations.

In the present example, needle exit ports (6134) are all arranged in a first plane extending transversely to the central axis of surgical access device (6100), and needle exit ports (6134) are all arranged in a second plane spaced distally from and extending parallel to the first transverse plane. Accordingly, needle exit ports (6134) are arranged with uniform (or equal) axial spacing relative to needle entrance ports (6130), such that needle channels (6128) and their corresponding suture paths define uniform suture path angles relative to the central axis of surgical access device (6100). In other versions of access device (6100), the axial spacing between needle entrance ports (6130) and needle exit ports (6134) may be nonuniform such that needle channels (6128) and their suture paths define nonuniform suture path angles relative to the central axis. In configurations in which each needle channel (6128) and its suture path defines the same suture path angle relative to the central axis, such as in the present example, needle channels (6128) and their suture paths may intersect one another at the central axis of access device (6100).

Surgical access device (6100) may further include an insufflation port (not shown) configured to direct insufflation fluid, such as carbon dioxide, from a fluid source into the body cavity to which surgical access device (6100) provides access. Access device (6100) may further include a plurality of sealing elements (not shown) arranged in one or more instrument channels (6124) and/or needle channels (6128) for maintaining insufflation. For example, one or more instrument channels (6124) may include a sealing element configured to sealingly engage the outer surface of a surgical instrument inserted therethrough, or a sealing element configured to maintain a generally air-tight seal when no instrument is arranged within instrument channel (6124), such as a duckbill seal. Additionally, one or more needle channels (6128) may include a sealing element, such as a pierceable sealing element, configured to sealingly engage the outer surface of a suture passer needle (6136) directed through needle channel (6128) and/or maintain a generally air-tight seal when no suture passer needle (6136) is arranged within needle channel (6128).

B. Exemplary Wound Closure Procedure Using Single-Incision Surgical Access Device Having Insert with Needle Entry Guide Members FIGS. 84A-84H show steps of an exemplary procedure for suturing closed a tissue opening (6142) (or wound) formed in tissue (6140) for placement of single-incision surgical access device (6100), using access device (6100) as a wound closure device. Like tissue (17) described above, tissue (6140) includes outward superficial layers and inward deeper layers. Superficial layers generally include an outer layer of skin (6144) and an inner layer of fat (6146). The deeper layers include layers of fascia (6148), which are fibrous and flexible with relatively higher tensile strength than the superficial layers. Tissue opening opens distally to a body cavity (6150). In exemplary procedures, tissue opening (6142) may be located in the patient umbilicus such that tissue opening (6142) opens distally to the abdominal cavity.

FIG. 84A shows surgical access device (6100) being positioned within tissue opening (6142). As described above, tissue retractor (6102) of access device (6100) is configured to elastically deform to facilitate insertion of access device (6100) into tissue opening (6142). Upon being fully positioned, tissue retractor (6102) resiliently returns to or toward its original shape, thereby securing tissue (6140) between proximal and distal flanges (6106, 6108) of tissue retractor (6102), as shown in FIG. 84B. Following placement of access device (6100) within tissue opening (6142), a surgical procedure may be conducted by inserting one or more surgical instruments (not shown) distally through respective surgical instrument channels (6124) to access tissue within body cavity (6150).

Following completion of the surgical procedure, the integrated suture guide features of surgical access device (6100) are utilized to guide application of multiple suture threads to tissue (6140) to thereby facilitate effective closure of tissue opening (6142). In particular, as shown in FIG. 84B, a suture passer needle (6136) carrying a thread end (6154) of a first suture thread (6152) is directed distally through surgical access device (6100) and adjacent tissue fascia (6148) along a first suture path. In particular, suture passer needle (6136) and thread end (6154) are directed through a first needle entrance port (6130) arranged on a first side portion of access device (6100), and along a respective first needle channel (6128) extending through insert (6104) and exiting through a corresponding first needle exit port (6134) arranged on a second side portion of access device (6100). Suture passer needle (6136) and thread end (6154) continue to be guided by needle channel (6128) to pass proximally over distal flange (6108) of tissue retractor (6102) and through a first portion of tissue fascia (6148), into body cavity (6150). Suture passer needle (6136) is manipulated to deposit thread end (6154) within body cavity (6150), and is then withdrawn proximally from surgical access device (6100) along the first suture path. In some examples, suture passer needle (6136) may include one or more steerable sections, such as a steerable tip (not shown), configured to direct thread end (6154) in a selected direction within body cavity (6150) to facilitate subsequent steps of the wound closure procedure, described below. It will be appreciated that any of the exemplary suture passer needles described below may include one or more steerable sections configured to facilitate application of a suture thread to tissue (6140) through a single-incision surgical access device disclosed herein.

As shown in FIG. 84C, suture passer needle (6136) is then directed distally through surgical access device (6100) and an adjacent second portion of tissue fascia (6148) along a second suture path. In particular, suture passer needle (6136) is directed through a second needle entrance port (6130) arranged on the second side portion of access device (6100), and along a respective second needle channel (6128) extending through insert (6104) and exiting through a corresponding second needle exit port (6134) arranged on the first side portion of access device (6100). Suture passer needle (6136) is further guided by second needle channel (6128) to pass proximally over distal flange (6108) of tissue retractor (6102) and through a second portion of tissue fascia (6148), into body cavity (6150). Suture passer needle (6136) is then manipulated, for example with the assistance of a steerable section thereof (not shown), to recapture thread end (6154) of first suture thread (6152) within body cavity (6150). Though not shown, one or more surgical instruments may be directed distally through instrument channels (6124) to engage thread end (6154) and assist in directing it from the first side of access device (6100) toward the second side so thread end (6154) may be effectively reached and recaptured by suture passer needle (6136) directed along the second suture path.

Suture passer needle (6136) and thread end (6154) are then withdrawn proximally from surgical access device (6100) along the second suture path, yielding the suture thread configuration shown in FIG. 84D. In particular, a first thread leg (6156) of first suture thread (6152) extends through access device (6100) and tissue (6140) along the first suture path to capture a first portion of fascia (6148); a second thread leg (6158) extends through access device (6100) and tissue (6140) along the second suture path to capture an opposed second portion of fascia (6148); and an anchoring loop (6160) extends between first and second thread legs (6156, 6158) within body cavity (6150).

Following application of first suture thread (6152) to tissue (6140), a second suture thread (6162) (see FIG. 84E) is applied to tissue in a similar manner. In particular, second suture thread (6162) is directed through surgical access device (6100) and adjacent fascia (6148) along third and fourth suture paths defined by third and fourth needle channels (6128), in a manner similar to that described above for first suture thread (6152). The resulting configuration of first and second suture threads (6152, 6162) is generally seen in FIG. 84E. As shown in FIG. 84E, following application of first and second suture threads (6152, 6) to tissue (6140) using the integrated suture guide features of surgical access device (6100), access device (6100) is withdrawn proximally from tissue opening (6142). Proximal withdrawal of access device (6100) allows the proximally extending legs of suture threads (6152, 6162) to slide distally through needle channels (6128), thereby freeing suture threads (6152, 6162) from access device (6100) and yielding the suture thread configuration shown in FIG. 84F. As shown in FIG. 84E, distal flange (6108) of tissue retractor (6102) may elastically deform to facilitate proximal removal of access device (6100) from tissue opening (6142).

As described above, needle channels (6128) are arranged uniformly within surgical access device (6100), and each needle channel (6128) and its corresponding suture path defines the same oblique suture path angle relative the central axis of access device (6100). Accordingly, each needle channel (6128) is configured to direct a respective thread leg of a suture thread (6152, 6162) to capture the same amount of tissue fascia (6148) (referred to as "tissue bite") on its respective side of access device (6100). As shown in FIG. 84F, "tissue bite" in the present context is defined by a distance (X) measured perpendicularly from the inner wall of tissue opening (6142), which may coincide with the outer surface of medial body portion (6110) of tissue retractor (6102), to the point at which suture passer needle (6136) and thus suture thread (6152, 6162) exits distally from tissue fascia (6148) into body cavity (6150). As described above, surgical access device (6100) may be configured in alternative examples such that needle channels (6128) are arranged non-uniformly in access device (6100). For instance, needle exit ports (6134) may be arranged with non-uniform axial spacing from needle entrance ports (6130), and/or one or more needle channels (6128) may define different suture path angles relative to the central axis of surgical access device (6100). In such alternative examples, resulting tissue bite distances (X) defined by the suture paths may be nonuniform.

As shown in FIG. 84G, the free legs of first and second suture threads (6152, 6162) are pulled proximally to draw together the captured portions of tissue fascia (6148). The suture thread legs are then tied together to form a suture knot (6164) at a location just proximally of fascia (6148). Optionally, the remaining free portions of suture threads (6152, 6162) may be directed through fat (6146) and skin (6144) using suture needles, for example as shown in FIG. 4D, to create an additional "superficial" suture knot to fully close tissue opening (6142) and promote optimal healing.

FIG. 84H schematically shows the exemplary arrangement of the first suture path (A), second suture path (B), third suture path (C), and fourth suture path (D) along which first and second suture threads (6152, 6162) are directed in the steps shown in FIGS. 84A-84E, described above. As shown in the present example, suitable needle channels (6128) of surgical access device (6100), defined by respective needle ports (6130, 6134), are selected such that first and second suture paths (A, B) extend in a first axial plane, and third and fourth suture paths (C, D) extend in a second axial plane that is generally perpendicular to the first axial plane. Consequently, each paring of suture paths (A, B and C, D) extends generally diagonally across tissue opening (6142). In other examples, suitable needle channels (6128) of surgical access device (6100) may be selected to yield various other arrangements of the suture paths along which first and second suture threads (6152, 6162) are directed. For instance, needle channels (6128) may be selected such that the first and second suture paths (A, B) for first suture thread (6152) are arranged in different axial planes, and third and fourth suture paths (C, D) for second suture thread (6162) are arranged in different axial planes.

C. Exemplary Suture Path Patterns

FIGS. 85A-85F show various exemplary suture path patterns along which first and second suture threads (6152, 6162) may be directed through surgical access device (6100). In that regard, it will be understood that the suture guide features of surgical access device (6100) described above may be suitably arranged as required to enable the exemplary suture path patterns of FIGS. 85A-85F.

FIG. 85A shows a first exemplary suture path pattern (6166) that is similar to the suture path pattern of FIG. 84H. In particular, first and second suture threads (6152, 6162) are applied to tissue (6140) such that each suture thread (6152, 6162) passes through first and second portions of fascia (6148) arranged on opposing sides of tissue opening (6142), and such that suture threads (6152, 6162) intersect each other diagonally when extending across tissue opening (6142) and through fascia (6148). FIG. 85B shows partial closure of tissue opening (6142) achieved by pulling proximally on free ends of suture threads (6152, 6162) applied according to suture pattern (6166) of FIG. 85A.

FIG. 85C shows a second exemplary suture path pattern (6168) in which first and second suture threads (6152, 6162) are applied to tissue (6140) such that each suture thread (6152, 6162) passes through first and second portions of fascia (6148) arranged on opposing sides of tissue opening (6142), and such that suture threads (6152, 6162) extend generally parallel to each other when extending across tissue opening (6142) and through fascia (6148). FIG. 85D shows partial closure of tissue opening (6142) achieved by pulling proximally on free ends of suture threads (6152, 6162) applied accord to suture pattern (6168) of FIG. 85C.

FIG. 85E shows a third exemplary suture path pattern (6170) in which first and second suture threads (6152, 6162) are applied to tissue (6140) such that first suture thread (6152) passes twice through a first portion of fascia (6148) arranged on a first side of tissue opening (6142), and second suture thread passes twice through a second portion of fascia (6148) arranged on a second side of an opposed second side of tissue opening (6142). FIG. 85F shows partial closure of tissue opening (6142) achieved by securing together first and second thread legs of first suture thread (6152) extending from the first portion of fascia (6148), and securing together first and second thread legs of second suture thread (6162) extending from the second portion of fascia (6148). Though not shown, threads legs of first suture thread (6152) may then be tied together with thread legs of second suture thread (6162) to thereby further close tissue opening (6142).

XVII. Exemplary Single-Incision Surgical Access Device Having Insert with Central Channel

A. Exemplary Single-Incision Surgical Access Device

FIGS. 86-88 show another exemplary single-incision surgical access device (6180) having integrated suture guide features configured to facilitate closure of a tissue opening in which access device (6180) is positioned for a surgical procedure. Surgical access device (6180) is similar to surgical access device (6100) described above except as otherwise described in detail below.

Similar to surgical access device (6100), surgical access device (6180) includes a tissue retractor (6182) and an insert (6184) supported within a central region of tissue retractor (6182). More specifically, tissue retractor (6182) includes a flexible annular body having a proximal flange (6186), a distal flange (6188), a medial body portion (6190) extending axially between proximal and distal flanges (6186, 6188), and a central passage (6192) extending axially through the annular body. Insert (6184) is supported within central passage (6192). Additionally, as shown in FIG. 89A, an outer lip of proximal flange (6186) houses a proximal resilient ring (6194) and an outer lip of distal flange (6188) houses a distal resilient ring (6196). Similar to surgical access device (6100), surgical access device (6180) may further include an insufflation port (not shown) and one or more sealing elements (not shown) configured to maintain insufflation during a surgical procedure.

Similar to insert (6104) of surgical access device (6100), insert (6184) of access device (6180) may be configured as a rigid assembly defining a generally cylindrical body having a proximal face (6198), a distal face (6200) (see FIG. 89A), a sidewall (6202), and a plurality of surgical instrument channels (6204) extending axially through the cylindrical body and opening to proximal and distal faces (6198, 6200). In the present example, insert (6184) includes four instrument channels (6204) arranged circumferentially with uniform spacing. Each surgical instrument channel (6204) is provided with an instrument entry guide member (6206), shown in the form of a ring structure, arranged on proximal face (6198) and configured to guide insertion of a surgical instrument into the entrance end of the instrument channel (6204). Unlike insert (6104), insert (6184) includes a central channel (6208) extending axially therethrough along the central axis of access device (6180) and opening to proximal and distal faces (6198, 6200) of insert (6184).

As best shown in FIG. 89A, surgical access device (6180) further includes four circumferentially arranged needle channels (6210) extending distally through access device (6180) and obliquely relative to the central axis. A proximal end of each needle channel (6210) opens to central channel (6208) to thereby define a respective needle entrance port (6212). Accordingly, needle entrance ports (6212) are accessible via central channel (6208). A distal end of each needle channel (6210) exits through a needle exit port (6214) arranged on a distal portion of medial body portion (6190) of tissue retractor (6182). Surgical access device (6180) further includes a plurality of flange ports (6216) arranged on a radially extending portion of distal flange (6188) of tissue retractor (6182). Each flange port (6216) aligns with a respective needle exit port (6214) and cooperates with the corresponding needle channel (6210) to define an oblique suture path along which a suture passer needle and a suture thread may be directed, as described below.

Similar to surgical access device (6100) described above, the suture guide features of surgical access device (6180) are arranged uniformly in circumferential, axial, and radial directions such that each suture path defined by a needle channel (6210) and its respective flange port (6216) defines the same suture path angle relative to the central axis of access device (6180). Unlike access device (6100), needle entrance and exit ports (6212, 6214) and flange ports (6216) of access device (6180) are circumferentially offset from surgical instrument channels (6204). Accordingly, needle channels (6210) pass distally between instrument channels (6204) rather than through instrument channels (6204). Other versions of surgical access device (6180) may include needle ports (6212, 6214) and flange ports (6216) arranged in various other quantities and configurations, which may define a variety of suture path angles.

As shown in FIGS. 86 and 87, tissue retractor (6182) of the present example further includes a plurality of perforation lines (6218) configured to facilitate release of suture threads from surgical access device (6180) during a wound closure procedure. Each perforation line (6218) is positioned in alignment with a respective needle exit port (6214) and a corresponding flange port (6216). In particular, each perforation line (6218) extends radially inwardly from a flange port (6216), and proximally along medial body portion (6190) to join with the respective needle exit port (6214). As shown in the present example, each perforation line (6218) may extend proximally beyond needle exit port (6214) and/or radially outwardly beyond flange port (6216).

As best shown in FIG. 88, perforation lines (6218) divide a distal portion of tissue retractor (6182) into a plurality of circumferential sections. In the present example, perforation lines (6218) define four circumferential sections (or quadrants) of tissue retractor (6182). In use, perforation lines (6218) are configured to rupture to thereby separate adjacent circumferential sections from one another. Advantageously, this enables suture threads to be easily released from tissue retractor (6182) during a wound closure procedure, for example as described below.

B. Exemplary Wound Closure Procedure Using Single-Incision Surgical Access Device Having Insert with Central Channel FIGS. 89A and 89B show steps of an exemplary procedure for suturing closed a tissue opening (6142) formed in tissue (6140) using single-incision surgical access device (6180) as a wound closure device. The steps of the present wound closure procedure are similar to those described above in connection with the wound closure procedure shown in FIGS. 84A-84G, except as otherwise described in detail below.

FIG. 89A shows surgical access device (6180) positioned within tissue opening (6142), and a first suture thread (6222) directed through access device (6180) and adjacent portions of tissue fascia (6148) along first and second suture paths. It will be understood that first suture thread (6222) may be directed through access device (6180) and fascia (6148) using any suitable suture passer needle, such as suture passer needle (6220). As described above, needle entrance ports (6212) open to central channel (6208) of insert (6184), such that suture passer needle (6220) accesses each needle entrance port (6212) via a proximal opening of central channel (6208). Suture passer needle (6220) directs first suture thread (6222) along a first suture path extending through a first needle channel (6210), an adjacent first portion of tissue fascia (6148), and a corresponding first flange port (6216), into body cavity (6150). Suture passer needle (6220) further directs first suture thread (6222) along a second suture path extending through an opposed second needle channel (6210), an adjacent second portion of tissue fascia (6148), and a corresponding second flange port (6216), yielding the suture thread configuration shown in FIG. 89A. Similar steps are then repeated for a second suture thread (6224) directed along third and fourth suture paths through third and fourth portions of tissue fascia (6148).

Following application of first and second suture threads (6222, 6224) to tissue (6140), surgical access device (6180) is withdrawn proximally from tissue opening (6142), as shown in FIG. 89B. Pulling access device (6180) proximally from tissue opening (6142) causes suture threads (6222, 6224) to tighten radially inwardly against tissue retractor (6182) and thereby rupture retractor (6182) along perforation lines (6218). Alternatively, or in combination, a surgeon may manually tear tissue retractor (6218) along one or more perforation lines (6218) by reaching distally through tissue opening (6142), for example with a surgical instrument. Rupturing and/or tearing of perforation lines (6218) operates to release suture threads (6222, 6224) from distal flange (6188), including flange ports (6216), thereby permitting suture threads (6222, 6224) to pass beneath distal flange (6188) as shown in FIG. 89B. Repositioning suture threads (6222, 6224) relative to tissue retractor (6182) in this manner facilitates proximal withdrawal of access device (6180) from tissue opening (6142) while ensuring that suture threads (6222, 6224) remain securely positioned within captured portions of fascia (6148). As surgical access device (6180) is fully withdrawn from tissue opening (6142), suture threads (6222, 6224) fully release from access device (6180), thereby yielding a suture thread configuration similar to that shown in FIG. 84F, described above. One or more suture knots (not shown) may then be formed to fully close tissue opening (6142), as described above in connection with FIG. 84G.

XVIII. Exemplary Single-Incision Surgical Access Device Having Insert with Needle Entrance Ports in Proximal Face A. Exemplary Single-Incision Surgical Access Device FIGS. 90-92 show another exemplary single-incision surgical access device (6230) having integrated suture guide features configured to facilitate closure of a tissue opening in which access device (6230) is positioned for a surgical procedure. Surgical access device (6230) is similar to surgical access device (6180) described above, except as otherwise described in detail below.

Similar to surgical access device (6180), surgical access device (6230) includes a tissue retractor (6232) and an insert (6234) supported within a central region of tissue retractor (6232). More specifically, tissue retractor (6232) includes a flexible annular body having a proximal flange (6236), a distal flange (6238), a medial body portion (6240) extending axially between proximal and distal flanges (6236, 6238), and a central passage (6242) extending axially through the annular body. Insert (6234) is supported within central passage (6242). Additionally, as shown in FIG. 93A, an outer lip of proximal flange (6236) houses a proximal resilient ring (6244), and an outer lip of distal flange (6238) houses a distal resilient ring (6246). Surgical access device (6180) may further include an insufflation port (not shown) and one or more sealing elements (not shown) configured to maintain insufflation during a surgical procedure.

Similar to insert (6184) of surgical access device (6180), insert (6234) may be configured as a rigid assembly defining a generally cylindrical body having a proximal face (6248), a distal face (6250), a sidewall (6252), and a plurality of surgical instrument channels (6254) extending axially through the cylindrical body and opening to proximal and distal faces (6248, 6250). In the present example, insert (6234) includes four instrument channels (6254) arranged circumferentially with uniform spacing. Each surgical instrument channel (6254) is provided with an instrument entry guide member (6256), shown in the form of a ring structure, arranged on proximal face (6248) and configured to guide insertion of a surgical instrument into the entrance end of the instrument channel (6254). Unlike insert (6184), insert (6234) of the present example omits central channel (6208), though in other versions a similar central channel may be provided.

As shown in FIG. 93A, surgical access device (6230) further includes four circumferentially arranged needle channels (6258) extending distally through access device (6230) and obliquely relative to the central axis thereof. As shown in FIGS. 90-92, a proximal end of each needle channel (6258) is defined by a needle entrance port (6260) formed in proximal face (6248) of insert (6234), and a distal end of each needle channel (6258) is defined by a needle exit port (6262) arranged on a distal portion of medial body portion (6240) of tissue retractor (6232). Like surgical access device (6180), access device (6230) further includes a plurality of flange ports (6264) arranged on a radially extending portion of distal flange (6238) of tissue retractor (6232). Access device (6230) also includes a plurality of perforation lines (6266) arranged circumferentially in a distal portion of tissue retractor (6232), similar to perforation lines (6218) described above.

Similar to surgical access device (6180), the suture guide features of surgical access device (6230) are arranged uniformly in circumferential, axial, and radial directions such that each suture path defined by a needle channel (6258) and its respective flange port (6264) defines the same suture path angle relative to the central axis of access device (6180). Similar to access device (6180), needle entrance and exit ports (6260, 6262) and flange ports (6264) of access device (6230) are circumferentially offset from surgical instrument channels (6254). Accordingly, needle channels (6258) pass distally between instrument channels (6204) rather than through instrument channels (6254). Other versions of surgical access device (6230) may include needle ports (6260, 6262) and flange ports (6264) arranged in various other quantities and configurations, which may define a variety of suture path angles.

B. Exemplary Wound Closure Procedure Using Single-Incision Surgical Access Device Having Insert with Needle Entrance Ports in Proximal Face FIGS. 93A and 93B show steps of an exemplary procedure for suturing closed a tissue opening (6142) formed in tissue (6140) using single-incision surgical access device (6230) as a wound closure device for applying first and second suture threads (6270, 6272). As will be readily apparent to one of ordinary skill in the art, the wound closure steps illustrated in FIGS. 93A and 93B in connection with surgical access device (6230) are substantially similar to the wound closure steps described above in connection with FIGS. 89A and 89B and surgical access device (6180).

In particular, first suture thread (6270) is directed along first and second suture paths extending through first and second needle channels (6258) and corresponding flange ports (6264) of surgical access device (6230), and adjacent first and second portions of tissue fascia (6148). Additionally, second suture thread (6272), shown in FIG. 97B, is directed along third and fourth suture paths extending through first and second needle channels (6258) and corresponding flange ports (6264) of access device (6230), and adjacent third and fourth portions of tissue fascia (6148). These steps differ from those described in connection with surgical access device (6180) shown in FIGS. 89A and 89B in that suture threads (6270, 6272) are directed into needle channels (6258) of access device (6230) via needle entrance ports (6260) arranged in proximal face (6248) of insert (6234), rather than via a central channel of insert (6234). Surgical access device (6230) may then be withdrawn from tissue opening (6142), and suture threads (6270, 6272) may be tied, in a manner similar to that described above in connection with surgical access device (6180).

XIX. Exemplary Single-Incision Surgical Access Device Having Segmented Distal Ring A. Exemplary Single-Incision Surgical Access Device FIGS. 94-96B show another exemplary single-incision surgical access device (6280) having integrated suture guide features configured to facilitate closure of a tissue opening in which access device (6280) is positioned for a surgical procedure. Surgical access device (6280) is similar to surgical access device (6230) described above, except as otherwise described in detail below. In that regard, like reference numerals in FIGS. 18-20B refer to like features described above in connection with FIGS. 90-92.

Surgical access device (6280) differs from surgical access device (6230) in that tissue retractor (6282) of access device (6280) includes a distal flange (6284) housing a segmented distal resilient ring (6286) that is divided into a plurality of independent circumferential ring segments (6288). As shown in FIG. 94, each ring segment (6288) includes a pair of end legs (6290) projecting radially outwardly from the two ends of ring segment (6288) and through an outer surface of distal flange (6284). Ring segments are arranged circumferentially such that each confronting pair of end legs (6290) of adjacent ring segments (6288) is aligned with a perforation line (6266) of tissue retractor (6282). More specifically, each confronting pair of end legs (6290) spans a respective perforation line (6266) such that perforation line (6266) extends radially between a circumferential gap formed between the confronting end legs (6290). As shown in FIG. 95, an arcuate body portion of each ring segment (6288) extending between its end legs (6290) is housed within a tubular member (6292), which in turn is housed within distal flange (6284). Ring segments (6288) may be formed of any suitable resilient material, such as nitinol, for example. Additionally, tubular members (6292) may be formed of any suitable polymeric material, such as silicone, for example. In exemplary configurations, distal flange (6284) may be formed as an overmold assembly.

Surgical access device (6280) further includes a plurality of coupling members shown in the form of caps (6294) configured to couple together each confronting pair of end legs (6290) of adjacent ring segments (6288). As shown in FIGS. 94 and 96A-96B, each confronting pair of end legs (6290) is received within a respective cap (6294). Each cap (6294) includes a perforation line (6296) extending radially therethrough and diving cap (6294) into first and second side portions, each side portion receiving a respective ring segment end leg (6290). As shown in FIGS. 96A and 96B, each cap (6294) is configured to be torn along its perforation line (6296) to thereby decouple adjacent ring segments (6288) from one another. Accordingly, when tissue retractor (6282) is also torn along its corresponding perforation line (6266), a suture thread (6298) extending through the corresponding flange port (6264) may be freed from distal flange (6284) and redirected over the top of distal flange (6284). As described below in connection with FIG. 97B, this feature of surgical access device (6280) provides advantages during a wound closure procedure. It will be appreciated that segmented distal ring (6286) and caps (6294) may be incorporated into the construction of any of the other exemplary single-incision surgical access devices described herein.

B. Exemplary Wound Closure Procedure Using Single-Incision Surgical Access Device Having Segmented Distal Ring FIGS. 97A and 97B show steps of an exemplary procedure for suturing closed a tissue opening (6142) formed in tissue (6140) using single-incision surgical access device (6280) as a wound closure device for applying first and second suture threads (6298, 6299). Those of ordinary skill in the art will appreciate that the steps of the present wound closure method are similar to those described above in connection with surgical access devices (6180, 6230), except as otherwise described below.

FIG. 97A shows a first suture thread (6298) after having been directed along first and second suture paths extending through first and second needle channels (6258) and corresponding flange ports (6264) of surgical access device (6280), and adjacent first and second portions of tissue fascia (6148). A second suture thread (6299), shown in FIG. 97B, is then directed along third and fourth suture paths extending through first and second needle channels (6258) and corresponding flange ports (6264) of surgical access device (6280), and adjacent third and fourth portions of tissue fascia (6148). Similar to wound closure methods described above in connection with surgical access devices (6180, 6230), access device (6280) is pulled proximally from tissue opening (6142). This proximal movement causes suture threads (6298, 6299) to exert a radially outwardly directed force against distal flange (6284) and thereby rupture retractor perforation lines (6266) as well as cap perforation lines (6296). A surgeon may assist this process by reaching distally through tissue opening (6142), for example with a surgical instrument, and manually tearing one or more perforation lines (6266, 6296). Rupturing of perforation lines (6266, 6296) operates to separate ring segments (288) from one another and thereby free suture threads (6298, 6299) from flange ports (6264) and enable suture threads (6298, 6299) to be repositioned over the top of distal flange (6284), as shown in FIG. 97B.

Repositioning suture threads (6298, 6299) relative to tissue retractor (6282) in the manner shown in FIG. 97B facilitates proximal withdrawal of surgical access device (6280) from tissue opening (6142) while ensuring that suture threads (6298, 6299) remain securely positioned within captured portions of fascia (6148). As surgical access device (6280) is fully withdrawn from tissue opening (6142), suture threads (6298, 6299) fully release from access device (6280), thereby yielding a suture thread configuration similar to that shown in FIG. 84F, described above. One or more suture knots (not shown) may then be formed to fully close tissue opening (6142), as described above in connection with FIG. 84G.

XX. Exemplary Single-Incision Surgical Access Devices Having Proximal Housing A. Exemplary Single-Incision Surgical Access Device Having Proximal Housing with Needle Guide Members FIGS. 98-100 show another exemplary single-incision surgical access device (6300) having integrated suture guide features configured to facilitate closure of a tissue opening in which access device (6300) is positioned for a surgical procedure. Surgical access device (6300) is similar to surgical access devices (6100, 6180, 6230, 6280) described above in that access device (6300) includes a tissue retractor (6302) having a flexible annular body with a proximal flange (6304) (see FIG. 100), a distal flange (6306), a medial body portion (6308) extending axially between proximal and distal flanges (6304, 6306), and a central passage (6310) extending axially through the annular body. Further, an outer lip of proximal flange (6304) houses a proximal resilient ring (6312), and an outer lip of distal flange (6306) houses a distal resilient ring (6314). Surgical access device (6300) may further include an insufflation port (not shown).

Surgical access device (6300) differs from the previously described surgical access devices (6100, 6180, 6230, 6280) in that access devices (6300) includes a proximal housing (6316) coupled to tissue retractor (6302) and configured to enclose a proximal portion of tissue retractor (6302), including proximal flange (6304) and a proximal opening to central passage (6310). Proximal housing (6316) includes an annular housing cover (6318) arranged proximally of proximal flange (6304), an annular housing support (6320) arranged distally of proximal flange (6304), and a circular housing base member (6322) accessible through a central opening of annular housing cover (6318). Housing cover (6318) is releasably coupled to housing support (6320) by latches (6324) arranged circumferentially about an outer perimeter of proximal housing (6316). In various examples, proximal housing (6316) may be configured as a rigid structure.

Housing base member (6322) includes a base plate (6326) and a plurality of instrument entry guide members (6328a, 6328b, 6328c, 6328d) supported by base plate (6326). Each instrument entry guide member (6328a, 6328b, 6328c, 6328d) is configured to guide a surgical instrument (not shown) through a respective surgical instrument channel extending axially through proximal housing (6316) and opening to central passage (6310) of tissue retractor (6302). In the present example, as shown best in FIGS. 98 and 99, proximal housing (6316) includes a first instrument entry guide member (6328a) providing access to an instrument channel of a large diameter, second and third instrument entry guide members (6328b, 6328c) each providing access to a respective instrument channel of a medium diameter, and a fourth instrument entry guide member (6328d) providing access to an instrument channel of a small diameter. Each instrument entry guide member (6328a, 6328b, 6328c, 6328d) includes a sealing element (6330) configured to sealingly engage a surgical instrument directed therethrough, and thereby maintain insufflation during a surgical procedure.

In the present example, first, second, and third instrument entry guide members (6328a, 6328b, 6328c) are movable relative to base plate (6326) of housing base member (6322) along respective tracks (6332a, 6332b, 6332c). Tracks (6332a, 6332b, 6332c) enable instrument entry guide members (6328a, 6328b, 6328c) to move relative to base plate (6326) along respective predefined paths in axial, radial, and/or arcuate directions. Advantageously, this mobility of instrument entry guide members (6328a, 6328b, 6328c), and their respective instrument channels, facilitates optimal positioning of surgical instruments directed distally therethrough during a surgical procedure. Proximal housing (6316), including base plate (6326), may include various additional or alternative features according to one or more teachings of U.S. Pat. No. 8,251,900, entitled "Surgical Access Device and Methods Providing Seal Movement in Predefined Paths," issued Aug. 28, 2012, the disclosure of which is incorporated by reference herein.

Similar to surgical access devices (6100, 6180, 6230, 6280) described above, surgical access device (6300) further includes integrated suture guide features configured to guide application of suture threads to tissue for closure of a tissue opening. In particular, proximal housing (6316) includes a plurality of circumferentially arranged needle entry guide members (6334) projecting proximally, angularly outwardly from a sidewall (6336). In the present example, each entry needle guide member (6334) is shown in the form of a tubular structure. As shown best in FIG. 100, each needle entry guide member (6334) defines a needle entrance port (6338) that communicates with a corresponding needle exit port (6340) formed on medial body portion (6308) of tissue retractor (6302) to define a corresponding needle channel (6342) extending through surgical access device (6300) and obliquely relative to a central axis thereof.

As shown in FIG. 98, and as further illustrated by cross-reference with FIGS. 104A-104F, described below, each needle channel (6342) is configured to guide a suture passer needle (6344) and a suture thread (6346) therethrough along an oblique suture path extending through surgical access device (6300) and adjacent tissue. Similar to surgical access devices (6100, 6180, 6230, 6280) described above, access device (6300) of the present example includes four needle channels (6342) arranged uniformly in a circumferential direction such that first and second needle channels (6342) lie in a first axial plane extending through the central axis of access device (6300), and second and third needle channels (6342) lie in a second axial plane extending through the central axis, perpendicularly to the first axial plane. Additionally, as best shown in FIG. 99, needle entry guide members (6334) and their respective needle channels (6342) are circumferentially offset from the surgical instrument channels defined by instrument entry guide members (6328a, 6328b, 6328c, 6328d) of proximal housing 6316). Accordingly, the resulting suture paths extend between, rather than through, the instrument channels. Further, needle entrance and exit ports (6338, 6340) are arranged uniformly in axial and radial directions such that each suture path defines the same suture path angle relative to the central axis. Those of ordinary skill in the art will appreciate that other versions of surgical access device (6300) may include needle ports (6338, 6340) arranged in various other quantities and configurations, which may define a variety of suture path angles.

B. Exemplary Single-Incision Surgical Access Device Having Proximal Housing with Needle Entrance Ports in Proximal Face FIGS. 101-103 show another exemplary single-incision surgical access device (6350) having integrated suture guide features configured to facilitate closure of a tissue opening in which access device (6350) is positioned for a surgical procedure. Surgical access device (6350) is similar to surgical access device (6300) described above, except as otherwise described in detail below. In that regard, like reference numerals in FIGS. 101-103 refer to like features described above in connection with FIGS. 98-100.

Surgical access device (6350) differs from surgical access device (6300) in that proximal housing (6352) of access device (6350) includes needle entrance ports (6354) arranged in housing base member (6356). Proximal housing (6350), including housing base member (6356), is otherwise similar to proximal housing (6316) described above, with needle entry guide members (6334) being omitted. In the present example, each needle entrance port (6354) is shown in the form of a generally semi-circular opening formed at an outer circumference of housing base member (6356), adjacent to an inner circumference of housing cover (6318). Like needle entrance ports (6338), needle entrance ports (6354) are arranged with uniform circumferential spacing therebetween, and are circumferentially offset from instrument entry guide members (6328a, 6328b, 6328c, 6328d). Additionally, each needle entrance port (6354) communicates with a corresponding needle exit port (6340) arranged on an opposed side of tissue retractor (6302) to define a respective needle channel (6358). Because needle entrance ports (6354) of surgical access device (6350) are arranged radially inwardly relative to needle entrance ports (6338) of access device (6300), needle channels (6358) may define slightly steeper suture path angles than needle channels (6342) of access device (6300).

C. Exemplary Wound Closure Procedure Using Single-Incision Surgical Access Device Having Proximal Housing FIGS. 104A-104F show steps of an exemplary procedure for suturing closed a tissue opening (6142) formed in tissue (6140) using single-incision surgical access device (6350) as a wound closure device. While these steps are shown and described in connection with surgical access device (6350), it will be understood that these steps may be similarly implemented in connection with surgical access device (6300) of FIGS. 98-100.

FIG. 104A shows surgical access device (6350) positioned within a tissue opening (6142). Following completion of one or more surgical procedures, a suture passer needle (6360) carrying a thread end (6364) of a first suture thread (6362) is directed distally through surgical access device (6350) and a first portion of tissue fascia (6148) along a first suture path. In particular, suture passer needle (6360) and thread end (6364) are directed through a first needle entrance port (6354) in proximal housing (6352), along a respective first needle channel (6358), through a corresponding first needle exit port (6340), and through an adjacent first portion of tissue fascia (6148) located proximally of (i.e., above) distal flange (6306), into body cavity (6150). Suture passer needle (6360) is then manipulated to deposit thread end (6364) within body cavity (6150), and is then withdrawn proximally from surgical access device (6350) along the first suture path.

As shown in FIG. 104C, a grasping instrument (6366) may be inserted distally through one of the instrument entry guide members (6328a, 6328b, 6328c, 6328d) of proximal housing (6352), and manipulated to grasp and move thread end (6364) toward an opposing side of surgical access device (6350) so thread end (6364) may be withdrawn proximally along a second suture path, shown FIG. 104D. Alternatively, or in addition, suture passer needle (6360) may be provided with one or more steerable sections, such as a steerable tip, configured to facilitate transfer of thread end (6364) between opposing sides of access device (6350) within body cavity (6150).

As shown in FIG. 104D, suture passer needle (6360) is directed distally through surgical access device (6280) along a second suture path extending through an opposing second needle entrance port (6354), a corresponding second needle channel (6358) and second needle exit port (6340), and an adjacent second portion of tissue fascia (6148), into body cavity (6150). Suture passer needle (6360) is then manipulated to recapture thread end (6364) of first suture thread (6362), and suture passer needle (6360) and thread end (6364) are withdrawn proximally along the second suture path, yielding the suture thread configuration shown in FIG. 104E. Similar steps are then repeated to apply a second suture thread (6368), shown in FIG. 104F, to tissue (6140) via third and fourth suture paths extending through surgical access device (6350) and corresponding third and fourth portions of fascia (6148).

As shown in FIG. 104F, following application of first and second suture threads (6362, 368) to tissue (6140), surgical access device (6350) is withdrawn proximally from tissue opening (6142). As access device (6350) is fully withdrawn from tissue opening (6142), suture threads (6362, 6368) fully release from access device (6350), thereby yielding a suture thread configuration similar to that shown in FIG. 84F, described above. One or more suture knots (not shown) may then be formed to fully close tissue opening (6142), as described above in connection with FIG. 84G.

XXI. Exemplary Single-Incision Surgical Access Device Having Tissue Retractor with Surgical Instrument Channels and Needle Entrance Ports FIGS. 105-107 show another exemplary single-incision surgical access device (6370) having integrated suture guide features configured to facilitate closure of a tissue opening in which access device (6370) is positioned for a surgical procedure. Surgical access device (6370) includes a tissue retractor (6372) having a flexible body defining a proximal flange (6374), a distal flange (6376), and a medial body portion (6378) extending therebetween. Unlike annular tissue retractors (6102, 6182, 6232, 6282, 6302) described above, tissue retractor 6372) omits a central passage extending fully through retractor (6372) along a central axis thereof. Instead, tissue retractor (6372) includes a central wall (6380) arranged radially inward of proximal flange (6374) and recessed distally from proximal flange (6374). Central wall (6380) may be arranged closer to proximal flange (6374) than distal flange (6376) so as to define a distal cavity (not shown) that opens distally to distal flange (6376).

Tissue retractor (6372) further includes a plurality of surgical instrument channels (6382) extending axially through central wall (6380). In the present example, tissue retractor (6372) includes three surgical instrument channels (6382) arranged circumferentially uniformly about the central axis of retractor (6372). In alternative examples, various other quantities and arrangements of instrument channels (6382) may be provided. Each instrument channel (6382) is configured to guide a surgical instrument distally through tissue retractor (6372) and into a body cavity. In the present example, surgical access device (6370) includes a plurality of cannula devices (6384) arranged within instrument channels (6382). Each cannula device (6384) includes a head (6386) and a shaft (6388) defining a lumen, and is configured to guide a surgical instrument distally through tissue retractor (6372) and into a body cavity (6150). Each cannula device (6384) may include an internal sealing element (not shown) configured to sealingly engaging the outer surface of a surgical instrument inserted therethrough to thereby maintain insufflation during a surgical procedure. In that regard, surgical access device (6370) further includes an insufflation port (6390) extending distally through central wall (6380) and configured to direct insufflation fluid distally through retractor (6372) and into a body cavity (6150).

Surgical access device (6370) further includes integrated suture guide features shown in the form of a plurality of needle entrances ports (6392) arranged circumferentially on proximal flange (6374); a corresponding plurality of needle exit ports (6394) arranged circumferentially on a distal portion of medial body portion (6378); and a corresponding plurality of needle guide notches (6396) arranged circumferentially on distal flange (6376). Each needle entrance port (6392) cooperates with a respective needle exit port (6394) to define a corresponding needle channel (not shown) extending through surgical access device (6370) and obliquely relative to its central axis. Each needle channel and its respective needle guide notch (6396) is configured to guide a suture passer needle (6398) and a suture thread (6400) along a suture path extending obliquely through access device (6370) and an adjacent portion of tissue fascia (6148).

Similar to surgical access devices (6100, 6180, 6230, 6280, 6300, 6350) described above, access device (6370) of the present example includes four sets of needle entrance ports (6392) and corresponding needle exit ports (6394) and needle guide notches (6396), the sets being arranged uniformly in a circumferential direction. Consequently, first and second suture paths defined by needle ports (6392, 6394) and guide notches (6396) lie in a first axial plane extending through the central axis of device (6370). Third and fourth suture paths defined by needle ports (6392, 6394) and guide notches (6396) lie in a second axial plane extending through the central axis, perpendicularly to the first axial plane. Additionally, needle ports (6392, 6394) are arranged uniformly in axial and radial directions such that each suture path defines the same suture path angle relative to the central axis. Those of ordinary skill in the art will appreciate that other versions of surgical access device (6370) may include needle ports (6392, 6394) and needle guide notches (6396) arranged in various other quantities and configurations, which may define a variety of suture path angles.

Any one or more of the exemplary single-incision surgical access devices and related methods described above, and variations thereof, may be implemented in conventional surgical procedures conducted by a medical professional as well as in robotic-assisted surgical procedures. For example, various teachings herein may be readily incorporated into a robotic surgical system such as one or more of the DAVINCI™ systems by Intuitive Surgical, Inc., of Sunnyvale, Calif., including their SP™ surgical system. Exemplary robotic surgical systems and related features, which may be combined with any one or more of the exemplary surgical access devices and methods disclosed herein, are disclosed in the following: U.S. Pat. No. 8,068,649, entitled "Method and Apparatus for Transforming Coordinate Systems in a Telemanipulation System," issued Nov. 29, 2011; U.S. Pat. No. 8,517,933, entitled "Retraction of Tissue for Single Port Entry, Robotically Assisted Medical Procedures," issued Aug. 27, 2013; U.S. Pat. No. 8,545,515, entitled "Curved Cannula Surgical System," issued Oct. 1, 2013; U.S. Pat. No. 8,551,115, entitled "Curved Cannula Instrument," issued Oct. 8, 2013; U.S. Pat. No. 8,623,028, entitled "Surgical Port Feature," issued Jan. 7, 2014, the disclosure of which is incorporated by reference herein; U.S. Pat. No. 8,771,180, entitled "Retraction of Tissue for Single Port Entry, Robotically Assisted Medical Procedures," issued Jul. 8, 2014, the disclosure of which is incorporated by reference herein; U.S. Pat. No. 8,888,789, entitled "Curved Cannula Surgical System Control," issued Nov. 18, 2014; U.S. Pat. No. 9,254,178, entitled "Curved Cannula Surgical System," issued Feb. 9, 2016; U.S. Pat. No. 9,283,050, entitled "Curved Cannula Surgical System," issued Mar. 15, 2016; U.S. Pat. No. 9,320,416, entitled "Surgical Instrument Control and Actuation," issued Apr. 26, 2016, the disclosure of which is incorporated by reference herein; U.S. Pat. No. 9,339,341, entitled "Direct Pull Surgical Gripper," issued May 17, 2016; U.S. Pat. No. 9,358,074, entitled "Multi-Port Surgical Robotic System Architecture," issued Jun. 7, 2016; U.S. Pat. No. 9,572,481, entitled "Medical System with Multiple Operating Modes for Steering a Medical Instrument Through Linked Body Passages," issued Feb. 21, 2017; U.S. Pat. No. 9,636,186, entitled "Multi-User Medical Robotic System for Collaboration or Training in Minimally Invasive Surgical Procedures," issued May 2, 2017; U.S. Pat. Pub. No. 2014/0066717, entitled "Surgical Port Feature," published Mar. 6, 2014, issued as U.S. Pat. No. 10,245,069 on Apr. 2, 2019, the disclosure of which is incorporated by reference herein; U.S. Pat. Pub. No. 2017/0128041, entitled "Laparoscopic Ultrasound Robotic Surgical System," published May 11, 2017, issued as U.S. Pat. No. 10,646,293 on May 12, 2020; and U.S. Pat. Pub. No. 2017/0128144, entitled "Laparoscopic Ultrasound Robotic Surgical System," published May 11, 2017, now abandoned, the disclosure of which is incorporated by reference herein; and U.S. Pat. Pub. No. 2017/0128145, entitled "Laparoscopic Ultrasound Robotic Surgical System," published May 11, 2017, issued as U.S. Pat. No. 10,603,127 on Mar. 31, 2021. The disclosure of each of these references is incorporated by reference herein.

XXII. Exemplary Trocar Assembly with Detachable Tissue Fastener

In some instances, inserting and pulling suture thread (60) through multiple portions of tissue opening (18) may be difficult, labor intensive, and/or time consuming. It may be thus be beneficial in such instances to close tissue opening (58) with an alternative suture prior to the removal of trocar assembly (10). For example, an alternative obturator (7114), like obturator (14) discussed above, includes a suture (7100), which may also be referred to herein as a tissue fastener (7100), that is preassembled and releasably connected to obturator (14) for closing tissue opening (18).

The following description provides various examples of a trocar assembly (7110) including various exemplary obturators (7114, 7214) with respective tissue fasteners (7100, 7200) releasably secured thereto. As will be described in greater detail below, each tissue fastener (7100, 7200) is configured to close tissue opening (58) by rotatably driving obturator (7114, 7214) within tissue opening (58) and then releasing tissue fastener (7100, 7200) for closure of tissue (17) and removal of obturator (7114, 7214). Tissue fasteners (7100, 7200) described below may be used with any obturator (12) and corresponding trocar assembly (10, 7110) described above and below and in any of the various procedures described in the various patent references cited herein. To this end, like numbers below indicate like features described above. Other suitable ways in which various trocar assemblies may be used will be apparent to those of ordinary skill in the art in view of the teachings herein.

A. First Securement Mechanism with a Detachable Tissue Fastener

FIGS. 108-109 show a trocar assembly (7110) including trocar cannula (12) and an exemplary alternative trocar obturator (7114). Like obturator (14) (see FIG. 1), trocar obturator (7114) is removably received within trocar cannula (12) through trocar housing (16). Trocar obturator (7114) includes a tissue fastener (7100), a distal tip (7120) and a cylindrical shaft (7148). Distal tip (7120) is positioned at a distal end of cylindrical shaft (7148). Tissue fastener (7100) is releasably attached to trocar obturator (7114) at distal tip (7120). Distal tip (7120) is substantially positioned within trocar cannula (12) at cannula distal end opening (36) when trocar obturator (7114) is initially positioned within trocar cannula (12). Cylindrical shaft (7148) of trocar obturator (7114) is configured to translate distally within trocar cannula (12) to allow distal tip (7120) to extend beyond cannula distal end opening (36) and thereby substantially expose tissue fastener (7100) from trocar cannula (12).

As shown in FIGS. 109-110, cylindrical shaft (7148) defines an internal channel (7116) with a longitudinal length that terminates on a distal end at a shaft opening (7118) and on a proximal end at handle head (46). Shaft opening (7118) is centered on distal tip (7120) and provides communication between internal channel (7116) and the external surroundings of distal tip (7120). Trocar obturator (7114) further includes a first securement mechanism (7130) extending within and along the longitudinal length of internal channel (7116). Securement mechanism (7130) terminates on a distal end at a hook member (7134) and on a proximal end at a handle (not shown). Hook member (7134) is configured to releasably engage distal tip (7120) at shaft opening (7118). Handle (not shown) is positioned adjacent to handle head (46) and is configured to slidably translate securement mechanism (7130) within inner channel (7116). Handle (not shown) is further configured to actuate hook member (7134) from a locked position (see FIGS. 113A-113B) to an unlocked position (see FIG. 113C) to thereby allow hook member (7134) to engage and disengage distal tip (7120) of trocar obturator (7114) for releasing tissue fastener (7100) as discussed below in greater detail.

As seen in FIG. 111, tissue fastener (7100) includes a base (7102) and a pair of arms (7106) extending outwardly therefrom. In the present example, tissue fastener (7100) is formed of an absorbable material configured to dissolve for absorption within the patient after a predetermined lapse of exposure to the tissue portions of tissue opening (58). As a merely illustrative example, tissue fastener (7100) is formed of an absorbable polymer material. Arms (7106) are integrally formed with base (7102) and extend longitudinally and angularly outwardly from base (7102). As shown in FIGS. 111-112, arms (7106) extend along respective helical paths. Base (7102) is configured to be received against distal tip (7120). Base (7102) has a diameter that is substantially equivalent to shaft opening (7118) and includes a slot (7103) that is configured to receive hook member (7134) to thereby allow securement mechanism (7130) to releasably attach tissue fastener (7100) to distal tip (7120) through shaft opening (7118). Although not shown, it will be apparent to those of ordinary skill in the art that tissue fastener (7100) may include more or fewer arms (7106) extending from base (7102).

Each arm (7106) terminates in a piercing tip (7107) that is configured to pierce and penetrate tissue. Each arm (7106) also includes a plurality of barbs (7108) extending outwardly therefrom. Although three barbs (7108) are shown extending from arms (7106), it should be understood that more or fewer barbs (7108) may be included on arms (7106). Barbs (7108) are configured to securely fix arms (7106) to tissue portions of tissue opening (58) as tissue fastener (7100) is rotatably driven within tissue opening (58) at a predetermined rotatable-release force. Arms (7106) are configured to draw the tissue portions of tissue opening (58) together upon rotation of distal tip (7120) and tissue fastener (7100) within tissue opening (58). Each barb (7108) of the present example extends at an obtuse angle relative piercing tip (7107) on each respective arm (7106) such that arms (7106) insert into tissue with relative ease. However, upon removal forces, barbs (7108) catch the tissue for securement of arms (7106) in the tissue. Thus, while barbs (7108) are configured to permit arms (7106) to be driven into tissue in a first respective direction, barbs (7108) are configured to prevent arms (7106) from being pulled from the tissue in a second respective direction after arms (7106) are driven into the tissue. In the present example, arms (7106) are sufficiently rigid for penetrating the tissue; but are configured to deflect upon application of excessive force.

FIGS. 112-113A illustrate the helical shape of tissue fastener (7100) through the outward and angular extension of arms (7106) from base (7102) such that arms (7106) lie in varying dimensional planes from each other. The helical shape of tissue fastener (7100) is configured to allow arms (7106) to coil around distal tip (7120) of trocar obturator (7114); and to allow arms (7106) to be rotatably driven into tissue like a corkscrew. Tissue fastener (7100) is releasably attached to distal tip (7120) through the engagement of hook member (7134) and base (7102) at shaft opening (7118). More particularly, base (7102) is releasably captured between hook member (7134) and distal tip (7120). Thus, upon disengaging hook member (7134) from base (7102), tissue fastener (7100) is released from trocar obturator (7114).

In the present example, after a clinician inserts trocar assembly (7110) through tissue (17) of a patient and achieves the diagnostic or therapeutic effect desired within cavity (18), the clinician slightly withdraws trocar cannula (12) and inserts trocar obturator (7114) within trocar cannula (12) rather than removing trocar assembly (7110) from tissue opening (58). At this stage, as shown in FIG. 113A, cannula distal end opening (36) is just proximal to the distal surface of the tissue defining tissue opening (58) (e.g., adjacent to one or more of the innermost layers of the fascia of the patient). As also seen in FIG. 113A, while trocar obturator (7114) is positioned within trocar cannula (12), distal tip (7120) is positioned adjacent cannula distal end opening (36). Distal tip (7120) is configured to project distally from cannula distal end opening (36) when trocar obturator (7114) is translated distally within trocar cannula (12).

Once trocar obturator (7114) is distally advanced within trocar cannula (12) to an extent where distal tip (7120) is positioned beyond cannula end opening (36), as seen in FIG. 113B, tissue fastener (7100) contacts tissue portions of tissue opening (58). In this instance, as further seen in FIG. 114A, arms (7106) press against the tissue portions of tissue opening (58). The clinician then rotates trocar obturator (7114) within trocar cannula (12) with sufficient force for arms (7106) to pierce the tissue and cause barbs (7108) to catch the tissue portions of tissue opening (58). As seen in FIGS. 113C and 114B, rotating trocar obturator (7114) and distal tip (7120) allows tissue fastener (7100) to draw the tissue portions of tissue opening (58) together to partially close tissue opening (58) as arms (7106) embed in the tissue. In the present example, tissue opening (58) is "partially closed" in the sense that the region of the region of tissue opening (58) at the fascia (56) is closed but not the region of tissue opening (58) that is proximal to the fascia (56).

With tissue opening (58) partially closed, the clinician disengages securement mechanism (7130) from distal tip (7120) and retracts trocar obturator (7114) proximally through trocar cannula (12). More particularly, as best seen in FIG. 113C and FIG. 114C, securement mechanism (7130) is rotated with handle (not shown) to align hook member (7134) with slot (7103) of base (7102). With hook member (7134) aligned with slot (7103) and disengaged from base (7102), handle (not shown) is translated proximally to thereby pull securement mechanism (7130) proximally. With hook member (7134) in the unlocked position, hook member (7134) releases tissue fastener (7100) from distal tip (7120). In this instance, retracting trocar obturator (7114) allows tissue fastener (7100) to maintain its secured position in closing tissue opening (58) at fascia (56). After fastener (7100) is used to close fascia (56) and trocar assembly (7110) is fully removed from the patient, skin (52) may be secured to close the proximal end of tissue opening (58) using conventional suture, stapling, adhesive, and/or any other suitable devices or techniques.

In versions where fastener (7100) is formed of a bioabsorbable material, after tissue fastener (7100) has been securely attached to tissue opening (58) (e.g., in the innermost layer(s) of fascia (56) tissue), tissue fastener (7100) is eventually absorbed by the tissue and thus effectively dissolves in the patient's body after the predetermined lapse of exposure. In the present example, the material forming tissue fastener (7100) does not degrade until the tissue associated with tissue opening (58) has scarred or otherwise healed to the point where tissue fastener (7100) is no longer needed to hold tissue opening (58) closed.

B. Second Securement Mechanism with a Detachable Tissue Fastener

FIGS. 115A-115C show another exemplary alternative trocar obturator (7214) including a cylindrical shaft (7248), a distal tip (7220) and a tissue fastener (7200). Distal tip (7220) is positioned along a distal end of cylindrical shaft (7248), and tissue fastener (7200) is releasably attached to trocar obturator (7214) at distal tip (7220). Cylindrical shaft (7248) is configured to translate distally within trocar cannula (12) (see FIG. 1) to allow distal tip (7220) to extend beyond cannula distal end opening (36) and thereby substantially uncover tissue fastener (7200) from trocar cannula (12). In some other versions, trocar cannula (12) is removed from the patient and then trocar obturator (7214) is subsequently inserted through the opening left by trocar cannula (12). Obturator (7114) may also be used in a similar fashion, such that it is not necessarily required in all versions for obturator (7114) to be disposed in trocar cannula (12) when obturator (7114) deploys fastener (7100) in tissue.

Trocar obturator (7214) is configured to releasably secure tissue fastener (7200) to distal tip (7220) through the engagement of tissue fastener (7200) to a second securement mechanism (7230), which includes a securement shoulder (7231') along a securement slot (7231). In particular, securement slot (7231) extends longitudinally and radially outwardly along a substantial longitudinal length of distal tip (7220) and is configured to hold tissue fastener (7200) on distal tip (7220) until the rotary application of a predetermined release force.

Tissue fastener (7200) comprises a pair of arms (7206) extending along respective helical paths from a base (7202) such that arms (7206) lie in varying dimensional planes from each other. Arms (7206) and base (7202) are generally similar to arms (7106) (see FIG. 114A) and base (7102) (see FIG. 114A) for engaging tissue with barbs (7108) (see FIG. 114A). However, base (7202) does not have slot (7103) (see FIG. 114A) and each arm (7206) further includes a catch member (7207) extending radially inwardly toward securement slot (7231). Each catch member (7207) is configured to fit within securement slot (7231) and releasably engage with distal tip (7220) for releasably attaching tissue fastener (7200) to distal tip (7220). Arms (7206) are configured to draw radially outwardly as the applied force increases toward the predetermined release force and thus similarly withdraw catch members (7207) radially outwardly from securement slot (7231). Once the applied force increases to the predetermined release force, catch members (7207) fully withdraw from securement slot (7231) to release tissue fastener (7200) from distal tip (7220). In the present example, each catch member (7207) is at least one barb (7108) (see FIG. 113A). However, the invention is not intended to be unnecessarily limited to the barb (7108) (see FIG. 113A) being catch member (7207).

In the present example, the clinician inserts trocar obturator (7214) within trocar cannula (12) (see FIG. 1) and translates cylindrical shaft (7248) distally therein to advance distal tip (7220) beyond cannula distal end opening (36) (see FIG. 1). With distal tip (7220) positioned beyond cannula end opening (36) (see FIG. 1), tissue fastener (7200) contacts against tissue portions of tissue opening (58) and arms (7206) press against the tissue portions of tissue opening (58), as seen in FIG. 115A-115B. In the present example, the tissue engaged by arms (7206) is fascia (56) tissue of a patient's abdominal wall. Upon rotation of trocar obturator (7214) with applied force less than the predetermined release force, barbs (7108) (see FIG. 114A) catch the tissue portions of tissue opening (58). As the force increases, arms (7206) radially deflect outwardly from the coiled, helical arrangement around distal tip (7220). Rotating distal tip (7220) draws the tissue portions of tissue opening (58) together as arms (7206) are driven into the tissue to partially close tissue opening (58) until the applied force increases to the predetermined release force. Catch members (7207) then withdraw from securement slot (7231) thereby releasing tissue fastener (7200) from trocar obturator (7214). With tissue opening (58) partially closed (e.g., the region of tissue opening (58) at the fascia (56) is closed but not the region of tissue opening (58) that is proximal to the fascia (56)), and with tissue fastener (200) completely freed from the releasable engagement with distal tip (7220) via securement slot (7231), the clinician retracts trocar obturator (7214) proximally through trocar cannula (12) as seen in FIG. 115C.

XXIII. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A trocar assembly, comprising: (a) a cannula assembly, including: (i) a housing having a proximal opening, (ii) a cannula extending distally from the trocar housing to a distal opening, and (iii) a working channel defining a longitudinal axis and extending from the proximal opening to the distal opening; (b) an obturator assembly, including: (i) a proximal head, (ii) a distal tip configured to penetrate tissue of a patient, and (iii) a shaft extending from the proximal head to the distal tip and configured to be received within the working channel of the cannula assembly such that the distal tip projects distally beyond the distal opening of the cannula; and (c) a catch arm selectively moveable from a retracted position to a first deployed position and a second deployed position and configured to releasably capture a suture thread from a needle, wherein the catch arm in the retracted position is positioned radially inward from the first deployed position for insertion into the patient, wherein the catch arm in the first deployed position is positioned radially outward from the retracted position for releasably capturing the suture thread, and wherein the catch arm is configured to be moved a predetermined distance from the first deployed position to the second deployed position and release the captured suture thread from the second deployed position for suturing the tissue.

Example 2

The trocar assembly of Example 1, wherein the cannula assembly further includes a needle channel extending across the longitudinal axis and configured to receive a needle with a suture thread for suturing a tissue of a patient, and wherein catch arm in the first deployed position linearly aligns with the needle channel to receive the suture thread therefrom.

Example 3

The trocar assembly of Example 2, wherein the catch arm includes a catch hole configured to align with the needle channel in the first deployed position and thereby receive the needle and releaseably capture the suture thread therein.

Example 4

The trocar assembly of any one or more of Examples 1 through 3, wherein the cannula defines an outer transverse profile, wherein the catch arm is generally within the outer transverse profile in the retracted position, and wherein the catch arm extends radially outward from the outer transverse profile in the deployed position.

Example 5

The trocar assembly of any one or more of Examples 1 through 4, wherein the catch arm in the retracted position is generally parallel with the longitudinal axis, and wherein the catch arm in the first deployed position is generally transverse to the longitudinal axis.

Example 6

The trocar assembly of any one or more of Examples 1 through 5, wherein the catch arm is configured to pivot from the retracted position to the first deployed position.

Example 7

The trocar assembly of any one or more of Examples 1 through 6, wherein the first deployed position is angularly opposite from the second deployed position about the longitudinal axis.

Example 8

The trocar assembly of any one or more of Examples 1 through 7, wherein the catch arm in the first deployed position is secured relative to the shaft of the obturator assembly such that the catch arm is configured to rotate to the second deployed position relative to the cannula of the trocar assembly in response to rotation of the shaft of the obturator assembly.

Example 9

The trocar assembly of Example 8, wherein the catch arm is pivotally connected to the shaft of the obturator assembly.

Example 10

The trocar assembly of any one or more of Examples 1 through 9, wherein the catch arm in the first deployed position is secured relative to the shaft of the obturator assembly in a first transverse direction, wherein the catch arm in the second deployed position is secured relative to the shaft of the obturator assembly in a second transverse direction, and wherein the first and second directions are respectively associated with opposing sides of the shaft of the obturator assembly.

Example 11

The trocar assembly of Example 10, wherein the catch arm is configured to pivot from the first deployed position to the second deployed position through the retracted position.

Example 12

The trocar assembly of Example 11, wherein the catch arm is pivotally connected to the shaft of the obturator assembly.

Example 13

The trocar assembly of any one or more of Examples 1 through 12, wherein the catch arm in the first deployed position is secured relative to the cannula such that rotating the cannula is configured to rotate the catch arm to the second deployed position.

Example 14

The trocar assembly of Example 13, wherein the catch arm is pivotally connected to the cannula of the trocar assembly.

Example 15

The trocar assembly of any one or more of Examples 1 through 14, further comprising an actuator operatively connected to the catch arm, wherein the actuator is configured to be selectively manipulated to thereby selectively move the catch arm from the retracted position to the first deployed position.

Example 16

An obturator assembly, comprising: (a) a proximal end portion; (b) a distal end portion having a distal tip configured to penetrate tissue of a patient; (c) a shaft extending longitudinally between the proximal end portion and the distal end portion; and (d) a catch arm connected to the distal end portion and selectively moveable from a retracted position to a deployed position and configured to releasably capture a suture thread from a needle, wherein the catch arm in the retracted position is positioned radially inward from the deployed position for insertion into the patient, and wherein the catch arm in the deployed position is positioned radially outward from the retracted position for releasably capturing the suture thread.

Example 17

A method of suturing a tissue opening with a suture thread and a trocar assembly, wherein the trocar assembly includes a cannula assembly, an obturator assembly, and a catch arm, wherein the catch arm is selectively moveable from a retracted position to a first deployed position and configured to releasably capture the suture thread from a needle, wherein the catch arm in the retracted position is positioned radially inward from the first deployed position for insertion into the patient, and wherein the catch arm in the first deployed position is positioned radially outward from the retracted position for releasably capturing the suture thread. the method including: (a) penetrating the tissue with the trocar assembly and positioning the catch arm within the patient while the catch arm is in the retracted position; (b) extending the catch arm radially outwardly to first deployed position; (c) inserting a thread end portion of the suture thread into the tissue with the needle; (d) releasably capturing the thread end portion of the suture thread with the catch arm; (e) moving the catch arm to a second deployed position with the thread end portion of the suture thread releasably captured thereto; (f) releasing the thread end portion of the suture thread from the catch arm; and (g) withdrawing the thread end portion of the suture thread from the patient to thereby suture the tissue opening.

Example 18

The method Example 17, wherein moving the catch arm further includes rotating the obturator assembly relative to the cannula assembly.

Example 19

The method any one or more of Examples 17 through 18, wherein moving the catch arm further includes rotating the cannula assembly relative to the patient.

Example 20

The method of any one or more of Examples 17 through 19, wherein moving the catch arm further includes pivoting the catch arm from the first deployed position to the second deployed position through the retracted position.

Example 21

A suture passer, comprising: (a) a needle extending longitudinally and configured to be manipulated between a catch position and a release position; (b) a first suture notch extending through the needle, wherein the first suture notch includes a first catch undercut configured to receive a suture thread therein and releasably capture the suture thread radially inwardly as the needle is manipulated toward a catch direction; and (c) a second suture notch extending through the needle, wherein the second suture notch includes a second catch undercut configured to receive the suture thread therein and releasably capture the suture thread radially inwardly as the needle is manipulated toward the catch direction.

Example 22

The suture passer of Example 21, wherein the first suture notch further includes a first release cam surface configured to urge the suture thread radially outwardly from the first catch undercut as the needle is manipulated toward a release direction.

Example 23

The suture passer of Example 22, wherein the needle further includes an outer radial surface and the first release cam surface projects between the first catch undercut and the outer radial surface of the needle.

Example 24

The suture passer of Example 23, wherein the first catch undercut defines a hooked surface within the first suture notch, wherein the first release cam surface extends continuously from the hooked surface to the outer radial surface of the needle.

Example 25

The suture passer of Example 24, wherein the first release cam surface extends distally and radially outwardly from the hooked surface to the outer radial surface of the needle.

Example 26

The suture passer of any one or more of Examples 21 through 25, further comprising a sheath having a longitudinal bore extending therethrough, wherein the longitudinal bore slidably receives the needle therein such that the needle is configured to move distally within the longitudinal bore relative to the sheath from a retracted position to an extended position.

Example 27

The suture passer of Example 26, wherein the sheath includes a radial wall extending distally to a distal sheath end, wherein the radial wall includes a first aperture in communication with the longitudinal bore, and wherein the first aperture is configured to longitudinally align with first suture notch and thereby expose the first suture notch for capturing the suture thread through the first aperture.

Example 28

The suture passer of Example 27, wherein the distal sheath end is configured to pierce a tissue.

Example 29

The suture passer of any one or more of Examples 21 through 28, further comprising a driver operatively connected to the needle and configured to selectively translate the needle longitudinally from the retracted position to the extended position.

Example 30

The suture passer of Example 29, wherein the driver is further configured to selectively rotate the needle from the retracted position to the extended position.

Example 31

The suture passer of any one or more of Examples 29 through 30, wherein the driver further includes a resilient member configured to bias the needle toward the retracted position.

Example 32

The suture passer of any one or more of Examples 21 through Example 31, wherein the second suture notch includes a second release cam surface configured to urge the suture thread radially outwardly from the second catch undercut as the needle is manipulated toward the release direction, wherein the needle extends along a longitudinal axis, and wherein first suture notch is positioned angularly opposite from the second suture notch about the longitudinal axis.

Example 33

The suture passer of any one or more of Example 32, further comprising a third suture notch extending through the needle, wherein the third suture notch includes a third catch undercut configured to receive the suture thread therein and releasably capture the suture thread radially inwardly as the needle is manipulated toward the catch direction.

Example 34

The suture passer of Example 33, wherein the third suture notch includes a third release cam surface configured to urge the suture thread radially outwardly from the third catch undercut as the needle is manipulated toward the release direction, wherein the needle extends along a longitudinal axis, and wherein first, second, and third suture notches are longitudinally and angularly positioned about the longitudinal axis in a helical arrangement.

Example 35

The suture passer of any one or more of Examples 21 through 34, wherein the distal needle end has a domed end extending distally therefrom.

Example 36

A suture passer, comprising: (a) a needle extending longitudinally along a longitudinal axis and configured to be manipulated between a catch position and a release position; (b) a first suture notch extending through the needle in a first position about the longitudinal axis, wherein the first suture notch includes: (i) a first catch portion configured to receive a suture thread therein and releasably capture the suture thread as the needle is manipulated toward the catch direction, and (ii) a first release portion configured to urge the suture thread from the first catch portion as the needle is manipulated toward the release direction; and (c) a second suture notch extending through the needle in a second position about the longitudinal axis, wherein the second suture notch includes: (i) a second catch portion configured to receive a suture thread therein and releasably capture the suture thread as the needle is manipulated toward the catch direction, and (ii) a second release portion configured to urge the suture thread from the second catch portion as the needle is manipulated toward the release direction, wherein the first position of the first suture notch is different than the second position of the second suture notch.

Example 37

The suture passer of Example 36, wherein first suture notch is positioned angularly opposite from the second suture notch about the longitudinal axis.

Example 38

The suture passer of any one or more of Examples 36 through 37, further comprising a third suture notch extending through the needle in a third position about the longitudinal axis, wherein the third suture notch includes: (i) a third catch portion configured to receive a suture thread therein and releasably capture the suture thread as the needle is manipulated toward the catch direction, and (ii) a third release portion configured to urge the suture thread from the third catch portion as the needle is manipulated toward the release direction, wherein the third position of the third suture notch is different than the first and second positions of the first and second suture notches, respectively.

Example 39

The suture passer of Example 38, wherein first, second, and third suture notches are longitudinally and angularly positioned in the first, second, and third positions about the longitudinal axis in a helical arrangement.

Example 40

A method of grasping a suture thread within a patient with a suture passer having a needle and a suture notch extending through the needle, wherein the suture notch includes a catch portion and a release portion, wherein the catch portion is configured to receive the suture thread therein and releasably capture the suture thread, and wherein the release portion is configured to urge the suture thread from the catch portion, the method comprising: (a) manipulating the needle from a catch position toward a release position; (b) urging the suture thread with the cam surface from the catch portion of the suture notch; and (c) releasing the suture thread from the catch portion of the suture notch.

Example 41

A surgical access device, comprising: (a) a cannula having a proximal end, a distal end, and a cannula lumen extending therebetween; (b) a housing assembly coupled to the proximal end of the cannula, wherein the housing assembly comprises: (i) a proximal housing, and (ii) a latch ring arranged distally of the proximal housing and having a user engagement feature, wherein the latch ring is rotatable by the user engagement feature to selectively couple and decouple the proximal housing with the cannula, wherein an interior of the housing assembly communicates with the cannula lumen to define a working channel extending from a proximal end of the surgical access device to a distal end of the surgical access device along a central axis thereof, wherein the working channel is configured to receive a surgical instrument therethrough; (c) a first needle port that opens to the working channel through a first side portion of the surgical access device; and (d) a second needle port that opens to the working channel through a second side portion of the surgical access device; wherein each of the first and second needle ports is configured to direct a suture passer needle through the surgical access device, across the working channel, at an oblique angle relative to the central axis of the surgical access device, wherein the user engagement feature of the latch ring is circumferentially offset from each of the first and second needle ports.

Example 42

The surgical access device of Example 41, wherein the housing assembly further comprises a distal housing coupled to the cannula, wherein the latch ring is arranged between the proximal housing and the distal housing, wherein the latch ring is rotatable relative to at least one of the proximal or distal housings to selectively couple and decouple the proximal housing with the distal housing.

Example 43

The surgical access device of any one or more of Examples 41 through 42, wherein the latch ring is rotatable to a position in which the user engagement feature is spaced circumferentially equidistantly between the first and second needle ports.

Example 44

The surgical access device of any one or more of Examples 41 through 43, wherein the latch ring is rotatable to a position in which the user engagement feature is circumferentially offset from each of the first and second needle ports by at least 90 degrees.

Example 45

The surgical access device of Example 44, wherein the first and second needle ports are diametrically opposed from one another, wherein the latch ring is rotatable to a position in which the user engagement feature is circumferentially offset from each of the first and second needle ports by 90 degrees.

Example 46

The surgical access device of any one or more of Examples 41 through 45, further comprising an insufflation port configured to direct insufflation fluid into the working channel, wherein the latch ring is rotatable to a position in which the user engagement feature is diametrically opposed from the insufflation port.

Example 47

The surgical access device of Example 46, wherein when the user engagement feature is positioned in diametric opposition to the insufflation port, the user engagement feature is spaced circumferentially equidistantly between the first and second needle ports.

Example 48

The surgical access device of Example 47, wherein when the user engagement feature is positioned in diametric opposition to the insufflation port, the user engagement feature is circumferentially offset from each of the first and second needle ports by 90 degrees.

Example 49

The surgical access device of any one or more of Examples 41 through 48, wherein the user engagement feature comprises an outwardly projecting knob.

Example 50

The surgical access device of any one or more of Examples 41 through 49, wherein the cannula includes a proximal hub having a larger diameter than medial and distal portions of the cannula, wherein the first and second needle ports extend through the proximal hub.

Example 51

The surgical access device of any one or more of Examples 41 through 50, wherein the first needle port comprises a first needle entrance port and the second needle port comprises a second needle entrance port, wherein the surgical access device further comprises a first needle exit port arranged distally of the first needle entrance port, and a second needle exit port arranged distally of the second needle entrance port, wherein the first needle entrance port and the first needle exit port together define a first suture path extending obliquely across the central axis of the surgical access device, wherein the second needle entrance port and the second needle exit port together define a second suture path extending obliquely across the central axis of the surgical access device.

Example 52

The surgical access device of Example 51, wherein the first and second needle entrance ports and the first and second needle exit ports are arranged such that the first and second suture paths extend through the central axis of the surgical access device.

Example 53

The surgical access device of any one or more of Examples 51 through 52, further comprising a first needle guide structure configured to guide a suture passer needle along the first suture path, and a second needle guide structure configured to guide a suture passer needle along the second suture path.

Example 54

The surgical access device of any one or more of the Examples 51 through 53, wherein each of the first and second needle entrance ports and each of the first and second needle exit ports is provided with a pierceable seal.

Example 55

The surgical access device of Example 54, further comprising a sleeve that encircles at least a portion of the cannula, wherein the sleeve defines the pierceable seals for the first and second needle exit ports.

Example 56

A surgical access device, comprising: (a) a cannula having a proximal end, a distal end, and a cannula lumen extending therebetween; (b) a housing assembly coupled to the proximal end of the cannula, wherein the housing assembly comprises: (i) a proximal housing, and (ii) a latch ring arranged distally of the proximal housing and having a user engagement feature, wherein the latch ring is movable by the user engagement feature to selectively couple and decouple the proximal housing with the cannula, wherein an interior of the housing assembly communicates with the cannula lumen to define a working channel extending from a proximal end of the surgical access device to a distal end of the surgical access device along a central axis thereof, wherein the working channel is configured to receive a surgical instrument therethrough; (c) a first needle port that opens to the working channel through a first side portion of the surgical access device; and (d) a second needle port that opens to the working channel through a second side portion of the surgical access device; wherein each of the first and second needle ports is configured to direct a suture passer needle through the surgical access device, across the working channel, at an oblique angle relative to the central axis of the surgical access device, wherein the user engagement feature of the latch ring is circumferentially offset from each of the first and second needle ports by at least 90 degrees.

Example 57

The surgical access device of Example 56, wherein the user engagement feature is movable to a position in which the user engagement feature is spaced circumferentially equidistantly between the first and second needle ports.

Example 58

The surgical access device of any one or more of Examples 56 through 57, wherein the user engagement feature comprises an outwardly projecting knob.

Example 59

A surgical access device, comprising: (a) a cannula having a proximal end, a distal end, and a cannula lumen extending therebetween; (b) a housing assembly coupled to the proximal end of the cannula, wherein the housing assembly comprises: (i) a proximal housing, and (ii) a latch ring arranged distally of the proximal housing and having an outwardly projecting knob, wherein the latch ring is movable by the outwardly projecting knob to selectively couple and decouple the proximal housing with the cannula, wherein an interior of the housing assembly communicates with the cannula lumen to define a working channel extending from a proximal end of the surgical access device to a distal end of the surgical access device along a central axis thereof, wherein the working channel is configured to receive a surgical instrument therethrough; (c) an insufflation port configured to direct insufflation fluid into the working channel; (d) a first needle port that opens to the working channel through a first side portion of the surgical access device; and (e) a second needle port that opens to the working channel through a second side portion of the surgical access device; wherein each of the first and second needle ports is configured to direct a suture passer needle through the surgical access device, across the working channel, at an oblique angle relative to the central axis of the surgical access device, wherein the outwardly projecting knob of the latch ring is circumferentially offset from each of the first needle port, the second needle port, and the insufflation port.

Example 60

The surgical access device of Example 59, wherein the user engagement feature is movable to a position in which the user engagement feature is diametrically opposed from the insufflation port and is circumferentially offset from at least one of the first or second needle ports by at least 90 degrees.

Example 61

A surgical access device, comprising: (a) a cannula having a proximal end, a distal end, and a cannula lumen extending therebetween (b) a housing assembly coupled to the proximal end of the cannula, wherein the housing assembly defines a housing interior in communication with the cannula lumen; (c) a working channel extending from a proximal end of the surgical access device to a distal end of the surgical access device along a central axis thereof, wherein the working channel is defined by the cannula lumen and the housing interior, wherein the working channel is configured to receive a surgical instrument therethrough; (d) an insufflation port configured to direct insufflation fluid into the working channel; (e) a first needle port that opens to the working channel through a first side portion of the surgical access device, wherein the first needle port is diametrically opposed from the insufflation port; and (f) a second needle port that opens to the working channel through a second side portion of the surgical access device, wherein each of the first and second needle ports is configured to direct a suture passer needle through the surgical access device, across the working channel, at an oblique angle relative to the central axis.

Example 62

The surgical access device of Example 61, wherein the second needle port is circumferentially offset from the insufflation port.

Example 63

The surgical access device of Example 62, wherein the second needle port is circumferentially offset from the insufflation port by at least 17 degrees.

Example 64

The surgical access device of any one or more of Examples 61 through 63, wherein the housing assembly includes a proximal housing and a latch ring configured to releasably couple the proximal housing with the cannula, wherein the latch ring includes a user engagement feature that is actuatable to release the proximal housing from the cannula, wherein the user engagement feature is circumferentially offset from the insufflation port throughout a full range of permissible motion of the user engagement feature.

Example 65

The surgical access device of Example 64, wherein the latch ring is movable to a position in which the user engagement feature is circumferentially offset from the insufflation port by at least 90 degrees.

Example 66

The surgical access device of any one or more of Examples 64 through 65, wherein the user engagement feature comprises an outwardly projecting knob.

Example 67

The surgical access device of any one or more of Examples 64 through 66, wherein the latch ring is rotatable about the central axis relative to the proximal housing.

Example 68

The surgical access device of any one or more of Examples 61 through 67, wherein the cannula includes a proximal hub configured to couple with the housing assembly, wherein the first and second needle ports extend through the proximal hub.

Example 69

The surgical access device of any one or more of Examples 61 through 68, wherein the first needle port comprises a first needle entrance port and the second needle port comprises a second needle entrance port, wherein the surgical access device further comprises a first needle exit port arranged distally of the first needle entrance port, and a second needle exit port arranged distally of the second needle entrance port, wherein the first needle entrance port and the first needle exit port together define a first suture path extending obliquely across the central axis of the surgical access device, wherein the second needle entrance port and the second needle exit port together define a second suture path extending obliquely across the central axis of the surgical access device.

Example 70

The surgical access device of Example 69, wherein the cannula includes a proximal hub and a cylindrical portion extending distally from the proximal hub, wherein the first and second needle exit ports open to the working channel through the cylindrical portion.

Example 71

The surgical access device of any one or more of Examples 69 through 70, wherein the first and second needle entrance ports and the first and second needle exit ports are arranged such that the first and second suture paths extend through the central axis of the surgical access device.

Example 72

The surgical access device of any one or more of Examples 69 through 71, further comprising a first needle guide structure configured to guide a suture passer needle through the first needle entrance port and along the first suture path, and a second needle guide structure configured to guide a suture passer needle through the second needle entrance port and along the second suture path.

Example 73

The surgical access device of Example 72, wherein the first and second needle guide structures comprise first and second needle guide tubes.

Example 74

The surgical access device of any one or more of Examples 69 through 73, wherein the first needle exit port is diametrically opposed from the first needle entrance port, wherein the second needle exit port is diametrically opposed from the second needle entrance port.

Example 75

The surgical access device of any of Examples 69 through 74, wherein the first needle entrance port, the first needle exit port, and the insufflation port lie in a plane extending axially through the surgical access device along the central axis thereof.

Example 76

A surgical access device, comprising: (a) a cannula having a proximal hub, a distal tip, and a cannula lumen extending therebetween; (b) a housing assembly coupled to the proximal hub of the cannula, wherein the housing assembly defines a housing interior in communication with the cannula lumen; (c) a working channel extending from a proximal end of the surgical access device to a distal end of the surgical access device along a central axis thereof, wherein the working channel is defined by the cannula lumen and the housing interior, wherein the working channel is configured to receive a surgical instrument therethrough; (d) an insufflation port configured to direct insufflation fluid into the working channel; and (e) a needle port that opens to the working channel through the proximal hub of the cannula, wherein the needle port is diametrically opposed from the insufflation port, wherein the needle port is configured to direct a suture passer needle through the surgical access device, across the working channel, at an oblique angle relative to the central axis.

Example 77

The surgical access device of Example 76, further comprising a second needle port that opens to the working channel through the proximal hub of the cannula, wherein the second needle port is circumferentially offset from the insufflation port.

Example 78

A surgical access device, comprising: (a) a cannula having a proximal end, a distal end, and a cannula lumen extending therebetween; (b) a housing assembly coupled to the proximal end of the cannula, wherein the housing assembly defines a housing interior in communication with the cannula lumen; (c) a working channel extending from a proximal end of the surgical access device to a distal end of the surgical access device along a central axis thereof, wherein the working channel is defined by the cannula lumen and the housing interior, wherein the working channel is configured to receive a surgical instrument therethrough; (d) an insufflation port configured to direct insufflation fluid into the working channel; (e) a first needle entrance port that opens to the working channel through a side portion of the surgical access device; (f) a first needle exit port that opens to the working channel through a side portion of the surgical access device, wherein the first needle exit port communicates with the first needle entrance port to define a first needle channel configured to guide a suture passer needle through the surgical access device, across the working channel, at an oblique angle relative to the central axis; (g) a second needle port that opens to the working channel through a side portion of the surgical access device; and (h) a second needle exit port that opens to the working channel through a side portion of the surgical access device, wherein the second needle exit port communicates with the second needle entrance port to define a second needle channel configured to guide a suture passer needle through the surgical access device, across the working channel, at an oblique angle relative to the central axis, wherein at least one of the first or second needle entrance ports and its respective needle exit port lie in an axial plane extending axially through the surgical access device along the central axis thereof, wherein the axial plane is offset from the insufflation port.

Example 79

The surgical access device of Example 78, wherein the first needle entrance port, the first needle exit port, and the insufflation port lie in a first axial plane extending axially through the surgical access device along the central axis thereof, wherein the second needle entrance port and the second needle exit port lie in a second axial plane extending axially through the surgical access device along the central axis, wherein the second axial plane is offset from the first axial plane.

Example 80

The surgical access device of Example 78, wherein each of the first needle entrance port and the second needle entrance port is circumferentially offset from the insufflation port.

Example 81

A surgical instrument comprising: (a) an outer sheath defining a lumen; and (b) an inner needle slidably disposed in the outer sheath, wherein the inner needle comprises: (i) a shaft, (ii) a driver configured to drive the shaft relative to the outer sheath from a first position to a second position, (iii) at least one suture capturing feature, wherein the at least one suture capturing feature is configured to cooperate with the outer sheath to thereby selectively capture and release a suture based on positioning of the shaft relative to the outer sheath, and (iv) a head secured to the shaft at an end opposite the driver, wherein the head is configured to transition between a contracted state and an expanded state.

Example 82

The surgical instrument of Example 81, wherein the at least one suture capturing feature comprises at least one notch formed in the head.

Example 83

The surgical instrument of any one or more of Examples 81 through 82, wherein the outer sheath comprises an outer needle having a distal tip.

Example 84

The surgical instrument of Example 83, wherein the distal tip of the outer needle has a pointed end such that the distal tip is configured to penetrate tissue.

Example 85

The surgical instrument of any one or more of Examples 83 through 84, wherein the distal tip of the outer needle has a sharpened edge such that the distal tip is configured to penetrate tissue.

Example 86

The surgical instrument of any one or more of Examples 83 through 85, wherein the head is configured to be confined within the tip when the inner needle is in the first position, wherein the head is configured to extend beyond the tip when the inner needle is translated to the second position by the driver.

Example 87

The surgical instrument of Example 86, wherein the shaft defines an inner lumen along a longitudinal axis, wherein the inner needle further comprises a cable slidably disposed within the inner lumen and operatively connected to an actuator.

Example 88

The surgical instrument of Example 87, wherein the cable is operatively connected to the head at an end opposite the actuator, wherein the cable is operable to radially expand the head from the contracted state to the expanded state when the inner needle is in the second position.

Example 89

The surgical instrument of Example 88, wherein the head has a blunt end such that the head is atraumatic.

Example 90

The surgical instrument of any one or more of Examples 88 through 89, wherein the head has a sharp end such that the head is configured to pierce tissue.

Example 91

The surgical instrument of Example 90, wherein the head is resiliently biased to the expanded state such that the head is configured to resiliently expand from the contracted state to the expanded state when the inner needle is translated from the first position to the second position.

Example 92

The surgical instrument of Example 91, wherein the outer needle defines an outer lumen having a first diameter, wherein the outer needle includes a bulbous shape having a second diameter, wherein the first diameter is smaller than the second diameter and the bulbous shape is proximal to the distal tip such that the head is configured to resiliently expand in the second diameter of the bulbous shape upon translation from the first position to the second position.

Example 93

The surgical instrument of any one or more of Examples 91 through 92, wherein the head includes at least one flex aperture, wherein the at least one flex aperture is configured to facilitate the resilient contraction of the head when in the contracted state.

Example 94

The surgical instrument of Example 93, wherein the at least one flex aperture is configured to reduce frictional resistance between the head and the outer needle upon translation of the inner needle relative to the outer needle.

Example 95

The surgical instrument of Example 94, wherein the at least one flex aperture is configured to be enlarged when the head is in the expanded state in the second position.

Example 96

A surgical instrument comprising: (a) a needle including at least one notch, wherein the notch is configured to capture a suture thread; and (b) a needle head fixedly attached to the needle, wherein the needle head is formed of a resilient material such that the needle head is operable to resiliently expand relative to a central axis from a contracted state to an expanded state.

Example 97

The surgical instrument of Example 96, further comprising a shaft including an opening at a distal end portion, wherein the needle is configured to be movably contained within the shaft when in a first position, wherein the needle is configured to protrude beyond the shaft through the opening when in a second position.

Example 98

The surgical instrument of Example 97, further comprising a cable movably contained within the needle, wherein the cable is operable to resiliently expand the needle head from the contracted state to the expanded state.

Example 99

The surgical instrument of any one or more of Examples 97 through 98, wherein the needle head includes one or more apertures configured to deform when the head is in the contracted state, wherein the one or more apertures is operable to reduce frictional resistance between the head and the shaft when the needle is in the first position.

Example 100

A method of indicating a tissue penetration site with an apparatus including a needle having a head configured to change profiles from a contracted state to an expanded state, the method comprising: (a) advancing the head proximate to the tissue penetration site; (b) forcing the head against a surface of the tissue; and (c) expanding the head from a contracted state to an expanded state to deform the tissue without penetrating the tissue, thereby indicate the tissue penetration site.

Example 101

An obturator configured for use with a trocar, the obturator comprising: (a) a head; (b) a shaft extending distally from the head along a central axis, wherein the shaft is configured to be received within a working channel of a trocar; (c) a distal tip configured to puncture tissue; (d) first and second needle entrance ports each arranged on at least one of the head or the shaft; and (e) first and second needle exit ports arranged on the shaft, wherein the first needle entrance port communicates with the first needle exit port to define a first suture path extending obliquely relative to the central axis, wherein the first suture path includes at least one first sealing element, wherein the second needle entrance port communicates with the second needle exit port to define a second suture path extending obliquely relative to the central axis, wherein the second suture path includes at least one second sealing element.

Example 102

The obturator of Example 101, wherein the first and second suture paths extend through a device interior of the wound closure device.

Example 103

The obturator of Example 102, wherein the head and the shaft collectively define the device interior, wherein each of the needle entrance ports and the needle exit ports opens to the device interior.

Example 104

The obturator of any one or more of Examples 101 through 103, wherein the first and second needle entrance ports are arranged on respective first and second side portions of the head.

Example 105

The obturator of any one or more of Examples 101 through 104, wherein the first and second needle entrance ports comprise first and second elongate slots.

Example 106

The obturator of any one or more of Examples 101 through 105, wherein the first and second needle exit ports comprise first and second elongate slots.

Example 107

The obturator of any one or more of Examples 101 through 106, further comprising third and fourth needle exit ports arranged on the cannula distally of the first and second needle exit ports.

Example 108

The obturator of Example 107, wherein the third and fourth needle exit ports are aligned axially with the first and second needle exit ports.

Example 109

The obturator of Example 101, further comprising at least one needle guide member arranged on the shaft distally of the first and second needle exit ports, wherein the at least one needle guide member is configured to guide a distal end of a suture passer needle directed along at least one of the first or second suture paths.

Example 110

The obturator of Example 109, wherein the at least one needle guide member comprises a pair of needle guide members, wherein each needle guide member is movable relative to the cannula between a retracted position and a deployed position in which the at least one needle guide member projects radially outwardly from the shaft.

Example 111

The obturator of any one or more of Examples 101 through 110, further comprising at least one anchor member arranged at a distal end portion of the shaft, wherein the at least one anchor member is movable relative to the shaft between a retracted position and a deployed position in which the at least one anchor member projects radially outwardly from the shaft.

Example 112

The obturator of Example 111, further comprising a plunger slidably arranged within a central lumen of the shaft, wherein the plunger is operatively coupled with the at least one anchor member, wherein the plunger is slidable axially within the shaft between a first axial position for placing the at least one anchor member in the retracted position and a second axial position for placing the at least one anchor member in the deployed position.

Example 113

The obturator of Example 112, wherein a distal end of the plunger is coupled to the distal tip of the obturator, wherein the distal tip is movable with the plunger relative to the shaft between the first and second axial positions.

Example 114

The obturator of Example 112, wherein the plunger is resiliently biased toward one of the first position or the second position, wherein the head is selectively decouplable from the shaft, wherein the head is configured to overcome a bias force associated with the plunger to thereby maintain the plunger in one of the first axial position or the second axial position when the head is coupled with the shaft.

Example 115

The obturator of any one or more of Examples 101 through 114, wherein the needle entrance ports are arranged on the shaft.

Example 116

An obturator configured for use with a trocar, the obturator comprising: (a) a shaft extending along a central axis; (b) a head releasably coupled to a proximal end of the shaft; (c) a distal tip configured to puncture tissue; (d) a first pair of needle ports configured to direct a suture passer needle through the obturator along a first suture path oriented obliquely relative to the central axis; and (e) a second pair of needle ports configured to direct a suture passer needle through the obturator along a second suture path oriented obliquely relative to the central axis.

Example 117

The obturator of Example 116, wherein the head includes a latch, wherein the latch is movable between a first position in which the latch is configured to secure the head to the shaft, and a second position in which the latch is configured to permit the head to be separated from the shaft.

Example 118

The obturator of any one or more of Examples 116 through 117, wherein the obturator further includes at least one anchor member arranged at a distal end portion of the shaft, wherein the at least one anchor member is movable relative to the shaft between a retracted position and a deployed position in which the at least one anchor member projects radially outwardly from the shaft.

Example 119

A trocar assembly, comprising: (a) a trocar including: (i) a housing assembly, (ii) a cannula extending distally from the housing assembly, and (iii) a working channel extending axially through the housing assembly and the cannula; and (b) the obturator of claim 16, wherein a proximal end of the obturator is configured to pass distally through the working channel when the head is removed from the shaft.

Example 120

A wound closure device, comprising: (a) a head; (b) a shaft extending distally from the head along a central axis; (c) a deployable member coupled to the shaft, wherein the deployable member is movable between a retracted position in which the shaft is configured to be inserted into a working channel of a trocar, and a deployed position in which the deployable member projects radially outwardly from the shaft and is configured to abut an adjacent structure to limit axial movement of the wound closure device relative to the adjacent structure; (d) a first pair of needle ports configured to guide a suture passer needle along a first suture path extending through the wound closure device obliquely relative to the central axis; and (e) a second pair of needle ports configured to guide a suture passer needle along a second suture path extending through the wound closure device obliquely relative to the central axis.

Example 121

A surgical access device positionable within a tissue opening, comprising: (a) a tissue retractor including a flexible body configured to engage tissue surrounding the tissue opening; (b) a plurality of surgical instrument channels arranged in a central portion of the tissue retractor, wherein each surgical instrument channel is configured to guide a surgical instrument distally through the surgical access device; (c) at least one needle entrance port arranged on a proximal portion of the surgical access device; and (d) at least one needle exit port arranged distally of the needle entrance port, wherein the at least one needle entrance port and the at least one needle exit port are configured to cooperate to define a needle channel extending distally through the surgical access device and obliquely relative to a central axis thereof, wherein the needle channel is configured to guide a suture passer needle through the surgical access device and adjacent tissue to facilitate closure of the tissue opening.

Example 122

The surgical access device of Example 121, wherein the flexible body of the tissue retractor includes a proximal flange, a distal flange, and a medial body portion extending between the proximal and distal flanges.

Example 123

The surgical access device of Example 122, wherein the at least one needle exit port is arranged at least partially on the medial body portion.

Example 124

The surgical access device of any one or more of Examples 122 through 123, wherein the distal flange includes a plurality of perforated regions arranged circumferentially about the central axis, wherein each perforated region extends radially inwardly from an outer edge of the distal flange.

Example 125

The surgical access device of Example 124, wherein the distal flange houses a resilient ring divided into a plurality of ring segments, wherein the perforated regions of the distal flange are arranged circumferentially at locations between adjacent ends of the ring segments.

Example 126

The surgical access device of Example 125, wherein the ring segments are releasably coupled together by a plurality of coupling members arranged at the adjacent ends of the ring segments.

Example 127

The surgical access device of any one or more of Examples 121 through 126, wherein the at least one needle entrance port is arranged on the tissue retractor.

Example 128

The surgical access device of any one or more of Examples 121 through 127, wherein the tissue retractor includes a central passage extending axially through the flexible body, wherein the surgical access device further includes an insert arranged within the central passage, wherein the plurality of surgical instrument channels extend through the insert.

Example 129

The surgical access device of Example 128, wherein the at least one needle entrance port is provided by the insert, wherein the at least one needle channel extends through the insert.

Example 130

The surgical access device of Example 129, wherein the insert includes at least one needle entry guide member protruding from a proximal end portion of the insert, wherein the at least one needle entry guide member defines the at least one needle entrance port.

Example 131

The surgical access device of any one or more of Examples 128 through 129, wherein the insert includes a central channel extending axially therethrough, wherein the at least one needle channel opens to the central channel to define the at least one needle entrance port Example 132

The surgical access device of any one or more of Examples 128 through 131, wherein the insert comprises a rigid structure.

Example 133

The surgical access device of any one or more of Examples 121 through 132, further comprising a proximal housing coupled to a proximal end of the tissue retractor, wherein the surgical instrument channels extend through the proximal housing, wherein the proximal housing is configured to provide the at least one needle entrance port.

Example 134

The surgical access device of Example 133, wherein the proximal housing includes at least one needle entry guide member protruding from an outer surface of the proximal housing, wherein the at least one needle entry guide member defines the at least one needle entrance port.

Example 135

The surgical access device of Example 133, wherein the at least one needle entrance port extends through a proximal face of the proximal housing.

Example 136

The surgical access device of any one or more of Examples 121 through 135, wherein the at least one needle entrance port comprises a plurality of circumferentially spaced needle entrance ports and the at least one needle exit port comprises a plurality of circumferentially spaced needle exit ports, wherein each needle entrance port is configured to cooperate with a corresponding needle exit port to define a respective needle channel extending distally through the surgical access device and obliquely relative to the central axis thereof, wherein each needle channel is configured to guide a suture passer needle through the surgical access device and adjacent tissue.

Example 137

The surgical access device of Example 136, wherein the plurality of needle entrance ports comprises first and second needle entrance ports arranged in a first axial plane, and third and fourth needle entrance ports arranged in a second axial plane angularly offset from the first axial plane, wherein the plurality of needle exit ports comprises first and second needle exit ports arranged in the first axial plane, and third and fourth needle exit ports arranged in the second axial plane, wherein the first, second, third, and fourth needle entrance ports are configured to cooperate with the first, second, third, and fourth needle exit ports, respectively, to define first, second, third, and fourth needle channels, respectively, extending through the surgical access device and obliquely relative to the central axis thereof.

Example 138

A surgical access device positionable within a tissue opening, comprising: (a) a tissue retractor including a flexible body configured to engage tissue surrounding the tissue opening, wherein the tissue retractor defines a central axis; (b) at least one surgical instrument channel configured to guide a surgical instrument distally through the surgical access device; (c) a plurality of needle entrance ports arranged circumferentially about the central axis on a proximal portion of the surgical access device; and (d) a plurality of needle exit ports arranged circumferentially about the central axis distally of the needle entrance ports, wherein each needle entrance port is configured to cooperate with a respective needle exit port to define a needle channel extending distally through the surgical access device and obliquely relative to the central axis, wherein each needle channel is configured to guide a suture passer needle through the surgical access device and adjacent tissue to facilitate closure of the tissue opening.

Example 139

The surgical access device of Example 138, wherein the needle exit ports are arranged on the flexible body of the tissue retractor, wherein the plurality of needle entrance ports includes at least four needle entrance ports and the plurality of needle exit ports includes at least four needle exit ports.

Example 140

A surgical access positionable within a tissue opening, comprising (a) a tissue retractor including a flexible body having a proximal flange, a distal flange, and a medial body portion extending between the proximal and distal flanges, wherein the proximal and distal flanges are configured to engage respective proximal and distal surfaces of the tissue, wherein the medial body portion is configured to engage an axial tissue wall defining the tissue opening; (b) at least one surgical instrument channel configured to guide a surgical instrument distally through the surgical access device; (c) a needle entrance port arranged on a proximal portion of the surgical access device; and (d) a needle exit port arranged distally of the needle entrance port on the medial body portion, wherein the needle entrance port is configured to cooperate with the needle exit port to define a needle channel extending distally through the surgical access device and obliquely relative to a central axis thereof, wherein each needle channel is configured to guide a suture passer needle through the surgical access device and adjacent tissue to facilitate closure of the tissue opening.

Example 141

A surgical instrument, comprising: (a) a shaft extending longitudinally and having a distal end portion; and (b) a tissue fastener releasably attached to the distal end portion of the shaft, wherein the shaft is operable to rotatably drive the tissue fastener about a longitudinal axis of the shaft, wherein the tissue fastener includes: (i) a base, (ii) a first arm extending longitudinally from the base, wherein the first arm is configured to be received within a first tissue portion, (iii) a second arm extending longitudinally from the base, wherein the second arm is configured to be received within a second tissue portion, wherein the first and second arms are configured to respectively draw the first tissue portion against the second tissue portion in response to rotation of the shaft about the longitudinal axis, and (iv) a plurality of barbs extending from the first and second arms, wherein the barbs are configured to anchor the first and second arms respectively within the first and second tissue portions, wherein the distal end portion of the shaft is configured to release the tissue fastener thereby securing the first tissue portion against the second tissue portion with the tissue fastener anchored therein.

Example 142

The surgical instrument of Example 141, wherein the tissue fastener is of a bioabsorbable material.

Example 143

The surgical instrument of any one or more of Examples 141 through 142, wherein the first and second arms lie in varying dimensional planes and are configured to coil around the distal end portion.

Example 144

The surgical instrument of Example 143, wherein the first and second arms extend from the base along respective helical paths.

Example 145

The surgical instrument of any one or more of Examples 141 through 144, wherein the shaft is configured to release the tissue fastener when rotated at a predetermined release force when the distal end portion abuts a first and second tissue portion.

Example 146

The surgical instrument of Example 145, wherein the first and second arms are configured to be directed radially outwardly upon the application of the predetermined release force.

Example 147

The surgical instrument of Example 146, wherein the distal end portion of the shaft has a securement shoulder configured to receive the first and second arms such that the tissue fastener is releasably clipped onto the distal end portion.

Example 148

The surgical instrument of Example 147, wherein the securement shoulder extends along a securement slot and at least one barb comprises a catch member configured to be received within the securement slot to thereby releasably clip onto the distal end portion.

Example 149

The surgical instrument of Example 148, wherein the catch member is configured to be directed radially outwardly with the first and second arms to thereby release the distal end portion upon the application of the predetermined release force.

Example 150

The surgical instrument of any one or more of Examples 141 through 149, wherein the shaft is configured to be received in a trocar.

Example 151

The surgical instrument of Example 150, wherein the shaft is configured to translate within a cannula of the trocar from a first position to a second position, wherein the tissue fastener is configured to be covered by the cannula when the shaft is in the first position, wherein the tissue fastener is configured to extend beyond the cannula when the shaft is in the second position.

Example 152

The surgical instrument of any one or more of Examples 141 through 151, further comprising a securement hook configured to releasably attach the tissue fastener to the distal end portion.

Example 153

The surgical instrument of Example 152, wherein the shaft has a channel extending through the distal end portion to an opening, and wherein the securement hook is slidably disposed through the channel.

Example 154

The surgical instrument of Example 153, wherein the base is configured to receive the hook member through the opening such that the hook member releasably attaches the tissue fastener to the distal end portion of the shaft.

Example 155

The surgical instrument of Example 154, wherein hook member is configured to rotate within the channel to disengage the securement hook from the tissue fastener.

Example 156

A tissue fastener, comprising: (a) a body including a slot, wherein the slot is configured to releasably attach the body to a surgical instrument; (b) a first arm angularly extending from the body in a helical formation, wherein the first arm includes at least one barb protruding laterally from the first arm; and (c) a second arm angularly extending from the body in a helical formation opposite of the first arm, wherein the second arm includes at least one barb protruding laterally from the second arm; wherein the first and second arms are configured to be rotatably driven within tissue; and wherein the at least one barb of the first and second arms are configured to securely close a tissue opening when the first and second arms are rotatably driven within the tissue.

Example 157

The tissue fastener of Example 156, wherein the body and the first and second arms are formed of a bioabsorbable material.

Example 158

The tissue fastener of any one or more of Examples 156 through 157, wherein the surgical instrument is configured to release the slot when the first and second arms abut the tissue opening and the body is rotated at a predetermined release force.

Example 159

The tissue fastener of any one or more of Examples 156 through 157, wherein the first and second arms are configured to curl around the surgical instrument in varying dimensional planes about the body.

Example 160

A method of closing a tissue opening in a patient using a barbed fastener and an obturator, wherein the barbed fastener includes a pair of arms with a plurality of barbs extending therefrom, wherein the obturator includes a securement mechanism configured to removably attach the barbed fastener to the obturator, the method comprising: (a) inserting the obturator with the barbed fastener thereon into a tissue opening with a surrounding tissue portion; (b) positioning the pair of arms against the tissue portion within the tissue opening site to securely fasten the plurality of barbs to the tissue portion along varying dimensional planes; (c) rotating the barbed fastener against the tissue portions with the obturator to thereby close the tissue opening with the tissue portion being pulled together along multiple dimensional planes; and (d) disengaging the barbed fastener from the obturator via the securement mechanism.

Example 161

A method of suturing a trocar path incision in a tissue of a patient with an obturator, wherein the obturator includes a proximal head, a distal tip configured to penetrate tissue of a patient, a shaft extending from the proximal head to the distal tip and configured to be received within a working channel of a cannula assembly, and a suturing feature configured to receive a suture, the method comprising: (a) inserting the obturator through the tissue such that the shaft extends through a tissue opening about the trocar path incision and the distal tip is positioned within a cavity of the patient; b) directing the suture via the suturing feature with the obturator inserted through the tissue in order to direct the suture relative to the tissue; and (c) closing the tissue opening about the trocar path incision with the suture.

Example 162

The method of Example 1, wherein the suturing feature of the obturator is a catch arm selectively moveable from a retracted position to a first deployed position and a second deployed position and configured to releasably capture a suture thread of the suture from a needle, the method further comprising: (a) extending the catch arm radially outwardly to first deployed position; (b) inserting a thread end portion of the suture thread into the tissue with the needle; (c) releasably capturing the thread end portion of the suture thread with the catch arm; (d) moving the catch arm to a second deployed position with the thread end portion of the suture thread releasably captured thereto; (e) releasing the thread end portion of the suture thread from the catch arm; and (f) withdrawing the thread end portion of the suture thread from the patient to thereby suture the tissue opening.

Example 163

The method of Example 162, wherein moving the catch arm further includes rotating the obturator relative to the cannula assembly.

Example 164

The method of Example 162, wherein moving the catch arm further includes pivoting the catch arm from the first deployed position to the second deployed position through the retracted position.

Example 165

The method of Example 161, wherein the suture is a barbed fastener with a pair of arms having a plurality of barbs extending therefrom and the suturing feature is a securement mechanism configured to removably attach the barbed fastener to the obturator, the method further comprising: (a) positioning the pair of arms against the tissue within the tissue opening to securely fasten the plurality of barbs to the tissue along varying dimensional planes; (b) rotating the barbed fastener against the tissue with the obturator to thereby close the tissue opening with the tissue being pulled together along multiple dimensional planes; and (c) disengaging the barbed fastener from the obturator via the securement mechanism.

Example 166

The method of Example 161, wherein the suturing feature includes a first needle entrance port, a second needle entrance port, a first needle exit port, and a second needle exit port, wherein the first and second needle entrance ports are each arranged on at least one of the proximal head or the shaft, wherein the first and second needle exit ports are arranged on the shaft, wherein the first needle entrance port communicates with the first needle exit port to define a first suture path extending obliquely relative to a central axis, and wherein the second needle entrance port communicates with the second needle exit port to define a second suture path extending obliquely relative to the central axis, the method comprising: (a) moving a needle with a suture thread of the suture thereon along the first suture path; and (b) moving the needle with the suture thread of the suture thereon along the second suture path.

Example 167

The method of Example 166, wherein the suturing feature includes a third needle exit port and a fourth needle exit port, wherein the third and fourth needle exit ports are arranged on the shaft distally of the first and second needle exit port, wherein the first needle entrance port communicates with the third needle exit port to define a third suture path extending obliquely relative to the central axis, and wherein the second needle entrance port communicates with the fourth needle exit port to define a fourth suture path extending obliquely relative to the central axis, and the method further comprises selecting from the first, second, third, and fourth suture paths to move the needle with the suture thread along at least one of the first, second, third, and fourth suture paths.

Example 168

The method of Example 167, wherein the third and fourth needle exit ports are aligned axially with the first and second needle exit ports.

Example 169

The method of any one or more of Examples 166 through 168, wherein the obturator further includes at least one needle guide member arranged on the shaft distally of the first and second needle exit ports, and the method further comprising guiding a distal end of the needle moving along at least one of the first or second suture paths.

Example 170

The method of any one or more of Examples 166 through 169, wherein the obturator further includes an anchor member movable relative to the shaft between a retracted position and a deployed position, and wherein the method further comprises moving the anchor member from the retracted position to the deployed position and projecting the anchor member radially outward from the shaft.

Example 171

The method of Example 170, wherein the obturator further includes a plunger slidably arranged within a central lumen of the shaft and operatively connected to the anchor member, and wherein the method further comprises sliding the plunger axially within the shaft from a first axial position to a second axial position to place the anchor in the deployed position.

Example 172

The method of any one or more of Examples 161 through 171, wherein a trocar assembly includes the cannula assembly and a housing assembly having a proximal housing, a latch ring, a first needle port, and a second needle port, wherein the latch ring is arranged distally of the proximal housing and has a user engagement feature, wherein the first needle port opens to the working channel through a first side portion of the trocar assembly, wherein the second needle port opens to the working channel through a second side portion of the trocar assembly, wherein each of the first and second needle ports is configured to direct a needle therethrough, across the working channel, at an oblique angle relative to a central axis, wherein the user engagement feature of the latch ring is circumferentially offset from each of the first and second needle ports, and wherein the method further comprises rotating the user engagement feature to couple or decouple the proximal housing with the cannula assembly.

Example 173

The method of Example 172, wherein rotating the user engagement feature further includes rotating the user engagement feature to a position in which the user engagement feature is spaced circumferentially equidistantly between the first and second needle ports.

Example 174

The method of Example 172, wherein rotating the user engagement feature further includes rotating the user engagement feature to a position in which the user engagement feature is diametrically opposed from the insufflation port.

Example 175

The method of Example 161, wherein a trocar assembly includes the cannula assembly and a housing assembly having a proximal housing, an insufflation port, a first needle port, and a second needle port, wherein the first needle port opens to the working channel through a first side portion of the trocar assembly and is positioned diametrically opposed from the insufflation port, wherein the second needle port opens to the working channel through a second side portion of the trocar assembly, wherein each of the first and second needle ports is configured to direct a needle therethrough, across the working channel, at an oblique angle relative to a central axis, and wherein the method further comprises directing an insufflation fluid from the insufflation portion to the working channel.

Example 176

The method of Example 175, wherein the second needle port is circumferentially offset from the insufflation port.

Example 177

The method of Example 175, wherein at least one of the first or second needle entrance ports and its respective needle exit port lie in an axial plane extending axially through the trocar assembly along the central axis thereof, and wherein the axial plane is offset from the insufflation port.

Example 178

The method of any one or more of Examples 161 through 177, further comprising: (a) manipulating a needle from a catch position toward a release position; (b) urging a suture thread of the suture with a cam surface of the needle from a catch portion of a suture notch; and (c) releasing the suture thread from the catch portion of the suture notch.

Example 179

The method of any one or more of Example 161 through 178, wherein a needle has a needle head configured to change profiles from a contracted state to an expanded state, the method further comprising: (a) advancing the head proximate to the tissue opening; (b) forcing the head against the tissue; and (c) expanding the head from a contracted state to an expanded state to deform the tissue without penetrating the tissue in order to indicate a tissue penetration site.

Example 180

The method of any one or more of Examples 161 through 179, wherein a surgical access device includes a tissue retractor including a flexible body, a plurality of surgical instrument channels arranged in a central portion of the tissue retractor, a needle entrance port, and a needle exit port arranged distally of the needle entrance port, the needle entrance port and the needle exit port defining a needle channel extending distally through the surgical access device and obliquely relative to a central axis thereof, the method comprising: (a) guiding a surgical instrument with at least one surgical instrument channel distally through the surgical access device; and (b) guiding a needle through the surgical access device and adjacent to the tissue to facilitate closure of the tissue opening.

XXIV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pat. No. 8,844,789, entitled "Automated End Effector Component Reloading System for Use with a Robotic System," issued Sep. 30, 2014, the disclosure of which is incorporated by reference herein; U.S. Pat. No. 8,820,605, entitled "Robotically-Controlled Surgical Instruments," issued Sep. 2, 2014, the disclosure of which is incorporated by reference herein; U.S. Pat. No. 8,616,431, entitled "Shiftable Drive Interface for Robotically-Controlled Surgical Tool," issued Dec. 31, 2013, the disclosure of which is incorporated by reference herein; U.S. Pat. No. 8,573,461, entitled "Surgical Stapling Instruments with Cam-Driven Staple Deployment Arrangements," issued Nov. 5, 2013, the disclosure of which is incorporated by reference herein; U.S. Pat. No. 8,602,288, entitled "Robotically-Controlled Motorized Surgical End Effector System with Rotary Actuated Closure Systems Having Variable Actuation Speeds," issued Dec. 10, 2013, the disclosure of which is incorporated by reference herein; U.S. Pat. No. 9,301,759, entitled "Robotically-Controlled Surgical Instrument with Selectively Articulatable End Effector," issued Apr. 5, 2016, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

The teachings presented herein may be further combined with various teachings of any one or more of the following: U.S. application Ser. No. 15/637,690, entitled "Needle Guide Instrument with Traverse Suture Capture Feature," filed Jun. 29, 2017, issued as U.S. Pat. No. 10,675,018 on Jun. 9, 2020, the disclosure of which is incorporated by reference herein; U.S. application Ser. No. 15/637,702, , entitled "Suture Grasping Instrument," filed on Jun. 29, 2017, issued as U.S. Pat. No. 10,639,029 on May 5, 2020, the disclosure of which is incorporated by reference herein; U.S. application Ser. No. 15/637,683, issued as U.S. Pat. No. 10,639,068 on May 5, 2020, incorporated by reference above; U.S. application Ser. No. 15/637,688, issued as U.S. Pat. No. 10,485,580 on Nov. 26, 2019, incorporated by reference above; U.S. application Ser. No. 15/637,712, entitled "Suture Passing Instrument with Puncture Site Identification Feature," filed on Jun. 29, 2017, issued as U.S. Pat. No. 10,709,440 on Jul. 14, 2020, the disclosure of which is incorporated by reference herein; U.S. application Ser. No. 15/637,696, entitled "Trocar Obturator with Transverse Needle Ports," filed on Jun. 29, 2017, issued as U.S. Pat. No. 10,869,690 on Dec. 22, 2020, the disclosure of which is incorporated by reference herein; U.S. application Ser. No. 15/637,707, entitled "Surgical Port with Wound Closure Channels," filed on Jun. 29, 2017, issued as U.S. Pat. No. 10,568,619 on Feb. 25, 2020, the disclosure of which is incorporated by reference herein; U.S. application Ser. No. 15/637,735, entitled "Trocar Obturator with Detachable Rotary Tissue Fastener," filed on Jun. 29, 2017, issued as U.S. Pat. No. 10,709,473 on Jul. 14, 2020, the disclosure of which is incorporated by reference herein; and/or other patents and patent application publications incorporated by reference above.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of suturing a trocar path incision in a tissue of a patient with a cannula assembly and an obturator, wherein the obturator includes a proximal head, a distal tip configured to penetrate tissue of a patient, a shaft extending along a longitudinal axis from the proximal head to the distal tip and received within a working channel of the cannula assembly, and a suturing feature configured to receive a suture including a suture thread, the method comprising:

(a) inserting the obturator and the cannula assembly through the tissue such that the shaft extends through a tissue opening about the trocar path incision and the distal tip is positioned within a cavity of the patient;

(b) inserting a thread end portion of the suture thread with a needle through a channel of the cannula assembly, into the tissue, and to the suturing feature such that insertion is obliquely oriented relative to the longitudinal axis of the shaft and the needle with the suture thread thereon simultaneously extends from the channel to the suturing feature;

(c) directing the suture thread via the suturing feature with the obturator inserted through the tissue in order to direct the suture thread relative to the tissue;

(d) rotating the suture feature about the longitudinal axis of the shaft thereby transitioning the suturing feature from a first deployed position toward a second deployed position;

(e) removing the thread end portion of the suture thread from the tissue such that the removal is obliquely oriented relative to the longitudinal axis of the shaft; and (f) closing the tissue opening about the trocar path incision with the suture.

2. The method of claim 1, wherein the suturing feature of the obturator includes a catch arm selectively moveable from a retracted position to the first deployed position and the second deployed position and configured to releasably capture the suture thread of the suture from the needle, the method further comprising:

(a) extending the catch arm radially outwardly to the first deployed position;

(b) inserting the thread end portion of the suture thread into the tissue with the needle;

(c) releasably capturing the thread end portion of the suture thread with the catch arm;

(d) rotating the catch arm to the second deployed position with the thread end portion of the suture thread releasably captured thereto;

(e) releasing the thread end portion of the suture thread from the catch arm; and (f) withdrawing the thread end portion of the suture thread from the patient to thereby suture the tissue opening.

3. The method of claim 2, wherein rotating the catch arm further includes rotating the obturator relative to the cannula assembly.

4. The method of claim 1, further comprising:

(a) manipulating the needle from a catch position toward a release position;

(b) urging the suture thread of the suture with a cam surface of the needle from a catch portion of a suture notch; and (c) releasing the suture thread from the catch portion of the suture notch.

5. The method of claim 1, wherein a surgical access device includes a tissue retractor including a flexible body, a plurality of surgical instrument channels arranged in a central portion of the tissue retractor, a needle entrance port, and a needle exit port arranged distally of the needle entrance port, the needle entrance port and the needle exit port defining a needle channel extending distally through the surgical access device and obliquely relative to the longitudinal axis of the shaft thereof, the method comprising:

(a) guiding a surgical instrument with at least one surgical instrument channel distally through the surgical access device; and (b) guiding the needle through the surgical access device and adjacent to the tissue to facilitate closure of the tissue opening.

6. The method of claim 1, wherein directing the suture thread via the suturing feature further includes directing the suture thread via the suturing feature with the obturator inserted through the tissue in order to direct the suture thread relative to the tissue while the cannula assembly is releasably secured to the obturator.

7. The method of claim 1, further comprising piercing the tissue with the distal tip of the obturator thereby forming a tissue opening in the tissue.

8. A method of suturing a trocar path incision in a tissue of a patient with an obturator and a needle, wherein the obturator includes a proximal head including a distal tip configured to penetrate tissue of a patient, a shaft extending from the proximal head to the distal tip and the shaft is configured to be received within a working channel of a cannula assembly, and a suturing feature configured to receive a suture, the method comprising:

(a) piercing the tissue with the distal tip of the obturator thereby forming a tissue opening in the tissue;

(b) inserting the obturator through the tissue such that the shaft extends through a tissue opening about the trocar path incision and the distal tip is positioned within a cavity of the patient;

(c) inserting a thread end portion of the suture through a first portion of the tissue with the needle;

(d) directing the suture via the suturing feature with the obturator inserted through the tissue in order to direct the suture distally through the tissue;

(e) removing the needle and the thread end portion of the suture proximally through another portion of the tissue with the needle, wherein the needle remains in contact with the thread end portion during the removal of the thread end portion from the tissue; and (f) knotting the suture to close the tissue opening about the trocar path incision.

9. A method of suturing a trocar path incision in a tissue of a patient with an obturator, wherein the obturator includes a proximal head, a distal tip configured to penetrate tissue of a patient, a shaft extending from the proximal head to the distal tip and received within a working channel of a cannula assembly, and a catch arm configured to receive a suture including a suture thread, the method comprising:

(a) inserting the obturator through the tissue such that the shaft extends through a tissue opening about the trocar path incision and the distal tip is positioned within a cavity of the patient;

(b) moving the suture thread with a needle into the catch arm while the obturator is releasably secured to the cannula assembly;

(c) manipulating the needle from a catch position toward a release position to release the suture thread;

(d) directing the suture thread via the catch arm with the obturator inserted through the tissue in order to direct the suture thread relative to the tissue;

(e) manipulating the needle from the release position to the catch position to grasp the suture thread and remove the suture thread from the catch arm, wherein the needle maintains contact with the suture thread while the suture thread is removed from the catch arm; and (f) closing the tissue opening about the trocar path incision with the suture.

\* \* \* \* \*